United States Patent [19]
Dolganov et al.

[11] Patent Number: 5,965,427
[45] Date of Patent: Oct. 12, 1999

[54] HUMAN RAD50 GENE AND METHODS OF USE THEREOF

[75] Inventors: Gregory Dolganov, San Carlos; Alexander Novikov, Foster City, both of Calif.

[73] Assignee: Genelabs Technologies, Inc., Redwood City, Calif.

[21] Appl. No.: 08/687,080

[22] Filed: Jul. 17, 1996

Related U.S. Application Data

[63] Continuation-in-part of application No. 08/592,126, Jan. 26, 1996.

[51] Int. Cl.$^6$ .............................. C07H 21/04; C12N 1/21; C12N 15/63
[52] U.S. Cl. .................................... 435/252.3; 435/320.1; 536/23.5; 536/24.31; 536/23.1; 935/9
[58] Field of Search .................................... 536/23.1, 23.5, 536/24.31; 435/320.1, 252.3; 935/9

[56] References Cited

PUBLICATIONS

Genbank Loci: R92967; L46900; N70974; H93370; L43399; L42096.
Clonetech 1995 Catalog pp. 32, 80–81 and 96–97.
Alani, E. et al., "Analysis of Wild–Type and rad50 Mutants of Yeast Suggests and Intimate Relationship between Meiotic Chromosome Synapsis and Recombination," *Cell.* 61: 419–436 (1990).
Alani, E. et al., "The Yeast RAD50 Gene Encodes a Predicted 153–kD Protein Containing a Purine Nucleotide–Binding Domain and Two Large Heptad–Repeat Regions," *Genetics.* 122: 47–57 (1989).
Baumann, P. et al., "Human Rad51 Protein Promotes ATP–Dependent Homologous Pairing and Strand Transfer Reactions In Vitro," *Cell.* 87: 757–766 (1996).
Beckett, M.A. and Weichselbaum R.R., "Southern Analysis of Human Head and Neck Cancer Cells for Homologous Sequences Using Yeast Gamma Repair Genes," *Journal of Surgical Oncology.* 38: 257–260 (1988).
Benson, F.E. et al., "Purification and Characterization of the Human Rad51 Protein, an Analogue of *E.coli* RecA," *The EMBO Journal.* 13: 5764–5771 (1994).
Dolganov, G.M. et al., "Human Rad50 Is Physically Associated with Human Mre11: Identification of a Conserved Multiprotein Complex Implicated in Recombinational DNA Repair," *Molecular and Cellular Biology.* 16: 4832–4841 (1996).
Glassner, B.J. and Mortimer, R.K., "Synergistic Interactions between RAD5, RAD16 and RAD54, Three Partially Homologous Yeast DNA Repair Genes Each in a Different Repair Pathway," *Radiation Research.* 139: 24–33 (1994).
International Search Report for PCT Application No. PCT/US97/01299 (Sep. 15, 1997).
Raymond, W.E. and Kleckner, N., "Expression of the *Saccharomyces cerevisiae* RAD50 Gene During Meiosis: Steady–State Transcript Levels Rise and Fall While Steady–State Protein Levels Remain Constant," *Mol Gen Genet.* 238: 390–400 (1993).
Raymond, W.E. and Kleckner, N., "RAD50 Protein of *S.cerevisiae* Exhibits ATP–Dependent DNA Binding," *Nucleic Acids Research.* 21: 3851–3856 (1993).
Allan, G.J., et al., "Loss of Heterozygosity on Chromosome 5 in Sporadic Ovarian Carcinoma is a Late Event and is Not Associated with Mutations in APC at 5q21–22," *Hum. Mutat.* 3:283–291 (1994).

(List continued on next page.)

*Primary Examiner*—Carla J. Myers
*Attorney, Agent, or Firm*—Charles K. Sholtz; Vincent M. Powers; Dehlinger & Associates

[57] ABSTRACT

Substantially-isolated polynucleotides encoding human RAD50 polypeptides, human RAD50 genomic sequences, and methods of use thereof.

12 Claims, 11 Drawing Sheets

OTHER PUBLICATIONS

Barrett, M.T., et al., "Determination of the Frequency of Loss of Heterozygosity in Esophageal Adenocarcinoma by Cell Sorting, Whole Genome Amplification and Microsatellite Polymorphisms," *Oncogene* 12:1873–1878 (1996).

Hsieh, L.L., and Huang, Y.C., "Loss of Heterozygosity of APC/MCC Gene in Differentiated and Undifferentiated Gastric Carcinomas in Taiwan," *Cancer Lett.* 96:169–174 (1995).

Largey, J.S., et al., "Loss of Heterozygosity Involving the APC Gene in Oral Squamous Cell Carcinomas," *Oral Surg. Oral Med. Oral Pathol.* 77:260–263 (1994).

Li, H., et al., "[Multiple Tumor Suppressor Genes in Esophageal Carcinoma Induced in Human Fetus Esophageal Epithelium by NMBzA]," *Chung Hua Chung Liu Tsa Chih* 17:170–174 (1995) (abstract).

Li, H., and Lu, S., "[Mutation of Tumor Suppressor Genes APC and MCC in Human Esophageal Cancer,]" *Chung Hua Chung Liu Tsa Chih* 17:9–12 (1995) (abstract).

Medeiros, A.C., et al., "Loss of Heterozygosity Affecting the APC and MCC Genetic Loci in Patients with Primary Breast Carcinomas," *Cancer Epidemiol. Biomarkers Prev.* 3:331–333 (1994).

Miura, K., et al., "Deletion Mapping in Squamous Cell Carcinomas of the Esophagus Defines a Region Containing a Tumor Suppressor Gene Within a 4–Centimorgan Interval of the Distal Long Arm of Chromosome 9," *Cancer Res.* 55:1828–1830 (1995).

Montesano, R., et al., "Genetic Alterations in Esophageal Cancer and Their Relevance to Etiology and Pathogenesis: a Review," *Int. J. Cancer* 69:225–235 (1996).

Nakashima, H., et al., "Microsatellite Instability in Japanese Esophageal Carcinoma," *Int. J. Cancer* 64:286–289 (1995).

Ogasawara, S., et al., "Frequent Microsatellite Alterations on Chromosome 3p in Esophageal Squamous Cell Carcinoma," *Cancer Res.* 55:891–894 (1995).

Ogasawara, S., et al., "Common Deleted Region on the Long Arm of Chromosome 5 in Esophageal Carcinoma," *Gastroenterology* 110:52–57 (1996).

Pederson, B., "5q–: Pathogenetic Importance of the Common Deleted Region and Clinical Consequences of the Entire Deleted Segment," *Anticancer Res.* 13:1913–1916 (1993).

Schnitzler, M., et al., "Quantitation of APC mRNA in Human Tissues," *Biochem. Biophys. Res. Commun.* 217:385–392 (1995).

Tamura, G., et al., "Two Distinct Regions of Deletion on the Long Arm of Chromosome 5 in Differentiated Adenocarcinomas of the Stomach," *Cancer Res.* 56:612–615 (1996).

Tavassoli, M., et al., "Loss of Heterozygosity on Chromosome 5q in Ovarian Cancer is Frequently Accompanied by TP53 Mutation and Identifies a Tumour Suppressor Gene Locus at 5q13.1–21," *Br. J. Cancer* 74:115–119 (1996).

>rad50-2.seq SEQ ID NO: 52
AGCAATAATGAAATTTCACAGTATGAAAGAAATCAATAAAATTATACGTGACCTGTGGCGAAGTACCTATCGTGGACAAG

Fig. 5A

>rad50-4.seq SEQ ID NO: 53
CAAGGAACTAGCTTCATCTGAGCAGAATAAAATCATATAAATAATGAACTAAAAAGAAGGAAGAGCAGTTGTCCAG
TTACGAAGACAAGCTGTTTGATGTTTGTGGTAGCCAGGATTTGAAAGTGATTTAGACAGGCTTAAAGAGGAAATTGA
AAATCATCAAAACAGCGAGCCATGCTGGCTGAGCCACAGCAGTTTACTCCCAGTTCATTACTCAGCTAACACGA
AAACCAGTCATCATGTTGCCCCGTTTGCTCCAGATAAACTCAAGTACACAGAATCAGAGCTAAAAAAGAAAAGCGGCTGATGA
GTCTAAACTGCGACTTGCTCCAGATAAACTCAAGTACACAGAATCAGAGCTAAAAAAGAAAAGCGGCTGATGA
AATGCTGGGACTTGTGCCCATGAGCAAAGCATAATTGATTTGAAGGAGAAGAATACCAGATTAAGAAACAAACT
GCAGAATGTCAATAGAGACATACAGCGCCTAAAGAACGACATAGAACAAGAAACACTCTTGGTACAATAATGCC
TGAAGAAGAAGTGCCAAGTATGCCTGACAGATGTTACAATTATGGAGAGGTTCCAGATGGAACTTAAAGATGTTGA
AAGAAAATTGCACACAACAAGCAGCTAAGCTACAAGGAATAGACTTAGATCGAACTGTCCAACAAGTCAACCAGGAGAA
ACAAGAGAAACAGCACAAGTTAGACACAGTTTCTAGTAGACACAAGCTAAATCGTAAGCTTATACAGGACCAGCAGGA
ACAGATTCAACATCAAAAGTACAACAAGAGCTAAAAATGAGCTAAAATCTGAGAAATCTGAGAAATCCACTAATTGCAACGTCG
TCAGCAACTGGAGGAGCAGACTGTGGAATTATCCACTGAAGTTCAGTCTTTGTTACAGAGATAAGGATGCTAAAGA
GCAGGTAAGCCCTTTGGAAACATTGGAAAAGTTCCAGCAAGAAGTTCCGGCTATATATGAAGAGACATTGA
CAACAAAATAGCCACAAGGATAAACTGAATGATATTAAAGAGAAGGTTAAAAATATTCATGCTATATGAAGAGACATTGA
GAATTATTCAAGATGGGAAGACGACTATAAGAAAGCAAAAAGAAACTGAACTTAATAAAGTAATAGCTCAACTAAG
TGAATGCGAGAACAACAAGAAAAGATAAATGAAGATATGAGACTCATGAGACAAGATATTGATACACAGAAG

Fig. 5B

>rad50-3.seq SEQ ID NO: 54
GTTGCTCAAGAAACAGATGTGAgAGCCCAGATTCGTCTCTGCAATTTCGTGATGTCAATGGAGAACTTATAGCTGT**GCAA
AGATCTATGGTGTGTACTC**AGAAAAGCAAAAGACAGAATTAAAACTCTGAAGGAGTCATTACTAGAACAAAGCAT
GGTGAAAAGGTCAGTCTGAGCTCTAAGTGTCAGAGAAATGACCGAGAAATGATCAGTCTCTTGGGTTTCCAAGCT
GTGCTAAATAATGTCATTTTCTGTCATCAAGAAGATTCTAATTGGCCTTAAGTGAAGGAAAGGCTTTGAAGCAAAAG
TTTGATGAGATTTTTCAGCAACAAGATACATTAAAGCCTTAGAAACACTTCGGCAGGTACGTCAGACACAAGGTCAG
AAAGTAAAAGAATATCAAATGAACTAAAATATCTGAAGCAATATAAGAAAAAAGCTTGTGAGATTCGTCAGATT
ACAAGTAAGGAAGCCCAGTTAACATCTTCAAAGGAAATTGTCAAATCCTATGAGAATGAACTTGATCATTGAAG

Fig. 5C

IP WITH 204/3p
1000 mM
300 mM
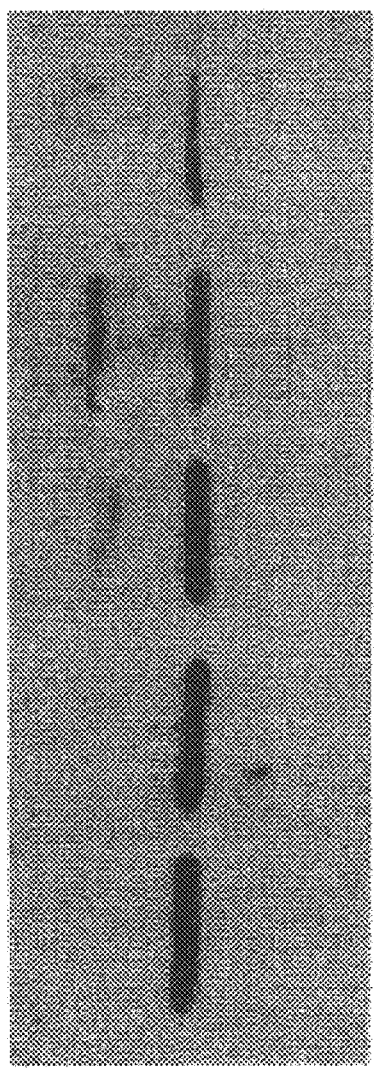
84
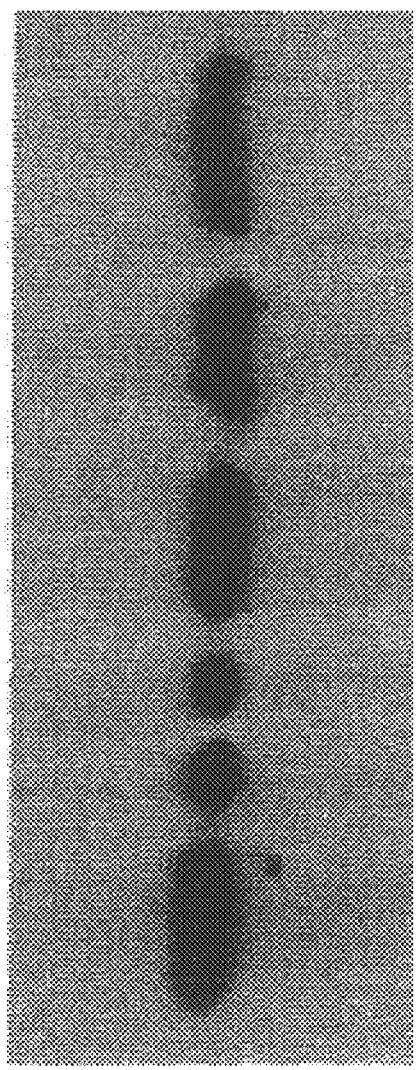
204/3p
IMMUNODETECTION REAGENT
Fig. 8

HUMAN RAD50 GENE AND METHODS OF USE THEREOF

This application is a continuation-in-part of co-owned U.S. patent application for "Transcripts Encoding Immunomodulatory Polypeptides", Ser. No. 08/592,126, filed Jan. 26, 1996.

FIELD OF THE INVENTION

The present invention relates to human RAD50 gene and protein compositions and to diagnostic and therapeutic methods of use thereof.

REFERENCES

Alani, E., et al., *Genetics* 122:47–57 (1989).
Alani, E., et al., *Cell* 61(3):419 (1990).
Ausubel, F. M., et al., in *CURRENT PROTOCOLS IN MOLECULAR BIOLOGY*, John Wiley and Sons, Inc., Media, Pa. (1988).
Bain, G. D., et al., *Dev. Biol.* 164:87–101 (1995).
Beames, et al., *Biotechniques* 11:378 (1991).
Bellanne-Chantelot, C., et al., *Cell* 70:1059–1068 (1992).
Boubnov, N. V., et al., *Proc. Natl. Acad. Sci. USA* 92:890–894 (1994).12
Boyum, A., *Scan J. Lab Invest* 21:77 (1968).
Burke, D. T., et al., *Science* 236:806–812 (1987).
Champlin, R. and D. W. Golde, "The Leukemias" in *HARRISON'S PRINCIPLES OF INTERNAL MEDICINE*, 12TH ED., J. D. Wilson, et al., Eds., McGraw-Hill (1991).
Chenchik, A., et al., *Clontechniques* X(1):5–8 (1995).
Chomczynski, P., and Sacchi, N., *Anal. Biochem.* 162:156 (1987).
Chumakov, I., et al., *Nature* 359:380–387 (1992).
Cotton, R. G., et al., *Proc. Natl. Acad. Sci. USA* 85:4397–4401 (1988).
Dayhoff, M. O., Ed., "A Model of Evolutionary Change in Proteins," in *MATRICES FOR DETECTING DISTANT RELATIONSHIPS*, National Biomedical Research Foundation, Washington, D.C. (1978).
Doetschman, et al., *Nature* 330:576 (1987).
Firnemich, A. A., et al., *Mol Cell Biol,* 15:1620 (1995).
Glisin, V., et al., *Biochemistry* 13:2633 (1974).
Georgopoulos, K., et al. *EMBO J.* 9:109–115 (1990).
Gorbalenya, A. E., and Koonin, E. V., *J. Mol. Biol.* 213:583–591 (1990).
Grompe, M., *Nature Genetics* 5:111–117 (1993).
Grunhaus, A. and Horowitz, M. S., *Semin. Virol.,* 3:237–252 (1992).
Guldberg, P., et al., *Genomics* 217:141–146 (1993).
Harlow, E., and Lane, D., in *ANTIBODIES: A LABORATORY MANUAL*, Cold Spring Harbor Laboratory Press, Cold Spring Harbor, Md. (1988).
Hays, S. L., et al., *Proc Nat Acad Sci, USA,* 92:6925 (1995).
Hertz, J., and Gerard, R. D., *Proc. Natl. Acad. Sci. U.S.A.,* 90:2812–2816 (1993).
Hirano, T., et al., *Current Opin. in Cell Biol.* 7:329–336 (1995).
Hogan, B., et al., *MANIPULATING THE MOUSE EMBRYO*, Cold Spring Harbor Laboratory, Cold Spring Harbor, N.Y. (1994).
Innis, M. A., et al., in *PCR PROTOCOLS*, Academic Press (1990).
Ivanov, E. L., et al., *Mol Cell Biol,* 14(5): 3414 (1994).
Jakobsen, K. S., et al., *Nucleic Acids Res.* 18:3669 (1990).
Jakobsen, K. S., et al., "Direct mRNA Isolation Using Magnetic Oligo(dT) Beads: A Protocol for All Types of Cell Cultures, Animal and Plant Tissues" in *ADVANCES IN BIOMAGNETIC SEPARATION*, M. Uhlen, et al., Eds., Eaton Publishing (1994).
Johzhuka, K., and Ogawa, H., *Genetics* 139:1521–1532 (1995).
Keller, G. M., et al., *Mol. Cell. Biol.* 13:472–486 (1993).
LeBeau, M. M., *Proc. Natl. Acad. Sci. USA* 90:5484–5488 (1993).
Lewis, D. B., et al., *Proc. Natl. Acad. Sci. USA* 85:9743 (1988).
Liber, H. L., and Thilly, W. G., *Mutat. Res.* 94:467–485 (1982).
Lipman, D. J., and Pearson, W. R., *Science* 227:1435–1441 (1985).
Longmire, J. L., et al., *GATA* 10:69–76 (1993).
Lupus, A., et al., *Science* 252:1162–1164 (1991).
Maniatis, T., et al., *MOLECULAR CLONING: A LABORATORY MANUAL*, Cold Spring Harbor Laboratory (1982).
Mansour, S. L., et al., *Nature* 336:348 (1988).
Martin, G. R., et al., *Proc. Natl. Acad. Sci.* 78:7634 (1981).
Michaud, J., et al., *Genomics* 13:389 (1992).
Miller, A. D., *Hum. Gene Ther.* 1:5 (1990).
Morgan, J. G., et al., *Nucleic Acids Res.* 20:5173–5179 (1992).
Mortensen, R. M., et al., *Mol. Cell. Biol.* 12:2391–2395, (1992).
Mullis, K. B., U.S. Pat. No. 4,683,202, issued Jul. 28, 1987.
Mullis, K. B., et al., U.S. Pat. No. 4,683,195, issued Jul. 28, 1987.
Myers, R. M., et al., *Meth. Enzymol.* 155:501–527 (1987).
Nadler, L. M., "The Malignant Lymphomas" in *HARRISON'S PRINCIPLES OF INTERNAL MEDICINE*, 12TH ED., J. D. Wilson, et al., Eds., McGraw-Hill (1991).
Nagamine, C. M., et al., *Am. J. hum. Genet.* 45:337–339 (1989).
Nimer, S. D., et al., *Blood,* 70:1705 (1987).
Petrini, J. H. J., et al., *Genomics* 29:80–86 (1995).
Ramirez-Solis, R., et al., "Guide to Techniques in Mouse Development" in: *Methods in Enzymology* vol 225, P. M. Wassarman and M. L. DePamphilis, eds., pp. 855–978, Academic Press, Inc., (1993).
Raymond, W. E. and Kleckner, N., *Mol. Gen. Genet.* 238:390–400 (1993a).
Raymond, W. E., and Kleckner, N., *Nuc. Acids Res.* 21:2851–3856 (1993b).
Reilly, P. R., et al., *BACULOVIRUS EXPRESSION VECTORS: A LABORATORY MANUAL*, 1992.
Robbins, J., et al., *Cell* 64:615–623 (1991).
Robertson, et al., *Nature* 323:445–448 (1986).
Rooney, D. E., and B. H. Czepulkowski, *HUMAN CYTOGENETICS: A PRACTICAL APPROACH*, IRL Press, NY, 1992.
Rosenfeld, M. A., et al., *Science* 252:431 (1991).
Rowley, et al., , *Proc. Natl. Acad. Sci. USA* 87:9358–9362 (1990).
Sambrook, J., et al., in *MOLECULAR CLONING: A LABORATORY MANUAL*, Second Edition, Cold Spring Harbor Laboratory, Cold Spring Harbor, N.Y. (1989).
Sheffield, V. C., et al., pp 1–149 in *ANALYSIS OF THE EFFICIENCY OF SINGLE BASE SUBSTITUTION DETECTION BY SSCP*, Cold Spring Harbor Laboratory, Cold Spring Harbor, N.Y. (1992).
Shinohara, A., et al., *Nat. Genet.* 4:239–243 (1993).
Siebert, P. D., et al., *Nuc. Acids Res.* 23(6):1087–1088 (1995).
Smith, D. B. and Johnson, K. S., *Gene* 67:31 (1988).
Smith, D. B. Methods Mol. Cell Biol. 4:220–229 (1993).

Tran, H. T., et al., *Mol. Cell. Biol.* 15:5607 (1995).
Tybulewicz, V. L. J., et al., *Cell* 65:1153–1163 (1991).
Weinberg, R. A., *Science* 254:1138 (1991).
Weiss, M. J., and S. H. Orkin, *J. Clin. Invest.* 97:591–595 (1996).
Zhang, F. R., et al., *Chromosoma* 99:436–439 (1990).

BACKGROUND OF THE INVENTION

A common genetic abnormality associated with malignant myeloid neoplasms in humans is the loss of whole chromosome 5 or 7 or a deletion of the long arm 5q or 7q of one of these chromosomes. In one reported study of 129 patients with therapy-related myelodisplastic syndrome (t-MDS) or therapy-related acute myeloid leukemia (t-AML), 75% of the patients had a loss or deletion of chromosome 5 or 7 (LeBeau). In addition, a deletion in 5q has also been observed in 10% of patients with AML arising de novo, and in 15% of patients who have MDS arising de novo (Nimer).

The 5q human chromosome region is known to contain a number of genes encoding growth factors, hormone receptors, and proteins involved in signal transduction or transcriptional regulation, and several of these genes are good candidates for tumor suppressor genes. The LeBeau study cited above investigated the possibility that deletion of a particular one or more of these genes, including the hematopoietic growth factors CSF2, IL3, IL4, IL5, and IL9, as well as EGR1, might be responsible for the predisposition to malignant myeloid neoplasms. The study was unsuccessful in identifying such a gene.

It has now been discovered, in accordance with the present invention, that at least one of the genes whose deletion in the 5q chromosome region correlates strongly with leukemia is a gene which is herein identified as a human RAD50 (hRAD50) gene, analogous to RAD50 gene in the yeast *Saccharomyces cerevisiae* (Sc).

In yeast, RAD50 is one of an epistatic group of genes whose products have been implicated in the recombinational repair of double-strand breaks (DSB's). The group of yeast genes include RAD50–57, MRE2, MRE11, XRS2, and RFA1 (Hays). Studies to date suggest that several genes in the group form a multi-protein complex (or complexes) that function in DSB repair, and participate in meiotic recombinational events (Firmenich, Hays).

Sc RAD50 itself appears to be required for recombinational repair of many types of DSB's (Tran), possibly in a complex with MRE11 (Johzuka, Ivanov). RAD50 functions in Sc is required during vegetative growth for recombinational repair of DSB, and during meiosis, for initiation of meiotic recombination (Raymond, 1993a). In light of the key role played by the protein, and the fact that the protein is known to bind to DNA in the presence of ATP (Raymond, 1993b), it has been proposed that the protein functions in chromosomal homology searching between interacting DNA molecules (Alani, 1989; 1990).

SUMMARY OF THE INVENTION

The invention includes, in one aspect, an isolated or substantially-isolated hRAD50 DNA composition capable of selectively hybridizing to a polynucleotide fragment having a sequence or the reverse complement of one or more of the DNA sequences identified by SEQ ID NO:55–115. The composition is at least 20, preferably at least 30 nucleotides in length.

In a general embodiment, the hRAD50 DNA composition is capable of selectively hybridizing under stringent conditions to a polynucleotide fragment having a sequence or the reverse complement of one or more of the DNA sequences identified by SEQ ID NO:55–115.

In one embodiment, the composition is capable of selectively hybridizing to a polynucleotide fragment (e.g., a fragment derived from a genomic library) corresponding to a hRAD50 exon and identified by one of the sequences SEQ ID NO:55, 56, 58, 61, 64, 66, 69, 71, 73, 75, 77, 79, 82, 84, 87, 89, 92, 95, 97, 99, 102, 104, 107, 110, 112, or 114.

In another embodiment, the composition is capable of selectively hybridizing to a polynucleotide corresponding to a hRAD50 intron and identified by one of the sequences SEQ ID NO:57, 59, 60, 62, 63, 65, 67, 68, 70, 72, 74, 76, 78, 80, 81, 83, 85, 86, 88, 90, 91, 93, 94, 96, 98, 100, 101, 103, 105, 106, 108, 109, 111, or 113.

In yet another embodiment, the composition is capable of selectively hybridizing to a polynucleotide derived from a cDNA library and identified by one of the sequences SEQ ID NO:44, 45 and 46.

In a related aspect, the invention includes a nucleic acid probe, at least 30 nucleotides in length, capable of selectively hybridizing under stringent conditions to a polynucleotide fragment having a sequence selected from the group consisting of SEQ ID NO:55–114. The probe has a sequence such that under typical hybridization conditions (see example provided in "definitions"), it does not hybridize to corresponding yeast RAD50 sequences, but does hybridize to the corresponding human RAD50 sequences. In a general embodiment, the probe is capable of selectively hybridizing to a polynucleotide fragment corresponding to a hRAD50 exon, such as a fragment having a sequence selected from the group consisting of SEQ ID NO:55, 56, 58, 61, 64, 66, 69, 71, 73, 75, 77, 79, 82, 84, 87, 89, 92, 95, 97, 99, 102, 104, 107, 110, 112, or 114.

DNA compositions and nucleic acid probes such as described above are useful in a number of screening applications, including but not limited to fluorescent in situ hybridization (FISH), Northern and Southern blot analyses, dot blot and slot blot analyses and the like.

The invention also includes a pair of single-stranded DNA primers useful for DNA amplification of a fragment of the human RAD50 (hRAD50) gene, wherein each primer of said pair is at least 15 nucleotides in length, and use of said pair in a polymerase chain reaction containing either human genomic DNA or suitable human cDNA target results in synthesis of a DNA fragment containing all or preferably part of the sequence of a human RAD50 gene. The primer pair is preferably capable of amplifying at least one exon of hRAD50 (or portion thereof), such as an exon having a sequence selected from the group consisting of SEQ ID NO:55, 56, 58, 61, 64, 66, 69, 71, 73, 75, 77, 79, 82, 84, 87, 89, 92, 95, 97, 99, 102, 104, 107, 110, 112, or 114. For example, the primers of the pair can have sequences derived from a sequence selected from the group consisting of SEQ ID NO:55–114, or SEQ ID NO:116–163.

Exemplary applications of such primer pairs include amplification of DNA fragments for use in single-strand conformational polymorphism (SSCP), denaturing gel electrophoresis (DGGE), or heteroduplex analyses (HA) of hRAD50 for the presence of mutations.

Also forming parts of the invention are (i) a method for screening an individual for predisposition to cancer, and (ii) a method for screening an individual for predisposition to hypersensitivity to electromagnetic (EM) radiation (e.g., X-rays, ultraviolet (UV) light). The methods include isolating genomic or cDNA fragments from the individual, testing the isolated fragments for an alteration in the polynucleotide sequence of the individual's hRAD50 gene relative to the polynucleotide sequence of a normal hRAD50 gene, and identifying the test individual as being predisposed to cancer or hypersensitivity to EM radiation if (i) an alteration is identified and (ii) the alteration results in a change in the amino acid sequence of the individual's hRAD50 protein relative to the amino acid sequence of a normal hRAD50 protein, or loss of the protein.

The predisposition to cancer screen may be applied, for example for screening for a predisposition to acute myeloid leukemia (AML), therapy-related acute myeloid leukemia (t-AML), therapy-related myelodysplastic syndrome, (t-MDS), and refractory anemia with excess blasts in transformation (RAEB-T).

The alteration in DNA sequence may be detected, for example, using hybridization analysis, such as in situ (e.g., fluorescent) hybridization, Northern and Southern blot analyses, dot blot or slot blot analyses. The alteration in DNA sequence may also be detected, for example, using single-strand conformational polymorphism (SSCP) analysis, denaturing gel electrophoresis (DGGE), or heteroduplex analysis (HA)

The invention also includes kits for detection of an alteration in the polynucleotide sequence of the individual's RAD50 gene. Hybridization kits include hRad50 hybridization probes, such as the probes identified above (e.g., probes suitable for Southern hybridization, dot blots, slot blots or FISH analysis), and may include other reagents as well as instructions for use. Polymerase chain reaction (PCR) amplification kits include primer pairs such as those described above, and may include additional reagents, such as Taq polymerase, amplification buffer and the like. Specific embodiments of the PCR amplification kits can include additional reagents specific for SSCP analysis, DGGE analysis or HA analysis.

In yet another aspect, the invention includes a gene therapy vector effective to transform human bone marrow cells. The vector includes an expression cassette containing an hRAD50 cDNA coding sequence identified by SEQ ID NO:44 or SEQ ID NO:45, under control of suitable control elements.

Also forming part of the invention is a method of decreasing the risk of a cancer in an individual having a defective hRAD50 gene, including the steps of: (a) isolating bone marrow stem cells from said individual, (b) transfecting cells of the individual with a gene therapy vector encoding a wild-type hRAD50 protein, and (c) introducing the transfected cells back into the individual, with the transfected cells now expressing wild-type hRAD50 protein.

In another aspect, the invention includes a substantially purified or substantially isolated hRAD50 polypeptide containing at least 11 consecutive residues in common with SEQ ID NO:51. The polypeptide may be produced by the protein expression vector constructed in accordance with another aspect of the invention, and containing, as a heterologous gene under the control of suitable control elements, an hRAD50 cDNA coding sequence portion effective to hybridize, under stringent hybridization conditions, with an hRAD50 cDNA having a sequence identified by SEQ ID NO:44.

hRAD50 polypeptides can be used, for example, to generate antibodies useful in assaying the presence of a hRAD50 protein in a sample, e.g., in a Western blot format. Such an analysis may be employed, for example, in a method of diagnosing an individual as being at increased risk for a cancer, described below.

The invention further includes an antibody (monoclonal or polyclonal) which is immunoreactive with hRAD50 protein identified by SEQ ID NO:51. The antibody is useful in methods of screening an individual for (i) predisposition to cancer, and (ii) predisposition to hypersensitivity to EM radiation. The methods include (a) obtaining from the individual, blood cells which in normal individuals contain hRAD50 as a soluble nuclear protein, (b) contacting soluble nuclear proteins from the cells obtained with an antibody which is immunoreactive with hRAD50 protein identified by SEQ ID NO:51, and (c) identifying the test individual as being predisposed to cancer or hypersensitivity to EM radiation if no normal immunocomplex between the cytosol proteins and the antibody is produced. A "normal" immunocomplex is defined as an association of the antibody with an antigen on a hRad50 polypeptide having the molecular weight of a wild-type hRad50 polypeptide (about 153 kD). The formation such an immunocomplex is described in Example 8 and shown in FIG. 7.

In another aspect, the invention includes a therapeutic method of decreasing risk of a cancer in an individual having a defective RAD50 gene. The method includes transfecting cells of the individual with an expression vector encoding a wild-type RAD50 protein, and expressing the protein in the cells. Exemplary cells amenable to such treatment include bone marrow stem cells. The cells can be transfected by a number of methods, including liposome-mediated transfection, $CaPO_4$ mediated transfection and electroporation. In one embodiment, the transfecting is done ex vivo or extracorporeally, by isolating selected cells (e.g., bone marrow stem cells or peripheral blood mononuclear cells (PBMC)), transfecting the cells ex vivo, and introducing the transfected cells back into the individual.

In a general embodiment, the expression vector used in the method is a viral vector, such as a retroviral vector, adenoviral vector or herpesviral vector. In another general embodiment, the vector is a mammalian expression vector.

The method is particularly amenable to decreasing risk for the following cancers: acute myeloid leukemia (AML), myelodysplastic syndrome (MDS), therapy-related myelodysplastic syndrome, (t-MDS), therapy-related acute myeloid leukemia (t-AML), refractory anemia (RA), and refractory anemia with excess blasts (RAEB).

An exemplary wild-type hRad50 protein suitable for use with the above-described method has the sequence represented as SEQ ID NO:51.

In still another aspect, the invention includes a human cell or cell line having a defective hRAD50 gene. The cell or cell line is useful in screening agents for the ability to promote DNA breaks in human cells. The screening is carried out by (a) exposing a human cell or cell line that is deficient for the wild-type hRAD50 gene to the test compound, (b) observing the morphology of the exposed cells, and (c) identifying a test agent as having the capability to promote DNA breaks if the observed morphology of the exposed cells differs from that of the same cells, but in the absence of exposure to the agent.

The invention further includes a transgenic mouse having a defective or missing RAD50 gene. The mouse is preferably homozygous for the defective or missing gene.

These and other objects and features of the invention will be more fully appreciated when the following detailed description of the invention is read in conjunction with the accompanying drawings.

BRIEF DESCRIPTION OF THE FIGURES

FIGS. 1A–1C are comparisons of the amino acid sequences of human Rad50 (hRad50) with *S. cerevisiae* Rad50 (ScRad50).

FIGS. 5A, 5B and 5C show DNA fragments used for primer design for determining the genomic sequence of RAD50. The sequences of these fragments are provided herein as SEQ ID NO:52, SEQ ID NO:53 and SEQ ID NO:54, respectively.

FIG. 8 shows immunoblots of immunoprecipitations carried out at NaCl concentrations ranging from 300 mM to 1000 mM, stained with hRad50 antiserum or hMre11 antiserum.

DETAILED DESCRIPTION OF THE INVENTION

I. Definitions

Figure 2A:
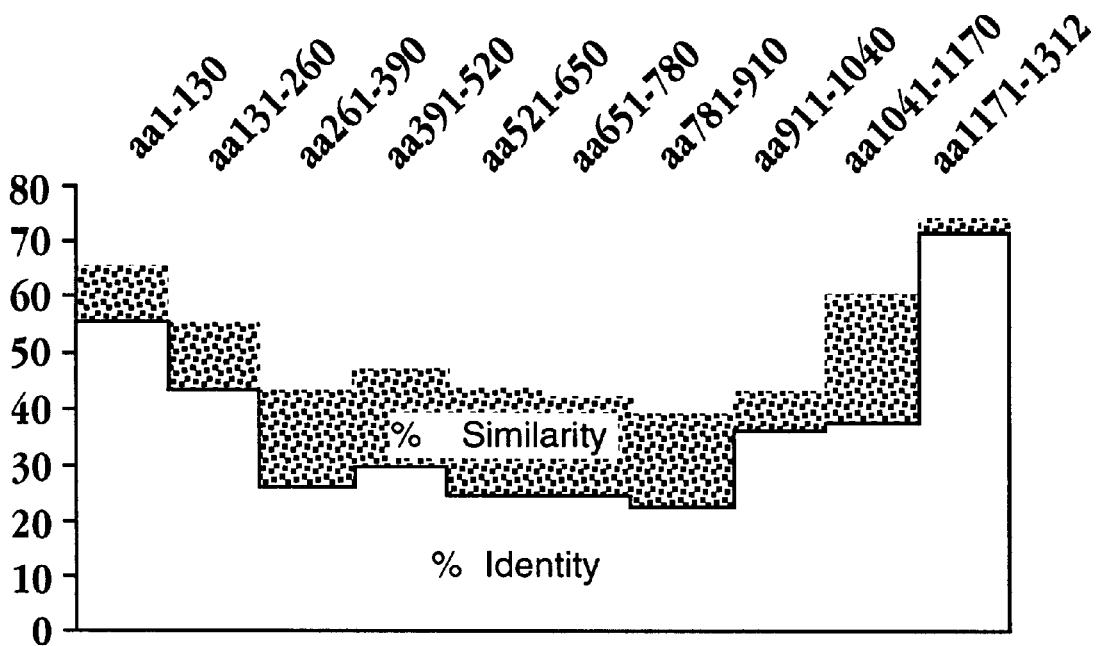
FIG. 2A shows the % similarity and % identity in a pairwise comparison of hRad50 and ScRad50.

"Substantially isolated" when used with respect to polynucleotide or polypeptides refers to the at least partial purification of such polynucleotides or polypeptides away from unrelated or contaminating components (e.g., cellular components other than the specified polynucleotide or polypeptide, and polypeptides or polynucleotides having a sequence different from that of the selected polypeptide or polynucleotide. Methods and procedures for the isolation or purification of compounds or components of interest are described below (e.g., recombinant production of polypeptides having immunomodulatory activity).

A nucleic acid fragment is considered to be "selectively hybridizable" to hRAD50 sequences if it is capable of specifically hybridizing to hRAD50 sequences but not to yeast RAD50 sequences (i) under typical hybridization and wash conditions, as described, for example, in Maniatis, et al., pages 320–328, and 382–389, or (ii) using reduced stringency wash conditions that allow at most about 25–30% basepair mismatches, for example: 2×SSC, 0.1 SDS, room temperature twice, 30 minutes each; then 2×SSC, 0.1% SDS, 37° C. once, 30 minutes; then 2×SSC room temperature twice, 10 minutes each.

"Stringent hybridization conditions" refer to hybridization under typical hybridization conditions as above, followed by stringent wash conditions, e.g., three washes in 0.1×SSC, 0.1% SDS at 65° C., 15 min each. "Stringent hybridization conditions" typically allow at most about 10–20% basepair mismatches.

A polynucleotide sequence or fragment is "derived from" another polynucleotide sequence or fragment when it contains the same sequence of nucleotides as are present in the sequence or fragment from which it is derived. For example, a bacterial plasmid contains an insert "derived from" a selected human gene if the sequence of the polynucleotides in the insert is the same as the sequence of the polynucleotides in the selected human gene. A polynucleotide sequence or fragment is also "derived from" another polynucleotide sequence or fragment if its sequence is the complement or reverse complement of the sequence from which it is derived (applicable, e.g., in the case or PCR primers "derived" from a target sequence, where the downstream primer is the reverse complement of the corresponding region in the target sequence).

Similarly, a polypeptide sequence or fragment is "derived from" another polypeptide sequence or fragment when it contains the same sequence of amino acids as are present in the sequence or fragment from which it is derived.

Percent (%) identity, with respect to two amino acid sequences, refers to the % of residues that are identical in the two sequences when the sequences are optimally aligned and no penalty is assigned to "gaps". In other words, if a gap needs to be inserted into a first sequence to optimally align it with a second sequence, the % identity is calculated using only the residues that are paired with a corresponding amino acid residue (i.e., the calculation does not consider residues in the second sequences that are in the "gap" of the first sequence). Optimal alignment is defined as the alignment giving the highest % identity score. Such alignments can be preformed using the "GENEWORKS" program. Alternatively, alignments may be performed using the local alignment program LALIGN with a ktup of 1, default parameters and the default PAM.

When a first polynucleotide fragment or polypeptide fragment is said to "correspond to" a second polynucleotide fragment or polypeptide fragment, respectively, it means that the fragments are essentially co-extensive with one another when the sequences representing the fragments (or complements or reverse complements thereof) are aligned using a sequence alignment program, such as "MACVECTOR" (IBI, New Haven, Conn.). "Corresponding" polynucleotide or polypeptide fragments typically contain a similar, if not identical, number of residues. It will be understood, however, that corresponding fragments may contain insertions or deletions of residues with respect to one another, as well as some differences in their sequences.

A cell or a cell line is "selectively deficient" for a copy of a selected gene, such as a wild-type copy of the hRAD50 gene, if (i) the cell or cell line contains no normal or wild-type functional copies of the selected gene, and (ii) the chromosome region in which the selected gene is normally contained is, in both chromosomes, substantially normal or wild-type with respect to all genes in that region with the exception of the selected gene. For example, a cell containing a large deletion on chromosome 5 encompassing hRAD50 as well as other genes is not selectively-deficient for hRAD50, whereas a cell containing a deletion of a portion of the hRAD50 gene is selectively-deficient for hRAD50 if the deletion prevents expression of functional protein and if the cell has no other functional copies of hRAD50.

A "defective" gene, such as a defective hRAD50 gene, is a gene that cannot cause expression of a functional gene product, i.e., a gene product having the biological activity associated with a gene product expressed by a normal, wild-type copy of the gene.

II. Direct Selection and Analysis of Chromosome 5-Specific cDNA Sequences

Experiments performed in support of the present invention detail the generation of cDNA samples enriched for sequences from the 5q23–31 region of human chromosome 5. This region has been identified as containing a tumor suppressor, which may be involved in the development of certain cancers and immunodeficiencies (LeBeau). The cDNA samples were derived from a variety of tissues, including human fetal brain and liver, adult bone marrow, leukemias, lymphomas, activated lymphocytes and cytokine-producing clones, as detailed in Example 1A. The samples were assayed for the presence of known cytokines as detailed in Example 1B using primers shown in Table 1. Results of these assays are shown in Table 2. Those samples showing increased expression of cytokines were combined to create "cDNA pools". The composition of the different pools is detailed in Example 1.

Pools containing relatively high levels of cDNAs encoding different cytokines (see Example 1, Table 2) were further processed using genomic "direct selection", as detailed in Examples 2 and 3. Here, yeast artificial chromosome (YAC) clones containing the 5q23–31 region of chromosome 5 were used to select cDNA that hybridized to sequences in that region. Analysis of approximately 3,000 cDNAs selected with the genomic region spanning 1.3 Mb of 5q23–31 revealed several hundred cDNA clones ranging from about 500 to about 800 bp in length. The sequences were further analyzed by mapping them to YAC clones containing fragments of the 5q23–31 region. About 79% of these clones were mapped to human chromosome 5 and starting YACs either by RT-PCR or Southern blot hybridization.

The data obtained from the physical mapping of the cDNAs to the starting YACs and chromosome 5-specific cosmids were used to group the cDNAs according to their location and partial overlap with one another, resulting in over 50 groups, or "bins", of cDNAs comprised of overlapping clones. Some of the selected cDNAs were also sequenced as described in Example 4 to facilitate placement into the bins.

The consensus cDNA sequences from one of these "bins" were homologous to the yeast RAD50 gene (he results of a "BLASTX" homology search against a protein sequence database (PIR +SWISS-PROT) showed that the human RAD50 homologue had a ~35% overall homology to *S. cerevisiae* Rad50: Score=390, P=3.8e-89.). Accordingly, the human gene from which these consensus sequences were derived was termed hRAD50 (human RAD50).

Three alternatively-spliced hRAD50 cDNA sequences were identified—SEQ ID NO:44, SEQ ID NO:45 and SEQ ID NO:46. SEQ ID NO:44 is a full-length cDNA sequence of hRAD50, and is about ten times more abundant than either of G18 (SEQ ID NO:45) or G102 (SEQ ID NO:46)

The hRAD50 consensus sequence (SEQ ID NO:44) was arrived at by analysis of a number of overlapping clones. In some cases, the clones overlapped only near their ends and the sequence between the overlaps was derived from a single cDNA. In such cases and some others, the consensus sequence may contain alternatively-spliced sequences from the same gene. It will be noted that two different alternatively-spliced transcripts G102 (SEQ ID NO:46) and G18 (SEQ ID NO:45), derived from the same region of the gene, were detected. G102 (SEQ ID NO:46) corresponds to sequences within the first intron (SEQ ID NO:57), while G18 corresponds to sequences in exon 11 (SEQ ID NO:79) and intron 11 (SEQ ID NO:80, 81). A proposed hRad50 alternatively-spliced isoform amino acid sequence encoded in part by G18 (SEQ ID NO:45) sequences is presented as SEQ ID NO:47. The first 597 amino acids of SEQ ID NO:47 are the same as the first 597 amino acids of SEQ ID NO:51 and the remaining amino acids of SEQ ID NO:47 are encoded in part by DNA sequences in G18 (SEQ ID NO:45). It is contemplated that G18 and/or G102 are fragments of cDNAs which encode truncated, alternatively-spliced forms of the hRad50 molecule.

Additional RAD50 sequences (e.g., other alternatively-spliced forms) may be obtained by one of skill in the art using the sequence information and teachings contained in the present specification combined with standard molecular techniques. For example, the cDNA clones described herein, or fragments thereof, may be used to screen a cDNA library constructed from, e.g., human T-cells using standard methods (e.g., Ausubel, et al., 1988). Such libraries are commercially available, for example, from Clontech (Palo Alto, Calif.). Full length clones may also be obtained by similar screening of cDNA pools generated as described herein.

III. Characterization of RAD50 cDNA

The expression pattern of hRAD50 cDNA was determined using RT-PCR with primers specific for the consensus sequence (SEQ ID NO:44). The details of the experimental methods are presented in Example 6B. Primers specific for the sequences to be amplified were constructed using standard methods. The primers were selected such that the expected amplification products were typically between 200 and 1000 bp in length. The following tissues were used for the RT-PCR reactions: total embryo (6, 8, 12 weeks of gestation), fetal liver, fetal brain, fetal muscle, placenta, adult heart, adult muscle, adult liver, adult brain, adult pancreas, adult kidney, adult aorta, adult spleen, adult testis, adult bone marrow, JY B-cell line, resting T-cells and activated T-cells.

Expression of hRAD50 sequences was also assessed using Northern blot analyses, as detailed in Example 6A. The Northern analyses were performed using probes derived from sequences SEQ ID NO:44 and SEQ ID NO:45. A non-coding 3'-flanking fragment of the gene corresponding to nucleotides 4333–5567 of SEQ ID NO:44 was used to probe a Northern Blot containing RNA derived from the same set of adult tissues as described above. mRNA species of 1.9 and 0.85 kb were detected in all tissues tested, with the strongest expression in testis, ovary and small intestine. Uniformity of RNA loading was confirmed using a beta-actin probe.

Similar experiments employing a probe corresponding to nucleotides 417–4353 of SEQ ID NO:44 revealed two mRNA species. A stronger signal was observed at about 5.8 kb and much lower signal was detected at about 6.5 kb in all tissues, with strongest expression in testis. The results of RT-PCR and Northern blot analyses taken together confirmed expression of the human RAD50 gene in activated T-cells, B-cells, placenta and multiple fetal tissues, including fetal liver. Genomic equivalent of this gene is about 100 kb.

In yeast, RAD50 encodes major and minor transcripts of 4.2 and 4.6 kb in length, respectively (Raymond and Kleckner, 1993a). Steady-state levels of both transcripts increase during meiosis, reaching maximal levels midway during meiotic prophase. Yeast RAD50 appears to be involved in DNA repair. It is required during vegetative growth for recombinational repair of double strand breaks and for efficient mating type switching, a direct recombination event promoted by a site-specific double strand break. Most *S. cerevisiae* mutants of Rad50 are deficient in repair of damage induced by X rays and in meiotic recombination.

The polypeptide predicted for *S. cerevisiae* Rad50 protein is 153 kDa (1312 aa) (Alani, et al., 1989). The protein contains an amino-terminal ATP-binding domain. Inactivation of this site by point mutations results in a null phenotype, and primary defects in meiosis. The remainder of the protein includes two long segments of heptad repeat sequence diagnostic of regions capable of forming alpha-helical coiled coils, one of which is similar to the S-2 domain of the myosin heavy chain. Since some mutations in the protein affect meiotic recombination but not the repair, it is likely that the protein has domains with different roles.

In accord with the present invention, human RAD50 is also involved in DNA repair. It will be appreciated that failure to express functional gene products of genes involved in DNA repair may be associated with cancer. In particular, an unrepaired double-strand (dbs) break of DNA can lead to a breakup of genomic DNA and culminate in any of a variety of cellular dysfunctions, including high sensitivity to ionizing radiation and impaired recombination. Defective recombination events (e.g., ones involving little or no sequence homology) have been implicated in carcinogenesis and severe immunodeficiencies.

Loss of human chromosome 5 as well as deletions of 5q have been associated with development of therapy-related acute non-lymphocytic leukemia (ANLL) or myeloid disorders (MDS). High resolution fluorescent in situ hybridization (FISH) has identified 5q31 as the most common cytogenetically deleted segment in t-MDS or t-ANLL (LeBeau, et al., 1993). Experiments performed in support of the present invention strongly suggest that hRAD50 is one of the genes involved in suppressing such disorders.

In particular, it is contemplated that hRAD50 has tumor suppression activity, i.e., that hRAD50 is a tumor suppression (TS) gene. Tumor suppressors (see review by Weinberg) are normal cellular genes that function by constraining the growth of cells. A number of tumor suppressor genes have been identified, including neurofibromatosis type I (NF-1), Wilms tumor (WT), the retinoblastoma susceptibility (RB) gene, the deleted in colon carcinoma (DCC) gene, the erbA gene and the p53 gene (Weinberg). According to the present invention, genes that when absent or when encoding nonfunctional gene product, predispose a cell toward neoplastic transformation, can also be considered tumor suppressor genes.

Genetic lesions that inactivate tumor suppressors liberate the cell from such constraints and lead to or predispose a cell to unregulated cellular proliferation, i.e., tumors. In other words, tumor suppressor genes contribute to oncogenicity through their loss rather than their activation. Accordingly, mutations in tumor suppressor genes are typically recessive with respect to precipitating the growth of a tumor—both copies of the gene must be inactivated for tumor formation to occur.

However, although both copies of a TS gene must typically be inactivated for tumor growth, individuals having one mutant or inactivated allele and one wild type allele of a particular TS gene are nevertheless at a significantly increased risk for developing a cancer precipitated by loss of that TS gene. This is due not only to the loss of the "backup" capability against deleterious effects of somatic mutations that two normal alleles provide for all non sex-linked genes, but also to the fact that evolving tumor cells employ genetic mechanisms to actively eliminate genes that interfere with their growth. In particular, when one allele of a TS gene is inactivated (e.g., by a germline mutation), the chromosomal region carrying the surviving wild-type allele may be replaced by a duplicated copy of the homologous chromosome region that carries the mutant allele. This replacement may be accomplished by, e.g., chromosomal nondisjunction, mitotic recombination, or gene conversion. These events typically occur with a frequency of as high as $10^{-3}$ to $10^{-4}$ per cell generations—a much higher rate than independent knockouts of the second copy, which occur on the order of $10^{-6}$ per generation.

Accordingly, in view of the above and the teachings of the present invention, deletion or inactivation of a single allele of the RAD50 gene has the effect of increasing the likelihood of cancer in a subject having such a deletion or inactivation. Such a deletion or inactivation also has the effect of increasing the likelihood that an individual will develop a hypersensitivity to electromagnetic (EM) radiation (e.g., X-rays, ultraviolet (UV) light), as discussed below.

The types of cancers and/or tumors which may be diagnosed and/or treated, or the risk of which may be assessed, using the methods and compositions of the present invention include hematological conditions (e.g., leukemias and lymphomas). In particular, the present inventions is particularly useful with respect to refractory anemias, acute non-lymphocytic leukemia, treatment-induced leukemias, lymphoproliferative disorders, and chronic myeloproliferative disorders. Specific examples of such hematological conditions which are manifested as cancers per se include but are not limited to acute myeloid leukemia (AML), therapy-related acute myeloid leukemia (t-AML), and therapy-related myelodysplastic syndrome (t-MDS). Specific examples of hematological conditions manifested as precancerous conditions include but are not limited to primary myelodysplastic syndrome (MDS), refractory anemia (RA), and refractory anemia with excess blasts (RAEB).

The sections below describe certain diagnostic and therapeutic methods enabled by the discoveries disclosed herein.

IV. hRAD50 Diagnostic Methods

In one aspect, the invention includes a method for diagnosing an individual as being predisposed to, or at increased risk for, cancer. The method includes detecting an alteration in the polynucleotide sequence of the individual's RAD50 gene relative to the polynucleotide sequence of a normal hRAD50 gene (e.g., SEQ ID NO:44), wherein the alteration results in a change in the amino acid sequence of the individual's Rad50 protein relative to the amino acid sequence of a normal hRad50 protein.

According to the present invention, an individual is at an increased risk for cancer, particularly a hematological cancer such as a leukemia or a lymphoma, if the individual contains at least one chromosome 5 with a defective or inactive or missing copy of hRAD50. For example, as illustrated in Example 9 and Table 4, individuals having deletions in the region of 5q23–q31 on one of their chromosomes have a hematological cancer (e.g., acute myeloid leukemia (AML), therapy-related acute myeloid leukemia (t-AML), and therapy-related myelodysplastic syndrome, (t-MDS)) or a precancerous condition (e.g., primary myelodysplastic syndrome (MDS), refractory anemia (RA), or refractory anemia with excess blasts (RAEB).

Several methods may be used to detect an alteration in the polynucleotide sequence of a RAD50 gene. Alterations as small as point mutations (i.e., single base-pair substitutions, insertions or deletions) can be detected using a number of different methods. A traditional approach to the detection of such alteration has been restriction fragment length polymorphism (RFLP) analysis, where the genomic DNA of a test individual is digested with different restriction endonucleases, probed with a fragment corresponding to the gene of interest, and the pattern of fragments analyzed.

Another exemplary method suitable for detection of point mutations is single-strand conformational (SSC) polymorphism (SSCP) analysis, as detailed in Grompe. SSCP is a conventional mutation screening technique where primer pairs are used to PCR amplify genomic DNA from a test subject, and the amplification products are resolved on a non-denaturing (e.g., glycerol-containing) polyacrylamide gel. The two single-stranded DNA molecules from each denatured PCR product assume a three-dimensional conformation dependent on the primary sequence. A difference in sequence between two such single-stranded molecules typically results in the molecules having different three-dimensional conformations, detectable as different bands on an SSCP non-denaturing gel. SSCP analysis typically detects 70–95% of mutations in PCR products that are 200 bp or shorter in length (Michaud, et al., Sheffield, et al.).

Subtle alterations in sequence (e.g., point mutations) may also be detected using denaturing gel electrophoresis (DGGE). This technique also uses differential electrophoretic migration of wild-type and mutant DNA to detect mutations. Double-stranded DNA (dsDNA) amplified by PCR is electrophoresed through a gradient of increasing concentration of a denaturant (e.g., urea and formamide). As they migrate through the gradient, the strands progressively dissociate in a sequence-dependent manner. Such partial melting of the duplex results in a marked decrease in mobility, allowing fragments differing in sequence by as little as one base-pair to be resolved (Myers, et al.). Accordingly, hRAD50 DNA from individuals with one normal and one mutant copy of hRAD50 would form normal/mutant heteroduplexes in the region of the alteration giving rise to the mutation. Such heteroduplexes can be resolved from the normal/normal and mutant/mutant homoduplexes using DGGE, and used to identify an individual as potentially at increased risk for cancer.

Heteroduplex analysis (HA) can also be used to detect mutations as subtle as single base-pair alterations. HA analysis typically employs PCR to generate amplification fragments corresponding to the region of a gene (e.g., hRAD50) being assayed. As described above for DGGE, when the target DNA contains two different sequences (e.g., one from a normal chromosome and one from a chromosome containing a mutant hRAD50 having an altered sequence with respect to wild-type hRAD50), and the sequences are similar enough to dimerize (i.e., the differences between the sequences are point mutations or small insertions/deletions), the amplification products will contain (i) homodimers consisting of either two strands having the wild-type sequence or two strands having the mutant sequence, and (ii) heterodimers consisting of one mutant strand and one wild-type strand. HA analyses are based on the observation that some such heteroduplexes have a different mobility than corresponding homoduplexes, even in regular polyacrylamide gels (Nagamine, C. M., et al.). HA analysis is facilitated, however, by use of specialized matrices, including "HYDROLINK" and "MDE", available from AT Biochem.

Other methods which may be used to detect heteroduplexes include RNase A cleavage (see, e.g., Ausubel, et al., Chapter 4) and chemical mismatch cleavage (Cotton, et al.).

Primer pairs used for SSCP, DGGE or HA analyses are typically designed based on sequences within introns adjacent splice junctions. Such primer pairs are then used to PCR amplify exons from target DNA (e.g., genomic DNA isolated from a subject in need of a diagnosis). The primers are preferably selected to generate amplification products in the range of 200-400 base pairs (bp). Exemplary primers suitable for SSCP, DGGE or HA analyses of the RAD50 gene include primers having sequences represented as SEQ ID NO:116 through SEQ ID NO:163. These primers correspond to the introns in vicinity of exon/intron splice junctions and are designed to amplify exon sequences from RAD50 genomic sequences. They are arranged in pairs corresponding to upstream and downstream primers. For example, primers r1 (SEQ ID NO:116) and r2 (SEQ ID NO:117) together constitute a primer pair effective to amplify a selected exon of the hRAD50 gene.

The selection of regions of a sequence suitable for serving as templates for PCR primer design is well known in the art (e.g., Innis, et al., 1990). In fact computer programs designed specifically for this purpose are commercially-available (e.g., "OLIGO" primer analysis software, NCBI, Inc., Plymouth, Minn.).

The methods described above can be used to detect several different types of mutations, including deletion mutations, insertion mutations and point mutations.

Deletion and insertion mutations may also be detected using hybridization methods, such as Southern blot hybridization, dot-blot hybridization, in situ hybridization (including fluorescent in situ hybridization (FISH)) and Northern blot hybridization. For example, extremely large (>1 megabase (Mb)) deletions and insertions can be detected by high resolution cytogenetics (Rooney, et al.) using FISH (Zhang, et al.), as described in Example 9. Smaller insertions and deletions, as well as some point mutations (e.g., point mutations that alter a relevant endonuclease restriction site) can be detected by Southern blot. Such hybridization analyses are also amenable to multiplex approaches, e.g., where probes to different portions of a gene are labelled with different dyes and used to probe a blot simultaneously.

An exemplary hybridization probe is a nucleic acid probe capable of selectively hybridizing to a polynucleotide fragment having a sequence selected from the group consisting of SEQ ID NO:55–114, wherein the probe is at least 30 nucleotides in length. Preferably, the probe is capable of selectively hybridizing to a polynucleotide fragment having a sequence selected from the group consisting of SEQ ID NO:55, 56, 58, 61, 64, 66, 69, 71, 73, 75, 77, 79, 82, 84, 87, 89, 92, 95, 97, 99, 102, 104, 107, 110, 112, or 114.

Deletion and insertion mutations may also be detected using a "multiplex" PCR approach, where a family of primer sets is designed to amplify a series of fragments (e.g., 200–400 bp fragments) having different lengths which together span substantially all of the cDNA encoding a selected gene (e.g., hRAD50). The fragments are then resolved on a gel, and insertions/deletions are detected by a change in the size of one or more fragments relative to fragments amplified using wild-type or normal hRAD50 as target.

hRAD50 DNA fragments having heterologous sequences (identified using, e.g., SSCP, DGGE or HA) are typically analyzed further using sequence analysis to determine if the nucleotide sequence alteration results in an alteration in the amino acid sequence. According to the present invention, hRad50 amino acid sequence alterations which predispose an individual to cancer or a precancerous condition are preferably ones that result in a substantial alteration in the activity of hRad50; i.e., alterations which represent mutations and not merely sequence polymorphisms among various individuals. For example, a missense point mutation resulting in conservative amino substitutions might not affect the biological activity of hRad50, and would be characterized as a sequence polymorphism rather than a mutation that is deleterious to the function of the protein. Examples of mutations having such a deleterious effect include point mutations that introduce a frame shift or a stop codon in the coding sequence of the cDNA.

DNA alterations having a substantial effect on the amino acid sequence can also be identified by analyzing the hRAD50 polypeptide itself, using, e.g., a Western immunoblot: Rad50 is a soluble protein confined to nucleus. A sample (e.g., a nuclear-enriched sample) from cells that in normal individuals express Rad50 (e.g., activated lymphocytes) can be used as a source for partially-purified Rad50 polypeptide, which can then be resolved on a polyacrylamide gel, the gel blotted and probed with anti-Rad50 antibodies, and the molecular weight and antibody-binding properties of the protein determined.

According to the present invention, alterations or mutations in the gene sequences of RAD50 which result in a functional change (e.g., non-conservative substitution, frame-shift, truncation or deletion) in the amino acid sequence of the Rad50 protein are indicative of the individual being at an increased risk for developing a precancerous condition or a cancer, particularly a hematological cancer such as a lymphoma or leukemia.

Lymphomas are neoplastic transformations of cells that reside primarily in lymphoid tissues. The two major forms of malignant lymphoma are Hodgkin's disease and non-Hodgkin's lymphoma (Nadler). Leukemias are a diverse group of neoplasms arising from the malignant transformation of hematopoietic cells. The transformed cells initially proliferate mainly in bone marrow and lymphoid tissues, where they interfere with immune function and hematopoiesis. Eventually, the leukemic cells migrate into the peripheral blood and infiltrate other tissues. Leukemias can be classified according to the affected cell types (myeloid or lymphoid) and as acute or chronic, depending on the history of the disease (Champlin and Golde).

Methods and compositions are particularly suitable for assessing the propensity or risk for contracting therapy-related malignant myeloid disorders. Specific examples of cancers amenable to analysis as described herein include acute nonlymphocytic leukemia (ANLL), which can include acute myeloid leukemia (AML), therapy-related acute myeloid leukemia (t-AML), and therapy-related myelodysplastic syndrome, (t-MDS).

Primary myelodysplastic syndrome (MDS) is a precancerous condition and includes a heterogeneous group of progressive, irreversible, multipotent stem cell disorders, including refractory anemia (RA), RA with ring sideroblasts (RARS), RA with excess blasts (RAEB), RAEB in transformation (RAEB-T) and chronic myelogenous leukemia (CMML). RA is not a cancer per se, unless it gains excessive blasts and becomes a RAEB-T, t-MDS or ANLL.

$5q^-$ syndrome is a distinct hematological disorder, occurring principally in elderly females. Its classical features includes macrocytic anaemia and mild infrequent progression to leukemias. Both t-MDS and $5q^-$ syndromes are possible undesirable consequences of successful chemotherapy following treatment of a previously-diagnosed malignant disease or non-neoplastic disorder. Their incidence varies with the different causative agents. For instance, $5q^-$ syndrome has been frequently reported in Hodgkin's disease patients treated with MOPP chemotherapy and radiotherapy and in myeloma patients treated with alkylating agents.

The above analysis can also be used in a method for diagnosing an individual as being predisposed to, or at increased risk for, hypersensitivity to electromagnetic (EM) radiation (e.g., X-rays, ultraviolet (UV) light), i.e., increased propensity for radiation-induced DNA damage. It is known, for example, that ultraviolet (UV) light and X-rays can cause DNA damage. According to the present invention, individuals who do not have two normal or wild-type copies of hRAD50 are at increased risk for suffering such damage. If diagnosed as being at increased risk, the individuals may take special precautions to minimize their exposure to potentially-risky radiation, such as avoiding certain routine X-rays and wearing extra protective clothing and UV-blocking sunscreen when outside in the sun.

The steps in the method are essentially the same as the steps of the method of diagnosing an individual for increased propensity for cancer.

V. hRAD50 Therapeutic Methods

In another aspect, the invention includes a method of decreasing risk of a cancer in an individual having a defective Rad50 gene, a method of treating a condition characterized by increased risk for developing a cancer in an individual, and a method of treating a cancer or cancerous condition in an individual.

According to the teachings herein, an individual suffering from a myeloid malignancy, where the transformed cells have no wild-type copies of hRAD50, can be treated using a gene therapy. Untransformed bone marrow stem cells are isolated from the individual and transfected with a gene therapy vector encoding wild-type hRad50. The individuals cancerous cells are then destroyed, and the transfected cells are infused or transplanted back into the individual, where they differentiate into cells expressing hRad50.

Exemplary gene therapy vectors of the present invention are effective to transform human bone marrow cells, and include an expression cassette containing an hRAD50 cDNA coding sequence identified by SEQ ID NO:44 or SEQ ID NO:45, under control of suitable control elements.

Any of a variety of gene therapy approaches may be used. One suitable approach is virally-mediated gene transfer, where host cells are transfected with chimeric genes or constructs of the present invention by infection with mature virions containing hybrid vectors (the chimeric genes along with selected viral sequences). The virions used to transfect host cells are preferably replication-defective, such that the virus is not able to replicate in the host cells.

The virions may be produced by co-infection of cultured host cells with a helper virus. Following coinfection, the virions are isolated (e.g., by cesium chloride centrifugation) and any remaining helper virus is inactivated (e.g., by heating). The resulting mature virions contain a chimeric gene of the present invention and may be used to infect host cells in the absence of helper virus. Alternatively, high titers of replication-defective recombinant virus, free of helper virus, may be produced in packaging cell lines containing those components for which the virus is defective (Miller).

Several types of viruses may be amenable for use as vectors with chimeric gene constructs of the present invention. Each type of virus has specific advantages and disadvantages, which are appreciated by those of skill in the art. Methods for manipulating viral vectors are also known in the art (e.g., Grunhaus and Horowitz; Hertz and Gerard; and Rosenfeld, et al.). Retroviruses may be particularly advantageous for use with the present invention—they are highly efficient at transfection (some vectors can stably transduce close to 100% of target cells), they stably integrate their DNA into the chromosomal DNA of the target cell and are suitable for use with proliferating cells, since they typically require replication of the target cells in order for proviral integration to occur.

The bone marrow are isolated using standard methods and transfected using a transfection system suitable for the vector. For example, transfection with certain viral constructs can be accomplished by simply incubating the construct or vector with the cells to be transfected. Other gene therapy vectors can be transfected into cells using liposome-mediated transfection, $CaPO_4$ mediated transfection or electroporation. The above-described methods can also be applied to treatment of other cells, such as peripheral blood mononuclear cells (PBMC) In addition to the diagnostic and therapeutic methods described above, the present invention enables the production of recombinant hRad5O, antibodies specifically immunoreactive with hRad5O, diagnostic methods using such antibodies and the construction of cell lines and transgenic animals defective for the RAD50 gene, as described below.

VI. hRAD50 Expression Vectors, Polypeptides and Antibodies

The present invention includes a recombinant expression vector capable of expressing hRAD50 sequences. Such a vector can then be used to express recombinant polypeptides in selected host cells, such as *E. coli*. Expression vectors such as described above typically contain control sequences, such as sequences containing promoter regions, enhancer elements, and the like, which are compatible with the selected host cell. These control sequences are operably linked to the insert sequence such that the insert sequence can be expressed in the selected host cell.

One example of an expression vector for recombinant production of hRad50 polypeptides is the plasmid PGEX (Smith and Johnson, 1988, Smith, 1993) and its derivatives (e.g., the pGEX series from Pharmacia Biotech, Piscataway, N.J.). These vectors express the polypeptide sequences of a cloned insert fused in-frame with glutathione-S-transferase. Recombinant PGEX plasmids can be transformed into appropriate strains of *E. coli* and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (Ausubel, et al., 1988).

Alternatively, affinity chromatography may also be employed for isolating β-galactosidase fusion proteins, such as those produced by cloning hRad50 polypeptide sequences in lambda gt11. The fused protein is isolated by passing cell lysis material over a solid support having surface-bound anti-β-galactosidase antibody.

Other suitable expression systems include a number of bacterial expression vectors, such as lambda gt11 (Promega, Madison Wis.), pGEX (Smith and Johnson, 1988), and pBS (Stratagene, La Jolla Calif.) vectors; yeast expression systems, such as the Pichia expression kit from Invitrogen (San Diego, Calif.); baculovirus expression systems (Reilly, et al.; Beames, et al.; Clontech, Palo Alto Calif.); and mammalian cell expression systems (Clontech, Palo Alto Calif.; Gibco-BRL, Gaithersburg Md.).

A number of features can be engineered into the expression vectors, such as leader sequences which promote the secretion of the expressed sequences into culture medium. The recombinantly produced polypeptides are typically isolated from lysed cells or culture media.

Isolated recombinant polypeptides produced as described above may be purified by standard protein purification procedures, including differential precipitation, molecular sieve chromatography, ion-exchange chromatography, isoelectric focusing, gel electrophoresis and affinity chromatography. Protein preparations can also be concentrated by, for example, filtration (Amicon, Danvers, Mass.).

In addition to recombinant methods, Rad50 proteins or polypeptides may be chemically synthesized using methods known to those skilled in the art.

hRad50 polypeptides, or immunogenic portions thereof, can be used as antigens in the generation of anti-sera or antibody preparations, as described in the Materials and Methods, herein. Typically, to prepare antibodies, a host animal, such as a rabbit, is immunized with the purified antigen or fused protein antigen. The host serum or plasma is collected following an appropriate time interval, and this serum is tested for antibodies specific against the antigen.

The gamma globulin fraction or the IgG antibodies of immunized animals can be obtained, for example, by use of saturated ammonium sulfate or DEAE Sephadex, or other techniques known to those skilled in the art for producing polyclonal antibodies.

Alternatively, a purified hRad5O antigen or fused antigen protein may be used for producing monoclonal antibodies. Here the spleen or lymphocytes from an immunized animal are removed and immortalized or used to prepare hybridomas by methods known to those skilled in the art (e.g., Harlow, et al.).

Antibodies secreted by the immortalized cells are screened to determine the clones that secrete antibodies of the desired specificity, for example, using Western blot (immunoblot) analysis. Example 8 describes the use of rabbit serum antibodies which are specific against hRad50 polypeptides in immunoprecipitation and immunoblot analyses.

Antibodies such as described above are useful in a method of screening an individual for predisposition to cancer. Blood cells, e.g., peripheral blood mononuclear cells (PBMC) are obtained from the individual using standard methods. These cells, in normal individuals, typically contain hRAD50 as a soluble nuclear protein. A protein fraction containing hRadSO is isolated from the cells, e.g., as described in the Materials and Methods under "Immunoprecipitation" and the soluble proteins in the fraction are contacted with an antibody which is immunoreactive with hRAD50 protein identified by SEQ ID NO:51. A polyclonal serum containing such an antibody was generated for used with experiments performed in support of the present invention as described in the Materials and Methods section.

Figure 7:
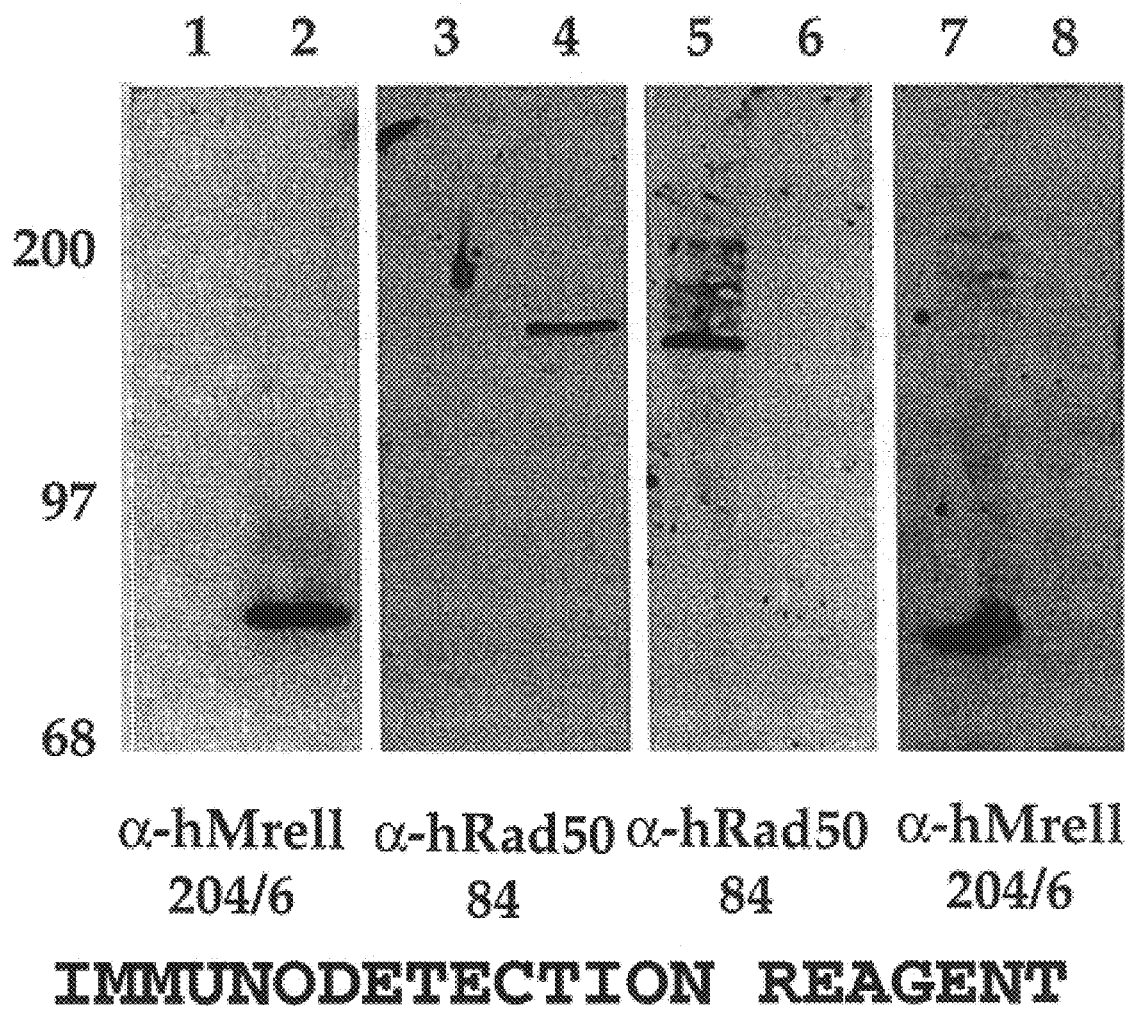
FIG. 7 shows immunoblots of immunoprecipitated material stained with hRad50 antiserum or hMre11 antiserum.

The individual is identified as being predisposed to cancer if no normal immunocomplex between the cytosol proteins and the antibody is produced. A "normal" immunocomplex is defined as an association of the antibody with an antigen on a hRad50 polypeptide having the molecular weight of a wild-type hRad50 polypeptide (about 153 kD). Examples of such normal complexes are shown in FIG. 7 with reference to FIG. 8.

VII. hRAD50-Deficient Cell Lines and Transgenic Mice

Also included in the invention are human cells, cell lines and transgenic animals selectively deficient for hRAD50 function. A convenient method for generating such "knockout" compositions (both cells and animals) is through the use of embryonic stem (ES) cell technology. ES cells are the derivatives of the inner cell mass of the blastocyst. ES cells are totipotent, nontransformed, primitive ectoderm-like cells that can be maintained in culture for many passages in an undifferentiated state. The cells have two advantageous characteristics with respect to the present invention: (ii) if ES cells are allowed to reach a high density in monolayers or to form aggregates in suspension, they will spontaneously differentiate to various cell types, and (ii) they can be reintroduced back into a 3.5 day blastocyst which, when placed into a suitable host (e.g., foster mother mouse) can colonize all tissues of the developing embryo, giving rise to a chimeric animal.

ES cells have many features in common with embryonal carcinoma (EC) cell lines: both are indistinguishable in their morphology and growth requirements, and their differentiation in vitro results in the formation of similar cell types (Martin, et al.). For example, it has been reported that ES cells can differentiate into parietal and visceral endoderm, cardiac muscle, as well as other cell types (Doetschman, et al., 1987).

As described in Example 10, the present invention enables the construction of cells, particularly human cells, that are null for the RAD50 gene. Such cells can be in the form of an immortalized cell line, or differentiated ES cells which can be passaged for several generation. hRAD50⁻ cells have a number of uses. For example, in view of RAD50's role in DNA repair, cells defective for RAD50 gene expression may be used to screen for carcinogenic compounds. In accordance with the invention, such cells are more sensitive to carcinogenic agents that cause DNA breaks or that render the DNA more prone to breakage by other causes (e.g., agents which increase the photosensitivity of the DNA), and may therefore be used to screen test compounds for the ability to promote DNA breaks.

In one embodiment, test compounds may be screened by exposing such a hRAD50⁻ cell (one that is deficient for the wild-type hRAD50 gene) to the test compound in a suitable carrier, and observing the morphology of the exposed cells. Controls preferably include (i) hRAD50⁻ cells exposed only to the carrier, and (ii) hRAD50⁺ cells identical to the hRAD50⁻ cells in all respects except for hRAD50 expression. The test compound can be left on the cells for an extended duration (e.g., for days), or may be used to briefly "pulse" the cells (e.g., for hours). The cells are allowed to grow for a selected period (e.g., 1–4 days) and are assayed for effects of the test compound.

Compounds which selectively induce changes in the morphology of the treated hRAD50⁻ cells, but not in the hRAD5⁺ control cells, are identified as having the capability to promote DNA breaks, i.e., as compounds which increase the rate of or cause DNA breaks, or which render the cells hypersensitive to other factors (e.g., UV light) which can cause DNA breaks.

The change in morphology that is typically associated with DNA breaks is apoptosis/cell death. Accordingly, in a preferred embodiment, viable cells in compound-exposed and control cultures are counted during the test phase, and compounds which cause an increase in cell death in hRAD50⁻ cells relative to hRAD50⁺ and unexposed control samples are identified as having the capability to promote DNA breaks. Other changes in morphology may also be indicative of DNA breaks. For example, exposure of cells to low doses of DNA-damaging carcinogens can transform cultured cells, and rapidly growing foci could be observed among untransformed cells.

Compounds which promote DNA breaks may affect cells in many ways, including cell-growth control, cell morphology, cell-to-cell interactions, membrane properties, cytoskeletal structure, protein secretion, gene expression, and cell mortality. As a consequence of such changes, cells may acquire different "transformed" phenotypes (e.g., rounded blast-like shapes) which depend on the dose and the exposure times of the reagents.

The above-described method may be applied to the screening of, e.g., chemotherapeutic drugs, and to test the carcinogenicity or mutagenicity of compounds or substances for which such carcinogenicity or mutagenicity data are needed.

Transfected ES may also be directly injected into the blastocoel of a host blastocyst or incubated in association with a zona-free morula, as described in Example 10, to generate a transgenic mouse. The host embryos are transferred into intermediate hosts or surrogate females for continued development. Using such an approach, it is possible to produce chimeric or transgenic mice with 30% of the live-borne stock containing tissue derived from the injected stem cells.

Other methods may be used to generate transgenic mice that are deficient for either one or both copies of the RAD50 gene. Such methods are described, for example, in the following U.S. Patents, all of which are incorporated herein by reference: (i) Ser. No. 5,491,283 ('283), issued Feb. 13, 1996, (ii) Ser. No. 5,487,992 ('992), issued Jan. 30, 1996 and (iii) Ser. No. 5,416,260 ('260), issued May 16, 1996. The '260 patent in particular discusses the modification of embryonic stem cells by homologous recombination to inactivate endogenous genes, and the use of such modified stem cells to produce a transgenic mouse.

It is contemplated that transgenic animals generated, e.g., as described above, can be used as models for human cancers associated with defective RAD50 function. For example, such animals may be useful in screens to identify therapeutic compounds effective to treat cancers such as acute myeloid leukemia (AML), therapy-related acute myeloid leukemia (t-AML), therapy-related myelodysplastic syndrome, (t-MDS), and refractory anemia with excess blasts in transformation (RAEB-T). Further, such animals may be useful in screens for or evaluation of compounds with the capability to promote DNA breaks, i.e., as compounds which increase the rate of or cause DNA breaks. Such screens may be useful, for example, in evaluating known compounds for their carcinogenicity.

The following examples illustrate but in no way are intended to limit the present invention.

MATERIALS AND METHODS

Unless otherwise indicated, restriction enzymes and DNA modifying enzymes were obtained from New England Biolabs (Beverly, Mass.) or Boehringer Mannheim (Indianapolis, Ind.). Nitrocellulose paper was obtained from Schleicher and Schuell (Keene, N.H.). Materials for SDS-polyacrylamide gel electrophoresis (SDS-PAGE) were obtained from Bio-Rad Laboratories (Hercules, Calif.). Other chemicals were purchased from Sigma (St. Louis, Mo.) or United States Biochemical (Cleveland, Ohio).

A. Buffers and Media

Phosphate-buffered saline (PBS)
   10×stock solution, 1 liter:
   80 g NaCl
   2 g KCl
   11.5 g $Na_2HPO_4$—$7H_2O$
   2 g $KH_2PO_4$
   Working solution, pH 7.3:
   137 mM NaCl
   2.7 mM KCl
   4.3 mM $Na_2HPO_4$—$7H_2O$
   1.4 mM $KH_2PO_4$
SSC (sodium chloride/sodium citrate), 20×
   3 M NaCl (175 g/liter)
   0.3 M $Na_3$citrate-$2H_2O$ (88 g/liter)
   Adjust pH to 7.0 with 1 M HCl
SSPE (sodium chloride/sodium phosphate/edta), 20×
   3.0 M NaCl
   0.20 M $NaH_2PO_4$
   20 mM EDTA, pH 7.4
Tris/EDTA Buffer (THE)
   10 mM Tris-Cl, pH as indicated
   1 mM EDTA, pH 8.0
AHC Medium and Plates (ura⁻, trp⁻)
   1.7 g yeast nitrogen base without amino acids and without ammonium sulfate (Difco Laboratories, Detroit, Mich.).
   5 g ammonium sulfate.
   10 g casein hydrolysate-acid, salt-free and vitamin-free (United States Biochemical, Cat. #12852, Cleveland, Ohio).
   50 ml (for medium) or 10 ml (for plates) of 2 mg/ml adenine hemisulfate (Sigma Chemical, Cat. #A-9126, St. Louis, Mo.).

Dissolve in a final volume of 900 ml $H_2O$, adjust pH to 5.8.

Autoclave 30 min, then add 100 ml sterile 20% (w/v) glucose. For AHC plates, add 20 g agar prior to autoclaving. Store at 4° C. for ≦6 weeks.

Denhardt solution, 100×
 10 g Ficoll 400
 10 g polyvinylpyrrolidone
 10 g bovine serum albumin (Pentex Fraction V, Miles Laboratories, Kankakee, Ill.)
 $H_2O$ to 500 ml
 Filter sterilize and store at −20° C. in 25-ml aliquots High Salt Buffer
 500 mM NaCl
 10 mM Tris, pH 7.5
 10 mM EDTA
 0.5% NP-40
 0.2 mg/ml PMSF Standard Lysis Buffer
 100 mM NaCl
 50 mM Tris, pH 7.4
 5 mM EDTA
 0.5% NP40

Strip Buffer
 62.5 mM Tris-HCl, pH 6.8
 100 mM p-mercaptoethanol
 2% SDS

B. Cell Lines

IMR90 primary fibroblasts were maintained in DMEM/10% FCS/1% Pen-Strep/2 mM L-Glutamine, and serially passed 1:3 from passage 8. Experiments utilizing IMR90 cells were performed using cells from passages 12–16. TK6 lymphoblastoid and K562 CML cells were grown in RPMI-1640/10% NBCS/1% Pen-Strep/2 mM L-Glutamine. All cells were grown at 37° C. in 5% CO2. IMR90 and TK6 cells were obtained from the American Type Culture Collection (ATCC; Rockville, Md.).

C. Irradiation

Cells were irradiated in a Mark I $^{137}$Cs source at a rate of approximately 200 cGy/min.

D. Immunoblots hRad50 and hMre11 antisera were raised in New Zealand White rabbits using bacterially produced histidine-tagged (hMre11) or GST (hRad50) fusion proteins using standard methods (Harlow, et al., Smith and Johnson, 1988, Smith, 1993). The resulting reagents were: preimmune serum 204pre and immune serum 204/6 (αhMre11); preimmune serum 84pre and immune serum 84 (αhRad50).

For Western blotting, $0.5-2\times10^6$ cells were lysed in SDS lysis buffer containing p-mercaptoethanol, aspirated through a 25 gauge needle to shear the genomic DNA and boiled before fractionation on SDS-PAGE gels. Immunoblot analyses were carried out with the indicated antisera at dilutions of 1:400 to 1:1000 using standard procedures (Harlow and Lane, 1988). Chemiluminescent detection of filter-bound antigen/antibody complexes was done with horseradish peroxidase-conjugated G+A protein in conjunction with Luminol reagent (Pierce, Rockford, Ill.). Where indicated, blots were stripped at 50° C. for 30 minutes in Strip Buffer and retreated with primary and secondary immunoblot reagents as described.

E. Immunoprecipitation $2.5\times10^6$ TK6 cells were lysed on ice for 30 minutes in High Salt Buffer. Lysates were then diluted 1:2 with Standard Lysis Buffer or with Lysis Buffer containing increased NaCl concentrations, and precleared for 1 hour at 4° C. with Protein A-Sepharose beads (Pharmacia, Piscataway, N.J.). Cleared lysates (final NaCl concentration 300 mM to 1000 mM) were incubated on ice for 1 hour with hMre11 serum 204/3p (affinity purified αhMre11), 204pre, hRad50 serum 84, or 84pre. Immune complexes were precipitated for 1 hour by rolling at 4° C. with Protein A-Sepharose beads. Bead-bound immunoprecipitates were washed 4 times with Standard Lysis Buffer, boiled in SDS sample buffer, and loaded on 8.5% polyacrylamide/SDS gels. Proteins were analyzed by immunoblotting using standard methods (Harlow and Lane, 1988) and detected as above.

F. Metabolic Labeling $5\times10^6$ K562 cells were removed from normal media, washed once with PBS, and resuspended in methionine- and phosphate-free RPMI1640 supplemented with 2% dialyzed NBCS, 8 mg/ml $Na_2HPO_4$, 85 μCi/ml [$^{35}$S]methionine (10 μCi/μl). Cells were incubated for 6 hours prior to harvesting for immunoprecipitation. Immunoprecipitates were fractionated on 8.5% SDS-PAGE gels. Gels were fixed for 30 minutes in 30% methanol/10% acetic acid, washed in dd$H_2O$, and incubated in 1 M sodium salicylate for 30 minutes prior to drying and autoradiography. Protein bands were readily visible within 7 hours.

EXAMPLE 1

Construction of cDNA Pools for Use in Direct Selection

Complementary DNA (cDNA) was prepared using standard methods from tissues and cell lines that expressed or were likely to express sufficient amounts of messenger RNA (mRNA) encoding proteins of interest. cDNA samples from several sources were sometimes grouped into "cDNA pools". For example, ionomycin-stimulated T cells, T cell clones, and T-lineage lymphomas were found be the best mRNA source for construction of a polymerase chain reaction (PCR) -amplifiable cDNA pool for direct selection due to high levels of corresponding cytokines expressed (first eight samples in Table 2, below). Similarly, a hybrid cDNA pool, termed pool #1, was constructed using mRNA isolated from a mixture of several activated T-cell clones and lymphomas (obtained from David Lewis, University of Washington, Seattle; Lewis, et al., 1988).

A complex primary cDNA pool, termed pool #2, was constructed from human fetal and adult tissues, including fetal brain and liver, adult bone marrow, and activated lymphocytes, as well as the following cytokine-producing cell lines, which, unless otherwise indicated, were obtained from the American Type Culture Collection (ATCC), Rockville Md.: A-10 cells (T cell clone), Jurkat cells (ATCC TIB-152), CEM cells (ATCC CCL-119), HUT-78 cells (ATCC TIB-161), JM cells (ATCC CRL-8294), Molt-4 cells (ATCC accession number CRL1582) and NG-1 cells.

Prior to isolating MRNA from "activated" T-cell samples, the cells were grown at $5\times10^6$ cells/ml in RPMI medium (GIBCO/BRL Life Technologies) supplemented with 5% human AB serum as previously described (Georgopoulos, et al., 1990) and activated using 50 ng/ml phorbol myristate acetate (PMA; Sigma, St. Louis, Mo.) in combination with either 25 μg/ml concanavalin A (Con A) (Pharmacia, Piscataway, N.J.) or 0.5 μM ionomycin (Calbiochem-Behring, San Diego, Calif.).

A. Cell Isolation and Synthesis of cDNA

1. Isolation of Primary T Cells and Thymocytes. Circulating adult T cells and thymocytes were isolated as previously described (Georgopoulos, et al., 1990) by Ficoll-Hypaque density gradient centrifugation and treated with CD4 Lymphokwik (One Lambda, Los Angeles, Calif.), a mixture of complement and monoclonal antibodies (mAb) directed against non-T-lineage markers and the CD8 surface antigen, following the manufacturer's instructions. The final purity of each T-lineage cell population was consistently >95% based on flow cytometric analysis after staining with appropriate mAbs.

2. Cell Activation. Cells were activated at $5\times10^6$/ml in RPMI medium supplemented with 5% human AB serum as previously described (Georgopoulos, et al., 1990) using 50 ng/ml phorbol myristate acetate (PMA; Sigma, St. Louis, Mo.) in combination with either 25 µg/ml concanavalin A (ConA) (Pharmacia, Piscataway, N.J.), 0.5 AM ionomycin (Calbiochem-Behring, San Diego, Calif,), or 2.5 µg/ml PHA (Sigma, St. Louis, Mo.).

3. RNA Isolation. Cell or tissue homogenates were prepared using a Polytron homogenizer as described (Chomczynski and Sacchi, 1987). Total RNA was isolated by the guanidinium isothiocyanate/CsCl method (Glizin, et al., 1974) or by the acid guanidinium isothiocyanate-phenol-chloroform extraction method (Chomczynski and Sacchi, 1987) using a commercial kit ("TRIZOL", Life Technologies, Inc., Gaithersburg, Md.). mRNA was isolated from the total RNA using oligo(dT)$_{25}$ "DYNABEADS" (Dynal Inc., Lake Success, N.Y.) following manufacturer's instructions ("mRNA Isolation Using "DYNABEADS" OLIGO(dT)$_{25}$", pp 35–60 in *BIOMAGNETIC TECHNIQUES IN MOLECULAR BIOLOGY—TECHNICAL HANDBOOK*, Second Edition, Dynal, A. S. (Oslo, Norway) (1995). Briefly, Poly-A$^+$ mRNA was selected using "MAGNETIC DYNABEADS OLIGO (dT)$_{25}$" (Dyndal A. S., Oslo, Norway) according to protocol 2.3.1 (Jakobsen, et al., 1990, 1994) as recommended by the manufacturer.

4. cDNA Synthesis. Cell or tissue Double-stranded (ds) cDNA was synthesized using the "SUPERSCRIPT" "CHOICE SYSTEM" kit for cDNA synthesis (GIBCO/BRL Life Technologies, Gaithersburg, Md.) according to the manufacturer's instructions, except that custom adapters (Adapter #3 and adapter #5, described below) were used in place of the EcoR1 adapters supplied with the kit. Approximately 5 µg of poly(A$^+$) mRNA were used with oligo dT15 or random hexamers to synthesize ds cDNA. The cDNA was purified from the primers and the low molecular weight products (<250 bp) on "WIZARD" PCR Preps DNA Purification System columns (Promega, Madison, Wis.) according to the manufacturer's protocol, and ligated to dephosphorylated adapters #3 (SEQ ID NO:1, SEQ ID NO:2) or #5 (SEQ ID NO:3, SEQ ID NO:4) using standard methods (Sambrook, et al., 1989). Typically, cDNA pools designed for direct selection contained adapter #3 at their ends to allow single primer PCR amplification (e.g., using primer #A3-2 (SEQ ID NO:5) or primer #AD3-CUA (SEQ ID NO:6; see below).

The adapters were made by combining oligonucleotides #4665 (SEQ ID NO:1) and #4666 (SEQ ID NO:2) (Adapter #3), or oligonucleotides #A5-1 (SEQ ID NO:3) and #A5-2 (SEQ ID NO:4) (Adapter #5), heating the mixtures to 95° C. for 5 minutes, and allowing the mixtures to gradually cool to room temperature over about 30 minutes. This caused the oligonucleotides in the mixtures to hybridize and form double stranded adapters with 3' overhangs as illustrated below. The adapters were then dephosphorylated with calf intestine phosphatase (CIP) using a standard protocol (Ausubel, et al., 1988), and the phosphatase inactivated by incubating at 70° C. for 10 min.

5'-biotinylated primer #A5-2b (SEQ ID NO:7) was designed to synthesize biotinylated subtraction probes (e.g.,
ribosomal, mitochondrial, Alu-, etc.) from cDNA fragments containing Adapter #5 using PCR. Primer #A3-2 (SEQ ID NO:5) was designed to synthesize similar probes from cDNA fragments containing Adapter #3. CUA-containing primer #AD3-CUA (SEQ ID NO:6) was designed to PCR amplify cDNAs that subcloned into the pAMP10 vector (GIBCO/BRL Life Technologies, Inc).

B. Screening of cDNA Samples with Cytokine PCR Primers

The presence of specific cytokine cDNAs in the different cDNA samples/pools was determined using PCR to provide an estimate of the degree to which such cytokine transcripts were present, i.e., to "validate" the cDNA samples/pools as sources for cytokine cDNAs. The PCR reactions were carried out using standard methods (Mullis, 1987; Mullis, et al., 1987) with the primer pairs presented in Table 1, below.

TABLE 1

| Primers | SEQ ID NO: | $T_{ann}$ | Sequence | Product Size |
|---|---|---|---|---|
| GM-CSF-2 | 8 | 60° C. | CCTTGACCATGATGGCC-AGCC | 187 bp |
| GM-CSF-1 | 9 | | CCCGGCTTGGCCAGCCT-CATC | |
| IL3-1 | 10 | 55° C. | CTCTGTGGTGAGAAGGC-CCA | 287 bp |
| IL3-2 | 11 | | CTTCGAAGGCCAAACCT-GGA | |
| IL4-3 | 12 | 55° C. | GGTTTCCTTCTCAGTTG-TGTT | 210 bp |
| IL4-4 | 13 | | CTCACCTCCCAACTGCT-TCCC | |
| IL5-1 | 14 | 55° C. | CACCAACTGTGCACTGA-AGAAATC | 213 bp |
| IL4-2 | 15 | | CCACTCGGTGTTCATTAC-ACC | |
| IL9-1 | 16 | 60° C. | AGCTTCTGGCCATGGTC-CTTAC | 360 bp |
| IL9-6 | 17 | | TCAGCGCGTTGCCTGCC-GTGGT | |
| IL13-1 | 18 | 55° C. | ATGGCGCTTTTGTTGACC-AC | 1013 bp |
| IL13-5 | 19 | | CCTGCCTCGGATGAGGC-TCC | |
| IRF1-7 | 20 | 55° C. | GAAGGCCAACTTTCGCT-GTG | 367 bp |
| IRF1-8 | 21 | | CACTGGGATGTGCCAGT-CGG | |
| TCF7-3 | 22 | 55° C. | CCGTTCCTTCCGATGACA-GTGCT | 898 bp |
| TCF7-4 | 23 | | GACATCAGCCAGAAGCA-AGT | |
| EGRI1-6 | 24 | 60° C. | CCACCTCCTCTCTCTCTT-CCTA | 750 bp |
| EGRI1-7 | 25 | | TCCATGGCACAGATGCT-GTAC | |
| CD14-5 | 26 | 65° C. | CCGCTGGTGCACGTCTCT-GCGACC | 1022 bp |
| CD14-6 | 27 | | CACGCCGGAGTTCATTG-AGCC | |
| CDC25-3 | 28 | 65° C. | GAGAGGAAGGAAGCTCT-GGCTC | 282 bp |
| CDC25-5 | 29 | | GTCCTGAAGAATCCAGG-TGACC | |

All cDNA samples and cDNA pools #1 and #2 were screened using PCR with the above primers, and the relative amount of specific amplification product determined. Prior to amplification, the samples were diluted such that the concentration of cDNA was the same in each sample (about 200 µg/ml). The results for individual cDNA samples are presented in the Table 2, below. Three pluses (+++) indicate a relatively high level of expression, (++) an intermediate level, (+) a relatively low level, (±) a very low but consistent level, (∓) a very low and inconsistent level, and (−) no detectable expression.

TABLE 2

| cDNA | IL13 | IL4 | IRF1 | IL5 | IL3 | GM-CSF | TCF7 | IL9 | EGR1 | CD14 | CDC25 |
|------|------|-----|------|-----|-----|--------|------|-----|------|------|-------|
| T-cells | ++ | +++ | +++ | +++ | +++ | ++++ | +++ | +++ | − | ± | − |
| A-10 | +++ | ++++ | +++ | ++++ | +++ | ++++ | ± | +++ | ++ | ± | ∓ |
| Jurkat | + | + | +++ | − | +++ | +++ | +++ | − | − | ± | + |
| CEM | ++ | ++ | +++ | ∓ | +++ | +++ | +++ | − | ++ | ± | ++ |
| HUT78 | ++ | ++ | +++ | + | +++ | ++++ | +++ | − | +++ | ± | ++ |
| JM | + | − | +++ | ∓ | +++ | ++++ | +++ | − | − | ± | +++ |
| Molt4 | + | ++ | +++ | − | − | − | +++ | − | − | ± | ++ |
| HNG-1 | ++ | − | ++= | − | − | ++++ | +++ | − | +++ | ± | ++ |
| Daudi | − | − | + | − | − | − | ± | − | − | ∓ | + |
| 816 | − | +++ | +++ | ± | − | − | ± | +++ | − | − | ∓ |
| Mono | − | − | +++ | − | − | +++ | − | − | − | +++ | − |

Daudi B-lineage cell lymphoma (Daudi); Monocytes stimulated with LPS for 6 hrs (Mono); Adult T cells stimulated with Con A and PMA for 6 hrs (T-cells); EBV-transformed B-cell line 816 (816); HNG-1 T-cell lineage lymphoma (HNG-1); Molt-4 T-cell lineage lymphoma (Molt4); JM T-cell lineage lymphoma (JM); HUT-78 T-cell lineage lymphoma (HUT78); CEM T-cell lineage lymphoma stimulated with ionomycin and PMA for 6 hrs (CEM); Jurkat T-cell lineage lymphoma (Jurkat); and Clone A-10 of T-cell origin, producing high levels of IL4 and IL5 and stimulated with Con A for 6 hrs (A-10).

The data in Table 2, above, suggest that a cDNA pool formed of cDNA samples in the first 6 rows of the table, along with the monocyte cDNA, may be particularly effective as a source of cytokine cDNAs. Accordingly, cDNA pool #3 was formed by combining equal fractions of these seven cDNA samples. cDNA pool #4 was formed by combining equal fractions of all eleven cDNA samples listed in Table 2, above, along with cDNA from adult bone marrow.

Eight additional cDNA pools, termed cDNA pools #5–12, were constructed by combining, at a 1:1 vol/vol ratio, cDNA pool #3 with cDNA samples of similar concentrations isolated from human tissues, including total embryo (6, 8, 12 weeks of gestation; pools #5, 6 and 7, respectively), fetal liver (pool #8), fetal brain (pool #9), adult bone marrow (pool #10), adult thymus (pool #11), and adult spleen (pool #12).

EXAMPLE 2

Preparation of Genomic DNA for Direct Selection

A. Mapping of Genomic Clones used for Direct Selection

Yeast artificial chromosome (YAC) clones containing sequences from the cytokine gene cluster area of chromosome 5 (5q23–31) were isolated and physically mapped to provide a template for the direct selection of the cDNA samples and pools described in Example 1. YAC clone A94G6 (~425 kb) was obtained from the YAC Washington University library (St. Louis, Mo.) (Burke, et al., 1987; Morgan, et al., 1992). Clones 259E7 (~490 kb) and 854G6 (~1.3 mb) were isolated from CEPH (Centre d' Etude du Polymorphisme Humain, France) regular and mega YAC libraries (Bellanne-Chantelot, et al., 1992).

To construct a physical map of the YAC clones, the clones were digested with NotI and run on a clamped homogeneous electrical fields (CHEF) mapper system ("CHEF-DR III" Variable Angle Pulsed Field Electrophoresis System, Bio-Rad Laboratories, Hercules, Calif.). The yeast clones were grown in liquid AHC medium (Bellanne-Chantelot, et al., 1992) for 48 hrs at 30° C. Cells were harvested, washed and embedded in 0.5% low melting temperature agarose (LMT) as described (Chumakov, et al., 1992). After the zymolase treatment and lysis, YACs were separated in 1% LMT agarose pulsed field gels in 0.5×TBE at 14° C. as described below.

All the separations were carried out in "CHEF-DR III" pulsed-field electrophoresis system (Bio-Rad) with following parameters: 1) small YACs (400–500 kb)—power OG V/cm; run time 24 hrs 4 min; initial switch time 21.41; final switch time 39.48; 2) mega YACs (1–1.5 mb)—power 0.6V/cm; run time$^1$ 22 hrs 30 min; switch time$^1$ 60.00; run time$^2$ 12 hrs 30 min; switch time$^2$ 90.00.

The CHEF gels were blotted and hybridized by standard Southern hybridization (Sambrook, et al., 1989) to probes for IL13, IL4, IL5, IRF1, IL3, GM-CSF, all of which are located in 5q23–31. The hybridization conditions, unless specified, were: 5×SSPE, 0.1% SDS, 5×Denhardt's, $^{32}$P-labelled probe, 65° C. overnight. The blots were washed first with 1×SSC+0.1% SDS at room temperature, and then with 0.1×SSC+0.1% SDS at 65° C. several times, 15 min each.

The results from the hybridizations were used to construct a physical map of the 1.3 megabase (Mb) region encompassed by YACs A94G6, 259E7 and 854G6. This map was confirmed and further refined by physically mapping a panel of chromosome 5-specific cosmids, as described in Example 5, below.

B. Direct Selection Protocol

DNA from the genomic clones was isolated as described in part C, below. The isolated DNA was labeled with biotin either by PCR using biotinylated primers SEQ ID NO:34 and SEQ ID NO:35, or by conventional labelling technique. For PCR labelling 5'-biotinylated primers were used that had been synthesized at Genosys Biotechnologies, Inc. (Woodlands, Tex.). For conventional labelling either photoactivatable biotin (PAB) or Biotin-21-dUTP nick translation labelling kits from Clontech (Palo Alto, Calif.) were used.

Biotinylated genomic DNA was hybridized in solution with complex representative cDNA pools #4–12. In selection with YACs A94G6 and 259E7, cDNA pool #4 was used. In selection with the mega YAC 854G6, a mixture of equal amounts of cDNA pools #4–12 was used. Hybridization was done at 65° C. in 20 μl of 5×SSPE, 1×Denhardt, 0.1% SDS to Cot=500. cDNAs that was close to saturation was efficiently-captured under these conditions. Specifically-bound cDNAs were captured with Dynal streptavidin beads and washed with 400 μl of 2×SSC, 0.5% SDS twice at RT, 10 min each and 4 times with 400 μl of 0.2×SSC+0.1% SDS at 65° C., 5 min each time.

Biotinylated genomic DNA-cDNA hybrids and free YAC DNA fragments were captured with streptavidin coated magnetic beads (Dynal A. S., Oslo, Norway) for 30 min at RT with occasional tapping. Two hundred μg of the beads (40 μl, 5 μg/μl) were added per each 5 pMoles of biotinylated PCR product (up to 4 kb in length). About 4 μg of the biotinylated PCR products within the range of 1–4 kb could be captured by this amount of beads. Dynabeads were washed twice with buffer containing 1M NaCl in preblocking buffer (THE pH 7.5+200 μg/ml Herring sperm DNA+ 0.1% BSA) and resuspended to 5 μg/μl in the same buffer without DNA or RNA. The suspension was incubated at room temperature (RT) for 30 min, and the beads were captured and isolated with the aid of a magnet. The isolated beads were then washed with 400 μl of 2×SSC, 0.5% SDS twice at RT, 10 min each and 4 times with 400 μl of 0.2×SSC+0.1% SDS at 65° C., 5 min each time.

After washing, specifically bound cDNAs were eluted from the hybrids of the biotinylated DNA-cDNA either by incubating the beads with 40 μl of 2.5 mM EDTA at 80° C. or with 100 mM NaOH at RT. The latter was followed by neutralization with 20 μl of 0.2 M HCl and 10 μl of 1M Tris-HCl pH 8.0.

Eluted cDNAs were PCR amplified by single primer amplification (SISPA) using either primer #AD3-2 (SEQ ID NO:5) or #AD3-CUA (SEQ ID NO:6). Primer #AD3-CUA was used when PCR products were to be cloned in pAMP10. This cloning system substantially reduced the background of "0"-insert and chimeric clones.

A second round of direct selection was usually performed following completion of the first round. The first round typically resulted in a several hundred to a thousand fold enrichment. The second round of selection enabled enrichment up to about a hundred-thousand-fold (Morgan, et al., 1992).

To determine whether a second round of selection was necessary, cDNA aliquots were SISPA-propagated the #AD3-2 primer (SEQ ID NO:5), cleaned up by "WIZARD" PCR column chromatography, quantitated, and run a on 1% agarose gel (about 1 μg/lane) both before and after selection. The gels were visualized, blotted, and hybridized with the probes known to reside within given genomic DNA. Alternatively, PCR was used to assess the enrichment by direct selection (Morgan, et al., 1992). If the degree of enrichment was less than about ten thousand-fold, a second round was performed.

C. Preparation of YAC DNA for Direct Selection

YAC clones A94G6, 259E7 and 854G6 were grown overnight in AHC medium at 30° C. Agarose blocks were prepared according to the protocol of LePaslier (Chumakov, et al., 1992). Briefly, yeast cells harboring the YACs were harvested, washed, counted and embedded in 0.5% Sea-Plaque GTG agarose (FMC, Rockland, Me.) as described in CHEF-DR$^R$III instruction manual and application guide. YAC DNAs or their restriction fragments were separated in 1% LMT agarose (FMC) pulsed field gels in 0.5×TBE at 14° C. according to the Bio-Rad protocols. For smaller YACs (400–500 kb), the following parameters were applied: power 0.6 V/cm; run time 24 hrs 4 min; initial switch time 21.41; final switch time 39.48. For mega YACs (1–1.5 mb), the following parameters were applied: power 0.6V/cm; run time[1] 22 hrs 30 min; switch time[1] 60.00; run time[2] 12 hrs 30 min; switch time[2] 90.00.

YAC DNA-containing bands (containing ~250 ng DNA) were excised, placed into tubes with 2 vol of 1×Sau3AI buffer (New England Biolabs (NEB), Beverly, Mass.), and treated with 12 U of Sau3AI (NEB) at 37° C. for 5 hrs.

The agarose containing the digested YAC DNA was then melted in 1 volume of THE at 68° C., and the DNA isolated using the "WIZARD" PCR Preps DNA Purification System (Promega, Madison, Wis.) at 37° C. following the manufacturer's instructions. DNA was eluted with THE (pH 8.0).

Due to steric hindrance of the incorporated biotin, one of the following adapters was ligated to the eluted YAC DNA to allow more efficient SISPA amplification and PCR controlled labelling with biotin: (i) Sau3A1 semiadapter #1, made of primers having sequences SEQ ID NO:42 and SEQ ID NO:43, (ii) Sau3A1 semiadapter #2, made of primers having sequences SEQ ID NO:30 and SEQ ID NO:31, or (iii) Sau3A1 adapter #S-1/S-2, made of primers having sequences SEQ ID NO:32 and SEQ ID NO:33. Sau3A1 semiadapter #2 provided better yields and specificity in ligations and subsequent PCRs.

Ligation of the linkers was typically carried overnight at +14° C. in 20 μl of the reaction mix, containing 100 ng of Sau3AI-digested YAC DNA, 100 pmoles of adapter, and 6 U of T4 DNA Ligase (New England Biolabs).

EXAMPLE 3

Direct cDNA Selection with the Genomic DNA Fragments Encompassing Cytokine Gene Cluster in 5q23–31

YAC clone DNA was PCR-amplified for 30 cycles using biotinylated primers SEQ ID NO:34 and SEQ ID NO:35. The amplified YAC DNA was then preblocked with Cot1 DNA (GIBCO/BRL Life Technologies, Inc.) and used for direct selection with cDNA samples as follows.

One hundred ng of the amplified biotinylated YAC DNA were mixed with either 5 μg Cot1 DNA and 5 μpg yeast host strain AB1380, or 10 μg Cot1 DNA, in 8 μl of water and denatured for 15 min under mineral oil at 98° C. in a heating block. The mixture was then supplemented with 2 μl of 25×SSPE+5×Denhardt+0.5% SDS to a final concentration of 5×SSPE, 1×Denhardt solution and 0.1% sodium dodecyl sulfate (SDS) in 10 μl, and hybridized for 2.0 hrs at 60° C. to Cot=20. In parallel, 10 μg of cDNAs were denatured in 8 μl of water for 15 min under mineral oil and treated as described above.

Ten μg of cDNAs from selected samples were denatured in 8 μl of water for 15 min under mineral oil as described above and supplemented to a final concentration of 5×SSPE, 1×Denhardt and 0.1% SDS. Direct selection was initiated by mixing 10 μl of the amplified cDNAs with 10 μl of the amplified and preblocked biotinylated YAC DNA (100 ng), and hybridization was conducted to a Cot=500 (about 4 hrs) at 65° C. under mineral oil. A Cot value of 1 is equivalent to 83 μg/ml of DNA×1 hour at 60° C. in 5×SSPE.

A. Isolation of cDNA/DNA Hybrids with Magnetic Beads

The hybridization mixture was then incubated with streptavidin coated magnetic beads (Dynal, Inc., Lake Success, N.Y.) in a buffer containing 1M NaCl in THE pH 7.5+0.1% BSA for 30 min at room temperature with occasional tapping to immobilize the biotinylated genomic DNA fragments, some of which contained hybridized cDNA species. Two hundred μg of the beads (40 μl, 5 μg/μl), effective to capture about 4 μg of the biotinylated PCR products (1–4 kb), were added per each 5 pMoles of biotinylated YAC DNA PCR product.

Following the incubation, the "DYNABEADS" were collected using a magnetic stand (Dynal, Inc.). The beads were then washed with 400 μl of 2×SSC, 0.5% SDS twice at RT, 10 min each, and 4 times with 400 μl of 0.2×SSC+ 0.1% SDS at 65° C., 5 min each. Specifically bound biotinylated DNA-cDNAs were incubated either with 40 μl of 2.5 mM EDTA at 80° C., or with 100 mM NaOH at RT with occasional tapping of the tube, eluted and neutralized with 20 μl of 0.2 M HCl and 10 μl of 1M Tris-HCl pH 8.0.

Specifically bound biotinylated DNA-cDNAs were eluted either with 40 μl of 2.5 mM EDTA at 80° C. or with 100 mM NaOH at RT with occasional tapping of the tube. In cases where NaOH was used, the eluted beads were neutralized with 20 μl of 0.2 M HCl and 10 μl of 1M Tris-HCl pH 8.0.

B. Subcloning of Selected cDNAs

The eluted material (~2 μl) was PCR-amplified for approximately 30 cycles in 100 μl tubes using approximately 50 pmoles each of primers SEQ ID NO:5 and SEQ ID NO:6, typically for 30 cycles using 2 μl of the eluate per 100 μl reaction. Primer SEQ ID NO:6 was used only when the PCR products were to be subcloned into the pAM10 vector. The PCR cycle parameters were as follows: 30 sec at 94° C., 30 sec at $T_{ann}$–5° C., and 2 min at 72° C. After the last cycle, the reactions were incubated for 7 min at 72° C., and then kept at 4° C. until further processing.

The PCR-amplified material was typically used for a second round of direct selection as described above, selected products were PCR amplified with primer SEQ ID NO:6, and ~1–5 μg of the selected cDNAs were subcloned into plasmid pCRTMII (Invitrogen Corporation, San Diego, Calif.) or the pAMP10 vector ("CLONEAMP" directional PCR cloning system, GIBCO/BRL Life Technologies, Inc). The pAMP10 vector is adapted for uracil DNA glycosilase (UDG) cloning. This approach does not require restriction endonuclease digestion, end-polishing, purification or ligation. With this system, PCR products should contain specified 12-base 5' sequence that contains dUMP residues instead of dTMP.

Treatment with UDG renders dUMP residues abasic, disrupting base-pairing which results in 3'-protruding termini. pAMP10 plasmid contains a modified multiple cloning site and 3' ends that are complementary to the 3' protruding termini of the UDG-treated PCR amplification products obtained with the primer SEQ ID NO:6. Linear vector and UDG both go to the selected amplified cDNAs, without ligase, and are complete in less than 30 min, producing recombinant molecules ready for transformation.

1 μl of 20 μl UDG-reaction mixture was typically used to electroporate 50 μl of electrocompetent JS5 E.coli cells (Bio-Rad) according to manufacture's protocol in a "GENE PULSER" apparatus (Bio-Rad), in 0.1 cm electrode gap cuvettes. After 1 hr incubation of electroporated cells in 1 ml of Luria Broth (LB), 100 μl of the culture was plated onto LB plates containing 100 μg/ml Ampicillin.

The quality of a direct selection was monitored by Southern blot hybridization using a probe known to reside on the YAC, when similar quantities of the PCR amplified cDNA were loaded on the gel before and after the selection. Usually up to 100,000-fold enrichment was observed in two rounds of selection. Before and after the selection cDNA aliquots were SISPA-propagated with the primer SEQ ID NO:5, cleaned up by Wizard PCR column chromatography, quantitated, and run in 1% agarose gel (about 1 μg/lane). The gels were visualized, blotted, and hybridized with the probes known to reside within given genomic DNA. Alternatively, quantitative PCR was used to assess the enrichment by direct selection. The enrichment ratios of direct selection were also monitored by plating cDNA aliquots before and after the selection, and counting the ratio of several marker clones to overall colonies. For example, if there was one IL3 positive clone in $10^6$ colonies before and one in 10 after the selection, the enrichment was considered to be around $10^5$ fold on this step. The selection process was controlled such that there was at least a 10 thousand-fold enrichment for at least one marker. Alternatively, negative selection was controlled for the markers known not to be on the YACs. In this case, the data were examined for a decrease in the ratio of this gene during selection.

EXAMPLE 4

Hybridization and Sequence Analysis of the Arrayed Region-Specific cDNAs

A. Analysis and Subcloning of the PCR Products

Individual colonies of PCR pAMP10 clones generated as described above were used to inoculate wells containing LB broth in 96-well plates. The cultures were incubated overnight at 37° C. and an aliquot from each well was transferred to an Immobilon-N membrane (Millipore, Bedford, Mass.), forming a grid corresponding to the locations of the samples in the plate.

The DNA was immobilized on the membranes using UV-crosslinking, and the membranes were then screened with $^{32}$P-labelled YAC, Cot1, mitochondrial, ribosomal and single copy probes known to reside on a starting genomic clone, in order to eliminate nonspecific or already known cDNAs from further analysis, as follows.

Membranes with the arrayed cDNAs were hybridized with different $^{32}$P-labelled probes: highly repetitive, high molecular weight human COT1 DNA (Life Technologies, Inc.), human mitochondrial and ribosomal probes, starting YAC probe, single copy marker genes, known to reside within the genomic region in question. Because starting total cellular RNA contained certain amount of heteronuclear, ribosomal and mitochondrial species, final cDNA pools still contained these species, and it was much easier to prescreen the arrayed libraries for them rather than to introduce additional steps into the selection protocol.

About 55% of the clones in arrayed selected cDNA libraries were eliminated in such a prescreening procedure. Single copy known genes from the genomic region in question were monitored as well, and were used to evaluate the quality of the selected material and the depth of the libraries. These statistics also aided in determining how many novel cDNAs might be expected. For instance, 18% of the clones in the A94G6 YAC selection library belonged to IRF1, IL13, IL3 and IL5.

Negative clones were subject to sequencing. Sequencing data confirmed that there were at least 7 novel gene candidates, one of which was assembled into a full-length clone of a human homolog of S.cerevisiae RAD50. After computer analysis of the sequencing data, PCR primers were designed for prospective novel gene cDNAs and were used both to evaluate the tissue-specificity of expression of the gene candidates and for physical mapping of cDNAs to human chromosome 5 and the starting YAC, as described below.

B. Sequence Analysis

Unique and presumably novel cDNA clones were sequenced and screened for similarity of their nucleotide and amino acid sequences using Fasta, BlastN, BlastX, tBlastN programs in known protein and nucleic acid databases. For efficient and quick identification of non-overlapping cDNAs, redundant cDNAs were eliminated by subsequent hybridization of the arrayed libraries with already identified individual cDNAs as probes and unique sequences were further analyzed as described below.

After two rounds of selection, ~66% of all clones mapped back to the starting genomic region, i.e., YAC or any other genomic DNA used to select these particular cDNAs. Each cDNA species comprised >1% of the selected material. The complexity of the selected cDNAs (i.e., the number of distinct species of DNAs) was dependent on the gene density in the region with respect to which the cDNAs were selected, and on the complexity of the starting cDNA sources.

EXAMPLE 5

Mapping Selected Clones to Chromosome 5: Physical Mapping of cDNAs to Cosmids A human chromosome 5-specific cosmid library was obtained from L. Deaven (Los Alamos National laboratories, N. Mex.) as arrayed individual clones in 96 well-plates that represented 8 x genome equivalents subcloned in the sCos1 vector (Longmire, et al., 1993). The E. coli DHS clones contained about 81% human inserts, 8% rodent inserts and 3% nonrecombinants. About 25,000 individual cosmid clones were microgridded onto "HYBOND-N" nylon membrane (Amersham Life Sciences, UK) using a "BIOMEK 1" (Beckman, Palo Alto, Calif.) robotic station. The filters with spotted clones were grown overnight on 96-well plate lids (Cat.#76-205-05, ICN Flow, Costa Mesa, Calif.) filled with 1.5% LB SeaKem GTG agarose (FMC Bioproducts, Rockland, Me.) supplemented with 20 $\mu$g/ml kanamycin (Sigma).

After treating the filters on Whatman 3mm paper saturated with 2xSSC/0.5% SDS for 2 min, the filters were microwaved for 2.5 min at ~750 W until dry. Then they were submerged in a buffer containing 50 mM Tris-HCl pH 8.0, 50 mM EDTA, 100 mM NaCl, 1% Na-lauryl-sarcosine, and 250 mg/ml Proteinase K (Boehringer). After incubation for 20 min at 37° C. the filters were UV-crosslinked on Fotodyne crosslinker for 35 sec. After washing, the microgrids were hybridized with different $^{32}$P-oligolabelled YAC, cDNA or terminal cosmid walking probes as described below. Many cDNAs selected with the above specified YACs were mapped to the clones on the microgrids. Other libraries may be similarly used for mapping purposes, including YAC, BAC, and P1 genomic libraries.

EXAMPLE 6

Determining Tissue Specific Expression

Tissue specificity of expression was performed using Northern blot analyses and PCR detection.

A. Northern Blot Analyses

Total RNA was isolated by the guanidinium isothiocyanate/CsCl method (Glisin, et al., 1974) or by the acid guanidinium isothiocyanate- phenol-chloroform extraction method using a commercial kit (Tri-reagent, Molecular Research Center, Cincinnati, Ohio), and was resolved on formaldehyde gels using standard methods (Sambrook, et al., 1989). The gels were blotted onto "HYBOND N" membranes (Amersham Life Sciences, UK), fixed by UV-crosslinking, and the membranes probed with radiolabeled probes corresponding to the clones. Conditions: Hybridization buffer, containing 5xSSPE, 2xDenhardt, 100 $\mu$g/ml sonicated salmon sperm DNA, 0.5% SDS; Hybridization temperature=65° C.

All probes consisted of DNA labeled by the random hexamer priming method using a commercial kit (Pharmacia, Piscataway, N.J.), with the exception of the IL4 probe, for which a single-stranded RNA probe was employed.

B. RT-PCR Analysis

About 1 $\mu$g of total RNA from different sources was reverse transcribed (RT) by random priming with "SUPERSCRIPT II" (GIBCO/BRL Life Technologies, Gaithersburg, Md.) in 20 $\mu$l of reaction mix as specified by the manufacturer. After heat inactivation, 1 $\mu$l of the RT-reaction was used in a 30 $\mu$l PCR of 30 cycles of conventional PCR with the primers and $T_{ann}$ specified below. Each PCR reaction contained 20 mM Tris-HCl pH 8.9 (at 25° C.), 16.7 mM $(NH_4)_2SO_4$, 1.5 mM $MgCl_2$, 200 AM dNTPs, 1 $\mu$M primers, and 0.8 U AmpliTaq (Cetus).

PCR-based detection of tissue-specific expression was performed using the following PCR-amplifiable primary cDNA pools: Total Embryo (6, 8, 12 weeks of gestation), Fetal Liver, Fetal Brain, Fetal Muscle, Placenta, Adult Heart, Adult Muscle, Adult Liver, Adult Brain, Adult Pancreas, Adult Kidney, Adult Aorta, Adult Spleen, Adult Testis, Adult Bone Marrow, JY B-cell line, Resting T-cells and Activated T-cells.

These cDNAs were either used directly as targets or PCR amplified for 30 cycles using primer SEQ ID NO:5. Amplified cDNAs were purified on a "WIZARD-PCR" column (Promega, Madison, Wis.), quantitated, and used in PCR reactions. Each PCR reaction contained 50 ng of one cDNA sample or pool (amplified or unamplified) as the target. After 30 cycles of PCR the products were separated on agarose gels and the intensity of the signals recorded.

EXAMPLE 7 hRAD50—Human Homolog of the Yeast Gene RAD50

A. Isolation of hRAD50

Three cDNA clones A106, G157, G170, selected with the YACs A94G6 and 854G6 as described in Example 3, were mapped to chromosome 5-specific cosmid 256E1 about 10 kb upstream of the IL13 gene.

A full-length cDNA, termed G10 (also referred to as "RAD50.seq"; SEQ ID NO:44), was obtained using marathon RACE (rapid amplification of cDNA ends; Chenchik, et al., 1995) techniques with activated T-cell and testis cDNA marathon pools. A marathon cDNA pool, in contrast to a regular cDNA pool, has a special adapter at the ends of cDNAs. Such cDNAs can not be SISPA amplified, because the adapter design suppresses PCR with a single adapter-specific primer (Siebert, et al., 1995). Exponential PCR is observed only if a gene-specific primer is employed along with the adapter-specific primer. Such cDNA pools allow both 5'- and 3'-RACE amplifications, and finally isolation of intact genes via combination PCR (Chenchik, et al., 1995).

Figure 1A:
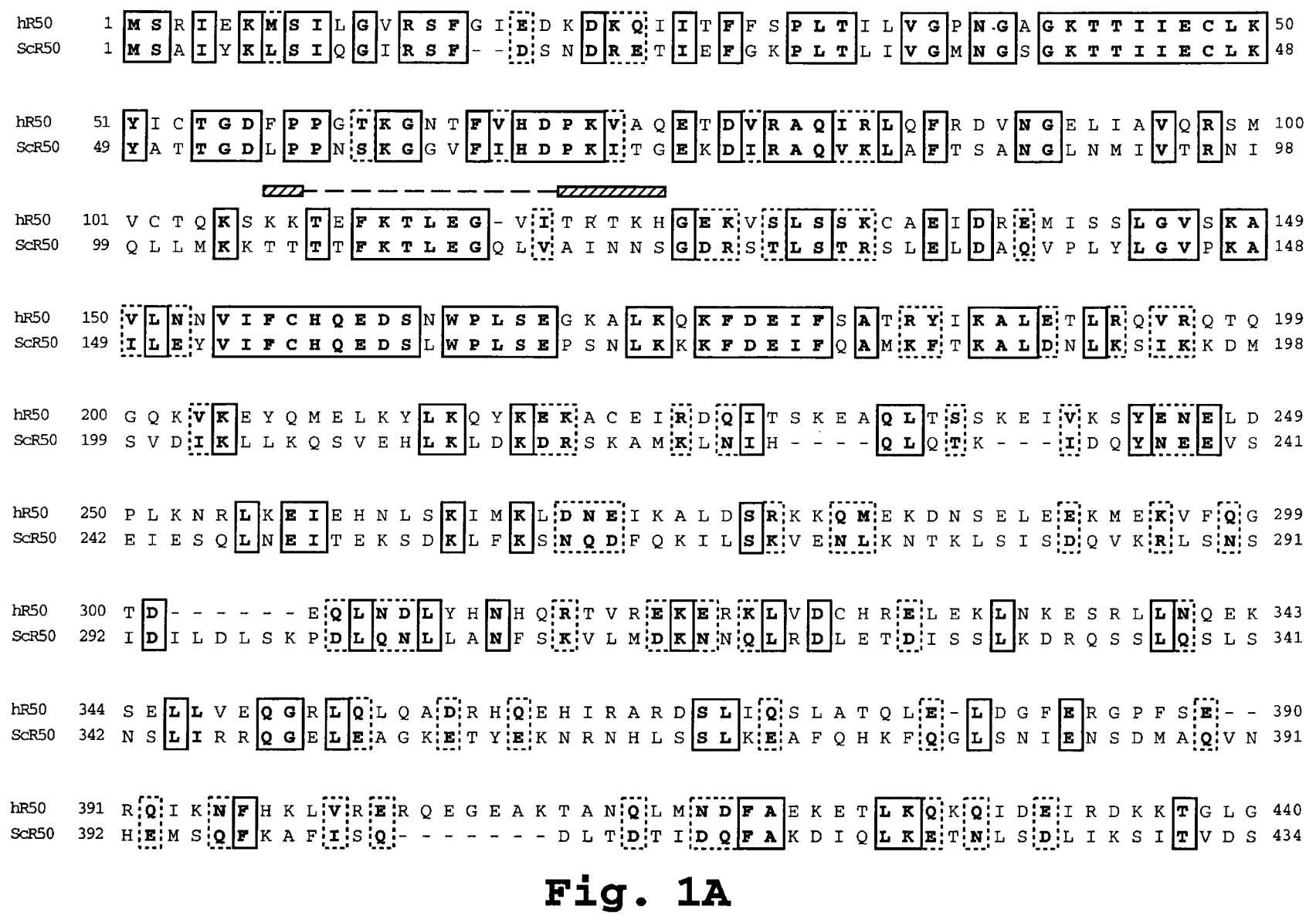
Figure 1B:
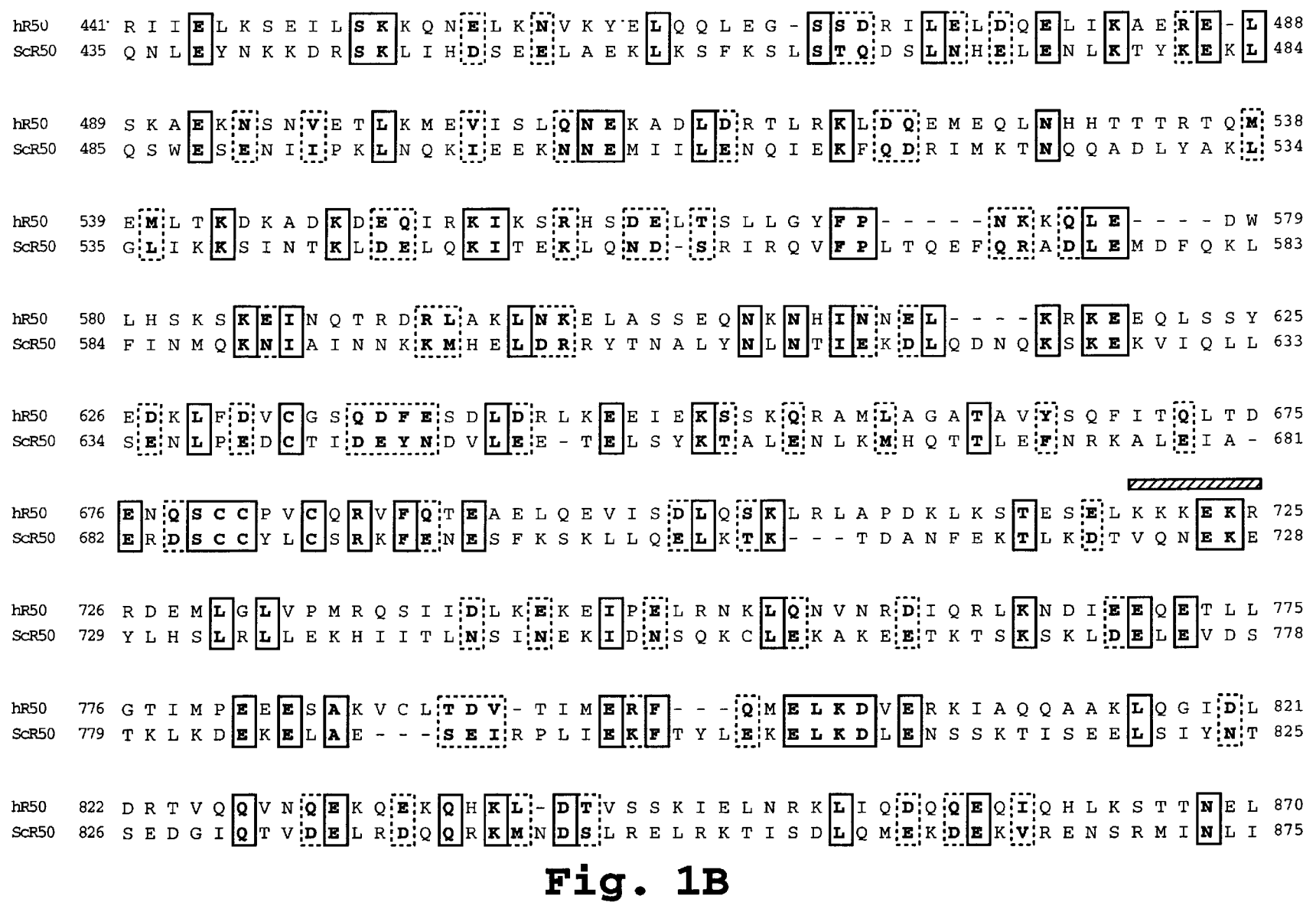
Figure 1C:
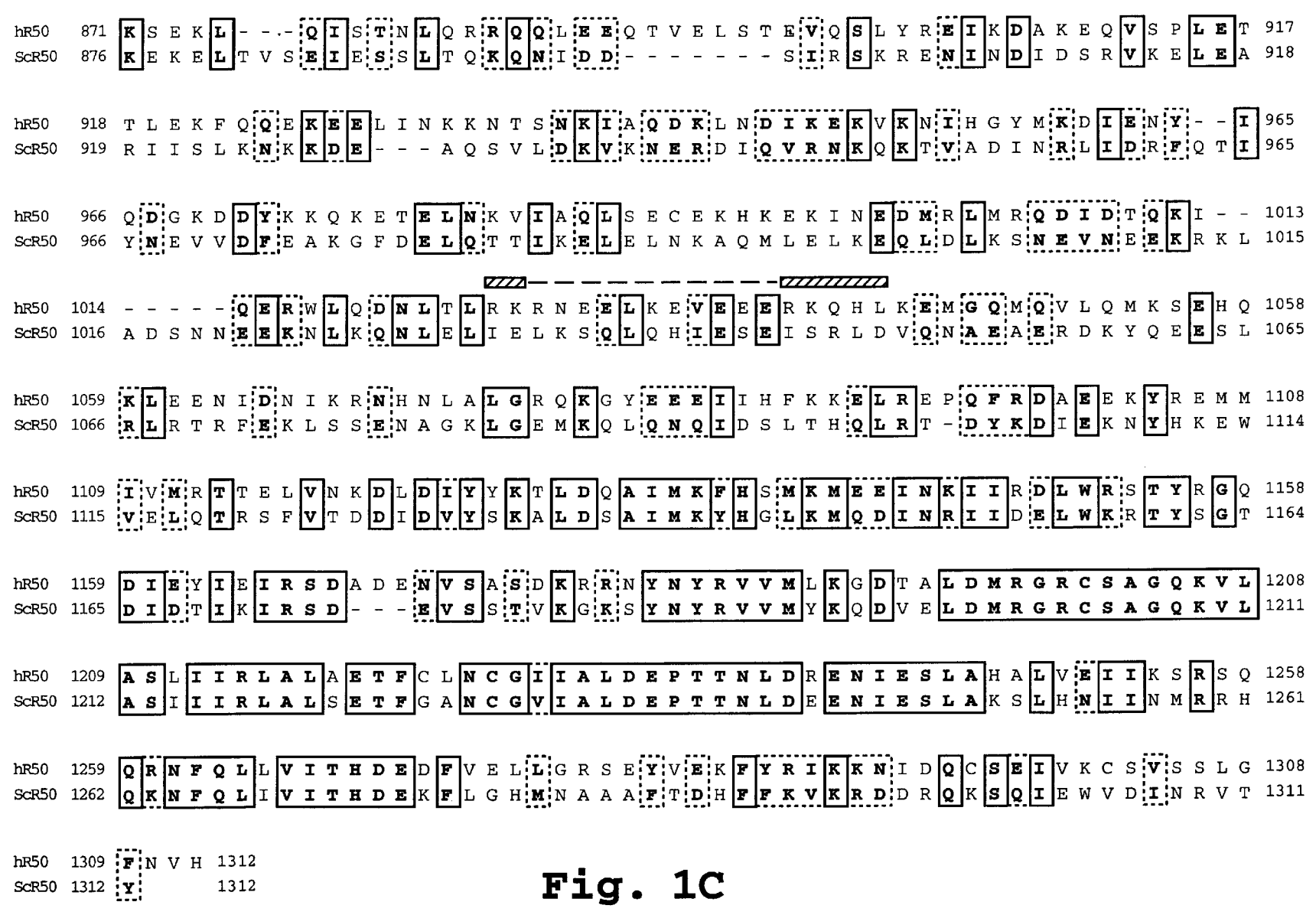

B. cDNA Sequence Analysis cDNA clone G10 is about 5,800 bp long and encodes a protein of 1312 aa (SEQ ID NO:51) with two highly-conserved domains with respect yeast RAD50 (>50% identity): an N-terminal ATP-binding domain and a conserved C-terminal domain. The locus corresponding to G10 was accordingly termed human RAD50 (hRAD50). FIGS. 1A–1C show an alignment of hRad50 and ScRad50. Identical amino acid residues are identified by solid-line boxes, and similar residues (as defined in the following paragraph) are identified by dashed boxes. Potential nuclear localization signals are indicated by hatched boxes over the hRad50 sequence. Two of these are bipartite (Robbins, et al., 1991) with a dashed line connecting the two segments. The Walker "A" and "B" NTP binding domains are overlined.

The two sequences were also compared pairwise in 130 amino acid segments using the Lipman-Pearson algorithm (Lipman and Pearson, 1985). The results are shown in FIG. 2A. Identical residues are indicated by solid white regions and similarities, with residues weighted according to the PAM250 matrix (Dayhoff, 1978), are indicated by filled boxes. The following amino acids were considered similar: {D, E, N, Q} {F, W, Y} {K, R} {A, G} {I, V} {L, M} {S, T} {C} {H} {P}.

hRad50 contains three potential nuclear localization signals (FIGS. 1A and 1B). The conserved N terminal domain includes the Walker A-type ATP binding signature (Alani, et al., 1989; Gorbalenya and Koonin, 1990), whereas the Walker B-type "DA" box is encoded by the C terminal conserved region (Gorbalenya and Koonin, 1990; Hirano, et al., 1995). The DA box-containing region of hRad5O is the most conserved region of the protein, exhibiting 68% identity over the C terminal 270 amino acids (FIGS. 1A, 1B and 2A).

The internal portion of ScRad50 is conserved to a much lesser extent. This region encodes the heptad repeat regions of the protein from amino acids 177–421 and amino acids 743–995 (Dayhoff, 1978). The heptad repeat motif in ScRad50 is likely to be significant for the assembly of ScRad50-containing protein complexes (Alani, et al., 1989; Raymond and Kleckner, 1993b).

Figure 2B:
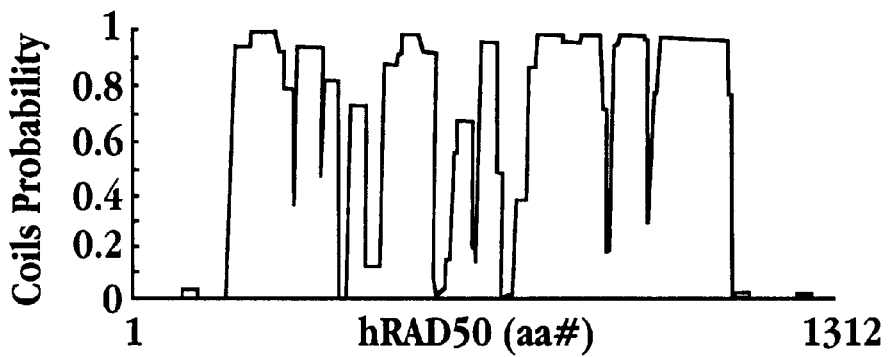
FIGS. 2B–2C shows the probability of coil formation as a function of amino acid position based on the amino acid sequences of hRad50 and ScRad50.
Figure 2C:
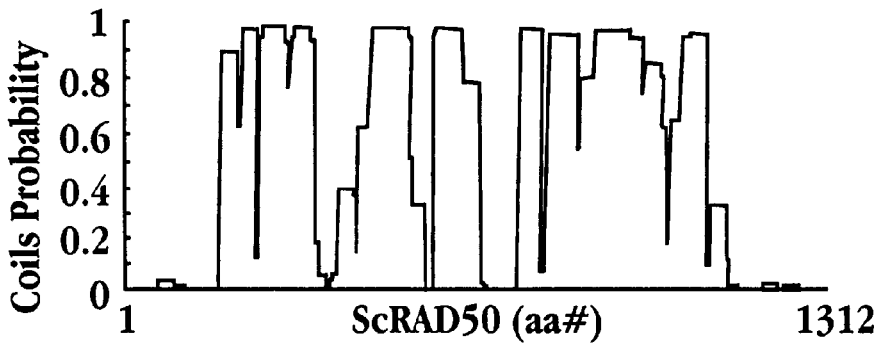

The COILS program (Lupas, et al., 1991; available over the World Wide Web (WWW) from Uniform Resource Locator (URL) http://ulrec3.unil.ch/software/COILS_form.html), which calculates the probability that a given segment of a protein will adopt a coiled coil conformation, was used to compare the predicted secondary structures of the two Rad50 homologues (Lupas, et al., 1991). Shown is the data at window width 28. The probabilities determined by the COILS program (Lupas, et al., 1991) (FIGS. 2B–2C). In spite of the relatively divergent primary sequence of the heptad repeat domains, these regions in hRad5O and ScRad50 are predicted to adopt very similar coiled coil structures.

C. Chromosomal Localization of the hRAD50 locus

Figure 3:
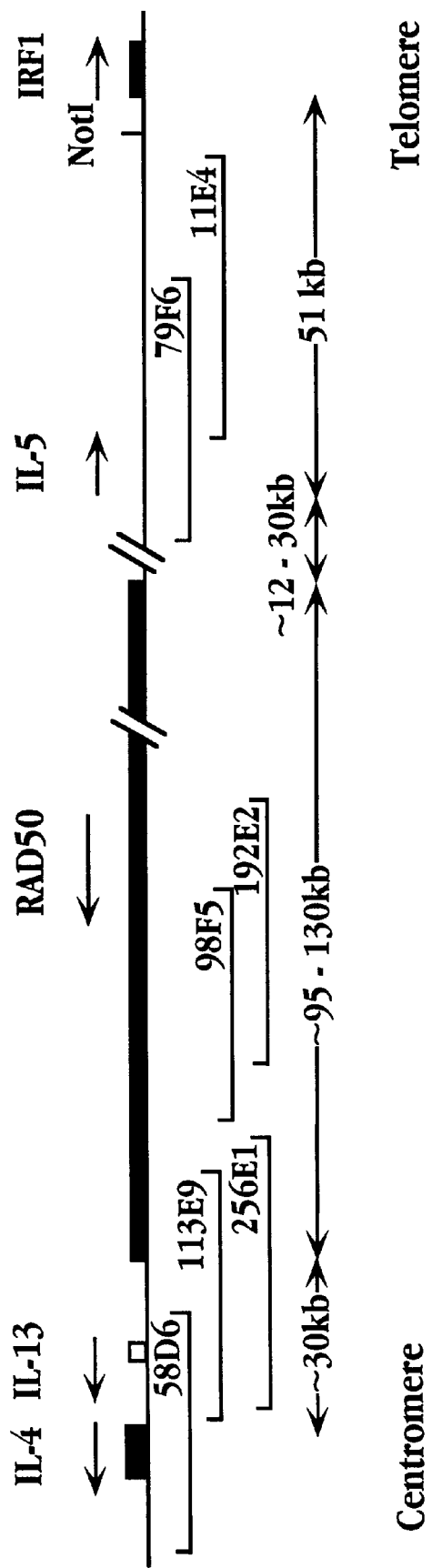
FIG. 3 shows the position of hRAD5O and selected cosmid clones with respect to other loci in the 5q23–31 region.

The chromosomal position of the RAD50 locus was determined using Southern blot analysis. The results are summarized in FIG. 3, which shows a physical map of the human RAD50 gene within the cytokine gene cluster in 5q23–q31. The genes depicted above map to a 320 kb NotI restriction fragment at 5q31. The distance between the IL4 and IL5 genes is about 150 kb. Because of the gaps in the chromosome 5-specific cosmid contig, represented by a double broken line, accurate estimation of the distance between the RAD50 and the IL5 genes, as well as of the size of the genomic RAD50 was not feasible. Some of the hRAD50 cosmid clones described herein are depicted below the map. Direction of gene transcription is indicated by the arrows. Cosmids 256E1, 113E9, and 58D6 placed the RAD50 locus approximately 14.0 kb upstream of the IL13 gene. Full-length hRAD50 cDNA was also used as a probe in Southern blot hybridization analysis of the YACs A94G6 and 854G6. This analysis confirmed that hRAD50 maps to the same 320 kb NotI restriction fragment as the IL4, IL13 and IL5 genes.

Figure 4:
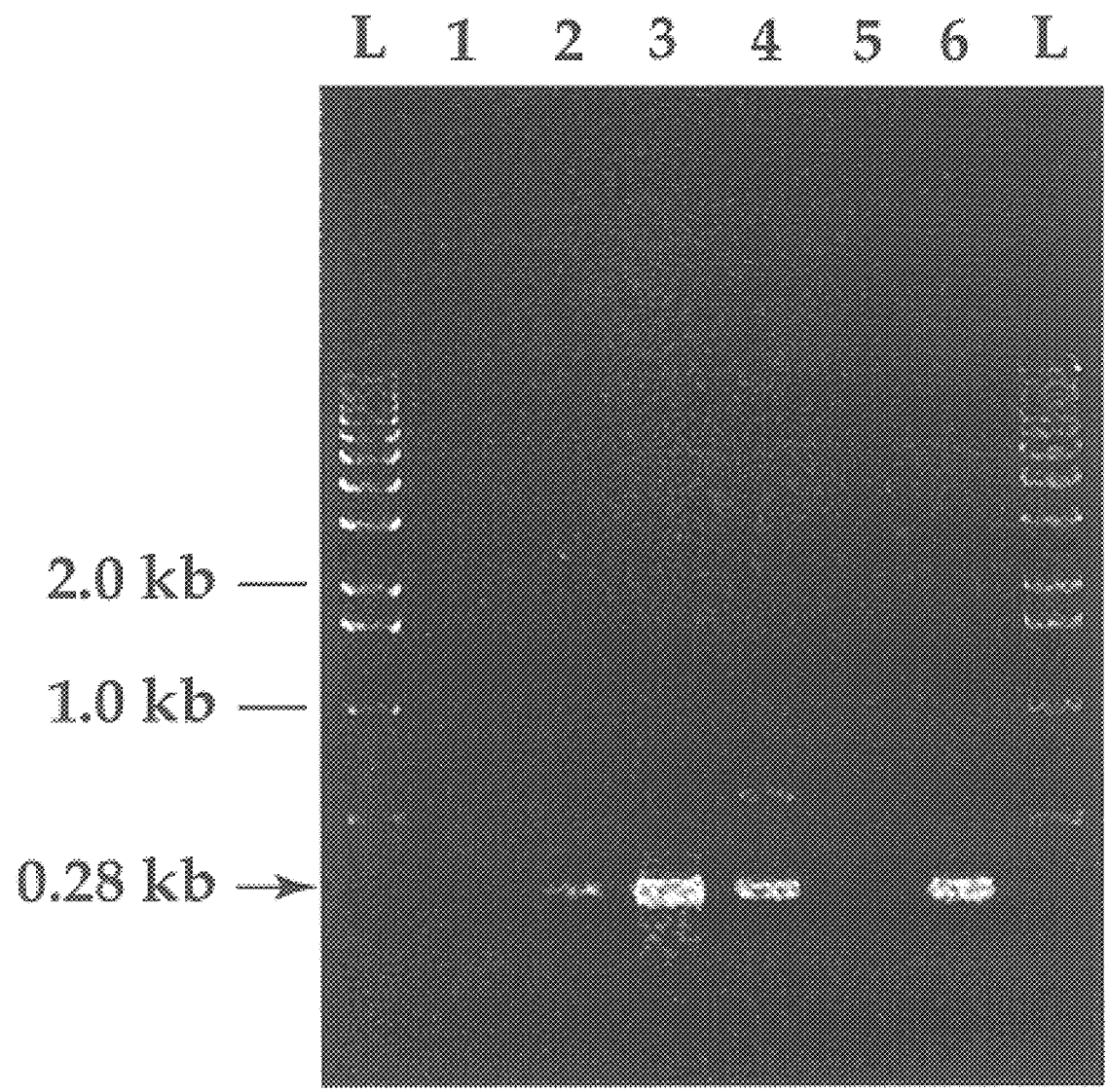
FIG. 4 shows the results of a PCR using primers directed to the 5' untranslated region of hRAD50.

Additional confirmation of this localization was established by PCR of DNA prepared from YACs A94G6 and 854G6, as well as from the chromosome 5-containing human/hamster hybrid cell line HHW105 with primers based on the 5' hRAD50 noncoding region. The data are presented in FIG. 4, which shows the results of PCR using primers G10-2 (SEQ ID NO:169) and G10-14 (SEQ ID NO:170), based on the 5' untranslated region of hRAD50. Template DNAs were as follows: Lane 1, No DNA control; Lane 2, Human genomic DNA; Lane 3, YAC 854G6; Lane 4, HHW105 human/hamster hybrid cell line DNA; Lane 5, CHO genomic DNA; Lane 6, YAC A94G6. L, 1 kb ladder. The hRAD50 primers amplified the expected products in the YAC clones derived from 5q31 and the human/hamster hybrid cell, whereas PCR with these primers on hamster genomic DNA failed to give any amplification products.

Four additional cosmid clones 54A2, 98F5, 192E2, and 32H4 were obtained by further screening of the chromosome 5-specific cosmid library with additional hRAD50 cDNA segments. By mapping various portions of the hRAD50 coding sequence to hRAD50-containing cosmids and YAC clones, the hRAD50 gene was estimated to span about 90–100 kb.

D. Genomic Sequence Analysis

All 25 exons, splice junctions, and portions of all 24 introns of the hRAD50 locus were sequenced. Primers for the genomic sequencing were designed from the cDNA sequence. The fragments used for primer design are presented in FIGS. 5A, 5B and 5C. The sequences of these fragments are provided herein as SEQ ID NO:52, SEQ ID NO:53 and SEQ ID NO:54, respectively. The regions used for design of upstream (5') primers are indicated in bold; regions used for design of downstream (3') primers are underlined.

The genomic sequence data are presented herein as SEQ ID NO:55–SEQ ID NO:114. Different SEQ ID NOs were assigned to each exon and each intron. Some introns were only sequenced at their ends, resulting in a "gap" in the central portion. These "gap-containing" introns are each represented by two SEQ ID NOs—one for the sequence at the 5' end and one for the sequence at the 3' end. The 5' and 3' ends of the genomic sequence were are presented herein as SEQ ID NO:55 and SEQ ID NO:114, respectively. The relationship of the SEQ ID NOs to the genomic structure is summarized in Table 3, below.

TABLE 3

Genomic Organization RAD50

| Exon # | SEQ ID # | #b.p. | Intron # | SEQ ID NOS. | #b.p. |
|---|---|---|---|---|---|
| 1 | 55, 56 | >516 | 1 | 57 | 1,829 |
| 2 | 58 | 84 | 2 | 59, 60 | 18,407 |
| 3 | 61 | 152 | 3 | 52, 63 | >1,800 |
| 4 | 64 | 186 | 4 | 65 | 359 |
| 5 | 66 | 205 | 5 | 67, 68 | >6,900 |
| 6 | 69 | 129 | 6 | 70 | 233 |
| 7 | 71 | 166 | 7 | 72 | 597 |
| 8 | 73 | 194 | 8 | 79 | 750 |
| 9 | 75 | 207 | 9 | 76 | 1,386 |
| 10 | 77 | 183 | 10 | 78 | 470 |
| 11 | 79 | 158 | 11 | 80, 81 | >2,400 |
| 12 | 82 | 176 | 12 | 83 | 535 |
| 13 | 84 | 238 | 13 | 85, 86 | >580 |
| 14 | 87 | 190 | 14 | 88 | 430 |
| 15 | 89 | 121 | 15 | 90, 91 | 741 |
| 16 | 92 | 194 | 16 | 93, 94 | 3,616 |
| 17 | 95 | 111 | 17 | 96 | 391 |
| 18 | 97 | 93 | 18 | 98 | 73 |
| 19 | 99 | 114 | 19 | 109, 101 | 6,606 |
| 20 | 102 | 128 | 20 | 103 | 1,939 |
| 21 | 104 | 225 | 21 | 105, 106 | 18,815 |
| 22 | 107 | 86 | 22 | 108, 109 | 880 |
| 23 | 110 | 143 | 23 | 111 | 2,448 |
| 24 | 112 | 134 | 24 | 113 | 1,371 |
| 25 | 114, 115 | 1,730 | | | |

E. hRAD50 expression hRAD50 expression was assessed by Northern blotting of mRNA prepared from various human tissues using A1

Figure 6:
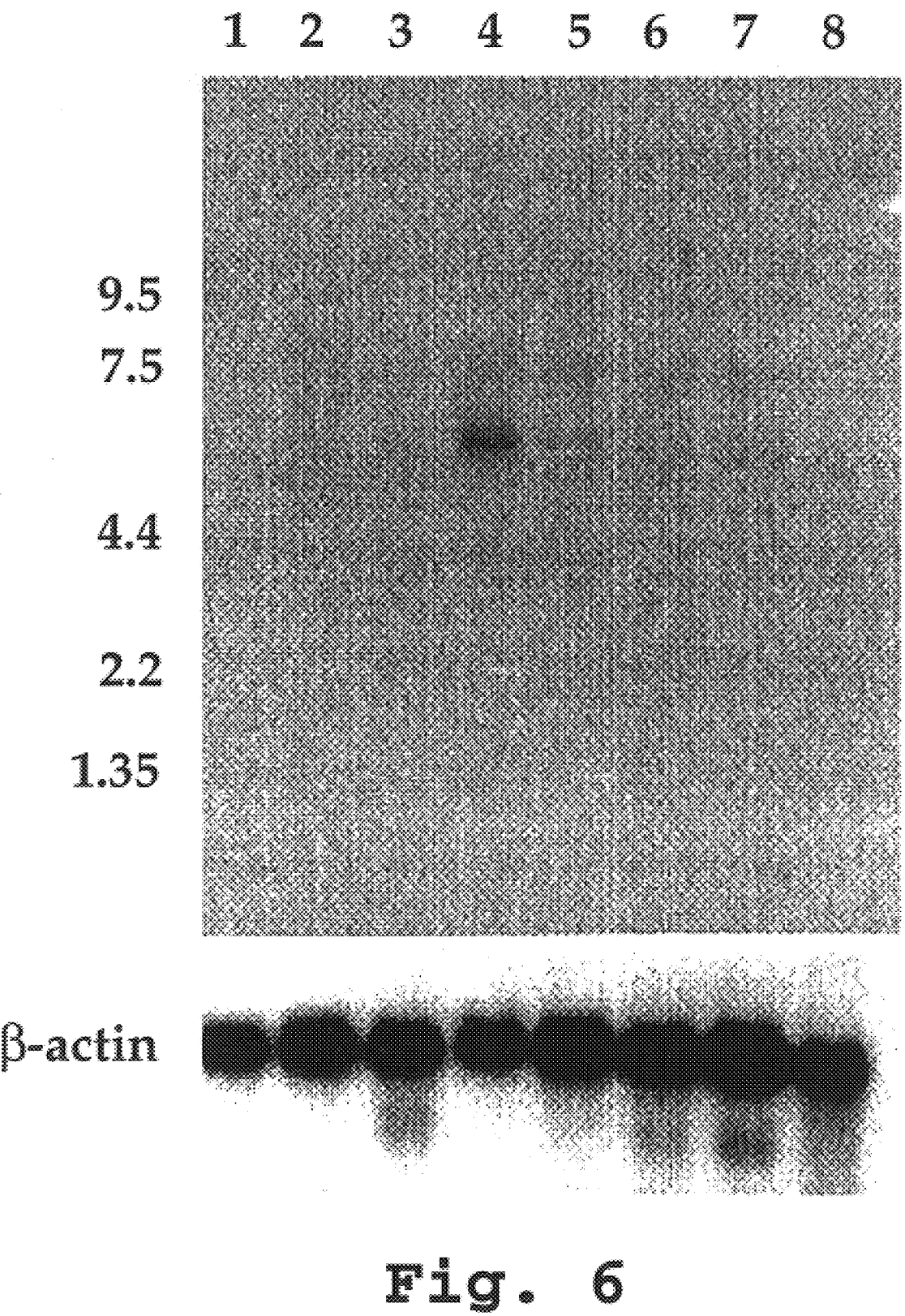
FIG. 6 shows a Northern blot of hRAD50 expression.

$^{32}$P-labelled probe, generated by PCR with the primers G10-N (SEQ ID NO:171)/G10-C1 (SEQ ID NO:172) on the G10 hRAD50 cDNA as a template (SEQ ID NO:44). A Northern blot filter was prepared with 1.5 μg of polyA+ RNA from various human tissues (Clontech, Palo Alto, Calif.). The results are shown in FIG. 6. The positions of RNA size standards are indicated. β-actin hybridization was included to control for mRNA abundance Lanes: 1, spleen; 2, thymus; 3, prostate; 4, testis; 5, ovary; 6, small intestine; 7, colon; 8, peripheral blood leukocytes.

The 5.5 kb hRAD50 transcript is seen in the testis, but is barely detectable in the other tissues examined. A faintly hybridizing band is also seen at 7 kb. The origin of this signal has not been established. Since a single protein species is observed with hRad50 antiserum (FIG. 6), the 7 kb band most likely corresponds to alternative 3' end processing of the hRAD50 transcript. Support for this explanation comes from the structure of the A106 cDNA which contains evidence of alternative 3' end processing. Increased expression of hRAD50 in the testis is reminiscent of the hMRE11 expression pattern, as well as that of another mammalian RAD52 epistasis group member, RAD51 (Petrini, et al., 1995; Shinohara, et al., 1993). hRAD50 transcripts were also detected in fetal liver and in activated T- and B-cells by RT-PCR.

A non-coding 3'-flanking portion of the gene, when used as a probe, detected mRNA species of 1.9 and 0.85 kb in multiple tissues. This may indicate either unusual alternative splicing of the RAD50 gene or an overlap with another gene.

The above results confirm that hRAD50 is expressed in activated T-cells, B-cells, total embryo, fetal muscle, fetal liver, placenta, adult heart, and adult bone marrow.

EXAMPLE 8

Association of hRad50 with hMre11—
Immunoprecipitation Analyses

It is recognized that S. cerevisiae Mre11 interacts with both ScRad50 and ScXrs2 in a two hybrid system (Johzhuka and ogawa, 1995). Experiments were performed to determine whether an analogous complex involving hMre11 and hRad50 exists in human cells. hMre11 antiserum or hRad50 antiserum was used to immunoprecipitate whole cell extracts of the human lymphoblastoid cell line, TK6 (Liber and Thilly, 1982). Since nuclear staining was observed with hMre11 and hRad50 antisera, whole cell extracts were prepared in high salt (500 mM NaCl) to increase the yield of chromatin-associated nuclear proteins (Boubnov, et al., 1995). The extracts were then diluted to 300 mM NaCl for immunoprecipitation as described in Materials and Methods.

TK6 cells (2.5×10$^6$/lane) were lysed in High Salt buffer and diluted 1:2 in Standard Lysis Buffer. Following incubation with the indicated antisera, immunoprecipitation was carried out with Protein A-Sepharose beads and immunoprecipitated material was analyzed by immunoblotting with hRad50 antiserum or hMre11 antiserum as described above. The filters were then stripped and retreated with the converse antiserum—hMre11 (following hRad50) or hRad50 (following hMre11).

The results are shown in FIG. 7. The positions of protein molecular weight standards are indicated. Lanes 1/2 and 3/4 are the same filter; lanes 5/6 and 7/8 are the same filter. Immunoprecipitation with 204pre (lanes 1 and 3) or αhMre11 204/6 (lanes 2 and 4) was followed by immunodetection with αhmre11 204/6 (Lanes 1 and 2) or αhRad50 84 (Lanes 3 and 4). Immunoprecipitation with 84pre (lanes 6 and 8) or αhRad50 84 (lanes 5 and 7) was followed by immunodetection with ahRad50 84 (lanes 5 and 6) or αhMre11 204/6 (lanes 7 and 8).

A single 153 kD band, corresponding to the predicted size of the hRad50 protein was precipitated by the hRad50 antiserum but not by the pre-immune serum (FIG. 7, lanes 5 and 6). The hRad50 antiserum also recognized an identical 153 kD band in the material immunoprecipitated by hMre11 antiserum (FIG. 7, lane 4). Conversely, a single 81 kD band corresponding to the hMre11 protein 3 was precipitated by the hMre11 antiserum as well as the hRad50 antiserum (FIG. 7, lanes 2 and 7). Immunoblotting the precipitated material with pre-immune serum produced neither the 81 kD nor the 153 kD signals observed with the specific antisera.

Association of these proteins in 300 mM NaCl demonstrates that hRad50 and hMre11 are in stable association. To assess the stability of this complex in more detail, immunoprecipitations were carried out at NaCl concentrations ranging from 300 mM to 1000 mM, followed by immunoblotting with hMre11 and hRad50 antisera as above.

The results are shown in FIG. 8. K562 cells (2.5×10$^6$/lane) were lysed in High Salt Buffer as above and diluted 1:2 in Lysis Buffer with increasing NaCl. Following incubation with 204/3p antiserum (affinity purified αhMre11 serum), immunoprecipitation was carried out with Protein A-Sepharose beads and immunoprecipitated material was analyzed by immunoblotting with 204/3p. Filters were then stripped and retreated with 84 (a hRad50 serum). From left to right, NaCl concentrations were: 300 mM, 500 mM, 750 mM, 850 mM, and 1000 mM.

As can be appreciated from the figure, the amount of hMre11 protein immunoprecipitated at increasing salt concentrations was unchanged. Similarly, the relative abundance of coimmunoprecipitated hRad50 remained essentially constant until the NaCl concentration exceeded 750 mM, and was still detectable at 1000 mM NaCl. These data demonstrate that hRad50 and hMre11 are tightly associated in cultured cells.

In S. cerevisiae, ScMre11 is associated with ScRad50 as well as the 96 kD protein, ScXrs2 (Johzhuka and Ogawa, 1995). Having demonstrated the association of hRad50 and hMre11, immunoprecipitation experiments were carried out using metabolically-labeled cells to determine whether the hRad50/hMre11 complex was associated with a protein corresponding to hXrs2.

K562 cells (5×10$^6$/lane) were grown in the presence of [$^{35}$S]Methionine for 6 hours and lysed in High Salt Buffer. Immunoprecipitation was carried out as described in the Materials and Methods using 204/3p (affinity purified αhMre11 sera) or 204pre antiserum. Immunoprecipitated material was analyzed by SDS-PAGE on 8.5% gels. The gels were then dried and autoradiographed for 13 hours. As expected, bands of 81 kD and 153 kD, corresponding to hMre11 and hRad50, were immunoprecipitated by the hNre11 antiserum. However, three additional bands (95 kD, 210 kD and ~350 kD) were also present in the immunoprecipitated material. These three proteins were not present in the control immunoprecipitation reaction, suggesting that hRad50 and three proteins of 95, 210, and 350 kD physically associate with hMre11. The detection of a 95 kD species in the immunoprecipitated material suggests that the human hRad50/hMre11 complex contains the human Xrs2 homologue.

EXAMPLE 9

Genetic Evidence for the Association of the hRAD50 with Myelogenous Leukemias

A. FISH Analysis

Fluorescence In Situ Hybridization (FISH) was performed as described by Rowley, et al., (1990), using an hRAD50 mixed probe, consisting of the cosmids 98F5, 192E2, and 256E1 (LANL chromosome 5-specific cosmid library) which span 80 kb of the C-terminal part of the gene, on chromosomes isolated from bone marrow cells, biopsy specimens or peripheral blood cells of patients who had previously been diagnosed with AML, MDS, t-MDS, t-AML, RA, or RAEB. These diagnoses were based on morphological and cytochemical studies of peripheral blood smears, bone marrow aspirates and biopsy specimens. The patients had also been previously characterized as having specific chromosome 5 deletions. The extent of the deletions, sex and ages of the patients, as well as the results of the FISH analyses are summarized in Table 4, below.

TABLE 4

Fluorescence In Situ Hybridization Analysis of Malignant Myeloid Disorders Characterized by a del (5q)

| Pt. | Age/Sex | DX | Chromosome Deletion | RAD50 Signal Normal 5 Homolog | del (5q) |
|---|---|---|---|---|---|
| 1 | 53/F | AML-M2 | del (5) (q13q33) | + | − |
| 2 | 44/M | t-MDS | del (5) (q15q33) | + | − |
| 3 | 67/F | MDS | del (5) (q15q33) | + | − |
| 4 | 86/F | MDS | del (5) (q22q34) | + | − |
| 5 | 41/M | t-MDS | del (5) (q14q33) | + | − |
| 6 | 68/F | t-AML | del (5) (q23q33) | + | − |
| 7 | 45/M | t-AML | del (5) (q11q34) | + | − |
| 8 | 64/M | RAEB | del (5) (q15q33) | + | − |
| 9 | 79/M | RA | del (5) (q13q33or34) | + | − |
| 10 | 64/F | RAEB | del (5) (q13q33) | + | − |

The results demonstrate that individuals heterozygous for the indicated deletions were also heterozygous for the RAD50 signal, i.e., they were missing sequences capable of hybridizing to the RAD50 probe on the chromosome containing the indicated deletion. The results support the role of RAD50 as a tumor suppressor gene which can be used (i) to diagnose an individual as being at increased for a cancer, and (ii) to decrease the risk of cancer in an individual having insufficient normal RAD50 function.

B. DGGE Analyses

Denaturing gel electrophoresis (DGGE) analyses using primers capable of amplifying hRAD50 exons are performed on genomic DNA samples from the patients listed above. The analyses are performed using primer pairs selected from primers having SEQ ID NO:116–163, where each two consecutive primers in the series form a primer pair. For example, primers r1 (SEQ ID NO:116) and r2 (SEQ ID NO:117) are used as one primer pair. The amplification products are resolved on a "D GENE" denaturing gel electrophoresis system (BioRad) as described by Guldberg, et al.

Amplification products containing heteroduplexes are sequenced to determine the nature of the mismatch.

EXAMPLE 10

Generation of Human Cell Lines and Transgenic Mice Deficient for Wild-Type hRad50

Am hRAD50 construct suitable for generation of transformed embryonic stem (ES) cells is designed using the method of Ramirez-Solis, et al. A positive-negative selection strategy (Mansour, et al., 1988) in combination with the PPNT vector (Tybulewicz, et al., 1991), containing PGKneo and PGKtk, is used to obtain targeted disruption of RAD50 gene. Both genes in this vector are under the control of the housekeeping mouse phosphoglycerate kinase-1 promoter. This strategy enriches for homologous recombination events by simultaneously selecting for a neo gene within the homologous DNA and against an HSV-tk gene placed at the end of the targeting vector.

A. Isolation of N-terminal Fragment of hRad50

PCR is carried out in 100 $\mu$l as described above, using hot start with "KLENTAQ1" (Ab Peptides, Inc., St. Louis, Mo.) and 50 ng of 854G6 YAC DNA as a template. The reaction is run on 1% agarose gel and a product of about 2.7 kb is excised from the gel, digested with NotI and XhoI, and ligated into NotI-XhoI linearized vector pPNT. Ligations and in vitro manipulations to generate PRAD50 are carried out according to Sambrook, et al.

A PCR fragment, generated with primers S1 (SEQ ID NO:174) and S2 (SEQ ID NO:175), encompasses 2.7 kb of the N-terminal region of the human RAD50 gene including the first and the second exons. This fragment is subcloned into the NotI and XhoI sites of PPNT.

A second C-terminal hRAD50 BamHI-EcoRI fragment (2.8 kb) of the cosmid 256E1 encompasses exon 24 and part of exon 25. This fragment is subcloned into BamHI-EcoRI sites of PPNT. The resulting plasmid (pRAD50-2) is linearized with restriction endonuclease NotI and used to electroporate ES cells as described below.

B. Transformation of Murine ES Cells

Linearized vector pRAD50-2 is used to electroporate the CCE line of ES cells (Robertson, et al., 1986) at passages 11–13, grown on STO feeder cells in Dulbecco's modified Eagle's medium supplemented with 10% fetal calf serum. To prepare cells for electroporation, confluent plates of ES cells are harvested by trypsinization, washed and resuspended in a buffer containing 20 mM HEPES (pH 7.0), 137 mM NaCl, 5 mM KCl, 0.7 mM $Na_2HPO_4$, 6 mM dextrose, and 0.1 mM 2-mercaptoethanol at $10^7$ cells per ml. Twenty five $\mu$g of the linearized pRAD50-2 plasmid are added to 0.9 ml of ES cell suspension, and the mixture is electroporated using the Bio-Rad Gene Pulser electroporator (Bio-Rad Laboratories, Hercules, Calif.) with a single discharge of 400 V at 25 $\mu$F.

After electroporation the cells are incubated for 5 min at room temperature and plated on 10-cm tissue culture plate with feeder cells. G418 (neomycin, 300 $\mu$g/ml) and gancyclovir (2 $\mu$M) are applied 48 hr after the electroporation. The cells are re-fed when the media starts turning yellow, typically daily for first 5 days. In ten days after electroporation, individual colonies are typically ready to be selected. Selected clones are propagated and assayed by PCR and Southern blot analysis to determine whether homologous recombination took place.

C. Blastocyst Injection of Transformed ES Cells

ES cells from selected clones testing positive for homologous recombination are used for blastocyst injection. Ten to fifteen disintegrated ES cells from a selected clone are collected with a microinjection needle and injected into intercellular space of a C57bl/6J blastocysts at 3 days postcoitum as described in Hogan, et al., (1994).

Chimeras are typically born 17 days after transferring 5–10 recombinant blastocysts back into one uterine horn of a single foster mother. Remaining manipulations to generate chimeric mice and test the breeding, as well as genomic analyses are performed according to Ramirez-Solis, et al., (1993) and Hogan, et al., (1994).

D. In Vitro Differentiation of Transformed ES Cells

ES cell lines can differentiate in vitro to form a variety of cell types in a sequence that recapitulates the first stages of mouse embryogenesis. Upon withdrawal of leukemia inhibitory factor (LIF) from the media and stromal contact, ES cells form embryoid bodies (Ebs)—spherical aggregates of differentiated cell types which appear in a well-defined temporal pattern. Hematopoiesis within Ebs has been well documented, as well as vasculogenesis, myogenesis, and development of neuronal-like cells (Bain, et al., 1995; see review by Weiss and Orkin, 1996).

Gearing ES cells development into blood cells is facilitated by a "two-step" replating assay in which Ebs are disaggregated into single cells and replated into methylcellulose cultures containing various cytokines. Following this protocol, precursor cells give rise to pure hematopoietic colonies that can be enumerated and analyzed (Keller, et al., 1993). A similar approach can be undertaken to gear the ES differentiation into, e.g., myocytes or fibroblasts.

Both alleles of a single copy gene (e.g., RAD50) can be inactivated in ES cells using, e.g., the method of Mortensen, et al. In vitro differentiation of resultant homozygous mutant ES cells can complement and extend gene knockout experiments in animals. In vitro differentiation of murine ES cells generates relatively large numbers of early embryonic specific type cells and their immediate precursors which can be isolated and used for further study. For example, ES cells lacking any functional copies of RAD50 can be used in a method of screening agents for the ability to promote DNA breaks in a human cell line.

While the invention has been described with reference to specific methods and embodiments, it is appreciated that various modifications and changes may be made without departing from the invention.

It is claimed:

1. A recombinant vector effective to transform human bone marrow cells, comprising
   an expression cassette containing a polynucleotide sequence that encodes (i) an hRAD50 protein encoded by nucleotides 389 to 4324 in SEQ ID NO:44 or (ii) an hRAD50 protein having the sequence identified by SEQ ID NO:47 under control of suitable control elements.

2. The vector of claim 1, wherein said polynucleotide sequence encodes an hRAD50 protein encoded by nucleotides 389 to 4324 in SEQ ID NO:44.

3. The vector of claim 1, wherein said polynucleotide sequence encodes an hRAD50 protein having the sequence identified by SEQ ID NO:47.

4. A protein expression vector containing, as a heterologous gene under the control of suitable control elements, a polynucleotide sequence that encodes (i) an hRAD50 protein encoded by nucleotides 389 to 4324 in SEQ ID NO:44 or (ii) an hRAD50 protein having the sequence identified by SEQ ID NO:47.

5. The vector of claim 4, wherein said polynucleotide sequence comprises nucleotides 389 to 4324 of SEQ ID NO:44.

6. The vector of claim 4, wherein said polynucleotide sequence encodes an hRAD50 protein having the sequence identified by SEQ ID NO:47.

7. An isolated polynucleotide fragment containing an open reading frame that encodes (i) an hRAD50 protein encoded by SEQ ID NO:44 or (ii) an hRAD50 protein having the sequence identified by SEQ ID NO:47.

8. The isolated polynucleotide of claim 7, wherein said open reading frame includes nucleotides 389 to 4324 of SEQ ID NO:44.

9. The vector of claim 7, wherein said open reading frame encodes an hRAD50 protein having the sequence identified by SEQ ID NO:47.

10. A host cell containing the vector of claim 4.

11. The host cell of claim 10, wherein said polynucleotide sequence comprises nucleotides 389 to 4324 of SEQ ID NO:44.

12. The host cell of claim 10, wherein said polynucleotide sequence encodes an hRAD50 protein having the sequence identified by SEQ ID NO:47.

* * * * *

```
SEQUENCE LISTING (1) GENERAL INFORMATION:

(iii) NUMBER OF SEQUENCES: 175

(2) INFORMATION FOR SEQ ID NO:1:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligonucleotide #4665 for adapter #3

(xi) SEQUENCE DESCRIPTION: SEQ ID NO:1:

GAGGATCCAG AATTCTCGAG TT                                                22

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligonucleotide #4666 for adapter #3

(xi) SEQUENCE DESCRIPTION: SEQ ID NO:2:

CTCCTAGGTC TTAAGAGCTC                                                   20

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA
```

(iii) HYPOTHETICAL: NO (iv) ANTI-SENSE: NO (vi) ORIGINAL SOURCE:
    (C) INDIVIDUAL ISOLATE: oligonucleotide #A5-1 for adapter #5

(xi) SEQUENCE DESCRIPTION: SEQ ID NO:3:

TGGATCCTCT AGAGAGTGTG GTT                                           23

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligonucleotide #A5-2 for adapter #5

(xi) SEQUENCE DESCRIPTION: SEQ ID NO:4:

ACCTAGGAGA TCTCTCACAC C                                             21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligo #AD3-2 for PCR amp of cDNAs (xi) SEQUENCE DESCRIPTION: SEQ ID NO:5:

ACTCGAGAAT TCTGGATCCT C                                             21

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligo #AD3-CUA for PCR amp of cDNAs (xi) SEQUENCE DESCRIPTION: SEQ ID NO:6:

CUACUACUAC UAACTCGAGA ATTCTGGATC CTC                                33

(2) INFORMATION FOR SEQ ID NO:7:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: oligo #A5-2b for PCR amp of cDNAs (xi) SEQUENCE DESCRIPTION: SEQ ID NO:7:

CCACACTCTC TAGAGGATCC A                                              21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GM-CSF-2

(xi) SEQUENCE DESCRIPTION: SEQ ID NO:8:

CCTTGACCAT GATGGCCAGC C                                              21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GM-CSF-1

(xi) SEQUENCE DESCRIPTION: SEQ ID NO:9:

CCCGGCTTGG CCAGCCTCAT C                                              21

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL3-1

(xi) SEQUENCE DESCRIPTION: SEQ ID NO:10:

CTCTGTGGTG AGAAGGCCCA                                              20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL3-2

(xi) SEQUENCE DESCRIPTION: SEQ ID NO:11:

CTTCGAAGGC CAAACCTGGA                                              20

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL4-3

(xi) SEQUENCE DESCRIPTION: SEQ ID NO:12:

GGTTTCCTTC TCAGTTGTGT TCT                                          23

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL4-4

(xi) SEQUENCE DESCRIPTION: SEQ ID NO:13:

CTCACCTCCC AACTGCTTCC C                                            21

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer IL5-1

(xi) SEQUENCE DESCRIPTION: SEQ ID NO:14:

CACCAACTGT GCACTGAAGA AATC                                                24

(2) INFORMATION FOR SEQ ID NO:15:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer IL4-2

(xi) SEQUENCE DESCRIPTION: SEQ ID NO:15:

CCACTCGGTG TTCATTACAC C                                                   21

(2) INFORMATION FOR SEQ ID NO:16:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer IL9-1

(xi) SEQUENCE DESCRIPTION: SEQ ID NO:16:

AGCTTCTGGC CATGGTCCTT AC                                                  22

(2) INFORMATION FOR SEQ ID NO:17:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer IL9-6

(xi) SEQUENCE DESCRIPTION: SEQ ID NO:17:

TCAGCGCGTT GCCTGCCGTG GT                                                  22

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL13-1

(xi) SEQUENCE DESCRIPTION: SEQ ID NO:18:

ATGGCGCTTT TGTTGACCAC                                        20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL13-5

(xi) SEQUENCE DESCRIPTION: SEQ ID NO:19:

CCTGCCTCGG ATGAGGCTCC                                        20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IRF1-7

(xi) SEQUENCE DESCRIPTION: SEQ ID NO:20:

GAAGGCCAAC TTTCGCTGTG                                        20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer IRF1-8

(xi) SEQUENCE DESCRIPTION: SEQ ID NO:21:

CACTGGGATG TGCCAGTCGG                                                  20

(2) INFORMATION FOR SEQ ID NO:22:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer TCF7-3

(xi) SEQUENCE DESCRIPTION: SEQ ID NO:22:

CCGTTCCTTC CGATGACAGT GCT                                              23

(2) INFORMATION FOR SEQ ID NO:23:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer TCF7-4

(xi) SEQUENCE DESCRIPTION: SEQ ID NO:23:

GACATCAGCC AGAAGCAAGT                                                  20

(2) INFORMATION FOR SEQ ID NO:24:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer EGRI1-6

(xi) SEQUENCE DESCRIPTION: SEQ ID NO:24:

CCACCTCCTC TCTCTCTTCC TA                                               22

(2) INFORMATION FOR SEQ ID NO:25:

(i) SEQUENCE CHARACTERISTICS:
             (A) LENGTH: 21 base pairs
             (B) TYPE: nucleic acid
             (C) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer EGRI1-7

(xi) SEQUENCE DESCRIPTION: SEQ ID NO:25:

TCCATGGCAC AGATGCTGTA C                                                     21

(2) INFORMATION FOR SEQ ID NO:26:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer CD14-5

(xi) SEQUENCE DESCRIPTION: SEQ ID NO:26:

CCGCTGGTGC ACGTCTCTGC GACC                                                  24

(2) INFORMATION FOR SEQ ID NO:27:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer CD14-6

(xi) SEQUENCE DESCRIPTION: SEQ ID NO:27:

CACGCCGGAG TTCATTGAGC C                                                     21

(2) INFORMATION FOR SEQ ID NO:28:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer CDC25-3

(xi) SEQUENCE DESCRIPTION: SEQ ID NO:28:

GAGAGGAAGG AAGCTCTGGC TC                                                    22

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer CDC25-5

(xi) SEQUENCE DESCRIPTION: SEQ ID NO:29:

```
GTCCTGAAGA ATCCAGGTGA CC                                           22
```

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer Sau3AI-2 for semiadapter #2

(xi) SEQUENCE DESCRIPTION: SEQ ID NO:30:

```
TCGCGGCCGA ATTCTAGAGC TCGCT                                        25
```

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer Sau3AI-3

(xi) SEQUENCE DESCRIPTION: SEQ ID NO:31:

```
CGCCGGCTTA AGATCTCGAG C                                            21
```

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO -continued (iv) ANTI-SENSE: NO (vi) ORIGINAL SOURCE:
         (C) INDIVIDUAL ISOLATE: Primer Sau3AI S-1

(xi) SEQUENCE DESCRIPTION: SEQ ID NO:32:

GATCTCGAGG ATCCTCAGAG AGTAGTAG                                        28

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Primer Sau3AI S-2 for adapter #S-1/2

(xi) SEQUENCE DESCRIPTION: SEQ ID NO:33:

AGCTCCTAGG AGTCTCTCAT CATC                                            24

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: 5'Biotin-YAC primer #1: PCR amp of
             YACs (xi) SEQUENCE DESCRIPTION: SEQ ID NO:34:

AGCGAGCTCT AGAATTCGGC CGC                                             23

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: 5'Biotin-YAC primer #2: PCR amp of
             YACs (xi) SEQUENCE DESCRIPTION: SEQ ID NO:35:

CTACTACTCT CTGAGGATCC TCGAGA                                          26

(2) INFORMATION FOR SEQ ID NO:36:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer A106-1 for RAD50

(xi) SEQUENCE DESCRIPTION: SEQ ID NO:36:

GTCATCCAGA CTCAGAGCTC                                                   20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer A106-2 for RAD50

(xi) SEQUENCE DESCRIPTION: SEQ ID NO:37:

CTGTCTAGGC AAACATGCTC                                                   20

(2) INFORMATION FOR SEQ ID NO:38:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G10-C for RAD50

(xi) SEQUENCE DESCRIPTION: SEQ ID NO:38:

GAGAGGAATT CTTTTAATGA ACATTGAATC CCAGGGAG                                38

(2) INFORMATION FOR SEQ ID NO:39:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G10-N for RAD50
```

(xi) SEQUENCE DESCRIPTION: SEQ ID NO:39:

GAGAGGATCC TTTGTGGACT CCAGGTCCCT GGTGAGATT                                  39

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G18-1

(xi) SEQUENCE DESCRIPTION: SEQ ID NO:40:

ATCAGACCAG GGACAGACTT GCC                                                  23

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G18-2

(xi) SEQUENCE DESCRIPTION: SEQ ID NO:41:

CATCTTCTTC ATGCCCTAAC TG                                                   22

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligonucleotide #4578

(xi) SEQUENCE DESCRIPTION: SEQ ID NO:42:

TAGGAGATCT CTTAAGAGCT                                                      20

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: oligonucleotide #4579

(xi) SEQUENCE DESCRIPTION: SEQ ID NO:43:

| | |
|---|---:|
| TCTCGAGAAT TCTCTAGAGG ATCC | 24 |

(2) INFORMATION FOR SEQ ID NO:44:

(i) SEQUENCE CHARACTERISTICS:
        (A) LENGTH: 5893 base pairs
        (B) TYPE: nucleic acid
        (C) STRANDEDNESS: double
        (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
    (C) INDIVIDUAL ISOLATE: RAD50 cDNA SEQUENCE, CDS: 389 TO 4324

(xi) SEQUENCE DESCRIPTION: SEQ ID NO:44:

| | |
|---|---:|
| CCAGGAGAGC GGCGTGGACG CGTGCGGGCC TAGAGGCCCA CGTGATCCGC AGGGCGGCCG | 60 |
| AGGCAGGAAG CTTGTGAGTG CGCGGTTGCG GGGTCGCATT GTGGCTACGG CTTTGCGTCC | 120 |
| CCGGCGGGCA GCCCCAGGCT GGTCCCCGCC TCCGCTCTCC CCACCGGCGG GGAAAGCAGC | 180 |
| TGGTGTGGGA GGAAAGGCTC CATCCCCCGC CCCCTCTCTC CCGCTGTTGG CTGGCAGGAT | 240 |
| CTTTTGGCAG TCCTGTGGCC TCGCTCCCCG CCCGGATCCT CCTGACCCTG AGATTCGCGG | 300 |
| GTCTCACGTC CCGTGCACGC CTTGCTTCGG CCTCAGTTAA GCCTTTGTGG ACTCCAGGTC | 360 |
| CCTGGTGAGA TTAGAAACGT TTGCAAACAT GTCCCGGATC GAAAAGATGA GCATTCTGGG | 420 |
| CGTGCGGAGT TTTGGAATAG AGGACAAAGA TAAGCAAATT ATCACTTTCT TCAGCCCCCT | 480 |
| TACAATTTTG GTTGGACCCA ATGGGCGGG AAAGACGACC ATCATTGAAT GTCTAAAATA | 540 |
| TATTTGTACT GGAGATTTCC CTCCTGGAAC CAAAGGAAAT ACATTTGTAC ACGATCCCAA | 600 |
| GGTTGCTCAA GAAACAGATG TGAGAGCCCA GATTCGTCTG CAATTTCGTG ATGTCAATGG | 660 |
| AGAACTTATA GCTGTGCAAA GATCTATGGT GTGTACTCAG AAAAGCAAAA AGACAGAATT | 720 |
| TAAAACTCTG GAAGGAGTCA TTACTAGAAC AAAGCATGGT GAAAAGGTCA GTCTGAGCTC | 780 |
| TAAGTGTGCA GAAATTGACC GAGAAATGAT CAGTTCTCTT GGGGTTTCCA AGGCTGTGCT | 840 |
| AAATAATGTC ATTTTCTGTC ATCAAGAAGA TTCTAATTGG CCTTTAAGTG AAGGAAAGGC | 900 |
| TTTGAAGCAA AAGTTTGATG AGATTTTTTC AGCAACAAGA TACATTAAAG CCTTAGAAAC | 960 |
| ACTTCGGCAG GTACGTCAGA CACAAGGTCA GAAAGTAAAA GAATATCAAA TGGAACTAAA | 1020 |
| ATATCTGAAG CAATATAAGG AAAAAGCTTG TGAGATTCGT GATCAGATTA CAAGTAAGGA | 1080 |
| AGCCCAGTTA ACATCTTCAA AGGAAATTGT CAAATCCTAT GAGAATGAAC TTGATCCATT | 1140 |
| GAAGAATCGT CTAAAAGAAA TTGAACATAA TCTCTCTAAA ATAATGAAAC TTGACAATGA | 1200 |
| AATTAAAGCC TTGGATAGCC GAAAGAAGCA AATGGAGAAA GATAATAGTG AACTGGAAGA | 1260 |
| GAAAATGGAA AAGGTTTTTC AAGGGACTGA TGAGCAACTA AATGACTTAT ATCACAATCA | 1320 |
| CCAGAGAACA GTAAGGGAGA AAGAAAGGAA ATTGGTAGAC TGTCATCGTG AACTGGAAAA | 1380 |

-continued

```
ACTAAATAAA GAATCTAGGC TTCTCAATCA GGAAAAATCA GAACTGCTTG TTGAACAGGG    1440

TCGTCTACAG CTGCAAGCAG ATCGCCATCA AGAACATATC CGAGCTAGAG ATTCATTAAT    1500

TCAGTCTTTG GCAACACAGC TAGAATTGGA TGGCTTTGAG CGTGGACCAT TCAGTGAAAG    1560

ACAGATTAAA AATTTTCACA AACTTGTGAG AGAGAGACAA GAAGGGGAAG CAAAAACTGC    1620

CAACCAACTG ATGAATGACT TTGCAGAAAA AGAGACTCTG AAACAAAAAC AGATAGATGA    1680

GATAAGAGAT AAGAAAACTG GACTGGGAAG AATAATTGAG TTAAAATCAG AAATCCTAAG    1740

TAAGAAGCAG AATGAGCTGA AAATGTGAA GTATGAATTA CAGCAGTTGG AAGGATCTTC    1800

AGACAGGATT CTTGAACTGG ACCAGGAGCT CATAAAAGCT GAACGTGAGT TAAGCAAGGC    1860

TGAGAAAAAC AGCAATGTAG AAACCTTAAA AATGGAAGTA ATAAGTCTCC AAAATGAAAA    1920

AGCAGACTTA GACAGGACCC TGCGTAAACT TGACCAGGAG ATGGAGCAGT TAAACCATCA    1980

TACAACAACA CGTACCCAAA TGGAGATGCT GACCAAAGAC AAAGCTGACA AGATGAACA     2040

AATCAGAAAA ATAAAATCTA GGCACAGTGA TGAATTAACC TCACTGTTGG GATATTTTCC    2100

CAACAAAAAA CAGCTTGAAG ACTGGCTACA TAGTAAATCA AAAGAAATTA ATCAGACCAG    2160

GGACAGACTT GCCAAATTGA ACAAGGAACT AGCTTCATCT GAGCAGAATA AAATCATAT    2220

AAATAATGAA CTAAAAAGAA AGGAAGAGCA GTTGTCCAGT TACGAAGACA AGCTGTTTGA    2280

TGTTTGTGGT AGCCAGGATT TTGAAAGTGA TTTAGACAGG CTTAAAGAGG AAATTGAAAA    2340

ATCATCAAAA CAGCGAGCCA TGCTGGCTGG AGCCACAGCA GTTTACTCCC AGTTCATTAC    2400

TCAGCTAACA GACGAAAACC AGTCATGTTG CCCCGTTTGT CAGAGAGTTT TTCAGACAGA    2460

GGCTGAGTTA CAAGAAGTCA TCAGTGATTT GCAGTCTAAA CTGCGACTTG CTCCAGATAA    2520

ACTCAAGTCA ACAGAATCAG AGCTAAAAAA AAAGGAAAAG CGGCGTGATG AAATGCTGGG    2580

ACTTGTGCCC ATGAGGCAAA GCATAATTGA TTTGAAGGAG AAGGAAATAC CAGAATTAAG    2640

AAACAAACTG CAGAATGTCA ATAGAGACAT ACAGCGCCTA AGAACGACA TAGAAGAACA     2700

AGAAACACTC TTGGGTACAA TAATGCCTGA AGAAGAAAGT GCCAAAGTAT GCCTGACAGA    2760

TGTTACAATT ATGGAGAGGT TCCAGATGGA ACTTAAAGAT GTTGAAAGAA AAATTGCACA    2820

ACAAGCAGCT AAGCTACAAG AATAGACTT AGATCGAACT GTCCAACAAG TCAACCAGGA     2880

GAAACAAGAG AAACAGCACA AGTTAGACAC AGTTTCTAGT AAGATTGAAT TGAATCGTAA    2940

GCTTATACAG GACCAGCAGG AACAGATTCA ACATCTAAAA AGTACAACAA ATGAGCTAAA    3000

ATCTGAGAAA CTTCAGATAT CCACTAATTT GCAACGTCGT CAGCAACTGG AGGAGCAGAC    3060

TGTGGAATTA TCCACTGAAG TTCAGTCTTT GTACAGAGAG ATAAAGGATG CTAAAGAGCA    3120

GGTAAGCCCT TTGGAAACAA CATTGGAAAA GTTCCAGCAA GAAAAAGAAG AATTAATCAA    3180

CAAAAAAAAT ACAAGCAACA AAATAGCACA GGATAAACTG AATGATATTA AAGAGAAGGT    3240

TAAAAATATT CATGGCTATA TGAAAGACAT TGAGAATTAT ATTCAAGATG GAAAGACGA     3300

CTATAAGAAG CAAAAAGAAA CTGAACTTAA TAAAGTAATA GCTCAACTAA GTGAATGCGA    3360

GAAACACAAA GAAAAGATAA ATGAAGATAT GAGACTCATG AGACAAGATA TTGATACACA    3420

GAAGATACAA GAAAGGTGGC TACAAGATAA CCTTACTTTA AGAAAAAGAA ATGAGGAACT    3480

AAAAGAAGTT GAAGAAGAAA GAAAACAACA TTTGAAGGAA ATGGGTCAAA TGCAGGTTTT    3540

GCAAATGAAA AGTGAACATC AGAAGTTGGA AGAGAACATA GACAATATAA AAAGAAATCA    3600

TAATTTGGCA TTAGGGCGAC AGAAAGGTTA TGAAGAAGAA ATTATTCATT TTAAGAAAGA    3660

ACTTCGAGAA CCACAATTTC GGGATGCTGA GGAAAAGTAT AGAGAAATGA TGATTGTTAT    3720

GAGGACAACA GAACTTGTGA ACAAGGATCT GGATATTTAT TATAAGACTC TTGACCAAGC    3780
```

```
AATAATGAAA TTTCACAGTA TGAAAATGGA AGAAATCAAT AAAATTATAC GTGACCTGTG    3840

GCGAAGTACC TATCGTGGAC AAGATATTGA ATACATAGAA ATACGGTCTG ATGCCGATGA    3900

AAATGTATCA GCTTCTGATA AAAGGCGGAA TTATAACTAC CGAGTGGTGA TGCTGAAGGG    3960

AGACACAGCC TTGGATATGC GAGGACGATG CAGTGCTGGA CAAAAGGTAT TAGCCTCACT    4020

CATCATTCGC CTGGCCCTGG CTGAAACGTT CTGCCTCAAC TGTGGCATCA TTGCCTTGGA    4080

TGAGCCAACA ACAAATCTTG ACCGAGAAAA CATTGAATCT CTTGCACATG CTCTGGTTGA    4140

GATAATAAAA AGTCGCTCAC AGCAGCGTAA CTTCCAGCTT CTGGTAATCA CTCATGATGA    4200

AGATTTGTG GAGCTTTTAG GACGTTCTGA ATATGTGGAG AAATTCTACA GGATTAAAAA     4260

GAACATCGAT CAGTGCTCAG AGATTGTGAA ATGCAGTGTT AGCTCCCTGG GATTCAATGT    4320

TCATTAAAAA TATCCAAGAT TTAAATGCCA TAGAAATGTA GGTCCTCAGA AAGTGTATAA    4380

TAAGAAACTT ATTTCTCATA TCAACTTAGT CAATAAGAAA ATATATTCTT TCAAAGGAAC    4440

ATTGTGTCTA GGATTTTGGA TGTTGAGAGG TTCTAAAATC ATGAAACTTG TTTCACTGAA    4500

AATTGGACAG ATTGCCTGTT TCTGATTTGC TGCTCTTCAT CCCATTCCAG GCAGCCTCTG    4560

TCAGGCCTTC AGGGTTCAGC AGTACAGCCG AGACTCGACT CTGTGCCTCC CTCCCCAGTG    4620

CAAATGCATG CTTCTTCTCA AAGCACTGTT GAGAAGGAGA TAATTACTGC CTTGAAAATT    4680

TATGGTTTTG GTATTTTTTT AAATCATAGT TAAATGTTAC CTCTGAATTT ACTTCCTTGC    4740

ATGTGGTTTG AAAAACTGAG TATTAATATC TGAGGATGAC CAGAAATGGT GAGATGTATG    4800

TTTGGCTCTG CTTTTAACTT TATAAATCCA GTGACCTCTC TCTCTGGGAC TTGGTTTCCC    4860

CAACTAAAAT TTGAAGTAGT TGAATGGGGT CTCAAAGTTT GACAGGAACC TTAAGTAATC    4920

ATCTAAGTCA GTACCCACCA CCTTCTTCTC CTACATATCC CTTCCAGATG GTCATCCAGA    4980

CTCAGAGCTC TCTCTACAGA GAGGAAATTC TCCACTGTGC ACACCCACCT TTGGAAAGCT    5040

CTGACCACTT GAGGCCTGAT CTGCCCATCG TGAAGAAGCC TGTAACACTC CTCTGCGTCT    5100

ATCCTGTGTA GCATACTGGC TTCACCATCA ATCCTGATTC CTCTCTAAGT GGGCATTGCC    5160

ATGTGGAAGG CAAGCCAGGC TCACTCACAG AGTCAAGGCC TGCTCCCTGT AGGGTCCAAC    5220

CAGACCTGGA AGAACAGGCC TCTCCATTTG CTCTTCAGAT GCCACTTCTA AGAAAAGCCT    5280

AATCACAGTT TTTCCTGGAA TTGCCAGCTG ACATCTTGAA TCCTTCCATT CCACACAGAA    5340

TGCAACCAAG TCACACGCTT TTGAATTATG CTTTGTAGAG TTTTGTCATT CAGAGTCAGC    5400

CAGGACCATA CCGGGTCTTG ATTCAGTCAC ATGGCATGGT TTTGTGCCAT CTGTAGCTAT    5460

AATGAGCATG TTTGCCTAGA CAGCTTTTCT CAACTGGGTC CAGAAGAGAA TTAAGCCCTA    5520

AGGTCCTAAG GCATCTATCT GTGCTAGGTT AAATGGTTGG CCCCCAAAGA TAGACAGGTC    5580

CTGATTTCTA GAACCCGTGA CTGTTACTTT ATACAGCAAA GGAAACTTTG CAGATGTGAT    5640

TAAAGCTAAG GACCTTAAGA CAGAGTATCC TGGGGGTGGT GGTGGGGTGG GGGGGGGTCC    5700

TAAATGTAAT CACGAGTAAG ATTAAGAGCA AATCAATTCT AGTCATATAT TAAACATCCA    5760

CAATAACCAA GATATTTTTA TCCCAAGAAT GCAAGATTTC AGAAAATGAA AAATCTGTTG    5820

ATAAATCCAT CACTATAATA AAACCGAAGG TGAAAAAAT TCTGAAAAAA AAAAAAAAA     5880

AAAAAAAAA AAA                                                       5893
```

(2) INFORMATION FOR SEQ ID NO:45:

(i) SEQUENCE CHARACTERISTICS:
        (A) LENGTH: 472 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
   (C) INDIVIDUAL ISOLATE: G18.seq (xi) SEQUENCE DESCRIPTION: SEQ ID NO:45:

| | | | | | |
|---|---|---|---|---|---|
| GTGGAAGAAT | GGTGAAATCA | TTGATACTTT | ACAACAAGTT | TATGAGATCA | ATGCCCCAAA | 60 |
| CAAATCAGCA | GTTTACAAAT | GGATAACTCA | GTTTAAGAAG | GGATGAGACG | ATATTAAAGA | 120 |
| TGAAGCCCAC | AGTGACAGAC | TGTTCACATC | AATTTGTGAG | GAAAAAAATC | ATCTTCTTCA | 180 |
| TGCCCTAACT | GAAGAAGATC | AATGATTAAC | AGCAGAAACA | ATAGCCAACA | CCATAGACAC | 240 |
| CTCAATTGAT | TCAGGTTACA | CAATTCTGAC | TGAAAAATTA | AAGTTGAGTA | AACGTTCTAC | 300 |
| TTGATGGATG | CCCAAATCAC | TGCTTCCAGA | TCAGCTGCAG | ACAACAGCAG | AACTTCCTCA | 360 |
| ATAAGTGGGA | TCAAGTTCCT | AAAGCATTTC | TTCAAAGAAT | TGTAACAGGA | GGTGATGGAA | 420 |
| TGTGGCTTTA | CCAGTACAAT | CTTCAATTTG | GCAAGTCTGT | CCCTGGTCTG | AT | 472 |

(2) INFORMATION FOR SEQ ID NO:46:

(i) SEQUENCE CHARACTERISTICS:
      (A) LENGTH: 371 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (C) INDIVIDUAL ISOLATE: G102.seq (xi) SEQUENCE DESCRIPTION: SEQ ID NO:46:

| | | | | | |
|---|---|---|---|---|---|
| GGGGGATCCA | GCTCAGAAGC | AGAGTGTCCA | CGCCAGGGAA | TAGTGTGGGG | ATTCAGAGCC | 60 |
| TGATAATGAT | GAGAAGGGGA | CCCACCTGAG | GGTTAAGTCG | GCTAGGGGGA | AGTCAGATCA | 120 |
| TAGAGTAGAG | ACGGCATTCT | TGCGAGAAGC | CACCTGGTAT | AAAGTATCAG | ACCGAGAAGA | 180 |
| GTGACCCTCT | CAGTGACACA | GATCTGGGGA | GATTCAGGTC | AGAGTACAGT | GGGCATCCCT | 240 |
| GCAAGAGGCC | ACCTGGTATC | AGAGAAGGGC | GGGGAATGAG | GACATGATCT | AGCACCAGAA | 300 |
| GTCAAAGTGT | ATACAGAATG | GAAAAGCATC | CCATGAGGGA | GTCGGAATGA | AGAGTCAAGA | 360 |
| GCCTACGCAG | G | | | | | 371 |

(2) INFORMATION FOR SEQ ID NO:47:

(i) SEQUENCE CHARACTERISTICS:
      (A) LENGTH: 645 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (vi) ORIGINAL SOURCE:
      (C) INDIVIDUAL ISOLATE: G18.pep (xi) SEQUENCE DESCRIPTION: SEQ ID NO:47:

```
Met Ser Arg Ile Glu Lys Met Ser Ile Leu Val Arg Ser Phe Gly
 1               5                  10                  15

Ile Glu Asp Lys Asp Lys Gln Ile Ile Thr Phe Phe Ser Pro Leu Thr
                20                  25                  30

Ile Leu Val Gly Pro Asn Gly Ala Gly Lys Thr Thr Ile Ile Glu Cys
                35                  40                  45

Leu Lys Tyr Ile Cys Thr Gly Asp Phe Pro Pro Gly Thr Lys Gly Asn
            50                  55                  60

Thr Phe Val Asn Asp Pro Lys Val Ala Gln Thr Asp Val Arg Ala
65                  70                  75                  80

Gln Ile Arg Leu Gln Phe Arg Asp Val Asn Gly Glu Leu Ile Ala Val
                85                  90                  95

Gln Arg Ser Met Val Cys Thr Gln Lys Ser Lys Lys Thr Glu Phe Lys
                100                 105                 110

Thr Leu Glu Gly Val Ile Thr Arg Thr Lys His Gly Glu Lys Val Ser
                115                 120                 125

Leu Ser Ser Lys Cys Ala Glu Ile Asp Arg Glu Met Ile Ser Ser Leu
        130                 135                 140

Gly Val Ser Lys Ala Val Leu Asn Asn Val Ile Phe Cys His Gln Glu
145                 150                 155                 160

Asp Ser Asn Trp Pro Leu Ser Glu Gly Lys Ala Leu Lys Gln Lys Phe
                165                 170                 175

Asp Glu Ile Phe Ser Ala Thr Arg Tyr Ile Lys Ala Leu Glu Thr Leu
                180                 185                 190

Arg Gln Val Arg Gln Thr Gln Gly Gln Lys Val Lys Glu Tyr Gln Met
                195                 200                 205

Glu Leu Lys Tyr Leu Lys Gln Tyr Lys Glu Lys Ala Cys Glu Ile Arg
210                 215                 220

Asp Gln Ile Thr Ser Lys Glu Ala Gln Leu Thr Ser Ser Lys Glu Ile
225                 230                 235                 240

Val Lys Ser Tyr Glu Asn Glu Leu Asp Pro Leu Lys Asn Arg Leu Lys
                245                 250                 255

Glu Ile Glu His Asn Leu Ser Lys Ile Met Lys Leu Asp Asn Glu Ile
                260                 265                 270

Lys Ala Leu Asp Ser Arg Lys Lys Gln Met Glu Lys Asp Asn Ser Glu
                275                 280                 285

Leu Glu Glu Lys Met Glu Lys Val Phe Gln Gly Thr Asp Glu Gln Leu
            290                 295                 300

Asn Asp Leu Tyr His Asn His Gln Arg Thr Val Arg Glu Lys Glu Arg
305                 310                 315                 320

Lys Leu Val Asp Cys His Arg Glu Leu Glu Lys Leu Asn Lys Glu Ser
                325                 330                 335

Arg Leu Leu Asn Gln Glu Lys Ser Glu Leu Val Glu Gln Gly Arg
                340                 345                 350

Leu Gln Leu Gln Ala Asp Arg His Gln Glu His Ile Arg Ala Arg Asp
            355                 360                 365

Ser Leu Ile Gln Ser Leu Ala Thr Gln Leu Glu Leu Asp Gly Phe Glu
            370                 375                 380

Arg Gly Pro Phe Ser Glu Arg Gln Ile Lys Asn Phe His Lys Leu Val
385                 390                 395                 400

Arg Glu Arg Gln Glu Gly Glu Ala Lys Thr Ala Asn Gln Leu Met Asn
                405                 410                 415
```

-continued

```
Asp Phe Ala Glu Lys Glu Thr Leu Lys Gln Lys Gln Ile Asp Glu Ile
                420                 425                 430

Arg Asp Lys Lys Thr Gly Leu Gly Arg Ile Ile Glu Leu Lys Ser Glu
            435                 440                 445

Ile Leu Ser Lys Lys Gln Asn Glu Leu Lys Asn Val Lys Tyr Glu Leu
        450                 455                 460

Gln Gln Leu Glu Gly Ser Ser Asp Arg Ile Leu Glu Leu Asp Gln Glu
465                 470                 475                 480

Leu Ile Lys Ala Glu Arg Glu Leu Ser Lys Ala Glu Lys Asn Ser Asn
                485                 490                 495

Val Glu Thr Leu Lys Met Glu Val Ile Ser Leu Gln Asn Glu Lys Ala
            500                 505                 510

Asp Leu Asp Arg Thr Leu Arg Lys Leu Asp Gln Glu Met Glu Gln Leu
        515                 520                 525

Asn His His Thr Thr Thr Arg Thr Gln Met Glu Met Leu Thr Lys Asp
530                 535                 540

Lys Ala Asp Lys Asp Glu Gln Ile Arg Lys Ile Lys Ser Arg His Ser
545                 550                 555                 560

Asp Glu Leu Thr Ser Leu Leu Gly Tyr Phe Pro Asn Lys Lys Gln Leu
                565                 570                 575

Glu Asp Trp Leu His Ser Lys Ser Lys Glu Ile Asn Gln Thr Arg Asp
            580                 585                 590

Arg Leu Ala Lys Leu Lys Ile Val Leu Val Lys Pro His Ser Ile Thr
        595                 600                 605

Ser Cys Tyr Asn Ser Leu Lys Lys Cys Phe Arg Asn Leu Ile Pro Leu
610                 615                 620

Ile Glu Glu Val Leu Leu Leu Ser Ala Ala Asp Leu Glu Ala Val Ile
625                 630                 635                 640

Trp Ala Ser Ile Lys
                645

(2) INFORMATION FOR SEQ ID NO:48:

(i) SEQUENCE CHARACTERISTICS:
        (A) LENGTH: 527 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: G65.pep (xi) SEQUENCE DESCRIPTION: SEQ ID NO:48:

Met Lys Leu Trp Val Ser Ala Leu Leu Met Ala Trp Phe Gly Val Leu
1               5                   10                  15

Ser Cys Val Gln Ala Glu Phe Phe Thr Ser Ile Gly His Met Thr Asp
                20                  25                  30

Leu Ile Tyr Ala Glu Lys Glu Leu Val Gln Ser Leu Lys Glu Tyr Ile
            35                  40                  45

Leu Val Glu Glu Ala Lys Leu Ser Lys Ile Lys Ser Trp Ala Asn Lys
        50                  55                  60

Met Glu Ala Leu Thr Ser Lys Ser Ala Ala Asp Ala Glu Gly Tyr Leu
65                  70                  75                  80
```

```
Ala His Pro Val Asn Ala Tyr Lys Leu Val Lys Arg Leu Asn Thr Asp
             85                  90                  95

Trp Pro Ala Leu Glu Asp Leu Val Leu Gln Asp Ser Ala Ala Gly Phe
            100                 105                 110

Ile Ala Asn Leu Ser Val Gln Arg Gln Phe Pro Thr Asp Glu Asp
            115                 120                 125

Glu Ile Gly Ala Ala Lys Ala Leu Met Arg Leu Gln Asp Thr Tyr Arg
            130                 135                 140

Leu Asp Pro Gly Thr Ile Ser Arg Gly Glu Leu Pro Gly Thr Lys Tyr
145                     150                 155                 160

Gln Ala Met Leu Ser Val Asp Asp Cys Phe Gly Met Gly Arg Ser Ala
                165                 170                 175

Tyr Asn Glu Gly Asp Tyr Tyr His Thr Val Leu Trp Met Glu Gln Val
            180                 185                 190

Leu Lys Gln Leu Asp Ala Gly Glu Ala Thr Thr Lys Ser Gln
            195                 200                 205

Val Leu Asp Tyr Leu Ser Tyr Ala Val Phe Gln Leu Gly Asp Leu His
            210                 215                 220

Arg Ala Leu Glu Leu Thr Arg Arg Leu Leu Ser Leu Asp Pro Ser His
225                 230                 235                 240

Glu Arg Ala Gly Gly Asn Leu Arg Tyr Phe Glu Gln Leu Leu Glu Glu
            245                 250                 255

Glu Arg Glu Lys Thr Leu Thr Asn Gln Thr Glu Ala Glu Leu Ala Thr
            260                 265                 270

Pro Glu Gly Ile Tyr Glu Arg Pro Val Asp Tyr Leu Pro Glu Arg Asp
            275                 280                 285

Val Tyr Glu Ser Leu Cys Arg Gly Glu Gly Val Lys Leu Thr Pro Arg
            290                 295                 300

Arg Gln Lys Arg Leu Phe Cys Arg Tyr His His Gly Asn Arg Ala Pro
305                 310                 315                 320

Gln Leu Leu Ile Ala Pro Phe Lys Glu Glu Asp Glu Trp Asp Ser Pro
            325                 330                 335

His Ile Val Arg Tyr Tyr Asp Val Met Ser Asp Glu Glu Ile Glu Arg
            340                 345                 350

Ile Lys Glu Ile Ala Lys Pro Lys Leu Ala Arg Ala Thr Val Arg Asp
            355                 360                 365

Pro Lys Thr Gly Val Leu Thr Val Ala Ser Tyr Arg Val Ser Lys Ser
370                 375                 380

Ser Trp Leu Glu Glu Asp Asp Pro Val Val Ala Arg Val Asn Arg
385                 390                 395                 400

Arg Met Gln His Ile Thr Gly Leu Thr Val Lys Thr Ala Glu Leu Leu
            405                 410                 415

Gln Val Ala Asn Tyr Gly Val Gly Gly Gln Tyr Glu Pro His Phe Asp
            420                 425                 430

Phe Ser Arg Arg Pro Phe Asp Ser Gly Leu Pro Thr Leu Gly Gln Arg
            435                 440                 445

Gly Ile Val Leu Ala Thr Phe Leu Asn Tyr Met Ser Asp Val Glu Ala
            450                 455                 460

Gly Gly Ala Thr Val Phe Pro Asp Leu Gly Ala Ala Ile Trp Pro Lys
465                 470                 475                 480

Lys Gly Thr Lys Leu Cys Ser Gly Thr Thr Ser Cys Gly Ala Gly Lys
            485                 490                 495

Val Thr Thr Glu Gln Asp Met Leu Pro Ala Leu Cys Leu Trp Ala Ala
            500                 505                 510
```

Ser Gly Ser Pro Ile Ser Gly Ser Met Asn Glu Asp Arg Ser Ser
    515                 520                 525

(2) INFORMATION FOR SEQ ID NO:49:

(i) SEQUENCE CHARACTERISTICS:
        (A) LENGTH: 727 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: TcA - N-terminal fragment (xi) SEQUENCE DESCRIPTION: SEQ ID NO:49:

| | |
|---|---|
| GTTGGTGTCA GCGGGCAACA GCCCACAGGA GTGTGCACCT CCTAGGACAG AGTTTGTCCT | 60 |
| CTCACTTCTG GAGAAGATGC AGACACAGGA GATCCTGAGG ATACTGCGAC TGCCTGAGCT | 120 |
| AGGTGACTTG GGACAGTTTT TCCGCAGCCT CTCGGCCACC ACCCTCGTGA GTATGGGTGC | 180 |
| CCTGGCTGCC ATCCTTGCCT ACTGGTTCAC TCACCGGCCA AAGGCCTTGC AGCCGCCATG | 240 |
| CAACCTCCTG ATGCAGTCAG AAGAAGTAGA GGACAGTGGC GGGGCACGGC GATCTGTGAT | 300 |
| TGGGTCTGGC CCTCAGCTAC TTACCCACTA CTATGATGAT GCCCGGACCA TGTACCAGGT | 360 |
| GTTCCGCCGT GGGCTTAGCA TCTCAGGGAA TGGGCCCTGT CTTGGTTTCA GGAAGCCTAA | 420 |
| GCAGCCTTAC CAGTGGCTGT CCTACCAGGA GGTGGCCGAC AGGGCTGAAT TTCTGGGGTC | 480 |
| CGGACTTCTC CAGCACAATT GTAAAGCATG CACTGATCAG TTTATTGGTG TTTTTGCACA | 540 |
| AAATCGGCCA GAGTGGATCA TTGTGGAGCT GGCCTGCTAC ACATATTCCA TGGTGGTGGT | 600 |
| CCCGCTCTAT GACACCCTGG GCCCTGGGGC TATCCGCTAC ATCATCAATA CAGCGGACAT | 660 |
| CAGCACCGTG ATTGTGGACA AACCTCAGAA GGCTGTGCTT CTGCTAGAGC ATGTGGAGAG | 720 |
| GAAGGAG | 727 |

(2) INFORMATION FOR SEQ ID NO:50:

(i) SEQUENCE CHARACTERISTICS:
        (A) LENGTH: 874 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: TcA - C-terminal fragment (xi) SEQUENCE DESCRIPTION: SEQ ID NO:50:

| | |
|---|---|
| GTGTGAGAGG ACCAAATGTG TTCAAAGGCT ACTTGAAAGA TCCAGACAGG ACGAAGGAGG | 60 |
| CCCTGGACAG CGATGGCTGG CTTCACACTG GAGACATCGG AAAATGGCTG CCGGCAGGAA | 120 |
| CTCTTAAAAT TATTGATCGG AAAAAGCATA TATTTAAACT TGCTCAGGGA GAATATGTTG | 180 |
| CACCCGAGAA GATTGAGAAC ATCTACATCC GGAGCCAACC TGTGGCGCAA ATCTATGTCC | 240 |
| ATGGGGACAG CTTAAAGGCC TTTTTGGTAG CATTGTTGT GCCTGACCCT GAAGTTATGC | 300 |

```
CCTCCTGGGC CCAGAAGAGA GGAATTGAAG GAACATATGC AGATCTCTGC ACAAATAAGG    360

ATCTGAAGAA AGCCATTTTG GAAGATATGG TGAGGTTAGG AAAAGAAAGT GGACTCCATT    420

CTTTTGAGCA GGTTAAAGCC ATTCACATCC ATTCTGACAT GTTCTCAGTT CAAAATGGCT    480

TGCTGACACC AACACTAAAA GCTAAGAGAC CTGAGCTGAG AGAGTACTTC AAAAAACAAA    540

TAGAAGAGCT TTACTCAATC TCCATGTGAA GTTCAAGGAA AGTTCTTCTC AGTGTAATGA    600

ACTGTCTAGC AATATTATAG TTATTCTTGA AAGTAATGAG TCAAAATGAC ACAGCTGAAA    660

ATGAATAAGC ATCTGATTTT ATGACTGAGC CTTTTCCTGT CCCAAGAGGT CTTTAACAAT    720

ATTTTCTCTA TCATCAATGA GTATATTTTA TTTTTATTAT AAAAATGATA TTGTGGTGGA    780

CTGCTAAAAA TATCACAAAT GGCAATGTAA AAATCAAGAC ATTTTCTCAA GAACTGTGTA    840

CCACTAAAAG TAATATATTG TCAATGTTCA CAGG                                874
```

(2) INFORMATION FOR SEQ ID NO:51:

(i) SEQUENCE CHARACTERISTICS:
        (A) LENGTH: 1312 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: TRANS. OF RAD50 cDNA (SEQ. 54), NT.
            389 TO 4324

(xi) SEQUENCE DESCRIPTION: SEQ ID NO:51:

```
Met Ser Arg Ile Glu Lys Met Ser Ile Leu Gly Val Arg Ser Phe Gly
1               5                   10                  15

Ile Glu Asp Lys Asp Lys Gln Ile Ile Thr Phe Ser Pro Leu Thr
                20                  25                  30

Ile Leu Val Gly Pro Asn Gly Ala Gly Lys Thr Thr Ile Ile Glu Cys
            35                  40                  45

Leu Lys Tyr Ile Cys Thr Gly Asp Phe Pro Pro Gly Thr Lys Gly Asn
50                  55                  60

Thr Phe Val His Asp Pro Lys Val Ala Gln Glu Thr Asp Val Arg Ala
65                  70                  75                  80

Gln Ile Arg Leu Gln Phe Arg Asp Val Asn Gly Glu Leu Ile Ala Val
                85                  90                  95

Gln Arg Ser Met Val Cys Thr Gln Lys Ser Lys Lys Thr Glu Phe Lys
            100                 105                 110

Thr Leu Glu Gly Val Ile Thr Arg Thr Lys His Gly Glu Lys Val Ser
            115                 120                 125

Leu Ser Ser Lys Cys Ala Glu Ile Asp Arg Glu Met Ile Ser Ser Leu
130                 135                 140

Gly Val Ser Lys Ala Val Leu Asn Asn Val Ile Phe Cys His Gln Glu
145                 150                 155                 160

Asp Ser Asn Trp Pro Leu Ser Glu Gly Lys Ala Leu Lys Gln Lys Phe
                165                 170                 175

Asp Glu Ile Phe Ser Ala Thr Arg Tyr Ile Lys Ala Leu Glu Thr Leu
            180                 185                 190

Arg Gln Val Arg Gln Thr Gln Gly Gln Lys Val Lys Glu Tyr Gln Met
            195                 200                 205
```

-continued

```
Glu Leu Lys Tyr Leu Lys Gln Tyr Lys Glu Lys Ala Cys Glu Ile Arg
    210                 215                 220
Asp Gln Ile Thr Ser Lys Glu Ala Gln Leu Thr Ser Ser Lys Glu Ile
225                 230                 235                 240
Val Lys Ser Tyr Glu Asn Glu Leu Asp Pro Leu Lys Asn Arg Leu Lys
                245                 250                 255
Glu Ile Glu His Asn Leu Ser Lys Ile Met Lys Leu Asp Asn Glu Ile
            260                 265                 270
Lys Ala Leu Asp Ser Arg Lys Lys Gln Met Glu Lys Asp Asn Ser Glu
        275                 280                 285
Leu Glu Glu Lys Met Glu Lys Val Phe Gln Gly Thr Asp Glu Gln Leu
    290                 295                 300
Asn Asp Leu Tyr His Asn His Gln Arg Thr Val Arg Glu Lys Glu Arg
305                 310                 315                 320
Lys Leu Val Asp Cys His Arg Glu Leu Glu Lys Leu Asn Lys Glu Ser
                325                 330                 335
Arg Leu Leu Asn Gln Glu Lys Ser Glu Leu Leu Val Glu Gln Gly Arg
            340                 345                 350
Leu Gln Leu Gln Ala Asp Arg His Gln Glu His Ile Arg Ala Arg Asp
        355                 360                 365
Ser Leu Ile Gln Ser Leu Ala Thr Gln Leu Glu Leu Asp Gly Phe Glu
    370                 375                 380
Arg Gly Pro Phe Ser Glu Arg Gln Ile Lys Asn Phe His Lys Leu Val
385                 390                 395                 400
Arg Glu Arg Gln Glu Gly Glu Ala Lys Thr Ala Asn Gln Leu Met Asn
                405                 410                 415
Asp Phe Ala Glu Lys Glu Thr Leu Lys Gln Lys Gln Ile Asp Glu Ile
            420                 425                 430
Arg Asp Lys Lys Thr Gly Leu Gly Arg Ile Ile Glu Leu Lys Ser Glu
        435                 440                 445
Ile Leu Ser Lys Lys Gln Asn Glu Leu Lys Asn Val Lys Tyr Glu Leu
    450                 455                 460
Gln Gln Leu Glu Gly Ser Ser Asp Arg Ile Leu Glu Leu Asp Gln Glu
465                 470                 475                 480
Leu Ile Lys Ala Glu Arg Glu Leu Ser Lys Ala Glu Lys Asn Ser Asn
                485                 490                 495
Val Glu Thr Leu Lys Met Glu Val Ile Ser Leu Gln Asn Glu Lys Ala
            500                 505                 510
Asp Leu Asp Arg Thr Leu Arg Lys Leu Asp Gln Glu Met Glu Gln Leu
        515                 520                 525
Asn His His Thr Thr Arg Thr Gln Met Glu Met Leu Thr Lys Asp
    530                 535                 540
Lys Ala Asp Lys Asp Glu Gln Ile Arg Lys Ile Lys Ser Arg His Ser
545                 550                 555                 560
Asp Glu Leu Thr Ser Leu Leu Gly Tyr Phe Pro Asn Lys Lys Gln Leu
                565                 570                 575
Glu Asp Trp Leu His Ser Lys Ser Lys Glu Ile Asn Gln Thr Arg Asp
            580                 585                 590
Arg Leu Ala Lys Leu Asn Lys Glu Leu Ala Ser Ser Glu Gln Asn Lys
        595                 600                 605
Asn His Ile Asn Asn Glu Leu Lys Arg Lys Glu Glu Gln Leu Ser Ser
    610                 615                 620
Tyr Glu Asp Lys Leu Phe Asp Val Cys Gly Ser Gln Asp Phe Glu Ser
625                 630                 635                 640
```

```
Asp Leu Asp Arg Leu Lys Glu Glu Ile Glu Lys Ser Lys Gln Arg
            645                 650                 655

Ala Met Leu Ala Gly Ala Thr Ala Val Tyr Ser Gln Phe Ile Thr Gln
            660                 665                 670

Leu Thr Asp Glu Asn Gln Ser Cys Cys Pro Val Cys Gln Arg Val Phe
            675                 680                 685

Gln Thr Glu Ala Glu Leu Gln Glu Val Ile Ser Asp Leu Gln Ser Lys
        690                 695                 700

Leu Arg Leu Ala Pro Asp Lys Leu Lys Ser Thr Glu Ser Glu Leu Lys
705                 710                 715                 720

Lys Lys Glu Lys Arg Arg Asp Glu Met Leu Gly Leu Val Pro Met Arg
                725                 730                 735

Gln Ser Ile Ile Asp Leu Lys Glu Lys Glu Ile Pro Glu Leu Arg Asn
            740                 745                 750

Lys Leu Gln Asn Val Asn Arg Asp Ile Gln Arg Leu Lys Asn Asp Ile
        755                 760                 765

Glu Glu Gln Glu Thr Leu Leu Gly Thr Ile Met Pro Glu Glu Glu Ser
    770                 775                 780

Ala Lys Val Cys Leu Thr Asp Val Thr Ile Met Glu Arg Phe Gln Met
785                 790                 795                 800

Glu Leu Lys Asp Val Glu Arg Lys Ile Ala Gln Gln Ala Ala Lys Leu
                805                 810                 815

Gln Gly Ile Asp Leu Asp Arg Thr Val Gln Gln Val Asn Gln Glu Lys
            820                 825                 830

Gln Glu Lys Gln His Lys Leu Asp Thr Val Ser Ser Lys Ile Glu Leu
        835                 840                 845

Asn Arg Lys Leu Ile Gln Asp Gln Gln Glu Gln Ile Gln His Leu Lys
850                 855                 860

Ser Thr Thr Asn Glu Leu Lys Ser Glu Lys Leu Gln Ile Ser Thr Asn
865                 870                 875                 880

Leu Gln Arg Arg Gln Gln Leu Glu Glu Gln Thr Val Glu Leu Ser Thr
                885                 890                 895

Glu Val Gln Ser Leu Tyr Arg Glu Ile Lys Asp Ala Lys Glu Gln Val
            900                 905                 910

Ser Pro Leu Glu Thr Thr Leu Glu Lys Phe Gln Gln Glu Lys Glu Glu
        915                 920                 925

Leu Ile Asn Lys Asn Thr Ser Asn Lys Ile Ala Gln Asp Lys Leu
    930                 935                 940

Asn Asp Ile Lys Glu Lys Val Lys Asn Ile His Gly Tyr Met Lys Asp
945                 950                 955                 960

Ile Glu Asn Tyr Ile Gln Asp Gly Lys Asp Asp Tyr Lys Lys Gln Lys
                965                 970                 975

Glu Thr Glu Leu Asn Lys Val Ile Ala Gln Leu Ser Glu Cys Glu Lys
            980                 985                 990

His Lys Glu Lys Ile Asn Glu Asp Met Arg Leu Met Arg Gln Asp Ile
        995                 1000                1005

Asp Thr Gln Lys Ile Gln Glu Arg Trp Leu Gln Asp Asn Leu Thr Leu
    1010                1015                1020

Arg Lys Arg Asn Glu Glu Leu Lys Glu Val Glu Glu Arg Lys Gln
1025                1030                1035                1040

His Leu Lys Glu Met Gly Gln Met Gln Val Leu Gln Met Lys Ser Glu
                1045                1050                1055

His Gln Lys Leu Glu Glu Asn Ile Asp Asn Ile Lys Arg Asn His Asn
```

```
            1060              1065              1070
Leu Ala Leu Gly Arg Gln Lys Gly Tyr Glu Glu Ile Ile His Phe
        1075              1080              1085
Lys Lys Glu Leu Arg Glu Pro Gln Phe Arg Asp Ala Glu Glu Lys Tyr
    1090              1095              1100
Arg Glu Met Met Ile Val Met Arg Thr Thr Glu Leu Val Asn Lys Asp
1105              1110              1115              1120
Leu Asp Ile Tyr Tyr Lys Thr Leu Asp Gln Ala Ile Met Lys Phe His
            1125              1130              1135
Ser Met Lys Met Glu Glu Ile Asn Lys Ile Ile Arg Asp Leu Trp Arg
        1140              1145              1150
Ser Thr Tyr Arg Gly Gln Asp Ile Glu Tyr Ile Glu Ile Arg Ser Asp
        1155              1160              1165
Ala Asp Glu Asn Val Ser Ala Ser Asp Lys Arg Arg Asn Tyr Asn Tyr
        1170              1175              1180
Arg Val Val Met Leu Lys Gly Asp Thr Ala Leu Asp Met Arg Gly Arg
1185              1190              1195              1200
Cys Ser Ala Gly Gln Lys Val Leu Ala Ser Leu Ile Ile Arg Leu Ala
            1205              1210              1215
Leu Ala Glu Thr Phe Cys Leu Asn Cys Gly Ile Ile Ala Leu Asp Glu
        1220              1225              1230
Pro Thr Thr Asn Leu Asp Arg Glu Asn Ile Glu Ser Leu Ala His Ala
        1235              1240              1245
Leu Val Glu Ile Ile Lys Ser Arg Ser Gln Gln Arg Asn Phe Gln Leu
        1250              1255              1260
Leu Val Ile Thr His Asp Glu Asp Phe Val Glu Leu Leu Gly Arg Ser
1265              1270              1275              1280
Glu Tyr Val Glu Lys Phe Tyr Arg Ile Lys Lys Asn Ile Asp Gln Cys
            1285              1290              1295
Ser Glu Ile Val Lys Cys Ser Val Ser Ser Leu Gly Phe Asn Val His
            1300              1305              1310
```

(2) INFORMATION FOR SEQ ID NO:52:

(i) SEQUENCE CHARACTERISTICS:
        (A) LENGTH: 86 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: RAD50-2

(xi) SEQUENCE DESCRIPTION: SEQ ID NO:52:

```
AGCAATAATG AAATTTCACA GTATGAAAAT GGAAGAAATC AATAAAATTA TACGTGACCT    60

GTGGCGAAGT ACCTATCGTG GACAAG                                        86
```

(2) INFORMATION FOR SEQ ID NO:53:

(i) SEQUENCE CHARACTERISTICS:
        (A) LENGTH: 1243 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
         (C) INDIVIDUAL ISOLATE: RAD50-4

(xi) SEQUENCE DESCRIPTION: SEQ ID NO:53:

```
CAAGGAACTA GCTTCATCTG AGCAGAATAA AAATCATATA AATAATGAAC TAAAAGAAG     60

GGAAGAGCAG TTGTCCAGTT ACGAAGACAA GCTGTTTGAT GTTTGTGGTA GCCAGGATTT    120

TGAAAGTGAT TTAGACAGGC TTAAAGAGGA AATTGAAAAA TCATCAAAAC AGCGAGCCAT    180

GCTGGCTGGA GCCACAGCAG TTTACTCCCA GTTCATTACT CAGCTAACAG ACGAAAACCA    240

GTCATGTTGC CCCGTTTGTC AGAGAGTTTT TCAGACAGAG GCTGAGTTAC AAGAAGTCAT    300

CAGTGATTTG CAGTCTAAAC TGCGACTTGC TCCAGATAAC CTCAAGTCAA CAGAATCAGA    360

GCTAAAAAAA AAGGAAAAGC GGCGTGATGA AATGCTGGGA CTTGTGCCCA TGAGGCAAAG    420

CATAATTGAT TTGAAGGAGA AGGAAATACC AGAATTAAGA AACAAACTGC AGAATGTCAA    480

TAGAGACATA CAGCGCCTAA AGAACGACAT AGAAGAACAA GAAACACTCT TGGGTACAAT    540

AATGCCTGAA GAAGAAAGTG CCAAAGTATG CCTGACAGAT GTTACAATTA TGGAGAGGTT    600

CCAGATGGAA CTTAAAGATG TTGAAAGAAA AATTGCACAA CAAGCAGCTA AGCTACAAGG    660

AATAGACTTA GATCGAACTG TCCAACAAGT CAACCAGGAG AAACAAGAGA ACAGCACAA     720

GTTAGACACA GTTTCTAGTA AGATTGAATT GAATCGTAAG CTTATACAGG ACCAGCAGGA    780

ACAGATTCAA CATCTAAAAA GTACAACAAA TGAGCTAAAA TCTGAGAAAC TTCAGATATC    840

CACTAATTTG CAACGTCGTC AGCAACTGGA GGAGCAGACT GTGGAATTAT CCACTGAAGT    900

TCAGTCTTTG TACAGAGAGA TAAAGGATGC TAAAGAGCAG GTAAGCCCTT TGGAAACAAC    960

ATTGGAAAAG TTCCAGCAAG AAAAAGAAGA ATTAATCAAC AAAAAAAATA CAAGCAACAA   1020

AATAGCACAG GATAAACTGA ATGATATTAA AGAGAAGGTT AAAAATATTC ATGGCTATAT   1080

GAAAGACATT GAGAATTATA TTCAAGATGG GAAAGACGAC TATAAGAAGC AAAAAGAAAC   1140

TGAACTTAAT AAAGTAATAG CTCAACTAAG TGAATGCGAG AAACACAAAG AAAAGATAAA   1200

TGAAGATATG AGACTCATGA GACAAGATAT TGATACACAG AAG                    1243
```

(2) INFORMATION FOR SEQ ID NO:54:

(i) SEQUENCE CHARACTERISTICS:
         (A) LENGTH: 543 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (vi) ORIGINAL SOURCE:
         (C) INDIVIDUAL ISOLATE: RAD50-3

(xi) SEQUENCE DESCRIPTION: SEQ ID NO:54:

```
GTTGCTCAAG AAACAGATGT GAGAGCCCAG ATTCGTCTGC AATTTCGTGA TGTCAATGGA     60

GAACTTATAG CTGTGCAAAG ATCTATGGTG TGTACTCAGA AAGCAAAAA GACAGAATTT    120

AAAACTCTGG AAGGAGTCAT TACTAGAACA AAGCATGGTG AAAAGGTCAG TCTGAGCTCT    180

AAGTGTGCAG AAATTGACCG AGAAATGATC AGTTCTCTTG GGGTTTCCAA GGCTGTGCTA    240
```

```
AATAATGTCA TTTTCTGTCA TCAAGAAGAT TCTAATTGGC CTTTAAGTGA AGGAAAGGCT    300

TTGAAGCAAA AGTTTGATGA GATTTTTTCA GCAACAAGAT ACATTAAAGC CTTAGAAACA    360

CTTCGGCAGG TACGTCAGAC ACAAGGTCAG AAAGTAAAAG AATATCAAAT GGAACTAAAA    420

TATCTGAAGC AATATAAGGA AAAAGCTTGT GAGATTCGTG ATCAGATTAC AAGTAAGGAA    480

GCCCAGTTAA CATCTTCAAA GGAAATTGTC AAATCCTATG AGAATGAACT TGATCCATTG    540

AAG                                                                 543
```

(2) INFORMATION FOR SEQ ID NO:55:

(i) SEQUENCE CHARACTERISTICS:
        (A) LENGTH: 2886 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 5' END OF RAD50 GENOMIC SEQUENCE (xi) SEQUENCE DESCRIPTION: SEQ ID NO:55:

```
ATTATGCTTC AATAAATCTG ACTTAAAAAA TGGTCTTGGC CAGGCGCAGT GGCTCACACC     60

TGTAATCCCA GCACTTTGGG AGGCCGAGGC GGGTGGATCA CAAGGTTAGG AGTTCGAGAC    120

CAGCTTGACC AACATGGTGA AACCCCGTCT CTACTAAAAA TACAAAAAAT TAGCCAGGTG    180

TGGTGCCACG TGCCTGTAAT CCCAGCTACT CAGGAGGCTG AGGCAGAAGA ATCACTTGAA    240

CGCGGGAGAT GGAGGTTGCA GTGAGCCAAG ATCGCACCAT TGCACTCCAG TCTGGGTGAC    300

AGAGTGAGAC TCCATCTCAA AAAAAAAAAA AAAAAAAGTC TCCACTTGAA TAGTCAATTA    360

TTCAAAGATA CACAAATGGC CAATAAACAC ATGAAATGAT GCTACTAATA ATTATTGAAA    420

TGCAAATCAA AATTACAATG AGGTATCACT TCACACTCAT CAGGATGGCT ACCATAAAAA    480

AACATAAAAT AACAAGTGTT GGCAAGCATA TGTAGAAATT GAAACCCTTA TGCACTATTG    540

GTGGGAATGT CAAATGGTAC AACCACTGTG GAAAACAGTA TGGCAGTTCC TCAAATAATT    600

AAAAATTGAA TTACTGTATG ATCTAATAAT TCCACTTCTG GGTATATACC CAAAAGAATT    660

GAAAGCAGGG TCCAGAAGTG ACATTTGTAC ACCAATATAT ATAGCCACAC TATTCACAAT    720

AGCTAAAATG TGAAAGTAAC CCAAATGTCC ATCAATAGAT GGATAAGCAA AATGTGATGT    780

GTATTGTAAT GAATCTTATT CAACCTTAAA AACGACCTGA ATTCTGATAT ATGCTACAGT    840

GGTCCCCAAC CTTTTTGGCA CCAGGGACCA GTCTCACGGA AGACAGTTTT TCCACAGACA    900

GGAGTGGGGT GATGGTTTTG GGATGAAACT GTTCGACCTC ACATCATCAG GCATTAGATT    960

CTCATAAGGA ATGGGCAAGC TAGATCCCTT GCATGGGCA  ACCTACATCT TTCTCATGGG   1020

CAGTTCAAAA TACGGTTTGT GCTCCTATGA GAATCTAATG CCCCCACTGA TCTGAGGCCC   1080

AGCTCGGGTG GTAATGTTCA CTCACCTGCT GCTCACCTCC TACTGTGCCA CCAGGTTCCT   1140

AACAGGCCAG GTATGCATAC TGGTCAGTGA CCCAGGGGTT GGGGACTGAG CTGCAACATG   1200

GATGAACCTT GAGGACATTA TAAGTGAAAT GAGCCAGTCA CAAAAGATA  AATACTGTAT   1260

GATTCCACTT ATATGAGGTA CTTAGTAAAA AATTATAGAG ACAGTAAGTA GAATGTTGGT   1320

TGTCAGGGTT TGGAGGATGT GGGGAGGAAA GGGTTATTGT TTAATGGGTA GTTTGTTTTG   1380

CAAAGTGAAA AGATTTGTAG AGGTTGAAAG GTGGTGACGG TTGTACGTGA GTATACTTAA   1440
```

| | |
|---|---|
| CACCACTGAA ATGTACACTT GGTTAAGATA GTAAATTCTT TTTGAGACGG AGTCTCGCTC | 1500 |
| TGTTGCCCAG GCTGGAGTGC AGTGGTGCGG TCTCGGCTCA CTGCAAGCTC CGCCTCCCGG | 1560 |
| GTTCATGCCA TACTCCTGCC TCAGCCTCCT GAGTAGCTGG GACCATCGGC GCCTGCCACC | 1620 |
| ATGCCCGGCT AATTTTTTGT GTTTTCAGTA GAGACGGGGT TTCACCGTGT TAGCCAGGAT | 1680 |
| GGTCTTGATT TCCTGACCTC GTGATCCACC CGTCTCGGCC TCCCAAAGTG CTGGGATTAC | 1740 |
| AGGCGTGAGC CACCGCGCCT GGCCAAGACA GTAAATTTTA TGTGTATTTT ACAATTTTTA | 1800 |
| AAATAAAAAA AGGTCTTTCG TCTTTTCCCA TTGTTTTATT ACATTTGCTT TGCCAAGTAA | 1860 |
| GACATTCCTA TATAATTTTA ATGTTTTGTT CCATTAGTTA TTTTAACTAT TTTGTAATAA | 1920 |
| CTGACACTTT CCGGTTTTTT TAACCTGGTA CAGCAAGAGA CTATTTCTCA CTGGTCTTCC | 1980 |
| CCACTTGCAT CCTTTGGCAC ATACATTTAT GTATTAGGTT CTGTAAATTA TTTGCTTGGG | 2040 |
| ATTGTATGAC TGGAGAAACA TTTCCTACAT TTTTCCAAGG CAGGCAGAGG CAAATTATAC | 2100 |
| CACTACAGTA ATTCCAAATT TGTGTTTCAT TTAAATGTCC TCCACTATTG TTTCAGTAAT | 2160 |
| TTTTATGTAT GTTTCTCTAG GCCCTTAAAT GTGATATCCC TCCATTAAGT TTGTTTCCAA | 2220 |
| GAAAGCAATA TTCTCAGTTA CTTCTGAGAC AGGTAACTTC TCTTTCCCTT ATTTTTAAAG | 2280 |
| ATATCTATTG CTGGGAGCAC TGATCGGAAT GGATTACCTC TACATTCTTC ATATTTGCAG | 2340 |
| ACTGCTTTTA GTTTTAGTTC CCAGACTTTT GGTCTTAAAG ACGCCTTTAC ACTAAAAAAT | 2400 |
| TACGGGGAC CTCAAAGAGC GTGTACGTGA GTTATAATTA TCAACATTTA CTCAATTAGA | 2460 |
| AATTAAAATT GGTATTTCTA AGCGCAAGAA TACACATGCG CACATTCCAT TAACCGCCAC | 2520 |
| TGCAATGGCG TCATCACATG TTATGTGATC ACTGGAAATT ACTACACGAA CGTTAGAGAG | 2580 |
| AGAATGAGAA TGAAAAGGAA AATAGTTTTG ACATGAACTG ACCCCGCTTC CTGGGTCTCC | 2640 |
| AATCCACCCC ACCACTACCC CCATTCCAGG AGTCCCAGGA TCAAGCTTTG GGAAGCGCCA | 2700 |
| TCCGTCACAG GTCTTGGTCT CCCCTTCCAA AAGTCAGTGC CTCTCCAGGC TGCCCATCCC | 2760 |
| CAGCAAAGAT CCGGAAGTCC GCTGCCCCTG GCAACAGCAC CCAGCACCTA GCCCTCTGCT | 2820 |
| TCGCCGTACC GCACCCGGAA GTCGGAGCTG CGCACGCACC GCGGGACTCT GATTTCCCGG | 2880 |
| CGTGCC | 2886 |

(2) INFORMATION FOR SEQ ID NO:56:

(i) SEQUENCE CHARACTERISTICS:
        (A) LENGTH: 516 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 1 OF RAD50 GENOMIC SEQUENCE (xi) SEQUENCE DESCRIPTION: SEQ ID NO:56:

| | |
|---|---|
| CCAGGAGAGC GGCGTGGACG CGTGCGGGCC TAGAGGCCCA CGTGATCCGC AGGGCGGCCG | 60 |
| AGGCAGGAAG CTGTGAGTGC GCGGTTGCGG GGTCGCATTG TGGCTACGGC TTTGCGTCCC | 120 |
| CGGCGGGCAG CCCCAGGCTG GTCCCCGCCT CCGCTCTCCC CACCGGCGGG GAAAGCAGCT | 180 |
| GGTGTGGGAG GAAAGGCTCC ATCCCCCGCC CCCTCTCTCC CGCTGTTGGC TGGCAGGATC | 240 |
| TTTTGGCAGT CCTGTGGCCT CGCTCCCCGC CCGGATCCTC CTGACCCTGA GATTCGCGGG | 300 |

```
TCTCACGTCC CGTGCACGCC TTGCTTCGGC CTCAGTTAAG CCTTTGTGGA CTCCAGGTCC      360

CTGGTGAGAT TAGAAACGTT TGCAAACATG TCCCGGATCG AAAAGATGAG CATTCTGGGC      420

GTGCGGAGTT TTGGAATAGA GGACAAAGAT AAGCAAATTA TCACTTTCTT CAGCCCCCTT      480

ACAATTTTGG TTGGACCCAA TGGGGCGGGA AAGACG                                516

(2) INFORMATION FOR SEQ ID NO:57:

(i) SEQUENCE CHARACTERISTICS:
        (A) LENGTH: 1829 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: INTRON 1 OF RAD50 GENOMIC SEQUENCE (xi) SEQUENCE DESCRIPTION: SEQ ID NO:57:

GTAAGTCTTC AGTAGCCGCC TTCAGTTTAC AGGTCGCTAC ATCTTTCGGA GAATAAAATG       60

GGAAGTTGAG AACTCTCCTT AGGAGCAGAA GCGTCCCTAG GGCTCCACAG GTGTAGGCCC      120

TTAAAGTGCC TTAGGGTGTG GCCTGCAGGC TACAGCGACC TTAGGAGTTT GCCTGAAGCA      180

GTCCCGGAAG GATGTCCGGA CCTGGCCTGG GGACAAGGTT TACTTAAGAA TCCCACGATA      240

CCGGGAGCTG TCGCCGCTCA CTCAGAGTTC AGTTCCCACT GGATGCCCTT TGGTCTGTAT      300

TGATGTTTTT AACGCTGTCT CCTTGCTTTC AAAGCATAGC ATTCACTTCC CAGTAGTTGT      360

CCCATACAAG AATTCCTTTA AAAGTTATAA AATGATACAT ACATGACTAA AGAGTTTCCA      420

AGTATGCCAA CTGTCCAGAC ATAATACATG GAAAATAAAT AAATTCAAAA TGTAACTGAT      480

GTAGTGGGGC TTAACTTGGA AAACTTCTCT TCTTAAAACT CAGTCAAAAA TTTAACGTTG      540

GTGCACGACT GACTTTTTTT TTTTTTTAAA GCCGTGGGAA TATTTATAAA TTTGAATGGA      600

AAGAATAACC AAGAGGCATT CTGGTCAGGA ATAGTGGCTT AAGAAAAAGC AAGACGATGT      660

CAGTATAGCA GGGAGAAGAG TCTAAAGGAA GGATTTGTGA AGAGTGTAGA AAGAGAGAAG      720

GTTGAGAATT GAATGCCAAA CTTGTTTACT TTTGTTTTTG TAAAAATGTT ATTTGTTGAA      780

TGCTTGTTAT GTACTTAGGA TTGTACTAAA TACTAGCAGA AGGGAGAGTA GTACTGTATA      840

GTGTTTATGA GGACTGGCTG CCTCAATACA GCTTTTTCGC TTCATTTATT AGTTGTCTGA      900

TTGTTTGCGA GTGACCTCAC TGCTCTGTGC CTTAGTTTTC TCATTTATAA AATGGAGATT      960

AAAAATAGTT TCTACAGCTG GCACGGTGG CTCACGCCTG TAATCCCAGC ACTTTGGGAG      1020

GCCGAGGCGG GTGGATCACC TGAGGTCAGG AGTTCGAGAC CAGCCTGGCC AACGTGGCGA     1080

AACCCCATCT CTAATAAAAA TACAAAAATT AGCCAGGCGT GGTGGCGCAT GCTGTAATCC     1140

TAGCTACTGG GGAGGCCGAG GCGGGAGAAT CGCTTGAACC GGGGAGGTGG AGGTTGCAGT     1200

GAGCCGAGAT CACGCCATTG CACTACACCA GCCTGGGTGA CAGAGGGAGA CTCTCTCCCC     1260

CCACAAAAAA AAAAAAAAAA AAAAAAAGT TTCTACAGGC TGGGCATGGT GGCTGACGAC      1320

TGTAATCCGA GCCGTTTGGG AGGCTGAGGC TGGGGGATTG CTTGAGCCCA GGAGGTCGAG     1380

AGGTCGAGGC TGCAGTAAGC CATGATCATG CAGCTGCACT GCAGCCTGGG CAGCAGAATG     1440

AGACCCTGTC TCTTAAACAA AAAGTTCCTA CAGCCTGGAG TTAATGTGAG AATTAAATAA     1500

ATGTATGTAA GAGTGCTTAG TACAATACAG TACTTAACTG TTAGCCATTC TTATTATTAA     1560
```

```
CTTAAATTAG TTTAAAGGGT TTCAGTTGAA AATAATTATT TTTTTCCCAA GTAACAATTC      1620

TTCATATTAG GATAACTTCT TAGTTATATA GCATTTCTGT GAACTTACAG CATTAACACT      1680

TAATCATATT TTTATTACAG GTTTTATAAT GTCAGATTTT ATCTTTTATA GTTTCCATGA      1740

TAAATAATAT TTTTGTAATG AATTCATATT TTATGGTAAA CTTCTGTGGT TCTCTTATAA      1800

CGAAATAATG TAATTTTCTA TTTCTTTAG                                        1829

(2) INFORMATION FOR SEQ ID NO:58:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 2 OF RAD50 GENOMIC SEQUENCE (xi) SEQUENCE DESCRIPTION: SEQ ID NO:58:

ACCATCATTG AATGTCTAAA ATATATTTGT ACTGGAGATT TCCCTCCTGG AACCAAAGGA        60

AATACATTTG TACACGATCC CAAG                                              84

(2) INFORMATION FOR SEQ ID NO:59:

(i) SEQUENCE CHARACTERISTICS:
        (A) LENGTH: 14855 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 5' END OF INTRON 2 OF RAD50 GENOMIC
            SEQUENCE (xi) SEQUENCE DESCRIPTION: SEQ ID NO:59:

GTAATGGTGC TAGTACAATT TTGTATTTTT ATAATTATAA AAATGATAAT AGCTTATTAT        60

AGAAAACTTG GCACTGGAAA ACTATAAAGA GAAATGAAAG TCAGCCCCAC ACAGTTTTAG       120

CACCCAGTAG TAACCGTTGT TGACATTTTC ATGTGTTTTC CTCCTCCTTT AAATACTGTT       180

TTATATAGCT GATGTCATAC TCTTAATTTT GTATTCTGGG TTTTTTTCCC CACTTAACAT       240

TATCATGAAG TCCTATGTCA TTAAAAAACT ATCATCTGGG TGTTTGGTAT GTAAGTGTTT       300

CTTTTAATCT TTATACTGCT TTGTATGTCT GAGATATTTT CTACTTAAAG TGCATGAACA       360

CTTTAGTAGT TATGTAATTT TCTTACATTA GATTGCTTTC AGTTTTTCAT TAAAATGTAC       420

CATGATAAGC CAGGCTTGGG GGTGTGTGCC AATACTCCCA GATAGCTCTA GAGGCTGAGA       480

TGGGAGGATT GCTTCAGCCC AGGAGTTCAA GGCTAGCCTG GACAATATAG TGAGACCCAC       540

TGTCTAGAAA AAAAGTATC ATGATAAAAA TCTTTGTGTA TGAATCATTG TTTGAATTAT        600

GGTGTTTATA CTATTCGTAT GTGTAAAGGA CATAGAATTT GGTCTATAGG TTTGTTTTTG       660

CACATATAGA AGTGAAACAA CAATACACAC ACACACACAC ACACACACAC ATATATATAT       720
```

```
AGTTTATTCG TTTTTAGTGG GGTCATGTGC CTCTCTAGCC GCTCCCTGAC CCCAGTTCCA       780

CTATGTTTTC GTTACGTATT CTTCCAAGCT TTTTTCTGCT TATAAAACCA TGTCTACGTG       840

AGCACATAAA TGCATTCACA CATACATATT TTAGCACATT AATATAATTT TATACTTCTA       900

TTTTATTGTT TTTAATTAGT AAATTGTATT CCATTGAGTT TATATCCTGT AGTTTATTAA       960

ATGACCCCCT GTTGATTATT ATTTGTTTCT ACCTTAGTGT GATTAAAGAT AACTCTGTAA      1020

TTATGAAAAT ATTTATGAAT TTTCCTCTTA GAAATGTAAT AGTATTTAGT ACATTTACTG      1080

AGTCCTCTCC ATAATGACTG TTTCCCACCT TCTCTCTCCT TAAATCTACA ATCTACTTTC      1140

CTTAATTGAT GATCTTGCTT TGTACTTTAT TGAGAAATAG GAAGAATCAA ATGAGAATTC      1200

CCTTATTTTC CAATCATCAC ATCTACGAAA CTACTGTACA TACGTGCCCA TACTGTTTTT      1260

TCTTGGATAA ATTATTTGTT GTTTTATCTA AACATGAACC AGCTCCTTGG AGGCTAGATC      1320

TCATTGATCC CTCTTATCCA CCCAAGGATT TTGCCCTTCA GTTTTTCCAT CTCTCTCCTG      1380

GATCAGCAGT TTCTCTTGAT GGATCATTCA CATCAGCATA TAAACATGCT CTGGTATCTC      1440

TAGTCTTCAA ACAAAAAACT CTCCCTTTAC TCCAATTTAC CCTCTAGCCA TTACCTTTTC      1500

TCTGTTCCAA TATATTTCAA AATTCATAAG ATTTGTATGT CCTCATTGTC TTTACTTCAT      1560

TGACTCCCAT TTTTCCCTCA ATCTACTCCA TTCAGGTTTT CTTTTTTTCC TCCACTAAAA      1620

GTGCCTTTGT AAGGTCACCA ATAATCTCAA TGTGCCAGAT AGAGTGGTCA GTTTCTAATT      1680

CTCATTAACA TCTTGTCAGA TTTGACACAG TTGGCTATTT CTTTTTTAAA ATATATTTCC      1740

TTCTTGGCTT TTGTGACACT ATAATCTCAT AGTTTCCTTC TTTCTCACTG GCTATACTTT      1800

AGTCTTTGTT GGGTCTACCT TTGCTTGATT TCTTTTTTTT TATGAGACGG AGTCTTGCAC      1860

TGTTGCCCAG GCTGGAGTGC AGTGTGGCAT GATCTTGGCT TACTGCAACC TCTGTCTCTC      1920

AGGTTCAAGC TATTCTTGTG CCTTAGCCTC TTGAGTAGCT GGGATTACGG GTGTGCCACC      1980

ACACCCAGCT AATTTTTGTA TTTTTAGCAG AGACGGGGTT TCATCATGTT GGCCAGGCTG      2040

GTCTCAACCT CCTCACCTCA GGTGATCCAC CTGCCTCAGT CTCCCAAAGT GCTGGGATTA      2100

CAGATGTGAG CCACTGCACC CAACCTGCTT GATTTCTAAA AGCCAGTGTG ACACAAGAGT      2160

TGGCCATCTT TGCATTAACC CTCTTCCCTA TCTCTCTTGG ATGAGCTTAT TCAGTCTAAC      2220

GGCTTTAAGT ACTGGTTATG TGCTGGTAAC TACCACATTT ATATATTTGA CCCTGACTTC      2280

TTTCCTTAAC TCTAGACATA TATGTCTAGC TGTTTGTTTG GATATTTAAT GGGCATCTCA      2340

AATTTAACAT GTTCAAAACA GAACTCTTGA TTCCTTGTAC CCACTTCCTG CCTACATTCT      2400

CAGCTCTGTT ACTACCTCAG TACCCCACCC CCGCCAGTTT TGTAAATGAT GTCATCATCC      2460

CTACATAAGC AATTCTTACC TACCCTTCTA AAATATGTCA GAATTTGTCT ACTTCATTCC      2520

ATCGGCCACT GTGTTCCTGT TCCAAGCCAC CATCATATTC CCTTTCAACT ATTAGAATCG      2580

TCTCCTAACT TATTTTCCTG CCCTCATTCT TGAAGCTCTC TCTTTCTCAC AGAGTAATCA      2640

GAGTTGTCTT TTAAATATTC ATTCAAGAGG GAATGAGTTG TTCAAAATCT GGGAAGAAAC      2700

ATTTCATTCA GTCTAGTTGC AGAGTCCCTG AGCATGGTTG GTGTGTTCAA GGAATGACAA      2760

GGAAGAACAA GGGAAAATGG TAGAAAATAA AGTTAGAAAG ATAGGAGAGA CTAGATCCTG      2820

TAGGTCCTTG GATTCTAGTC TTATTTAAAT AGGAATCTGT CTATTGGGAG ATTTTGAGCA      2880

GGGAAAGGAC ATGGTCTGAT TTATCTTTTA AAGTGCTCAG TCTGGTTGCT GAGAGAAGAC      2940

TGTCCGTAGG TAGCAAAGAT AGGGCAGAGA CAAATTAAGA AGATTTTGTG ATGATCCAGG      3000

TGAGAAATAT AGGTGGCTTC ATTAAGGTAG TGGTAGAATG GTGAGAAATG TTTGGATTTA      3060

GGATGTATTT TGAAGATAGA ACCAACAAAT TAGCTAATGG TTTGGATAAT GGTGTATGAA      3120
```

-continued

| | |
|---|---|
| AGAAGTAAAA GCATCAAGCA TAACTCCAAA GTTTTTGGCT TGAACAACTG GATAAAATAG | 3180 |
| TTTTGTCATT TATTATAATA GGGGCACTAT GGAAAAAATA TTTGGGTGGA TCTGGTTTAA | 3240 |
| ACATGCAAAT TAGGGATATG TGTTAAATAT CCAAAGGAGA TGTCCAGTTG GCAAGCAGAA | 3300 |
| GTCTGTTCAG GAAAGAGATT AGGACTGGAG AAAGAAAATT AGGAATCATT AGTGTATACA | 3360 |
| GGTAGTTCCA CATAGTTAAT TTTTAAAGCC TGATGAGATC AAATAGAGAG TGAATATGGA | 3420 |
| AAAGATATTC AAGACCTTAA CCTAGAGCAC TAGAGCCGAT GATGCCTTTA GAAATTGGGA | 3480 |
| AGAGGAGGAG AAGCTAGTAA AAGAGCAATT CGTTAAGTAA GGAAAACTGA GAGAGTGGTG | 3540 |
| TCTTGGAAGA CAAGAGAATA AAGTGTTATA AGGAGGAAAT CATCAACTGT GTCAAATATG | 3600 |
| TTGATAGCTC AAGAAAGAAG AGGAGTGTTT GGATATGTGG AGTCCGTTGT TGCTCTTGAC | 3660 |
| AAAACCAGTT CCAGTAATCA GAGAAAAGAT AAAGAAGTGA AACAGAATTA TTTTATGAAT | 3720 |
| TTTGTTGTAA GTGGACACAG ACATAGGACA GTAGCTGAAG AGGTTAACAG GATAAAGGAA | 3780 |
| AGTTTTGTTG TTGTTGTTTT ATTGTGTTTT TAAAAGTGGG ATATACTAGA GCATTTGTAG | 3840 |
| ACTGTTGGGA ATGACTCTGG ACAGAAACAT TGATGCAGGA GAGGGGATAA TTACAGAGCA | 3900 |
| CAATTCTTGA GTAGGCAAAA AGAGATAAGA TCCATTGCCC AACTGGAGGG GATACCAGGA | 3960 |
| ACATCCACTG TTATCCATTG TAACAGGGAT TTAGGCAGAT TATATGATTG GAAACTTTAG | 4020 |
| TGGTGAAAGA ATGAGTAAGT TCTCTTTTGA TTGCTTTTAT ATTCTCAAAT GAAAAAGAA | 4080 |
| ATGAAGTTAC TGGTTGAGAG TGGCAGAAGG GGTTGATTGA GCCTAGAAAA CATAGAATAG | 4140 |
| TTTTTAACCT CAGTAAGTAA ATTGATTAAG GGAGGTGTTC TGGGATTACA TGACAGTGTC | 4200 |
| AGGGGTTTTG TGAAAATTTA AAGAGAGACC AGCCATCATG GTTATGTATG TTTTTTCAGT | 4260 |
| CTTGTTCAGC CCAAGCACTG AATAAATTGG AAAGTTGCAT TTATCCATGG TTGGGGATTT | 4320 |
| GGTAAATACT ATGAAGGTAA TGAGAAGCAA GGAATTGAGT ACCGATATGG TTTGAATTTG | 4380 |
| TATCTGCCCA AATCTCATGT CAAATTGTAA CCCCCATTGT TGGAGGAGGG GCCTGGTGGG | 4440 |
| AGGTGATTGA ATCATGGAGG TGGATTTCCC CCTTGCAGTT CTTGTGATAG TAAGTTCTCA | 4500 |
| TGAGATCTGA TTGTTTAAAA GTGTGTAGCA CCTCCCCCTT CACTCTCTTC CTCCTGTTCT | 4560 |
| GGCCGTGTAA GATGTGCCAG CCTCCTCTTC ACCTTCTGCC ATGATTGTAA GTTTCCTGAG | 4620 |
| GCCTCCGCAG TCATGCTTCC TGTACAGCCT GCAGAACCGT GAGCCAATTA AACCTCTTTT | 4680 |
| CTTTAACCAG TTTCAGGTAT TTCTTTGTAG CAGTGAGAAA ACAGACTAAT GCAGAAAGTT | 4740 |
| GGTACCGAGA GTAGGGTATT GCTATAAAGA TAGCTGAAAA TGTGGAAGTG ACTTTGGAAC | 4800 |
| TGGGTAATGG GTAGAGGTTG GAACAGTTTG GAGGGCTCAA AAGAAGACAG GAAGATGAGG | 4860 |
| AAAAGTTTGG AACTTCCTAG AGACTTGTTA AATTATTTTG ACCAAAATGC TGACAGTGAT | 4920 |
| ATGAATAATG AAGTCTAGGC TGAGGAGGTC TCAGATGGAG ATAAGGAGCT TACTGAGAAC | 4980 |
| TGGAGTAAAG GTCACTCTTG CGATGCTTTA GCAAAGAGAC TGGCAGCATT GTGCCCCTGC | 5040 |
| TCTAGGAATC TGTGGAACTT TGAACTTGAA AGAGATGATT TAGAGTATTT GGTGGAAGAA | 5100 |
| ATTTCCAGGC AGCAAAACTT TCAACATGTG GCCTGGCTGC TTCTAGCAGT ATATGCTCAT | 5160 |
| ATGTGCAAGC AAAGAGATCT GAAACTGGAA CTTATATTTA AAAGGGAAGC AGAGCATAAA | 5220 |
| AGTTTGGAAA ATTTGCACCC TGATCATGTG GTAGAAAAGA AAAACCCATT TTCTGGGGAG | 5280 |
| GAATTCAAGC CGGCTGCAGA AATTTGCATA AGTAAAGAGG AGCAGAATGT TAATAGCCA | 5340 |
| AGACACTGGG GAAAATGGCT AGAAGGCATT TCAGAGATCT TCACAGCAGC CCCTCCCATT | 5400 |
| ACAGGACACT ACTCCCTGTG TTTCAGCCAC TCCAGCTCCA GCCATGGCTA AAAGGGCCCC | 5460 |
| AGATATATCT TAAGCTGCTG CTCCAGAGGC TGCAAGCTGT AAGCCTTGGC AGCTTCCACA | 5520 |

```
TGGTGTTAAG CCTGGGGTTG CGCAGAGAAC AAGAGTTGAG GCTTGGGAGC CTCCACCTAG      5580

ATTTCAGGGG ATGTATGGAA ACGTCTGGAT GTCCAGGCAG AAGTCTGCAG GACTTGTTGC      5640

AGGAGGGACC TGGTTGGGGT GATTGGATCA TGGGGGTAGA TTTCCCCCTT GCTGTTCTCA      5700

TGATAGTGAG TAAATTCTCA TGAGATCTGG TTGTTTAAAA ATCTGTCACA ATTCCCCCTT      5760

TACTCTTTTT CTTCTGCTCC AGCCATGTAA GATGTGCCAG CATCCCCTTT GCCTTCTGCC      5820

ATGATTGTAA GTTTCCTGAG GTCTCCCCAG TCTTGCTTCC TGTATAGCAT GTGGAACTGT      5880

GAGCCAATTA AACCTCCTTT CATTATAAGT TACCCAGTTT CAGGTTTTTT TTTTATAGCA      5940

GTGCAAGAAT GTACTTATAC AACCATAATC TTAATATATT GACTTAATCA ATCCTCCTGT      6000

ATGTAATCAA TGTCTCATCG TTGCATCAGG GCCCTAGCAC CTCATATGGG CTGACTCCAT      6060

CCCTGTATGC CAGTCTTCCT TATCCTGCGT AGGCTCTTGA CTCTTCATTC TGACTCCCTC      6120

ATGGGATGCT TTTCCATTCT GTATACACTT TGACTTCTGG TGCTAGATCA TGTCCTCATT      6180

CCCCGCCCTT CTCTGATACC AGGTGGCCTC TTGCAGGGAT GCCCACTGTA CTCTGACCTG      6240

AATCTCCCCA GATCTGTGTC ACTGAGAGGG TCACTCTTCT CAGTCTGATA CTTTATACCA      6300

GGTGGCTTCT TGCAAGAATG CCGTCTCTAC TCTATGATCT GACTTCCCCC TAGCCGACTT      6360

AACCCTCAGG TGGGCCCCCT TCTCATCATT ATCAGGCTCT GAATCCCCAC ACTATTCCCT      6420

GGCGTGGACA CTCTGCTTCT GAGCTGGATC CCCCCTATTT GTGGATTCCT CTTTCATCCT      6480

GCTGGAACTC TGATACCATT GGACTCTTGA AACTCTGTCT ATGCCAAGCT GTTTCCCCAT      6540

GAGGGTACCC TTCTCAGCCT ACTCAAGCTC ATTTATTCCA CTCTAGGCTG AGTTATAGGT      6600

GCCTTAACCT TCAGCTGGCA TGAACACGCA CCTTCTTCTG CCCCACCTAA TGGTTTTACA      6660

ACTAGATTGT TTGGAGAAAG AAGGGTTTTT CTTATTTTTT ATTTTATTCT TTTTGATAGA      6720

AATTGTTCTG AAGTATAATA CACATTTCTT TGTTTTAATA ATTCAATCTA AATTACACTT      6780

CACTTTTGAA GTGACTCTTC TTCAATAAGA GTGTCAACAA CAATGTAGTG ATAGAAATGC      6840

TACAAGATAG CCCTTGCTTG AATTCTATTT ACTAATTTGA TGTTTGCCGG GTAGCTAGGT      6900

CCTCGAAAAG TAGATGCCAT GGAGAAAGAG TATGTGTATT TGGCTTGCTA CTCAGGAACA      6960

CTGTAAACAA ATTAATTTTT TGCTGCATAA ATACATAGCT CCTTAGTTCA ACTACTGTGG      7020

ATTAAACCTT CAGCAGAATG CTCTCCTTAT GATGAAATGA CAGAGTCAAG TCTGGGCTTT      7080

CAAAGCTTTA TACTGACCTC TGGCCACCTC CTCATTGAAA TGTCTGTATC CTAAGAGGCT      7140

GTTTCTGAGT AGCCAGTTCA GCGACTTCTT CCTCTTTACC TCCATCCTCA ACCCTTGTCC      7200

AGGCTGCCTT CCTATCTCTC CTCGATTATT CCCTGCTTCA TGTCTTGTCT CAGTTCACTC      7260

TGTTCACCCT AAAGACAAAA TAATTCTTCT AAAATGCATA TCTACTTCAT GCAATTCCCC      7320

TGGTTCAAAC CATTTAGTGC CATCACCTTA AATCCAAAAG CCTTACCAAG TTTAGAAGGC      7380

TGTTAATTTC TGAAACATTT TAGGTTGATA CTCTTCTTTT CCCTACTTTC TATGCCAAAC      7440

ATTCTGAAAT TTCTGTAGTC ACGTAGTGAC TCAGATCTTC TCATCTGGTT AACTTCTACC      7500

CAGATTGGTA GAAGTTTCAT TTAAACATTC ACTTCCTTTA GACTACCTTC CCTGAGCTGT      7560

CCTAGATAGG TTAGATGCTC CTGCTTTGTA CTCCCAGATT ATCCTGTGCT TATGATGGTG      7620

TTTAGCACAC CTTGTCTACA TTTAACCTAT CTTGCATGCT TCAAAGGAAA AAAAGTCTGT      7680

CAGTTTGAAC CAAAACAACA CATGAAACCT ACAAAGTGCC TGTAAATATT TGTTGAATGA      7740

TTAATTGAAT TAGTATCAAA GTTAAATTCA TGCCAAGAAG TCATTAAAAA GTCAGCAAAG      7800

GATCTTTAAT GATTTTTTTT TTTTAAAGCA GAATCCAGTA CTTGTGATTT GGGTTGCAAC      7860

AAAATAATGA GTATCACACT TATACTCGCA AGATGAATAA CTGTAACACT GGAAAAGTAT      7920
```

```
GTGAAACAAC TATTTTCAGG CATTGGACCA CAGATAATGC AGGGCTATAT TCTTTGAGAA    7980

AGGAGAAACA TAAAAGGTGA TTCTGCATTC ATTCCAGCTT TCTACCTGGG AACACTTTGT    8040

AAACTTTGGC ACATGGAATT GGAATCCAGT AGAGAGCTGG GCAGAATTGG GCATCACTAG    8100

GCAGATGAAA CAAAGATAGG ATTTTGGATT TGCTAAAGTG ACTGGAAATT GTAGAGCAGA    8160

GTACTGAAGT AGGGTTGTTG TGCAGAGATG GTGTACCAGA AATCTGCATA AGGATCTTTT    8220

GAGTCTTTGG CCAAATACTA AGCTATCCAT GTATAGGATG AGATTTAATG AGGGCTAGTA    8280

GAGAACAACT ACCAAGGTGG CAAGTGGGGC TGTGAGTGTT GTATTCTAAA GGTCACACAA    8340

TGCTGTGAGA CATTTGAGTC CTGATGTGCC AGAATGGAGT GACCTTGTGG AACTCTCCAG    8400

TGTTCACTTG AGACCTCAGA AAGGCCCACC TAACAAATAC TGAAACCAGG TTTTGATAGA    8460

ATCAAGCTGA GTTGCCAGTA AATTAACTGG CTGCTAGAAC AAAACTCAAG ACTTTTTAAA    8520

GGAAGCCTAC TCAGTCGAAG CTCTCAATGT GGCATCTACA ATGTGCAGAA TATAATTTTA    8580

AAAATTAATG GGAATATGCA AAAGAAAATG TGGTCTATAC CTGAGAAGGG AAAAGTGAGT    8640

AGAAGCAGAT CCAGAGATGA CAGATTTTGG AATTAGCAGA CAAGGATTTT TTTTTAAATT    8700

TTTTTTAAAT TTTTTTTTTT GAGATGGAGT CTCACTCTGT TTCCCAGGCT GGAGTGCAGT    8760

GGCACAATCT CGGCTCACTG CAACCTGTGC CTCCCAGGTT CAGGCAATTT TCCTGCCTCA    8820

GCCTCCCGAG TAGCTGGAAC TACAGGTGCC CACGACCATG CCCGGCTGAT TTTTTATTTT    8880

TTTATTTTTT ATTTTTAGTA GAGACGGGGT TTCACCATAT TAGCCAACCT GGTCTCGAAC    8940

TCATGACCTT GTGATCCGCC TGCCTCGGCC TCCCAAAGTG CTGGGATTGC AGGCATGAGC    9000

CACGACGCCC GACCGGATTT TTTTAAAGCT ATGATAGATA AGCTCAAGGA CTTAAAGGAA    9060

AAGATGGACA TAATGTGTGG GAAGACATCT AAACAGAGTA ATAAAAACTA TAAAAAAAGA    9120

CCCAAGAAGC TGAATGCATC ACAAGCAGCA TAAACATAAC TATGTTGTAC ATTACATTCA    9180

AATTGTTCAA AACTAAATAT AAAATCTTAA AAACAGGTGG AGGAAAAAGT AACACATCAT    9240

GCAGAGGGAA AGAATAATGA GTATGATTAC TTCTTAGGAA AAGCAATCTA AACCTGAAAA    9300

CAGTGGGACA GCACCTTTAA GGTGCTAGGG AATAAAAGTT AAACTCCTAT ATCCAGCAAA    9360

AATATTCTTT GAAAATTGGA GGTGAAATGG AGGACATTTT CAGATTTAAA ACAAAATGGT    9420

AGAGGTAATT TGTTACAGAC AGGCTTGCAC TATAGTAATT GTTAAAGAAA GTTTTTGAGG    9480

CTGAAGGAAA ATGTCGAAAA TGATTGTAAA TTAGTCCTAG AGTAAAAGCT GCTCTAGGTC    9540

CCCCTTTACA GACCTTAACA ACAAAGGTTC AAAAGAATCC AACTGTTTGT TGCTCAAAAA    9600

ACTTAACTGC ATGCCAGAAC AAAGTTCAGT ACTCATTAAA GGAATAAAAC AAAATCTTTC    9660

ACCCAACAAT ACAAAATTCA CAATCAAAAG TTAACAGGCA TCCAAAGAAG CAGGGAAATA    9720

GGACCCATAA TCAGAGAAAA ATCAATCATA TGAACAGATC CAAAATGAAA GAAATAATAG    9780

AATTAGTAGA TAAGAACCCT AAAACCTTAT TATAACTCTT ATAAATATGC TCATAGATAT    9840

AAAGGAAAAC ATAAGCATAA TGAGAAAAAT GGAAAATAAT TTTAAAAACC CAAATAAACG    9900

GAATAATGGT GTTTTGTATA TAATGGTACA AATAGGTTAA AAGCAAAAGG ATTGAAAAAA    9960

TATACTGTGC CAGCTAATGA AAAGAAAGCT GAAGTGACCA TATTAATACC AGACAGAAGA   10020

CATCAGAACT AGGGAAAATG AAACATTTTA TGATGAGAAG AGGTCAATTT AATGCAAGGA   10080

CACAAAAATT CTAAATGTAA AACTTCCAAA TATATGAGGC AGAAACCTAT GGAACAGAAT   10140

GGAGAAATAC ACAAATCTGC AAGGTCAATT GGAGATCTCA ATACCCCTCT CAGTAGAGAA   10200

AAGAAGCAGA TGAAATATCA GTAAGTATAT GGAAAATTTT AACAACACTG TTAACCAAAT   10260

CAACCTGATT GACATTTATA GGACATTCCA TTGAACGATA GCAGAATACA CTTTATTTTC   10320
```

```
AAGTGCATGT GGAACATTCT GTAAGATAGA CCAACATTCT GGACTGTAAA ACAAGTGTCA    10380

ATAAATTTAT AAGGAGTAAA GTCATAGATA ATGTATTCTG TGACTACACC AGAATCAGTA    10440

GCAGAAAAGT ATCCGGAAAA TCCCCAAATA ATTGAAAAAT TAAGCAGCAT ACTTCTAAAT    10500

ATTACATGGA TCAAAAAAGG AATCACAAGG GAAATTAGAA AAAATACTTT AAATGAATCA    10560

AAAATATAGC ATGTAAAAAT ATGTGGGGTG CAGCTAGATA ATGCTTAGAG AGATACGGTA    10620

GAAAAGAAAC CAATCAGTAT AATTTGCCAC ATTAACAGAA TAAAAAGAA ATATCATATG    10680

AACACCAATA GATACAGAAA ACGCATTTCA ATTTAATAGT CTTTCGTGGT AAAAACCCTC    10740

AGCATAACTG ATGGAGGAAT ATTAATTCCT GAATAATTCA GTCCAAAATC CGTTAGGTGT    10800

GGCTGAGTGA GGAAGGCATC CACAAAAACA AGCTGTGACA GCCTGGTGGG GGATTGGAGC    10860

CCAAGTAAGG AATCTATGAG TTTATACTGA TACAAGAAAA TGGGGGGGGA AATGGAGAAA    10920

GAGCAAAGCC CCTTATACTA GAACCTTAAC TAATATAAAA GGAATAATGG AACTAGAAAA    10980

TTACTATAGG CATACCTTAG ATATTGCAGG TTAAGTTCTA ATGGATGGCG GTCTTGTCTA    11040

CATTGAAAAT CTGTTGTTTA GTGTAGCTAC CTTCATCAAT TACCTGAGCT AGATCTTCTG    11100

GATAACTTGC TGCAGCTCCT GCATCAGCAC TTGCTGCTTC ACCTCGCACT TTTATGTTGT    11160

GGAGACAGCT TCTTTCTTTA AGCCTCATGA ACCAACCATT GCTAGCTTCC AACTTTTCTT    11220

TGCAGCTTCT TTACTTCTCT CAGCCTTCAT AGAATTGCAG AGAGTTGGGG CTTTGCTCTG    11280

GATTAGGTTT TGGCCTGAGG GAATGTTGTG GCTGGTTTAA TCTATCCCAA CTACTAAAAC    11340

TTTCTCCATA TCAGCAGTAA GGCTGTTTCA CTTTCTTATC ATTTGTGTGT TCACTAAAGT    11400

AGCACTTTTA ATTTTATTCA AGAACTTTTC CTTTGCCCTC ACAACTCAGC TAACTGATGA    11460

AAGAGGCCTA ACTTTCAACC TGTTTTGGAT TTTGACATGC TTTTCTCAAC TAAGCTTAAT    11520

CATTTCTAGT TTTTGATTTA AAACGAGATG TTTGACTCTT CTTTCGCTTA AACACTTAGG    11580

GGCTGTTGTA GGGTTACTAA TTGGCCTAAT TTCCATATTA TTGTGTCTCA GGCAATCAGG    11640

TTCCAAGGAG AGGGAGAGAG ACGGGAATGG CAGGTCAGTA AAGCAGTCAG GACACACACG    11700

TTAATGGATT AAGTTCACCT CTTATATGTG GATGGTTTGT GGCACACAAA CAATTACAGT    11760

AGTAACATCA AAGATCACTT ATCACAGATC ACTATAACAG ATACAATAAT AATGAAAAAG    11820

TTTGAAATAT TGTGAGAATT ACCAAAATGT GACACAGAGA CACAAAGTGA GCACATGCTG    11880

TTGGAAAAAT GGCACCGATA GACTTGTTAG ATGCAGGGTT GCCACAAACC TCTGAAGAGC    11940

ACAATAAGAT GGGGTATGCC TGTATTTGAT AGCTGTCATA ATAATAATTC ATTCAGGTAA    12000

GAAACAGTAG ATGCTAAAAC TAATGGAAGA AAGTTTGATG AAGTATGAGA TAGTTGTATG    12060

GTCTCTGCAT CTCTCCCTCA AATTATTAAT TAATTGTAAA GAAAAATTTT TTGGTGAAGC    12120

TAGGAGATAC ACCTTTATCA AGAGATTGAA GTTAGTCTAG GCAACATGGT GAACCACATC    12180

TCTACAAAAA CTACAAAAAT TGGCGGGGTG TGGTGGCATG CACCTATAGT CCCAGCTACT    12240

TGGGGGCTG AGGTAGGAGG ATTGCTTATG ACTCAGAGGT CGTGGATGCA GTGAGCTGTG    12300

TTCATGCCAC TGCACTCCAG CCTGGATGAC AAAGTGAGAC CCTGTCTCAA AAAATAAAT    12360

AAAGGGATTG AAGTTAATAC CCTCCGTAAT GAGATAAATG GAAATGATGT CCTGTCTGAT    12420

GAGATGCAGT AAAAGGAACT CATCATCGCT TGTATAATAT TCTTGCCAAA GATACATAAC    12480

CTGATTCTAG TCGTGAGGAA ATATTACCCA AATTTTGGGA GGTATTCTGC AAAATAATGG    12540

TCTGTACTTT TCAAAATTAT CAGTCATGAA AGTCAAGGAA AATCTGAGCA ACTATTTCAG    12600

GCTGAAAGAA AGTAAAGAGA CATAACCACC AAATACAAAG TGTAATTCTG AACTGAATCC    12660

TTTTGCTCTA AAGGACGTAC TGGGACAAGT GAATTAGGCT GTAGAAAAAG AAAAAAACAA    12720
```

-continued

```
TCAGTATAAT TTGCCACAGT AATAGAATAA AGAAGAAAAA TCATATGAGC ATCAATAGAT   12780

ACAGAAAAAG CTTTTCAATT TAATACTCAT TCATGATAAA AACTCTCAGC ATAACTAATG   12840

GATGAATAGT TATTCATTCC TGATTAATTC AGTCCAAAAG CCATTAGGTA GGACTGAGTG   12900

AGGAAGGCAT CCACAGAAGT ACCCTAGGGA TGAATAGATG ATAGAATTAG TAGATAAGAA   12960

CCTTAAAATC TTATTATAAA TCTTATAACT ATGTTCATAG ATATAAATAA AAACATAAAA   13020

ATAAAAACAT GAGAAAAATG GAGGACAATA ACCAAAAAAC CCTAAATAAA GTAAAAGGAA   13080

TAACAGTGTT TTTATATATA ATAGTACAGA TGGGTTTAAA ACAAAAGGAT GGGAAAAATA   13140

TACCGTGCCA GCTAATGAAA AGAATGCTGA AGTGACCATA TTAATATAAG ACAGAAGACA   13200

TCAGAAAAAA TAGGTGATTA TATGATATTT GAATGTCTGT TCATTGTTGG TCTTTTAGGT   13260

CTTATAAGAT GATGGTCATT TTCTACTACT TTAAGGGAGC ATATTAAATT TTTTTCAACA   13320

GACTTTAAAC TTTATTTTGT AGATCAGCTT CGGGTTTATA GCAAAATTGA GCAGAAAGTA   13380

CAGTTTCTGT ATATTCCCTG CCTGTACACA CACAACCTCC TCTACTATCA GCATCTAACT   13440

TTTTGTAGAT ACTTTGCCTC ATTCAAATAA TCCAGGGTAA TCTTTCTATT TTAAAGTCAA   13500

GTGATTGACA CCCCAGTTCC ATCTGTAATG TTAATTCTCT TTTGCTGTGT AATGTAACAT   13560

TCACAAATTC AAGGGATTAG AATGTGGACA TCTTTGGAGA ACCATTATTT TATATGCCAC   13620

AGCTGAGTTA ATGGTAACTT ATCACATTTT GGAACAACTG GCAAAACTTG AATGGGATTT   13680

GTGGACCATG TGGTAATAAT ATATCAGTAT CAGTTTCCTG ATTTTTGTTG TTGAAAATGT   13740

CCTTGTTTTG TAGGAAATAC TGGTGTTGGG ACATCAGATC AGCAACTTAC TCTCATGTGG   13800

TTTGGGGGGC AGGAAAGCTA TGTATACTGT AGTTCTGTGT ATTACTCCAT TTTCACACTG   13860

CTGTTAAAGA CATACCCAAG ACTGGGCAAT TTACAAAAGA AAGAGGTTTA ATGGACTTAC   13920

AGTTCCACGT GGCTGGGGAG GCCTCACAAT CATGGTGGAA GGTGAAAGTC ATGTCTCACA   13980

TGGTGGCAAA TGAGAGCTTG TGCAGGAAAA TTCCCCCTTA TAATGACCAT CAGATCTCGT   14040

GAGACTTACT ATCATGAGAA CAGCACAGGA AAGACCTGCC CCCGTGATTC AATTATCTCC   14100

CACCTGGTTT CTCCCACAAC ACATGGGGAT TCAAGATGAG ATTTGAGTGG AGACACAGCC   14160

AAACCATATG ATTCCACCCC TGGCCCCTCC CAAATCTCAT GTCCTCACAT TTCAAACCA    14220

ATCATGCCTT CCCAACAGTC CCCCAAAGTC TTATTTTAGC ATTAATTCAG AAGTCCACAG   14280

TCCAGAGTCT TACCCAAGAT AAGGCAAGTC CCTTCTGCCT ATGCGCCTGT AAACTCAAAA   14340

GCAAGTTAGT TACTTCTTAG ATACAATGGG GATACAGGCA TTGGGCAAAT ACAGCCATTC   14400

CAAATGGGAG AAATTGGCCA AAACAAAGGG GCTACAGGCC CCGTGCAAGT CCGAAATTCA   14460

GTGGGGCAGG TGTATCTTAA AGCTCCAGAA TGATCTCCTT TGACTCCATG TCTCACATCC   14520

AGGTCACTCT GATGCAAGAG GTGGGCTTCC ATGGCCTTGG GCAGCTCCAC TTCTGGCTTT   14580

GCAGGGTATA GCCTCCTTCC TGGCTGTTTT CACAGGCTGG TGTTGAGTGC CTGCAGTTTT   14640

TCCAGGTGCA CAGTGCAAGC TGTCAGTGGA TCTATTATTC TGGGGGATCT ACCAGTCTGG   14700

AGGACAGTGG CTGTCTTCTC ACAGCTCCAC TAGGCAGTCC CCTCCATAGG AACTCTGTGG   14760

GGTTTCAACC CCACATTTCC CTTCCATATT GCCCTAGCAG AGGTTTTCCA TAAGGGCCCC   14820

ACCCCTGCAG CAAACATCTG CCTGGGCATC CAGGT                            14855
```

(2) INFORMATION FOR SEQ ID NO:60:

(i) SEQUENCE CHARACTERISTICS:
        (A) LENGTH: 231 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (C) INDIVIDUAL ISOLATE: 3' END OF INTRON 2 OF RAD50 GENOMIC
        SEQUENCE (xi) SEQUENCE DESCRIPTION: SEQ ID NO:60:

```
ATACCTGATC TCCTAATGAT GCTGAATAAA GGAGGTAGAT AGTATATCAT TTTTGTAAAT      60

TAATTAAACA GTATTCTTCT ATATTTTGGA TAGCATGTAA AAATATCACT CATTTTGGAT     120

GTTTTTCTTT TTGTTCCCTC ATTTTGGGTA AGATTGCTTA TGCCTTTTTC TCAGAACCAA     180

CACTGGTGCT TATTAAAGTA ACATAAGTTT TTTCTGTGTT TTCCTTCAAA G              231
```

(2) INFORMATION FOR SEQ ID NO:61:

(i) SEQUENCE CHARACTERISTICS:
      (A) LENGTH: 152 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (C) INDIVIDUAL ISOLATE: EXON 3 OF RAD50 GENOMIC SEQUENCE (xi) SEQUENCE DESCRIPTION: SEQ ID NO:61:

```
GTTGCTCAAG AAACAGATGT GAGAGCCCAG ATTCGTCTGC AATTTCGTGA TGTCAATGGA      60

GAACTTATAG CTGTGCAAAG ATCTATGGTG TGTACTCAGA AAAGCAAAAA GACAGAATTT     120

AAAACTCTGG AAGGAGTCAT TACTAGAACA AA                                    152
```

(2) INFORMATION FOR SEQ ID NO:62:

(i) SEQUENCE CHARACTERISTICS:
      (A) LENGTH: 266 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (C) INDIVIDUAL ISOLATE: 5' END OF INTRON 3 OF RAD50 GENOMIC
          SEQUENCE (xi) SEQUENCE DESCRIPTION: SEQ ID NO:62:

```
GTAGGTGTTT ATATGATATT TGAATTTCTG TTCATTTTCA GTCTTTTAGG TCTGTAAGTT      60

GATGGTTGTT TTCTACTATA AGTTTAGGGG AGCATATTAA ATTTTTTTCA ATAGACTTTA     120

GACTTTATTT TTTTAGAGCA GTTTTGGGTT TATAGCAAAA TTGGGCAGAA AGTACTGAGC     180

TTCCATTTTC TCCCTACCCC CACGCACACA CAGCCTCCTC CACTATGAAC ATTTGATTTT     240

TTGTGGATAC TATTTGTCAG TTAAAT                                          266
```

(2) INFORMATION FOR SEQ ID NO:63:

(i) SEQUENCE CHARACTERISTICS:
        (A) LENGTH: 250 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 3' END OF INTRON 3 OF RAD50 GENOMIC
            SEQUENCE (xi) SEQUENCE DESCRIPTION: SEQ ID NO:63:

GTCCCAAATA TGTAAAAAAT AAATTCTGGC TTCCTTTCCT GAACTACTTT GTTTTACATA      60

TCTTTTCATC TGTGAACCGT TAAATAGTTT AAGAGTTACA CTTTTTAGCA TGATGAAGCC     120

ATTTCTAACG GGATAGGTGA AGGGCCTTTT TTTTTATTCT TTTAAAGAAG TACAGTATGA     180

ATTGATTAAG CAATAGAATA GATACACTGA AGGTTATTTT ACATATATTC TTGATTTTCA     240

TTTTCTGTAG                                                           250

(2) INFORMATION FOR SEQ ID NO:64:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 4 OF RAD50 GENOMIC SEQUENCE (xi) SEQUENCE DESCRIPTION: SEQ ID NO:64:

GCATGGTGAA AAGGTCAGTC TGAGCTCTAA GTGTGCAGAA ATTGACCGAG AAATGATCAG      60

TTCTCTTGGG GTTTCCAAGG CTGTGCTAAA TAATGTCATT TTCTGTCATC AAGAAGATTC     120

TAATTGGCCT TTAAGTGAAG GAAAGGCTTT GAAGCAAAAG TTTGATGAGA TTTTTTCAGC     180

AACAAG                                                               186

(2) INFORMATION FOR SEQ ID NO:65:

(i) SEQUENCE CHARACTERISTICS:
        (A) LENGTH: 359 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: INTRON 4 OF RAD50 GENOMIC SEQUENCE (xi) SEQUENCE DESCRIPTION: SEQ ID NO:65:

GTTTGTAACC CTTAAATAGA CTTTGTAGTC CATTAAGTTA TTGAACTGTG TTTGCAATTT      60

GGATGCTTCT TTTTAACAGA AAAAATTTAA AAAGCAGAAA GGTCATCAGT TACTACCTCT     120

CATCCAGCAG CAACCATTGG GCATATTTTC TTTCACTTGT CTTTCTGTGC GTATATTTAT    180

TTACCTGATT GACAGTATAA ATGTAATTTT TTTCACTTAC CATTATGTCA TAGGCATTTT    240

ACAAGTTATT AAAAACTCAT TGTAACTGTA ATCTTAGTGA CAGCATAATA TCCCACTGTA    300

TGAATATATA CCATAATTTA CTTTGCCAGA AATTTGATTT TTGTTTCATA TCTTCAAAG    359

(2) INFORMATION FOR SEQ ID NO:66:

(i) SEQUENCE CHARACTERISTICS:
        (A) LENGTH: 205 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 5 OF RAD50 GENOMIC SEQUENCE (xi) SEQUENCE DESCRIPTION: SEQ ID NO:66:

ATACATTAAA GCCTTAGAAA CACTTCGGCA GGTACGTCAG ACACAAGGTC AGAAAGTAAA    60

AGAATATCAA ATGGAACTAA AATATCTGAA GCAATATAAG GAAAAAGCTT GTGAGATTCG    120

TGATCAGATT ACAAGTAAGG AAGCCCAGTT AACATCTTCA AAGGAAATTG TCAAATCCTA    180

TGAGAATGAA CTTGATCCAT TGAAG                                         205

(2) INFORMATION FOR SEQ ID NO:67:

(i) SEQUENCE CHARACTERISTICS:
        (A) LENGTH: 243 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 5' END OF INTRON 5 OF RAD50 GENOMIC
            SEQUENCE (xi) SEQUENCE DESCRIPTION: SEQ ID NO:67:

GTAACTTGAT TTTATTTTTA ATTGACAAAA ATTGTATATC TTTATGGTAT ACAGCATGAT    60

GTTTTGATAT AAGTATACAT CGTGGACTGG CTAGGTGATG CTGCCAACTT ACTGATTTAG    120

TGTATGATGG TGTTTTTGAG GTGCTCCAGT GGCTTCTGTT TCTATCAGCT GTCCCTCCTG    180

TTCAGCTACT GACGGGGTGG TGCGTAACGG CAAAAGCACC GCCGGACATC AGCGCTATCT    240

CTG                                                                 243

(2) INFORMATION FOR SEQ ID NO:68:

(i) SEQUENCE CHARACTERISTICS:
        (A) LENGTH: 6623 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: 3' END OF INTRON 5 OF RAD50 GENOMIC SEQUENCE (xi) SEQUENCE DESCRIPTION: SEQ ID NO:68:

```
TTTGAATCAT GAAGTAGAAA ATATATATAT ATTTTTAATG ATGGCCATGC ATAGAAATAT      60
ATTGCAAGGG CTTCTGGGAG GAGGTAGGGC TGAGGTGGGC CTTGAAGAAT GGGAAGAAAT     120
CAAGTCAGCA AACTAGAAGA CATTTTATAC ATGTTTGTAT TTATTTATTT ATTTATTTTT     180
GAGATGGAGT TTCACTTTTG TTGCCCAGGC TGGAGTGCAG TGGCACGATC TCGGCTCACT     240
GCAACCTCTG CCTCCCGGGT TCAAGCAATT CTCCCACTTA GCCTCCAGGG TAGCTGGGAT     300
TACAGGCATG AGCCACCACG CCCGGCTAAA TAAAAAAAAA AAATAGAATT TTTTGTATTT     360
TTAGTAGAGA CGGGGTTTCT CCATGTTGGT CAGGCTGGTC GCGAACTCCC GACCTCAAGT     420
GATCTGCCCG CCTCGGCCTC CCAAAGTGCA GGATTACAG GCGTGAGCCA CCGCACCTGG      480
AAATGTTTGT ATTTATTTTG ACTTTTCTTT TAAAAGTAAT ATGTGCCCCT AGTAAAAAAG     540
TTATAAAGG ATATTAGGTG AAAAGTAAAA GATAGTCTTC CATTTCTCAT CTCTAACCTT      600
CCAGAGTATA TTTTACCTGC AACTTTTTTT AACTGCATAT ATACAATACA TATGTATATA     660
CAAACATTCA CTTGTATGTA TGTGCATATT TACCTTTACA AGCTTAATCA GAACAGGATT     720
ATGAGAGGAA GAGTCTGGGT TAAGTAAATC AATATAAAAG GAGTAAATGA CCAATATGAA     780
TCGGGGTCAG ATTATAGAAA GCTAATGGAT TTCAGACTTA GTTCAATAGA CAGAAGAGTG     840
GAAGACTATG TTATATTTTA GGATGAGTTG TCCTGATAAC TCTGTGTGGG TCCCGTGGTA     900
ATTACCAAGA TATTAGAACA GATTTCCTTT TTTTTTCTTC TTTCCCCCTT GCCCCACTCC     960
ACGTTTTATT TTCTTGAGGA GCATCTTGGT TGGAGAGATG ACAAGCACAT GTAATGGTAA    1020
GGCAGAGAAA AAAACAAGAC CTGTAGGAGC TCTGAGGATA AGAAAGAGA ATTTCTATCT     1080
GAGGTAGCCA GAGAGGATTT CATAGGACTG AATTTGGCCA TGACTTTTTT GATCATAAAT    1140
GAGTAAGTCA TTGGAGACAT AGAGACAGTA AAATCCAAGC TGTCTTTGAA CACTGTCAAG    1200
GAAATCCATA TTGTTGAAAT GAAGCATTTA TATTGGAAAT GATGTCAAGG TAGGGCTAAA    1260
TGATAATACC TAGGATTTAG TGAGTGGTGC CAAGATTCTA ACCAAGGCTG TAGCAGAGGT    1320
TGAGGTATTT ATTTACTTGT TTGTGTTTAA TTGTGAGTAA TTCTCCAAGG GTTTAATATT    1380
CTTCTCTGTA TCCTCAGAGC CTAGCCTAGT GCCTGGCACA TAGCAGGTGG TTCAATAAAT    1440
GTTTATTAAG TAGATGACTT CCAAAGTCCT TTTTTTTAGC TCTGACATGT GAAGATTCTT    1500
CCCTTCATAG AACCCAATTA AAGTTTGGGT CAAATCACCT TCCCAGAAAA GACTACGTCC    1560
TTTCAACCAT GCACTAGAAT GCATCCTTTC CCATTTTTAC TGATTCCCTT TATCTTCGGG    1620
AACTCTCACT CTCTCATAAA CTACTTTATT ACCATCCCAC CATATCCTGT CCTCTTTTTT    1680
TGGCCTACTT AGATCTGTTT TCCTTTCTTG CCTTAAATGG GAATTGCTAG AGGAATATGT    1740
TTCTAACTTT TTTTTTCTGC ACACAAGTTC ATGGTCCTTC TATACTTGAT AGCCCAGCTG    1800
CTCTATTTTT TTTATCTCAT TTCACACTGG CACCTAAGCT TTAAACCCTT GGCTGTTTTT    1860
GTTATTGTTG TCTGCCTGCT TGTCCTAGCT CCTTTTACTA GGTGTGTACT CTGGGGATAG    1920
AACCTATGTT TTGTGCTCTG AGATTAGAAC CAAAACACAG ATGTCAAAGA AGGAATTCAG    1980
GGGATCTGGT GACTGGCTGG ATTTAAGGAA TGAAGCAGGT AGAGATGTCA TGAAAGATCC    2040
AAGCCCAGAT GATTATCATA ATGTTTGTGC TACCAAGAGG CAGTGAAAAC ACTGATGGAA    2100
AGAAACTGAG CACTTTGTAG AGTATCATAG TAGAGCTGTT AGTATTCATT GCTCTTAAGT    2160
```

```
ATCCATCCAG TTATATTTGT TAGACTCTAC TCAAAAGGTA TTTTCTGAGT ACAGAATTTT    2220

TTTCACAAGT GGTGCAAATG GTCTCATTAA TTGAATGTTT ACTGCCTAAC ACTAACCCGA    2280

GTGCTTTAAA ATGTATAATG TAAACTCCAT AGTAACTGTG AGGTTGTATA GGCAGGAAAA    2340

CTGAGGTACA GGTATTCACA GTGGAAATAA GGGTTAAAGG TAGGATTTGA GTCCTCTGAT    2400

TCCTAAGTTT ATACCTTTTT TTCTTTTTAA GTCAAGTTTA TTAAGGTATA ATATATATAT    2460

GGTAAAATCC ACCCTTTTTA GAGTATAAAT TCTATGAGTT AGGACATATG CATACAGTAG    2520

CATAACCATC ACTAAAATGA AGATGTAGAA TATTTCAGTC ACTCCAAAAA GTTCTCTCAA    2580

AGTCCTTGCA GTCAGTCCTC TCCCCTGCTC CCATCCATAG TAACCACTAA TTTGTTTTCT    2640

GTCATTATAG TTTTGCCTTT TCCAGAGAGT GGCACATATA TAGAATCATA CAGTATGCAG    2700

ACTTTTGTGT CTGGGATTTA TCTATGTTGC TGCATGTGTG AGTAATTCAT TCCTTTTTTT    2760

TTTTTTTTTT TTTGAGACGG AGTTTCACTC TTATTGCCCA GGCTGGAGTG CAATGGCATG    2820

ATCTCGGCTC ACTGCAACCT CCGTCTCCCA GGTTCAAGCA ATTCTCCTAC CTCAGCCTCC    2880

CAAGTAGCTG GGATTACAGG CATGTGCCAC CATACCCAGC TAATTTTTTT TGTATTTTTA    2940

GTAGAGACGG GGTTTCTCCA TGTTGGTCAG GCTGGTCTCG AACTCCCAAC CTCAGATGAT    3000

CTGCCCACCT CGGCCTCCCA AAGTGCTGGG ATTACAGGTG TGAGCCACTG TGCCCGGCAA    3060

TTCATTCCTT TTTATTGTGG AGGAGCATTC CTTCCATTGT ATCATGTATT ATAATTTTTT    3120

TCCTCATCCA TTCTGTGGCT GATGGACATT AAGTTGTTTT TGGTTGAACT AGTTTACAGT    3180

CCCTCCAACA GTGTAAAAGT GTTCCTCTTT CTCCACATCC TCTCCAGCAC CTGTTGTTTC    3240

CTGATTTTTA TTGATCGCCA TTCTAACTGG TGTGAGATGA TATCTCATTG TGGTTTTGAT    3300

TTGCATTTCT CTGATGGCCA GTGATGATGA GCATTTTTTC ATGTGTCTGT TGTCTGCATA    3360

AATCTCTTCT TTTGAGAAGT GTCTGTTCAT ATCCTTCACC CACTTTTTGA TGGGGTTGTT    3420

TGTTTTTTTC TTGTAAATTT GTTTGAGTTC TTTGTAGATT CTGGATATTA GCCCTTTGTC    3480

AGATGAGTTG ATTGCAAAAA TGTTCTCCCA TTCTGTAGGT TGCTTGTTCA CTCTGATGGT    3540

AGTTTCTTTT GCTGTGCAGA AGCTCTTTAG TTTAATTAGA ACCCATTTGT CAGTGTGGCG    3600

ATTCCTCAAG GATCTAGAAA TAGAAATACC ATTTGACCCA GCCATCCCAT TACTGGGTAT    3660

ATACCCAAAG GATTATAAAT CATGCTGCTA TAAAGACACA TGCACATGTA TGTTTATTGC    3720

AGCACTACTC ACAATAGCAA AGACTTAGAA CCAACCCAAA TGTCCAATGA TGATAGACTG    3780

GATTAAGAAA ATATGGCACA TATACACCAT GGAATACTAT GCAGCCATAA AAAATGATGA    3840

GTTCATGTCC TTTGTAGGGA CATGGATGAA GCTGGAAACC ATCATTCTCA GCAAACTACC    3900

GCAAGAACAA AAAACCAAAC ACCGCATGTT CTCACTCATA GGTGGGAATT GAACAATGAG    3960

AACACTTGGA CAGACACAGG AAGGGAACA TCACACACTG GGTCCTGTTG TGGGGTGGGG    4020

GGAGGGAGGA GGGATAGCAT TAGGAGATAC ACCTAATGTA AATGACGAGT TAATGGGTGC    4080

AGCACACCAA CATGGCACAT GTATACATAT GTAACAAACC TGCATGTTGT GCACATGTAC    4140

CCTCGAACTT AAAGTATAAT AAAAAGAAAT AAGTTGTTTT CGGCTTTGGG TTGTTACAGA    4200

TAAAACTGCT ATAAACTTCT GTATACAGGT CTTTGGATAA CTTTAGGACT CGGGTTGCTA    4260

GGTCGTGTGG TAAATATATG TTTAACCTTA TAAGTTACCA GATGGCTGTA CCATCTGGTA    4320

CCACTTCATA GTCCTACCAA CAATATACCA ACAATTTATG GGAATGTAAT TGCTCTGCAT    4380

TCTCATCCCC ACTTAGTACT GTCAGTCTTT TTCATTTTAG CCATAACAGT AGGGGTGTGG    4440

TAGTGTCTCA TTGTGACATT GTGAGGTTGT ATTTCTTTAT ATTTTTAATT TGTGTTTTCC    4500

TAGTTGATCA GTCAATTGAT TATTGATTTT GAGCATCTTT TCATGTATTT ATTTGCCACC    4560
```

| | |
|---|---|
| TGAATATCTT CGTTAGTAAA ATATAAAAGT CTTTTGCCTA TTTTTCAATG TTATTTATTT | 4620 |
| ATTGGTCATT TTATTATTGA GCTGTGAGAG TTCTTTTTTT TTTTTTTTTT TTTCTTGTTT | 4680 |
| TTTGAGACAG GGTCTCGCTG TCTTACCCAG GCCAGAGTGC AGTGGTGTGA TCTTGGCTCA | 4740 |
| CTGCAACCTC TGACTCCCAG GCTCAAGTGA TCCTTCCACC TCAGTCTCCC ACGTAGCTGG | 4800 |
| GACTACAGGC ACACACTCAC CACACCGGTG AGACTTGTAG AGGCAAGGTC TCACCAGGTT | 4860 |
| ACCCAGGCTG GTCTCAAACT TCTGGGCTCA AGCAATCAGC CTGCCTCAGT CTCCCAAAGT | 4920 |
| GCTGGGATTA CAGGTGTGAG CTACAGTGCC AGGCAGAGAG TTCTAAATAT GTTCTGGATA | 4980 |
| CAAGCCCTTT ATCAGATATT GGTTTTGCAG ATATTTCTTA ACTGCTTTTC AGAGGACAGG | 5040 |
| AGTTTTAAAT TTTGATCAGG TACAGTTTAT AAACTTTTTT CTCTTATGGT TTATACTTTT | 5100 |
| TGTTTATTAT TTAGGAAGTC TTTGACCCAG TGTCACAAAA ATATTCTTCA GTGTTTTCCT | 5160 |
| CTAAAAGTTT TATAGTTTGA GTTCTTACAA TTAAGTATAT GCTTCATTTC AGAATCTTAA | 5220 |
| TATGATATGA GGTAAAAGTT GAGGTTTACT TTCTTACATA CAAATGTCCA CTTCTTCTAG | 5280 |
| CACCCAGAGC CTAGTCATTA TGATACCCTG CCTTCTAATC TTATTGTTAT CTTGTCTCCC | 5340 |
| AATCTTAACT ATACAATTTT GTACAAGTCA GTTAAGTCCT TTGAATTTCC TGCTTAGTAT | 5400 |
| ATACTTTTGT GAGGATTAGA GAGAATTTAT AGCAGCACCT AGTACAGTGT CTGGAACATA | 5460 |
| GCAGACATTC AATCAGTGAT ACCTGTGACT GTTGCTCTTG GTAAAATTAT TTTTTTCAAA | 5520 |
| TCTCTCTTTC GTTAGCTAA CATTGAACAC CTATTGCATG TTCTGGGGAT ACATTAGGGA | 5580 |
| ACAAAGTAAA CAAAGTTTCT GTTTTTAGGT TCATTTGTAT ATGAACGTTT ACGTTCATAT | 5640 |
| ACAAATCACA AGCTATACTA TTAGTATAAT TTTAATAAAT TATGTTAAAG TCGAGGATGC | 5700 |
| ATTTTGGTGC AATTATGAAA GCTTGCAATT GCTGTCTAAG CATTCCAATA ACTTCATATG | 5760 |
| TTAGTTTAAA ATTAGGTTCT GCTGGGCATG GTGGTACATA CTTATAGTCT CAGCTACTTG | 5820 |
| GAGGCTGAGG TGGGAGGAAC ACTTGAGCCC AGGAGTTCAA GTTGTATTGC ACTGTTATTG | 5880 |
| CACCTGTGAA TAGCCACTCC AGCCAGGGCA ACATAGCAAG ACCTTGTCTC TGCATTTGAA | 5940 |
| ATAATAATAA TAAAAGTAGG TTGTAAAAAT GTCTTAGAAG AAGAGTTGGT CAGTTTTGGA | 6000 |
| ATCATAGAGG CAAACACTAG AAGAATATCC CCAGCATCAT CCAATAAGAG AATGCCCCGA | 6060 |
| ACCAGATCCC AGTATTCCTG GGAGATGAGG CAACCAGCTG TCTCTGGAAG CGAGCCTCAG | 6120 |
| AGCAGGCCAC TGAGCTCCCT TGTTGTACTT TACTTGCTCA GAGTCCTCTG TGGTTGAGCA | 6180 |
| AGCTTTGGAT TAAAGTATAC TCTTCATGTA AATTTGCCTA TAGGCTCAGA ATGCATTGGT | 6240 |
| AACTCACCAT GAATTTCTAG CCTTCTCAGT AGTCCTGACT TAAAAAAATA CATTAAATAG | 6300 |
| TTACCTTTTT AAGGATTAAG TAACTCTAAA TGCCCAATGA ATGAATAATG ACTTTTGTGG | 6360 |
| CAGGTGTTGA GGACAGGACA TGGTGTTTGG AGTTAGAAGT GGAATTTAAT TCCTGCTTCT | 6420 |
| CTCTACTAGC TGTGAGGACT TGGGCCAAGT TACTTAATGT CTCTGAACTT CAGTTTCTCT | 6480 |
| AGGCCTGCTC TACAGTGTTA TTGTTAGCCT TAAATGAGAT CACTTTTACT AAATGCCTGG | 6540 |
| ACCTGGAGTA TCTTACTTGT CTTCATCTAT CAGCCATGTA AGCTATAGTG AGTTTTATTT | 6600 |
| ATGTAATGTT TCTTTATTTT CAG | 6623 |

(2) INFORMATION FOR SEQ ID NO:69:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (C) INDIVIDUAL ISOLATE: EXON 6 OF RAD50 GENOMIC SEQUENCE (xi) SEQUENCE DESCRIPTION: SEQ ID NO:69:

```
AATCGTCTAA AAGAAATTGA ACATAATCTC TCTAAAATAA TGAAACTTGA CAATGAAATT    60

AAAGCCTTGG ATAGCCGAAA GAAGCAAATG GAGAAAGATA ATAGTGAACT GGAAGAGAAA   120

ATGGAAAAG                                                           129
```

(2) INFORMATION FOR SEQ ID NO:70:

(i) SEQUENCE CHARACTERISTICS:
       (A) LENGTH: 233 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (C) INDIVIDUAL ISOLATE: INTRON 6 OF RAD50 GENOMIC SEQUENCE (xi) SEQUENCE DESCRIPTION: SEQ ID NO:70:

```
GTTTGTGGTG GTAGAATTTT GTTCTGCTTC AAAATTTTGG GATTATTGTA ATGAACTTTA    60

TTTGAATCCA TTTTGCCATC CACATTGGAA AAAAACAAAT ACAGATCTTG TTACTTCTAT   120

GTATATGTTA AAATGAAGGA TATTGAATAA GGTTTGGTTT ATATTTGATA CCTCAAAGTG   180

ATCATATTTT CTTATGTTTG TACATTAAAG CTTTTTATTT TGGTGTTACA CAG          233
```

(2) INFORMATION FOR SEQ ID NO:71:

(i) SEQUENCE CHARACTERISTICS:
       (A) LENGTH: 166 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (C) INDIVIDUAL ISOLATE: EXON 7 OF RAD50 GENOMIC SEQUENCE (xi) SEQUENCE DESCRIPTION: SEQ ID NO:71:

```
GTTTTTCAAG GGACTGATGA GCAACTAAAT GACTTATATC ACAATCACCA GAGAACAGTA    60

AGGGAGAAAG AAAGGAAATT GGTAGACTGT CATCGTGAAC TGGAAAAACT AAATAAAGAA   120

TCTAGGCTTC TCAATCAGGA AAAATCAGAA CTGCTTGTTG AACAGG                  166
```

(2) INFORMATION FOR SEQ ID NO:72:

(i) SEQUENCE CHARACTERISTICS:
       (A) LENGTH: 597 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (C) INDIVIDUAL ISOLATE: INTRON 7 OF RAD50 GENOMIC SEQUENCE (xi) SEQUENCE DESCRIPTION: SEQ ID NO:72:

```
GTAGGACAAA ATGTTTATTT GGTCGTTTTT CCTACTATGA TGTTATACAT TTTCTGTATG      60

AATGAAGAAT CTCCAAGGAC TTATGCTGAG TGAAAAGCCA ATCTTAAAAG GCTATACACA     120

GTATGTTTCC ATTTATATAA CATTTTTATA ATGTCAAAAT TTTAGAAATA GTGGAGAAAT     180

TAGTGGTTGC CAGGGATACT GGGTAAGAGA AGGACAGGA GGGAGCTAGG TATGGTTATG      240

ATTAGAACAA AAAGAGAGTC CTTGTAGTAT TGGAACTGTT CAGTATCTTG ACTGCCATAG     300

TGATATATG AACCGACACA GGTGATAAAA TTATATAGAA CTTAATATAC ACACATCCAC      360

ATGCTCAGGG GTACAAATAA AATTGGGGAA ATTTGAATAA GATTGATGAA TTATATCAAT     420

ATCAGTATTC TGGTTGTGAT ATTTTACTGC AGTTTTGCAA AATGTTATCA TTGGGAGAAA     480

CTGGGCAAAA TGTACAAGAG ACACACTGCA TTATTTTTA TAACTCGTGA ATCTGCAGCT      540

ATCTCAACTT TTTAAGCACC AGTTGAAAAA AAAATTATGA GATTTTTTTT TTAAAAG        597
```

(2) INFORMATION FOR SEQ ID NO:73:

(i) SEQUENCE CHARACTERISTICS:
            (A) LENGTH: 194 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (C) INDIVIDUAL ISOLATE: EXON 8 OF RAD50 GENOMIC SEQUENCE (xi) SEQUENCE DESCRIPTION: SEQ ID NO:73:

```
GTCGTCTACA GCTGCAAGCA GATCGCCATC AAGAACATAT CCGAGCTAGA GATTCATTAA      60

TTCAGTCTTT GGCAACACAG CTAGAATTGG ATGGCTTTGA GCGTGGACCA TTCAGTGAAA     120

GACAGATTAA AAATTTTCAC AAACTTGTGA GAGAGAGACA AGAAGGGGAA GCAAAAACTG     180

CCAACCAACT GATG                                                      194
```

(2) INFORMATION FOR SEQ ID NO:74:

(i) SEQUENCE CHARACTERISTICS:
            (A) LENGTH: 750 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (C) INDIVIDUAL ISOLATE: INTRON 8 OF RAD50 GENOMIC SEQUENCE (xi) SEQUENCE DESCRIPTION: SEQ ID NO:74:

```
GCAAGTATTT TGAAATACAG TATTTGTTAT TTTGTTTGCA TCATATTCTC TACTTGAATT      60
```

```
GTTTTAATTT TTGGTTGGAC TCCATTTTGG CATATTTTTC TATTAGTGTT AGGATAAAAT      120

CTGCTACAAG GCAGAAAAAC CTTTATTGAA GCAAATGTTC TTAAGTGTAT AAAGATAAAA      180

ATATGAAGAA AATGTAAACC TACATTTTTT ATTTGGTTTT AAGTAAAAAT TTTTAAAAAC      240

TAATTGCAGA GAAAACATTT GCTCACAGTT AATGATTATC TCTGGGTAAT GGTTTTGATT      300

GTTTTTAAAA TACAGTCTTG AACCACATGT TTTGGTCAGT GATAGACCAC ATATTTGACA      360

TTGGTCCCAT AAAATTATAA TACTGTATTT TACTGTATGT TTTCTGTGTT TAGATATGTT      420

TAGATACATA AATACTTATC ATCATGTTAC AGTTGCCAAA GTATTCAGTA CAGTAATATG      480

CTGTATAGGT TTGTAGCCCA TAAACAATAG GCTATACCAT ATAGTCTATG TGTGTATTAA      540

ACTATACCAT GTAGGCTTAT GTAAATACAT TCTGATGTTC ACACAATGAT AAAATTGCCT      600

AATGATGCAT TTCTTGGAAT ATATCCCTGC TGAGCAACAC ACGACTGTAC TTTTTTGTAT      660

TTTCTTCAGT GTACATATAT TCCTTTTGCA ATTAAAAAAC TTAAATTGTT TAGTAAATTA      720

TTAATGCTCA TTCTTTACAT ATGCATTTAG                                      750

(2) INFORMATION FOR SEQ ID NO:75:

(i) SEQUENCE CHARACTERISTICS:
        (A) LENGTH: 207 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: EXON 9 OF RAD50 GENOMIC SEQUENCE (xi) SEQUENCE DESCRIPTION: SEQ ID NO:75:

AATGACTTTG CAGAAAAAGA GACTCTGAAA CAAAAACAGA TAGATGAGAT AAGAGATAAG       60

AAAACTGGAC TGGGAAGAAT AATTGAGTTA AAATCAGAAA TCCTAAGTAA GAAGCAGAAT      120

GAGCTGAAAA ATGTGAAGTA TGAATTACAG CAGTTGGAAG GATCTTCAGA CAGGATTCTT      180

GAACTGGACC AGGAGCTCAT AAAAGCT                                         207

(2) INFORMATION FOR SEQ ID NO:76:

(i) SEQUENCE CHARACTERISTICS:
        (A) LENGTH: 1386 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: INTRON 9 OF RAD50 GENOMIC SEQUENCE (xi) SEQUENCE DESCRIPTION: SEQ ID NO:76:

GTAAGATATT GTTTGAATAA TCTAATAATT TTAAGATATA ATACTTTTAG AAGTATTTTG       60

TCTATTTTTG ATCCTAAGAT TATAGCATTT TAATAAAAAC ATCAACTTTG TCTTATTCTC      120

ATGTAAAATG AATTCATCTG AATATCTTGA TCTTCTGACT CTTTGGTTCT ACAACCCGAT      180

AGCCTGAAAA TTAGAATCAC ATAGGGAGCT TTTTAAAGAT ACTGTACTCA GACCTTAAAG      240
```

```
CTTCAGACCT TCCAAATCAA AATCTCTGAG AATGGGGCAT AGAAATGTAC ATTCAAAACA      300

CAACAAAACT GGCTAATTCT TATGAGCACC TTGATTAAGA ACACTTACCA GGCCGGGTGC      360

GGTGTCTCAC ACCTGTAATC CCAGCACTTT GGGAAGCCAA GGCAGGCAGA TAACGTGAGG      420

TCAGGAGTTC AAGACCTGTC CAGCCAACAT GGTGAAACCC CGTCTCTACT AAAAATACAA      480

AAATTAGCTG GGCGTGGTGG CGTGTGCCTG TAATCCCAGC TACTTGGGAG GCCAGGGCAG      540

GAGAATCGCT TGAACCTGGG AGGCAGAGGT TGCAGTGAGC CAAGATTGCG CCACTGCTCT      600

CCAGCCTGGG TGACAGAGTG GGACTCCATC TCAAAAAAAA GAAAAAGAAC ACTTGCCAAA      660

GTTTTAAAAA AGCAAGTATT TTTCCTCTAG GTCACACACG TTGTAATTCT AGATGATTTT      720

TGCTGTATTA TTACTTTTTC TGTGTTAAAA ACTTTCTTAG CCAATCTTTT CAGGTATTTC      780

CATATTTTCT TTCTTGCTTC TAGTCTGTCC TCCTTCTTCA CATCTCCATT ACCAAAGTAA      840

GCATTCTAAA GCATGGCAAA CTTCTTAAAG CCCATCTTGA TAATTTATGT AAACATTTAT      900

TTTTGCTCCA TAACTCACCA TTGTAGCATA CATTTTTGTC AGTTTAGCAC TTCATCAGTG      960

TTGTCTTGTT GGGGTGGGGA GATACTTGGT CAGGGACCAC ATCACACTAT TTTTATAGTT     1020

TCTACATACC AGGCAATATA GTGAATTACA TGGGGACATA ATAAATATTT AATTGTTGAC     1080

TGAGGACTCA CTAATCTGTG TACTTAGACA CATGTCTCCT AATTTTACAG TAATTCTCAC     1140

ATTTCTTTCC TGTTTGACCC TTCTAGGTTT ATTTACTAAT TCTCTACCAT TATAACATAG     1200

TAAGGTCACT TTAATAAGAT ATACCTTAGA GCATATATAG TGCCTTATGT TTTTTTCTCT     1260

TGTTGGATGC AAACAGTAAT ATTTGGAACA TTCTGAGGAG TAGTTAATTT CTAATACACT     1320

TTGTCATTAT TTTAATTCTT GCACAAAATA TATAACACCT TTGCATTTGT ATGAATTATT     1380

GACTAG                                                                1386

(2) INFORMATION FOR SEQ ID NO:77:

(i) SEQUENCE CHARACTERISTICS:
        (A) LENGTH: 183 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 10 OF RAD50 GENOMIC SEQUENCE (xi) SEQUENCE DESCRIPTION: SEQ ID NO:77:

GAACGTGAGT TAAGCAAGGC TGAGAAAAAC AGCAATGTAG AAACCTTAAA AATGGAAGTA       60

ATAAGTCTCC AAAATGAAAA AGCAGACTTA GACAGGACCC TGCGTAAACT TGACCAGGAG      120

ATGGAGCAGT TAAACCATCA TACAACAACA CGTACCCAAA TGGAGATGCT GACCAAAGAC      180

AAA                                                                    183

(2) INFORMATION FOR SEQ ID NO:78:

(i) SEQUENCE CHARACTERISTICS:
        (A) LENGTH: 470 base pairs
        (B) TYPE: nucleic acid
        (C) STRANDEDNESS: double
        (D) TOPOLOGY: linear (ii) MOLECULE TYPE: DNA (genomic)
```

(iii) HYPOTHETICAL: NO (iv) ANTI-SENSE: NO (vi) ORIGINAL SOURCE:
         (C) INDIVIDUAL ISOLATE: INTRON 10 OF RAD50 GENOMIC SEQUENCE (xi) SEQUENCE DESCRIPTION: SEQ ID NO:78:

```
GTATGATTTT TCTTTTTGTT CTAATTATAC TGTCTGGTAC TTAAAATAGC CTACCTTGCA      60

CTCATAAGTC ATAGACTATA AGGTATTAAG TTGGTATTGA CTATATTTTA GAGGCTAAGT     120

GAGCTTAGTA CTCTATATAA TAGACTTTCA AGCTTAAAAG TTATTGTTTA ATTACAAAAA     180

GTTAATACAG AAATGTATAT ATATGTATAT ACACACATGC ACATTACTGT TAACTTTTAA     240

CATACACAAA TTTTAAAATT TTATATTGTT CGACTTGGTA CTCCACTCTT AAGGCTTAGA     300

AAGACCATCC CCACTTGAAG ACTTTAAGAA CTTTAAGAAA TTTTATATTT TATTTTCATA     360

TTTTTATAGT TTTAAGCTTA GAACTTTAGT CAGTCTAGAA TTTATTTTTG TTCTTGATAT     420

AATGTGGAGA TATAGACTTT ATTTTTAAAA GATTTTTTTT TTACCTATAG                470
```

(2) INFORMATION FOR SEQ ID NO:79:

(i) SEQUENCE CHARACTERISTICS:
        (A) LENGTH: 158 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: EXON 11 OF RAD50 GENOMIC SEQUENCE (xi) SEQUENCE DESCRIPTION: SEQ ID NO:79:

```
GCTGACAAAG ATGAACAAAT CAGAAAAATA AAATCTAGGC ACAGTGATGA ATTAACCTCA      60

CTGTTGGGAT ATTTTCCCAA CAAAAAACAG CTTGAAGACT GGCTACATAG TAAATCAAAA     120

GAAATTAATC AGACCAGGGA CAGACTTGCC AAATTGAA                             158
```

(2) INFORMATION FOR SEQ ID NO:80:

(i) SEQUENCE CHARACTERISTICS:
        (A) LENGTH: 386 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: 5' END OF INTRON 11 OF RAD50 GENOMIC
             SEQUENCE (xi) SEQUENCE DESCRIPTION: SEQ ID NO:80:

```
GTAAGTTGCA ACATTTGGAG ATGTAATAGA AATCTCTTAT TTCATGCTTA CCTGTTTAAT      60

TGTTTTAAAA TAATTTATTG TCATGAAATG GTATGTTATA TTGATAAACT TTAGTTCTTA     120

CATACAAGGA GACTTCAGAA AGTTCATGGA AAAATGGAAT TAAAAGATAA AAATTTTAAA     180

TAAACTGTAT TTCTCAACAT AAGCTCCATC AAGTTCAAGA CTCTTCTGAG CAGTGATACC     240
```

```
AGCAATTTAG TTCAGTCCTA AAGAACTGAG GGTCCTGGGA ATTTAACCAT GTCAGTGTAG          300

TCTTTTTTAC ATTGCTAGCA TAAAAATGGG TGCCCTTTAA AGATTTTTTT AAGATTAAGA          360

AACTAGAAGA CAGGAGGAGC CAAATC                                               386
```

(2) INFORMATION FOR SEQ ID NO:81:

(i) SEQUENCE CHARACTERISTICS:
        (A) LENGTH: 247 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 3' END OF INTRON 11 OF RAD50 GENOMIC
            SEQUENCE (xi) SEQUENCE DESCRIPTION: SEQ ID NO:81:

```
CAGGCAGAAT TCTGTGTACA TTTTTCTGGG AGCAGGCCCA TGAGTAGGAC TGGCAGGTGA           60

GTCAGTGTCC TAGGGGAGA GTTAAGGCAG AAGTGGACTA GTCCCTCAAC TTCTGAAAAA          120

AATTATTTGG TCATACCAAA CTCTTGTCAT GATTTGTTGG CAGAATTTGT CTTGTTTTTG          180

CCTACTCAAA TTTTCAAACT AATTTCTCCT ATTTTAAAAT GAAAATCCAT ATTTGCTCTT          240

ATTTTAG                                                                   247
```

(2) INFORMATION FOR SEQ ID NO:82:

(i) SEQUENCE CHARACTERISTICS:
        (A) LENGTH: 176 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 12 OF RAD50 GENOMIC SEQUENCE (xi) SEQUENCE DESCRIPTION: SEQ ID NO:82:

```
CAAGGAACTA GCTTCATCTG AGCAGAATAA AAATCATATA AATAATGAAC TAAAAGAAA           60

GGAAGAGCAG TTGTCCAGTT ACGAAGACAA GCTGTTTGAT GTTTGTGGTA GCCAGGATTT         120

TGAAAGTGAT TTAGACAGGC TTAAAGAGGA AATTGAAAAA TCATCAAAAC AGCGAG             176
```

(2) INFORMATION FOR SEQ ID NO:83:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: INTRON 12 OF RAD50 GENOMIC SEQUENCE (xi) SEQUENCE DESCRIPTION: SEQ ID NO:83:

```
GTAAGTTGTC TACTTTATAT TATCAGGATA CTTTGACACC TTTGAATTTT CATTCACAGG      60

TAACTGTTAA GGATGGGGAA TTTAAAAACC TGGTTATGGA GCCTAATGGC TTGGATTTCA     120

GTCCTGGCTC TACAACTTAC TCACTGTGTG ACTTTAGGCA AGTTACTGAA ACCTTCCTGT     180

GTTTCATTGT CTATAAAATG AGGACACAAC TACCACCTGT GGTACTGAGG TGTGAATGAG     240

ATTGTAATTA TAAAGCCCTT AGAACAGTGC CTGGCACATA GAAAGCTCTC AGTAGGCATT     300

TTGTTATACT TATAATGTGT TACCAAAAAA TATTTATACA AATCTGAATG TATCATGCTC     360

TTTGGAAGCG AATATCGGAA TTTTAAATAT CAGAATTTTT ATTTCTTTTA TAATATATTT     420

ATAAAGCAAG AATAATCATA TATTTATAGA AAAAGATACA ACCGTATTCA GAATACTGTA     480

TTTTATGTTT TTTTCTCATT GGTGATATAA TTTATTTTCT TAAAATAG                  528
```

(2) INFORMATION FOR SEQ ID NO:84:

(i) SEQUENCE CHARACTERISTICS:
        (A) LENGTH: 238 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 13 OF RAD50 GENOMIC SEQUENCE (xi) SEQUENCE DESCRIPTION: SEQ ID NO:84:

```
CCATGCTGGC TGGAGCCACA GCAGTTTACT CCCAGTTCAT TACTCAGCTA ACAGACGAAA      60

ACCAGTCATG TTGCCCCGTT TGTCAGAGAG TTTTTCAGAC AGAGGCTGAG TTACAAGAAG     120

TCATCAGTGA TTTGCAGTCT AAACTGCGAC TTGCTCCAGA TAAACTCAAG TCAACAGAAT     180

CAGAGCTAAA AAAAAAGGAA AAGCGGCGTG ATGAAATGCT GGGACTTGTG CCCATGAG      238
```

(2) INFORMATION FOR SEQ ID NO:85:

(i) SEQUENCE CHARACTERISTICS:
        (A) LENGTH: 267 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 5' END OF INTRON 13 OF RAD50 GENOMIC
            SEQUENCE (xi) SEQUENCE DESCRIPTION: SEQ ID NO:85:

```
GTAAGAATGG GATTTACCTT CACTGTACAT GTAGCAGCAC ATTGTAAAAG GTACCCATCT      60

CATGCCTGGG CAGATGGTAG TTACTCAGTA AGGACTCTGA GCTGGTATGC CCTGTCTTAT     120

ATCACTTCTA TGATAAGAAG ATTCAATTAT TTTGTTAAA GATAAGCTTG TTTCCTGTCT      180

TTTTTTCTTT TTCTTTTTTT TTCCTGAGAC AGAGTCTCTC TCTGTCACCT AAGCTGGAGT     240

GCAGTGGCAT GATCTTGGCT CCATTGC                                          267
```

(2) INFORMATION FOR SEQ ID NO:86:

(i) SEQUENCE CHARACTERISTICS:
        (A) LENGTH: 266 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 3' END OF INTRON 13 OF RAD50 GENOMIC
            SEQUENCE (xi) SEQUENCE DESCRIPTION: SEQ ID NO:86:

```
TCTCTCCTTA AGATACTTGT TAATTACAAA GACTAAAACA GTAACTTTAC AGTGGAGAAA      60
CCTGGCCAAC ACCATCTAAG CCAAGTGAAT AAGGATTAAC ATCATCAGTA ATAAGACATA     120
TTGATATCAT GATTCCATAT CCACTGTATAT GATACCCTGA AAAGAACACA ATGTCACTTC    180
TGTGGTATTC TTCCTAAAAA TACATAACCT CAGTCTAACT GTGAGAAACA TCAGATACTT     240
TATTTTTAAT TGTGTTTTCT ATTTAG                                          266
```

(2) INFORMATION FOR SEQ ID NO:87:

(i) SEQUENCE CHARACTERISTICS:
        (A) LENGTH: 190 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 14 OF RAD50 GENOMIC SEQUENCE (xi) SEQUENCE DESCRIPTION: SEQ ID NO:87:

```
GCAAAGCATA ATTGATTTGA AGGAGAAGGA AATACCAGAA TTAAGAAACA AACTGCAGAA      60
TGTCAATAGA GACATACAGC GCCTAAAGAA CGACATAGAA GAACAAGAAA CACTCTTGGG     120
TACAATAATG CCTGAAGAAG AAAGTGCCAA AGTATGCCTG ACAGATGTTA CAATTATGGA     180
GAGGTTCCAG                                                            190
```

(2) INFORMATION FOR SEQ ID NO:88:

(i) SEQUENCE CHARACTERISTICS:
        (A) LENGTH: 430 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: INTRON 14 OF RAD50 GENOMIC SEQUENCE (xi) SEQUENCE DESCRIPTION: SEQ ID NO:88:

```
GTAAGTTTAT TGTAGTTTAA GGCAGAATAA AACTTGTTCC ATGGTGGCTT GAATTTGAAG      60
```

```
TGTGAGAGTT AAAAATAGTA GCTAGTATTC AGGTACAGGT TGTGTTTAGA ATTCCCCATC      120

CTGAATTTCA GATACCCTCA GGGAGAAACT GCTTAGTTTA CATCCCTGGG TTTAAACTTT      180

TTAATTCATA AATTTAAAAA TTAAGACAGT TCTGTTTGTT TTTCATCTTT AGTCAGCTTC      240

CTTTTGTTTA CATCATTTGA ATTGCTGATA ATTAATTTCA CTTTTATCCT ATTAAACTTT      300

GCTAAAATTG TATCTAGAAA TGGTTTATAA GTTTAGATTT AAAAAATAAA TGATAAGAGC      360

AATTAATTTT TAAAGATTTT GAATAATGCA GTAAGTTTAT TAAAGGAAAT CATTTTGTTA      420

TATTCTTAAG                                                            430
```

(2) INFORMATION FOR SEQ ID NO:89:

(i) SEQUENCE CHARACTERISTICS:
        (A) LENGTH: 127 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 15 OF RAD50 GENOMIC SEQUENCE (xi) SEQUENCE DESCRIPTION: SEQ ID NO:89:

```
ATGGAACTTA AAGATGTTGA AGAAAAAATT GCACAACAAG CAGCTAAGCT ACAAGGAATA       60

GACTTAGATC GAACTGTCCA ACAAGTCAAC CAGGAGAAAC AAGAGAAACA GCACAAGTTA      120

GACACAG                                                               127
```

(2) INFORMATION FOR SEQ ID NO:90:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 5' END OF INTRON 15 OF RAD50 GENOMIC
            SEQUENCE (xi) SEQUENCE DESCRIPTION: SEQ ID NO:90:

```
GTAATACAGT CTGTGTCCTT CTGTACTCAT AGAGACTTTG ACATTGCGAG CACATGCCTT       60

TTACAGTCAA TTTTATATCT GTTACATGGA CAACGAAGTT CCTTCCTGTC CACATATATT      120

TGCTCTTTTT TTCTGAAAAG CATCACTTCT CTTTGTTCTC TTACTTTGCA CAACAGATTT      180

TGAACAGTAG GAGAGTATGA AATAAGCTGT ATTCTCTTTT CCTTTTTTTT TTTTTTAAGA      240

TAGAGTTCAC TTTTGGTCGC C                                               261
```

(2) INFORMATION FOR SEQ ID NO:91:

(i) SEQUENCE CHARACTERISTICS:
        (A) LENGTH: 284 base pairs
        (B) TYPE: nucleic acid
        (C) STRANDEDNESS: double
        (D) TOPOLOGY: linear -continued (ii) MOLECULE TYPE: DNA (genomic)

(iii) HYPOTHETICAL: NO (iv) ANTI-SENSE: NO (vi) ORIGINAL SOURCE:
   (C) INDIVIDUAL ISOLATE: 3' END OF INTRON 15 OF RAD50 GENOMIC
       SEQUENCE (xi) SEQUENCE DESCRIPTION: SEQ ID NO:91:

```
CCCCAAAGTG CTGGGATAAC AAGTGTGAGC CAGTGCGCCT GGCCATGAGC TGTATTCTTT    60

CTCATTCATA CCTGCCCTGT AAGCTTTTCC CTGTGAGTGG CCAGCAGGGA ACATCAAGCT   120

GATTTGAGAA CTAGCAGGGT TCTCATTGTA TTTTTGTTGC AGTGGGTGGG GCCCACAGAA   180

ATAGCATTTG TGGATTCCAT AGACCGATAA AAATGGAAG AATGATACAA ATAGTATTTT    240

CTATGCCCTT ACATTAATTA CTGTGATAAT ATGTTTTTGT GTAG                    284
```

(2) INFORMATION FOR SEQ ID NO:92:

(i) SEQUENCE CHARACTERISTICS:
       (A) LENGTH: 194 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (C) INDIVIDUAL ISOLATE: EXON 16 OF RAD50 GENOMIC SEQUENCE (xi) SEQUENCE DESCRIPTION: SEQ ID NO:92:

```
TTTCTAGTAA GATTGAATTG AATCGTAAGC TTATACAGGA CCAGCAGGAA CAGATTCAAC    60

ATCTAAAAAG TACAACAAAT GAGCTAAAAT CTGAGAAACT TCAGATATCC ACTAATTTGC   120

AACGTCGTCA GCAACTGGAG GAGCAGACTG TGGAATTATC CACTGAAGTT CAGTCTTTGT   180

ACAGAGAGAT AAAG                                                     194
```

(2) INFORMATION FOR SEQ ID NO:93:

(i) SEQUENCE CHARACTERISTICS:
       (A) LENGTH: 239 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (C) INDIVIDUAL ISOLATE: 5' END OF INTRON 16 OF RAD50 GENOMIC
           SEQUENCE (xi) SEQUENCE DESCRIPTION: SEQ ID NO:93:

```
GTAAGAATAT CCATACATGT TTTTTGTAAA ATTATTTTAA TTATTTATTT TTATTTTTAT    60

TTTTTGAGAC AGTCTCGTTC TGTCACCCAG GCTGGAGTGC AGTAGCACGA TCTCGGCTCA   120

CTGCAACCTC CATCTCCTGG GTTCAAGTGA TTCTCTTGCC TCAGCCTCTG GAGTAGCTGG   180

GATTACAGGC GTGCACCACC ATGCCTGGCT AATTTTTGTT CTTTTAGTAG AAACGGGTT    239
```

(2) INFORMATION FOR SEQ ID NO:94:

(i) SEQUENCE CHARACTERISTICS:
        (A) LENGTH: 367 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 3' END OF INTRON 16 OF RAD50 GENOMIC
            SEQUENCE (xi) SEQUENCE DESCRIPTION: SEQ ID NO:94:

```
GTTGAAGCCA CACGCTAATA TAATTGGGAG CACATGGCCT AGATTAAGAT CAAATTAGTG      60

GTTGATGCAG TATAGCATGC GTAGTGGTTA AGAGCGTGAA CTCTGGAGCT GGACTGGGTT     120

AAAATCTTGG CTGCTTCATT TACTGGCTGT TGTGACCCTG GACAAATCAT TCTCTGTGTC     180

TGTTTGCTCG TTTGAAATAT AGGACTGAAA ATGATGGTAC TGTCCTCATA GGGTCATTGA     240

AAGGAGCAAA TGAGTTGACT TTTAGAGCCT GGCACATAGA AAGTGCTTTT ATTAAGACTG     300

TGAAGTCTGA CCCCTAAAGT AAGATAATGG AATATTATAT AATACTTTAT CTTTTTTATA     360

TTTTTAG                                                               367
```

(2) INFORMATION FOR SEQ ID NO:95:

(i) SEQUENCE CHARACTERISTICS:
        (A) LENGTH: 111 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 17 OF RAD50 GENOMIC SEQUENCE (xi) SEQUENCE DESCRIPTION: SEQ ID NO:95:

```
GATGCTAAAG AGCAGGTAAG CCCTTTGGAA ACAACATTGG AAAAGTTCCA GCAAGAAAAA      60

GAAGAATTAA TCAACAAAAA AAATACAAGC AACAAAATAG CACAGGATAA A              111
```

(2) INFORMATION FOR SEQ ID NO:96:

(i) SEQUENCE CHARACTERISTICS:
        (A) LENGTH: 391 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: INTRON 17 OF RAD50 GENOMIC SEQUENCE (xi) SEQUENCE DESCRIPTION: SEQ ID NO:96:

```
GTAAGATTTC ATTTATATAT TTACTTATCA AATATCTGTA TTAAACTTAT GTTCATAGCA      60
```

```
CCACGTCGGA CACTTATTTC ACATGAAATT AAATAGCATA AGATAAATAG TATTTTCAGA      120

TTCATGGTAT AATTTTGACA TTAGAAATTC TTGTTAGAAC AAGGATTTGA TGTAAATTAT      180

TTTGCTGCTT GATCTACAAT AGAAGTTAAG AAATGAGACT AATTAATCAA TTCCTATAGG      240

TGAGAAAGGG ACTTGTCTGC GATCATAAAA TTCAGTAGTG GTGGAAACTG GAACCCAATG      300

TTCATAACTT CCCAGCCAGT GTTTTACTGT GCTCTCCTGT TATGTGCCCT TAAGTACAAC      360

CAGTGTAAAT TTAATGAATA TTTTTCTACA G                                    391

(2) INFORMATION FOR SEQ ID NO:97:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 18 OF RAD50 GENOMIC SEQUENCE (xi) SEQUENCE DESCRIPTION: SEQ ID NO:97:

CTGAATGATA TTAAAGAGAA GGTTAAAAAT ATTCATGGCT ATATGAAAGA CATTGAGAAT       60

TATATTCAAG ATGGGAAAGA CGACTATAAG AAG                                   93

(2) INFORMATION FOR SEQ ID NO:98:

(i) SEQUENCE CHARACTERISTICS:
        (A) LENGTH: 73 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: INTRON 18 OF RAD50 GENOMIC SEQUENCE (xi) SEQUENCE DESCRIPTION: SEQ ID NO:98:

GTAATTTAAA ACTTAAAATT ATTTATTTGA TTGTATTTTT ATTCATGTGC TTAAAGAATT       60

TTCTTTTTTG TAG                                                         73

(2) INFORMATION FOR SEQ ID NO:99:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 19 OF RAD50 GENOMIC SEQUENCE (xi) SEQUENCE DESCRIPTION: SEQ ID NO:99:
```

CAAAAAGAAA CTGAACTTAA TAAAGTAATA GCTCAACTAA GTGAATGCGA GAAACACAAA    60

GAAAAGATAA ATGAAGATAT GAGACTCATG AGACAAGATA TTGATACACA GAAG          114

(2) INFORMATION FOR SEQ ID NO:100:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 5' END OF INTRON 19 OF RAD50 GENOMIC
            SEQUENCE (xi) SEQUENCE DESCRIPTION: SEQ ID NO:100:

GTAGGTCTGT TTTGCTTATG ATATCACTTA CACCTATGAC ATTCTTTTCT ATAGTTTTAT    60

TTTCAATAGA AGATCCATTG AATAGAAATG CAAAAAGGAA AGAGGCCAAG CGTGGTGGCT   120

CACACCTGTA ATCCCTGCAC TTTGGAAGGC CGAGGCGGGT GGATCACTTG AGGCCAGGAG   180

ATCAAGACCA GCCTGGCCAA CACAGTGAAA CCCTGTCTGT ACTGAAAATA CAAAAATTAG   240

CTGGCCGTG                                                           249

(2) INFORMATION FOR SEQ ID NO:101:

(i) SEQUENCE CHARACTERISTICS:
        (A) LENGTH: 5543 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 3' END OF INTRON 19 OF RAD50 GENOMIC
            SEQUENCE (xi) SEQUENCE DESCRIPTION: SEQ ID NO:101:

TCACATGCTT TATGCAAGCA TGGTAGTTAA TGCCTTTAAA AACTATACCA TTTCTCTGTT    60

CTTACTGTTT TAAACAAAAT TTACTATTTG AATGCCTTAA CCACTTGGTT ATAAGTGGTT   120

GCTTAAAATC ATTTGGAAGA TTAGTTACAT TAGTTTTCTG CTGGGTCTCT TTCTGTACCA   180

CCAAGAATTT CAAATATATG AAATATCAGT CAAAGGGAGA TCAAATCTCT GCCTGGCCTA   240

ATACATATTG AATAACTGTA TAAATTTATG ATGCATATAT AACAAAATAA TTATCACTAG   300

CTTTTATGTA GTTGCCTATA TAAAAATCAC AATCTGTAAA TTCGCAGCAG CTCTCTGTAT   360

ATATATACGA AATTGTTAAG ATTAATGATC TATGACCCCT TTTAAAGTGA TGGTCTAAAC   420

TTAGTGGATC TGATGGTATT AGTTTACTTT GTAACCTTCC TTGTTCCAGA AATTATTTAC   480

TTAGTTATAT ACAATAGAGC AAAGATAAAT GTATTTCAAA TTAATGGGAA AACAAGGCAG   540

TGTAGAAATA AGGGCAAGAA AGTAATGAAA CCAGGAGAGA AGTGTATAAA AAGTATGCAT   600

GAAGTCTGAT ATGCTTGCTG AAGATTCTAG TAGTCAAATA AAGAGAGGAG GCCAGGCGCA   660

GTGACTCATG CCTGTAATCC CAGCACTTTG GGAGGCCAAG GCAGACGGAT CACCTGAGGT   720

```
CAGGAGTTCA AGACTAGCCT GGCCAATATG GTAAAACCCC ATCTCTACTG AAAATAGAAA    780

AATTAGCCAG GTGTGGTGAC ACGCGCCTGT AATCCCAGGT ACTCAGGAGG CTGAGGCAGG    840

AGAATCGCTT GAACCTGGGA GGCAGAGATT GCAGTGAGCC GAGATCACAC CATTGCACTT    900

CAGCCTGGGT GACAAGAGTG AAACTCCGTC TCAAACAAAC AAACAAACAA ACAGAAACAA    960

AAACAGCCAG GCGTGGTGGC TCACGCCTGT AATCCCAGCA CTTTGGGAGG CCAAGGCGGG   1020

CAGATCACGA GGTCAGGAGA TCGAGACCAT CCTGGCTAAC ACGCCGAAAC CCCGTCTCTA   1080

CTAAAAAATA CAAAAAATTA GCCAGGCCTG GTGGTGGGCG CCTGTAGTCC CAGCTACTCA   1140

GGAAGCTGAG GCAGGAGAAT GGCGTGAACC TGGGAGGCAG AGCTTGCAGT GAGCCGAGAT   1200

CGCACCACTG CACTCCAGCC TGGGTGACAG AGCCAGACTC CGTCTTAAAA AAAAAAAAA   1260

AAAAAAAAAA GTCACAATTA GTCAAGATTC ACATTGTGTC AATGCTAAAA GAAAACCAGT   1320

TTCCTATACT GACTACAGGA TAATGTCTCT ATTCATAGAA AGGAAGACAT GTATAGTCTT   1380

CAACAGACTT CGCAGGGCTT TAAAAAAAAT ACAGTGTATC TCAGCATCAT TATTCCTTGA   1440

TACGAGGTTC TGTAGAGGGT GGTATGATTG AAGCCTGAAG TAAATGTTAA TGTTTAGAAA   1500

GCAAAGGTTC TTAGCTAGGG GCACCTGTAA ATCGTCTGAG TTTTTCCACT TCTAGGTATA   1560

GAACTAAGAA AATTGAAAAC ATATGTTCCC ACAACAACTT GTACAAGAAT GCTCATAGCA   1620

GCATTATTTG TAATAGTCAA AATATGGACA CACCCAAATG GCCATCAACT GATGATCAGA   1680

TAAACAAAAT GTGGTATACC CATACAATGG AATATTATTC AGCCATAAAA AGGATACATG   1740

CTACCACATG AATGAACCCT TAAAACATGC TAAGCAAAAG AAGCCAGTCA CAAAAGGTCA   1800

CATAATGTAC GATTCCACTT ATAATAAATG TACAGATTAG GTAAATCCAG TGACAGCAGA   1860

TTAATGTTTC CAGGGGGCTA GAGGTGAGGA AGGAATAGAG TGACTGCTAT TGAATATGAG   1920

ATTTCCTTTT GGGATGATCA AATGCTCTGG AATTGGATAG TGGTGATGGT TGTATAACCT   1980

TGTAAATAAA GTAAAACTGC TAAATTGTAC ACGTTTAAAC AGTGAATTTT GTGGAATATT   2040

AATTACATCT CAGTTTTTAA AAAATGACTT AGGTTATTAA AAATACATGT GTTGGCCGGG   2100

CACAGTGGCT CATGCCTGTA ATCCTAGCAC TTTGGGAGGC CGAGGCGGGC AGATTGCTTG   2160

AGCCTGGGAG TTCCAGACTA TCCTGGGCAA TATGGCGAAA CCCCATCTCT ACAAAAAAAT   2220

TAGCCAGGTG TGATGGTGCA TACCTGTAGT CCCAGCTACT CAGGAGGCTG AGGTGGGAGG   2280

ATTGCTTGAG CTGGGGAGTT CAAGGCTGCA GTGAGCCCTT ACTACGCCAC TGCACTCCAG   2340

CCTGGGCAAC AGAGCAAGAC CCTGTCTCAA AAAATATATA TATATATATG TCTATGTCTC   2400

CAATCCACAC CAGTAAATCA GAATCTTGGG GGTTTGGGCA GAGATATGTG TGTTTTGTTG   2460

AAATTCCTTA GAGGTTCTAA TATATCCCTT TAGCTGTCAA TAACTGAGCC AGCACTGGAT   2520

GGACTGCATA GCTTTCAGGC AGTCTTGTAG AAGTGGTGTT ATTCCCAGCT AGACTTTTGG   2580

TGGACATTGG ACTGTAATCT GTTCAGCATG CCACTCTCTC ACAGGTATCT AGAATGCAGC   2640

TAATTTTTAT GTTTCCATAG GTGACCAGCT GCATGCATTA ACTGTCATCT GAGTTGGATG   2700

ATTGGGGTTA ATATTTAAGA GCTGAGGAGC CTAACAGTCA CTTATTTACG TACTGATTTA   2760

AGCCCTGCTA AATTTAGTCC ACAGAATAAA ATAATTTGGA AACTTAACTG CCTTTCTCAG   2820

TTTTCAGCTG AAGGAATATA TGAAGAGAAC TGTAGGTGAC CTGACTTGTC CAAGGTCACA   2880

AAAAGTAGTA ACAGGTAGAA CTGGACCCTA CACTATCAAA TTTCTAGTAG AATGGAAAAA   2940

CATTTGTGGT ATACTATAAC TGCATCTGAT TTTTTTTCCC TTCCTTTCTC TGATACATTT   3000

TGTAGACTAT AATTGGAATT CTCACTGCTT ACAGTACAAA GGACAAATTT GACCCAAAAG   3060

GCATTTATT AGCAATTATT GAGTCAGGCA CTATACTGAT TACATACACT CATTCCTTTA   3120
```

```
ATCTTCACAA TAGTCTTTTT TTTTTTTTTT TTTTTTTTAA ATTAGATGGA GTCTTGCTCT    3180

CTCACCCAGG CTGGAGTGCA GTGGCACAAT CTCGGCTCAC TGCAACATTC GCCTCCCGGG    3240

TTCAAGTGAT TCTCCTGCCT CAACCTGCCT GGGGCTACAG GCGAGTGCCA CCAGGCCTGG    3300

CTAATTTTTG TATTTTTAGT AGAGGTGGGG TTTCACTATG TTGGCCAGGA TGATCTCGAA    3360

CTCCTGACCT CAAGTAATCC ATCTGCCTTG GCCTCCCAAA GTGCTGGGAT TACAGGTATG    3420

AGCCACCACG CCCGGCCACA CAATAGTTCT TTATGATAGA TAGTATCATT ATTGACCATG    3480

TTATAAGCAA ACTGAGGTTC AGAGAATTTA AACTAATTTG CCCAAAGTTA TCCAGTTTAA    3540

AAGTAATAAC ACTGTGATTT GAGCCTAGAT GTATCTGACT TCAAAGCATT ACACTCTTGA    3600

TGTGGTATAT ACTGTCTTTC AAAACTAGAA GAATAATGGA AGCTGACCTA AAACAAAGAA    3660

ATGCCTAGCT GTCTGGTAAC AATGCAGGTA GACAGACCAG CAACAATATT TTGTGCCAAA    3720

AATCAGTCTC ATCTAAAAAT GTGATAGCAC TTTAAAGAGT CCTTTCATGC AATTGTGAAA    3780

ACAAATTCAA ATGTTCTGGG GTATTAGATG AAAGTAAGCA GTAGCACATT CCCTTGTTCC    3840

TAATAAGGAA CAACAAGCAT AGTACCCCAT AGTAGAACCT TGGTAAGTCA CACCAGCTAC    3900

AGTGGTACAT TAGATTGCTT TAGCAACAAA GGACATTTAT AACCATGTCA TTTTAGTCAC    3960

CTTTAACTGC CTATAATAAT GCCTTTAGTA GATACATATT CAGTTGTCTC GGTATCTCTG    4020

GGAGGGATTG GTTCCAGGAT CCCCCGATAA ACAGATACC  GAAATCTAGG ATGCTCAAGT    4080

CCCTTATATA AAATGGCATA TCTAGTGTTT ACATATAGCC TATCCATATC CTCTGATATA    4140

CTTTAATCTC TAGATTGCTT TTGATATTAA TATGTAAATG ATACGTAGTT TTTATATTGT    4200

ATTATTTTAA ATTTGTATTT TTTTATTGTA CTATTACTTT TTATTTTTTT TCCCCAATAT    4260

TTTTGATCCA TGGTTAGTTG AATCCGTAGA TGTGGACCCT GTGGATAAAT TGTATGTTTA    4320

TATTATTTCC AGGAAAAATG AAAGTAGCCT TACTTTGTGA CTGTTAAAAA AGAAAAAAAA    4380

AACTCTAAAA ATAGTCACGC ATAGAGGGGC AGGATTGGAT ATGAACATTA AGCATGTGAG    4440

AGAAATCCTT GATTTCCCTC TCTCATCTAC CAGTCCCTGG CCTTTACTGT TGGTGCAAGA    4500

TATTGCCACA GGTCTGTCCA TCTCTCTCAC TTCCCATGTC ACTGAGTTTA GCTTAGCTGC    4560

AAGGGCTATT GCAGGAGGGT CCCAGCTCCC TCTTTGAGAA ATCCTTACTC CAAATTCAGA    4620

ATAAGTTTTC TATACACATG ATTTGTGGGC CAAATCACCC TTCTTTCTGC AGGAAATTTT    4680

TTTTCCTCTA AATTCCAAAG AATCAACTTA AAAACTGTTT TCTAATGATT GTCTCTTGAC    4740

AACATAGTTC ATTTTAATCA CCAGGAAAAC CACTGAAATA ATTTTGTTGT TGTTGCTGCT    4800

GCTGCTAAGT GTTATTGAGT CTCTTTTGAA GGACAAAACT ACTCAACAAG AACAGCCAAT    4860

TTTTTGAAAT TTCATTTCGG TGGCTAAGGA GGTACCAAGT TCATAGATAT ATGCTACTAT    4920

TGTGGCACTT CTTACTGCCT TGAGTGATTA CAATTTGTCA ACCTAAAGGT AGAAGTTGCA    4980

GGTAACATAT ACCTAACAGG TTCTAATGGT CTTGGTACAT GTTGGGAGAC AGAACTAGGA    5040

CGAAAAAGTT GGGGAAGACT TCAGTAGTAG TATTGATCTC TTATAATCTT TCAGGTCAGT    5100

AGGCTTTATC ATGGGGTTCC TATGCAAAAT GATCCACTGG GGATGTAGGT ATTAAAATAT    5160

CTAGTTATAT TTTTAATTTC ACCATTTAAA ATGTCTGTTT TGTATGTTTT TAATACTTTA    5220

TAAGTAAATA AGTACACAGA TATATGCTCA AATCTTTATG AGACTCCCCA TCAAACAGTA    5280

GACCTGGTTT TTAGATTATG GTTGTGAAAG AGCAGTAAAA GCTGCGCTAC AGGAGGTATT    5340

ACACTTGTCA CTGTGGATGG GGATGGGCCA TCCAGATTGC CCCAGACCTG TAGATTCCTT    5400

CACACTGGCT TATTCTCCCT CTGTTGAATT TCACATGATT CTAAGTAAGA CAGAAATGGC    5460

ACTTGCTGTC ACCAGTTGCC TGTTACAGAT TTCATGTTAG TAACTTGGTT ATTTTTGTTA    5520
```

ACTAATTTAA TGTTTACCTT TAG                                          5543

(2) INFORMATION FOR SEQ ID NO:102:

(i) SEQUENCE CHARACTERISTICS:
        (A) LENGTH: 128 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 20 OF RAD50 GENOMIC SEQUENCE (xi) SEQUENCE DESCRIPTION: SEQ ID NO:102:

ATACAAGAAA GGTGGCTACA AGATAACCTT ACTTTAAGAA AAAGAAATGA GGAACTAAAA    60

GAAGTTGAAG AAGAAAGAAA ACAACATTTG AAGGAAATGG GTCAAATGCA GGTTTTGCAA   120

ATGAAAAG                                                          128

(2) INFORMATION FOR SEQ ID NO:103:

(i) SEQUENCE CHARACTERISTICS:
        (A) LENGTH: 1939 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: INTRON 20 OF RAD50 GENOMIC SEQUENCE (xi) SEQUENCE DESCRIPTION: SEQ ID NO:103:

GTATGCTTTT AAAATAATCT TCAGTTTAAA TAAACGTCTT TATTACTGGA ATGTGAAGAA    60

TATTAAATAC CTGTTTTAAA AGAATTTTAG CCTCAGCCTG GTATCCTTTG AGAGTTACTA   120

GAAGGTGAAC AGTGTTTGGA TACAATTATA TTTCATGGCC TTAAGAACTT TATTACTGAA   180

GAAGTGATAT AGAATTGGTA ATCACACTGT AGTGATGGGC CTTAGTTATT CAGTATTGAA   240

CATGCTTAGC CCCCATACAT CTGCTAGCCT GCTGCACAGA ATAGTGGTAC TAAGCATAAA   300

GAATATGGAG CTGTGGACCT TGTCTGGGTC AGAGCTTGTA CAGTCTATAA TATTGTCAAT   360

GGAGTTGTTG CCAGAGTGAT TTATCCACAG AGATTCATTT TAGATTTTCT CATTTGTAAT   420

TATGTGTCCA CCAGAGCATT TCTTTTGAAA GATGAGCCTC ATTCTTCCTT TATCTGGTCT   480

TATTGTTACT TATTGTAGTT GCTACCTTCC TGGTACAGCA GAAAAGATTT TATTCCTGCC   540

TTGACTGCCT TAGAGTTAGT TGCCTTAGGA ATTCTGTAAG AACCTTGTTG ATGCTAAGGC   600

ACTAGACTGG TATAAAAGGT TGTACTAGGC AAATACTTAG ATTGTCAACC ACCTCAGCTG   660

GTTAAATCCA GGCCTCTCAT TTATTAAACC CTTCCTTGTA GAGTTTTCAT GTCTTCTTGA   720

ATTTATACAG AAATCTGAAT GAAAAATGC CCAGGCTTTT CTAAAGGATA TAGTAAAGTG    780

AATTTTAATT TATAAAGCCT AACAAATGGT TAATCCTGTG TTTTGGTTAA GTACTCTTAG   840

CTATTTAAAA TCTCTTTCCT ATATCAGGGA AATCAGATTT TTAACTAGAA GAGCTCATCA   900

TCTTCAGAGT CTTCATTTTT GTATGCATTA TGCACACTTA GACCCAGAAA AATCACAGAG   960

-continued

```
GAAATTATGA TGAAAGCCAA GAATGTGACC CTAATATCCT AGTTCCCAAG CCTCAGTTCT      1020

TTTACACGAT ACTCTCCATG GCAAGTTGGA AAAGTAATGC TTCTAGAAGA AATTTTGATA      1080

TAAAATAATA TATTCGTGGC TACTAAAGAC CAAAACCAGA TATTTAAAAA ATTTCTTCTG      1140

TAATTGGTAC ATAACAGTAC TTTTTACATT CATTCACATT ACTAAGTACA ACTATTTTTC      1200

AAACGTTTCT TCAACCAGGA CATAACAGAA ATGCCAACAA GACTTGTAAT CCAGTCGACT      1260

CTGTAAGGAT GCCCATAAGC TTGAGAGTAG TGCCTGACAC ATAAGAGGAT GCTTAATAAG      1320

TGATAATAAA TAAATGAAGA TTTTTAAAGC ATACATTGAA ATTTGTATAA TCTGCCAAAA      1380

TATCAGAAAA GTTTGAATAT TTTACTTTTT TGGTCATTAT TATGGTTTTT ACACTTGTGC      1440

AAGAGAAATT TTGTTTTCAT GGAGGAATCT AAATTTTTAA TAAGTATTAC TGCAGAAAAT      1500

TAATATATGA TTTAATTCGT ATTGTGCCTT TGACATGAGC AAAATGATGA TGAAGCCTGT      1560

TATCCATAAC TTCTTAGTGT TGATAATTGT GCATTCTCAG TTCACAATCA GAAGATTGTG      1620

AATTTGTAAT ATTAATCACC AGAGTGCTTT ACTTAGCGTC TAAAGGCCAG GAACTTTATC      1680

AGTGATCACA TGCTATGAGG GTTCTGTAAT ACACAAAATT AGCTATTTAG CAACCTATGT      1740

GCGGCAGAGA TATGGAAGGA AGAGAGGGGT TTTCTTTAGT ACCAAAGCCC TAAATAATAA      1800

GCAAGGAGAG ACTCTGTTAT AATATACTGA TTGCTAAGGA GAATGATACT TAACCTATCT      1860

AAAGAAATCT ATGACTTTTC CACTTCAGGT TGTTAAAAGC TAAAAAATGG TCCTCATTTG      1920

TCATTTTTCT TTTTTACAG                                                  1939
```

(2) INFORMATION FOR SEQ ID NO:104:

(i) SEQUENCE CHARACTERISTICS:
        (A) LENGTH: 225 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 21 OF RAD50 GENOMIC SEQUENCE (xi) SEQUENCE DESCRIPTION: SEQ ID NO:104:

```
TGAACATCAG AAGTTGGAAG AGAACATAGA CAATATAAAA AGAAATCATA ATTTGGCATT        60

AGGGCGACAG AAAGGTTATG AAGAAGAAAT TATTCATTTT AAGAAAGAAC TTCGAGAACC       120

ACAATTTCGG GATGCTGAGG AAAAGTATAG AGAAATGATG ATTGTTATGA GGACAACAGA       180

ACTTGTGAAC AAGGATCTGG ATATTTATTA TAAGACTCTT GACCA                      225
```

(2) INFORMATION FOR SEQ ID NO:105:

(i) SEQUENCE CHARACTERISTICS:
        (A) LENGTH: 13158 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 5' END OF INTRON 21 OF RAD50 GENOMIC

SEQUENCE (xi) SEQUENCE DESCRIPTION: SEQ ID NO:105:

| | | | | | |
|---|---|---|---|---|---|
| GTAAGTATTA | GACTGGGGAT | TTTCTTATTG | CAGTTAATAT | TAACTAACAT | ACTTTAGTCA | 60
| TCTTTTCTCT | CATTTTTTTC | TTTTTTTCTT | TTTTATTTTT | TGAGACAGAG | TTTCACTCTT | 120
| GTTTCCCAGG | CTGGAGTGCA | ATGGCACGAT | CTCAGCTCAC | TGCAACCTCT | GCCTCCCGGG | 180
| TTCAAATGAT | TCTCCTGCCT | CATCCTCCCA | AGTAGCTGGT | ATTACAGGTG | CATGCCACCA | 240
| CGCTGGGCTA | ATCTTGTATT | TTTAGTAGAG | ACGGGGTTTC | TCCATGTAGG | TCAGGCTGGT | 300
| CTCGAACTCC | TGACCTGAGG | TGATCCACCC | GCCTCGGCCT | CCCAAAGTGC | TGGGATTACA | 360
| GGCATGAGCC | ACTGCGCCCA | GCCCCTCATT | TTTTCTCTTT | AAATATGGTA | TTTTATGTAT | 420
| ACCATGGATT | GGAAAATATA | TGTATGTATG | TATGTAAACA | CACACTAGCT | TAAGTTATGA | 480
| AGTTAAGATA | TAAAGCATAT | TAATATCTAC | GAGTATTCAT | GATACTACCT | CCCTCTAACC | 540
| AATCTACCAT | TATCACTGAT | TGGCATCCAC | TTAGATGCTC | CCTTCTTATC | TCAACCTTCT | 600
| GTCATCCCCA | TTCCCTATAA | CCAGTGACAA | AGATTTTTAC | TTTCTCTGCT | TTTTTAAAAA | 660
| ACAGTTTTAT | CATATATATG | TCATATTTTG | AGCTTTTTAA | AAATGATATG | ATATTCTAGG | 720
| ACTTGCTTTT | TTATTTGGAT | TTGCTTTTGT | TTATCCATGT | TGTTTATGGC | CGTAGTTGAT | 780
| TCATTTTCAC | TGATGTACAT | AATCTACTAT | GGGAATAGAC | CACAATGCAT | TCATTCTCCT | 840
| ACAGATGGAC | ATTTGGGGTT | TTTTTCCAGG | TCTTGTCATG | TCTTCTGGAG | GAAAGGTATA | 900
| AGGTTATATT | TGTGGGAGTG | CATTGTGGAG | TATGCTCAAT | TTTACAAAAT | AATATTGTTT | 960
| TCCAGAAATG | ACTACTGATT | TATACCACTA | GCAGTATATA | AGGGTTTATT | TGATGGATCC | 1020
| TCTGACATTG | GTTTTATAAA | TTTCTTAATG | TTTGCCAACC | TCATAGGTTT | AAAATGATGA | 1080
| ATCGTTGTTT | ATACATTATT | AGTCTTGTCT | TTTTGTGTGT | TTTGGGACAG | AGTCTCTCTT | 1140
| TGTCACCTAG | GCTAGAGTGC | AATGGTGCAA | TCATAGTTCA | GTGTAACCTC | AAACTCCTGG | 1200
| GCTCAGGCAT | TCCTCCCACT | TCGGCCTCCC | AAAGTGCTGG | GGTCACAGGT | GTGAGGCATT | 1260
| GTTCCTGGCC | CTATTGGTCT | TTTCTTATTG | ATTTAAATGT | GTTCTTTATC | TCTTCTGCAT | 1320
| TTCAATTCCT | TTTCAGTTAT | ATGTATTACA | AATGTCTTTT | CAAACATTAT | GCTTATCTTT | 1380
| TTTACTTAGC | ATCTTTTGAT | GACACTGGAT | TTGATTTTGA | GTTAGTTGAA | TTTAGCAGCC | 1440
| TTTTCTGGTT | AGCTCTTTGT | GTGTCTTGTT | AAGAAATCCT | TCCCTACTCC | TCTCTCTCTC | 1500
| TCTCTCTCTC | TCTCTCTACT | CCTCTCTCTC | TCTCTCTCTC | TCTATATATA | TATATATAAA | 1560
| GATATATATA | TATAAAGATA | TATATATATA | TAGAGAGAGA | GAGAGAGAGA | TATATCTTTT | 1620
| TTTTTTTTGA | GACGGAGTCT | CACTCAGTCG | CCCAGGCTGG | AGTGCAGTGG | CGCCATCTCG | 1680
| GCTCACTGCA | AGCTCTGCCT | CCCAGGTTCA | CGCCATTCTC | CTGCCTCAGC | CTCCTGAGTA | 1740
| GCTGGGACTA | CAGGCGCCCG | CCACTACGCC | CGGCTAATTT | TATTGCATTT | TTAGTAGAGA | 1800
| TGGGGTTTCA | CCGTGTTAGC | CAGGATGGTC | TCGATTTCCT | GACCTCGTGA | TCCACCTGTA | 1860
| TTGGCCTCCC | AAAGTGCTGG | GATTACAGGC | GTGAGCTGCC | ACGCCCTACT | TCTATATTTT | 1920
| TGTCTAAAAG | TTTTAAATTT | TGCCTTTCAC | ATGTAAGTAC | ATTTAAGTAT | TTAATTCTAA | 1980
| GTTGAATTTT | TTCCGTTATG | AATAACTGGT | TGTCTTGGCT | CTATTTATTG | TAGACTATCC | 2040
| TTCTCTCAGT | GACCTACAGT | GTCATTTCTG | TCATATATCA | GAATTCCCTA | TGTGCCTGGG | 2100
| TTGGCCTGGG | TTCTCTGTTC | TACTTAATTC | ATCACTTTGT | CTATCTCTGT | GCCATTTCTC | 2160
| TCACCATCTT | AATTACATAT | AGCAGAATTT | TCTTTATCCA | GTGTATGTCT | GTCTTTTAAC | 2220
| CAGTGAATTT | AGGCCTTTCA | TATTCATTCT | GATTACTCAA | TTGAGTTGGA | TTTATTTCTG | 2280

```
CCATCTTTTT TTCCTTTCCT GCCTTTTTGA GATGGATTTA TTTTTCTTGA CTCCTCCTTT      2340

TTCCCTTCTT TGGGTTATCC AGTTGACCAT ATAACATGGG GATTAGGGAC ACTAAGCCCC      2400

CCACGCAGTC AGAAATCCAC ATATAACTTT TGATTCCCTC AGAACTTAAC TACTAATAGC      2460

CTACTGTTGA CTGGAAGCCT TACTGATAAC AGAAACAGTT GATTAACATA TATTTTGTAT      2520

GTTATGTGTA TTATATGCAG TATTCTTTCA CAATAAAGTA AACTGGAGAC AAGAAAAAAT      2580

TATAAGGGAA AATATATTTT CTGTTAAGTG GAAATGAATC ATCATAAAGG TCTTCATCCT      2640

TGTCCTCTTC ACATTGAAGA GGAGGAGGAA GAAGAGGAGG GGTCAGTCTT GCTGTCTCGG      2700

ATGGCAGAGG TGGAAGAAAA TCTACATAAA CATAGACCCA CATGGTTCAA ACCTGTGTTC      2760

AAGGATCGGT TGTATTCTAC TTTAGTTATT TGAGTGTTTA CTTTTTAATT TTTAAATACT      2820

TATTTGACTT AAAATCATAT GCATTAGTTC TCAAAGTGGT CGTGGAGCAC CATTATCAGT      2880

ATCACCTTGG AACATGTTAG AAATGCCTCT CAGCTTCTAC CCCAGACCTC GATCAAAAAT      2940

TTGAGAGGTA GGGCCCAGCA GTCTATTTTT GACAGACATT TTGGGTGATT CTGATGCACA      3000

TCAAAGTTTA AAAACCATAG CTTTAATGTG AATTGTTTTA TCTTTTTCCT GAATACTAAT      3060

TATCTTCTCT CATCTGCATT ATTTCTTTTG TCTAATATTT TAGTTTTACC TTGTTTTTAA      3120

ATCATCACAA ATGAGTAATA ATTATTGTGG TGGTTTCATA AGCCCGCATG TTTCCCAATT      3180

TCTTTGTTCA TTCTTGCTTT TTAAATCCCA CTCCTCCCTT CTTTAGGTTC AGTTTTCTTT      3240

TTTTGGAGTA TATTCTTCAA TAGTTTTTTC AGTGAATGAC TGTTAGTGGT AAACAATCAG      3300

TCTTTGAGAA GTTTTTCCCC TTAATTTGAT AGTTTAGCTG AGCATAGAGT TCTAGATTGA      3360

CAGTTTTGTT CTCTTGGCAC TTTGAAAATA TTTCATTTTT TGTTGGCCTC TATGGTTACA      3420

GTTGAGAAAT CATTTTAATT ATTCCTTTAA AAGTAATCTG CCTTTTTCCC CTGGTTCTCT      3480

TAGGATTTTT CCCTTTGTCT TCAGTGTTCT GTATTTTTAT AATAGTGTGT CTAGACTCAG      3540

CTTTAGTTCT TCTGCTCATA AATTATGCTT TTTGATCTGA GGATTGATAT CTTCCATCAA      3600

TTTTGGGGAT TTTTCATACA TTATCTCTTC AAATATTATT CTTTCTCCAT TTCTCACTAT      3660

TTTCCCCTTC TTCACTTTTT ATTAGACATA ACCTCCTCTT TCCTCTACAT TGCTTAACCC      3720

CTCTTGCATA TACTGGGCTC TGGGTAAATA TCTTGTTAAA TAAATTATTT AGCTGCTACT      3780

TATACTGCCT ATTGAGTTGT CATTTTTTCC TCCATTTTTT TCTATAAGTT CTATTTTGTT      3840

CTTTTTCAGA AACTCACATG GTTTTTTTAT AATTTTTTTT TTTAAAACA GAGTCTGGCT       3900

CTGTCGCCCA GGCTAGAGTG CAGTGGCATG ATCTCGGCTC ACTGCAGCCT CCACCTCCTG      3960

AGTTCAAGCA GTTCTCATTC CTCAGCCTCC CAGATAGCTG GAATTACAGA TGCATGCCAC      4020

CACTCGGCTA ATTTTTGTAT TTTTATTACA GATGGGGTTT TGTCATGTTG CCCCGGCTGG      4080

TCTTGAACTC CTGGCCTCAA GCGATCCTCC TGCCTAGGTC TCCCAAAATG CTAGGATTAC      4140

AGATGCGAGC CACTGCGCCA GGCCTATGAT GTATTTTCTT CCTTTGTATT TTGATTCCTT      4200

CTTGAATGTG TCTTTACTCA TTTTATACAC ATTTTATACC TAGGCCTCCC AAAGTGCTAG      4260

GATTACAGAT GTGAGCCACT GTGCCAGGCT TATGATGTAT TTTCTTCCTT AGTATTTTGA      4320

TTCCTTCTTG AATGTGTCTT TACTCATTTT AACTATACAC ATTTTATATT CTCTTTCAGA      4380

TTGTTATTTT TTAATTTCAC ATTTTGAGGA GTCTGCTTCT GCTGTTTTGT ATGTTGATTC      4440

TATCCCCTAG TGAAGTTTCT GTGTTTTATT AACATTTAAT TGTGTGCTTA TCTTTAGTAG      4500

TGTTGTTTTT TCTATGAGAC TCCCTTGTGA CCTTTCCTTG TAGAGGTCCA TCTACACAGA      4560

AATTTTGGTT TTATATTAAC TAAGAGCTCC AGAGAAAACA TTGGCCTGCA TGTAGGGTTT      4620

TTGTTAATTT CTTAGTTGGT AGGTTCCTAG ACTATACTCA CTGGTAGCAT AACTTTGAAC      4680
```

```
CCCAAAACTA TATAAAGCAT TTGCCCAAGA CTTTGAATTT TCAACTCATT AATTTTCCAC    4740

TCTTTCATTG AGGATTGATG TTATAGCTCT TGAAGAGTCC CATTTTTTGT GTGTTGGGAG    4800

TCACTTCTAA TCTTCTTCCT TACTTGGGTC CTATCCTTCA TCTTCTGTCC TGGATGATAA    4860

GAACCAATCC CTAGGTTATA AAAACAATAA CGCCAAGTTC ATGGCTGGGC ACGGTGGCTC    4920

ATGCCTGTAA GCCCAGCACT TTGGGAGACC GAGGTGGGCG GATCACTTGA GGTGAGGAGT    4980

TCAAGACCAG CCTGGCCAAC ATGGTGAAAC CCCGTCTGTA CTAAAAAAAA TACAAAAATT    5040

AGCTGGCTGT AGTGGTGCAC ACCTGTAATG CCAGCTACTC AGGAGGCTGA GGCAGGAGAA    5100

TCGCTTGAAC TGGGAAGTAG AGGTTGCAGT GAGCCAAGAT TGCACCACTG CACTCCAGCC    5160

TGGGCAACAG AACGAGACTC TGTCTCAAAA CTAACAATAA CAGTAATAAT AATAACCCCA    5220

AGTTTAGTTT GTCTGTCAGG TTACATACTG ACTGGTCTGG TTTTCACTTC TATCTTCGTT    5280

TCTATTATGT AGGGATTTCC CTTTCTTTCT TGTGAGCTCA ACTATGAATT TAAAATAAGT    5340

TTTGTTATAA GTCTATCTAG TAGTTCTGTT CATTTGTGGC AGGAGAATTA TTACTTACCT    5400

TAGATTTTGG TGGTGGTTGT TTTTTCCAGA ATGGCAAATA TCTTCCTTAG CACTAAGAGA    5460

GTTACACAGA GAGCTTCTCT TCTAAGACTT CTGGTCAGAT ACAGCATAGT CAACAGACCA    5520

ACCTGAGCAG TGGCATTCAG ACCACAGGGC TCAGGAAGAC AGGAGAACTC TGGTTTCAGT    5580

ATGAGGACTT TTTTAGTTAG TGATGATAAC AAAGGTGGTC CCAGAATTGC CTAGGCATAT    5640

TTTTGGCATA TACAAGTTTT AGGAAGTACG TAATCATGTA AGACAAATTA GATCCATTTA    5700

CTGTGAAATA TTGGGAGTGA GCCAATTAAC ATGTTATTTT TTAAAAATAA ATTATACTAA    5760

GATTTTGTT AGATTAAGTT TAACTTTTAA AACAATTTTT TGAGAGTATT CCATGGATAT    5820

ATCTTTTGTC CCATTTCATT GTGAGTGGGT ACGTTAACAT TACAATGTTC CCTGGGTCCA    5880

AAATGGCTCA TAGAATTATA TGCCTGCACC AAATGAGAAC TTTTGTTTTT TAACTTCTTT    5940

GAATATTGCC ATCTCTCCTA GATATTAGAT CCAGCAGTTT AAAGTGGTTA GTCTTGGAAT    6000

TTAAGGTGCT GAAACAAGAA CATAAGCAAA ACTTAAGGAA TTCTTGCCCA GTAGACTACA    6060

CATACATATA TTTGTTTTTT GTTTTTTGGT TTTTTTGCC TTTAATAATT CTTTTTAGTC    6120

TTCTCAGCTA CCTCATTTAT GCCTTTAGGG GACTTTTTAG TTTTTCTTAG TTCTTTAACA    6180

ACAGATGCTG TGTATCTAAT AGACTTATCA AACATTCATT GAGCATTAAG GAATAGGAGA    6240

TCCAGTAACT TCTAGCAAGG ATATTATAGT TTATTTGAAG AGACACAAAT CAAAACAGAT    6300

TTTTGTTGGT AAAAACCTAT TTGCCAGGC TTAGTGCTTA CGCCTGTAAT CCTAGCACTT    6360

TGGGAGTCCA AAGTGGGTGG ATTGCTTAAG TCCAGGAGTT TGAGACCAAC CTGGGCAACA    6420

TGGCGAAACC CCATCACTAC AAAAAAATAC AAAAATTATC TGGGCGTGGT AGCACACACC    6480

TGTAATCCCA GCTACTCAGA AGCCCGTGGC GGGTTGCAAT GAGCCAAGAT TGTGCCAGTG    6540

CACTCCAGCG TGGGTGACAG AAAGAGACCC TGTCTCAAAA AAAAAAAAA AAAAAAAATC    6600

ACCAAAACTT CTTTTTGGAA TAAGATAAGT TGGTTGTGAT GGAAAAATAA AAATGGATAT    6660

TAAAAGCAAG ACATTGGACT TTGTATAAAA GTCCAACATG ATAAGTTTTA CCTTTTTTAA    6720

AAAGCCTCAG AAGTCCATAA TACATGGTTA AAAGTGCTGT CTCTGAACAC TACAGATGTC    6780

CAGATTTTGA ATTCTTTTTT TTTTTTTTTG AGACGGAGTC TCGCTCTGTC GCCCAGGCTG    6840

GAGTGCAGTG GCGGGATCTC GGCTCACTGC AAGCTCCGCC TCCCGGGTTC ACGCCATTCT    6900

CCTGCCTCAG CCTCCCAAGT AGCTGGGACT ACAGGCGCCC GCCACTACGC CCGGCTAATT    6960

TTTTGTATTT TTAGTAGAGA CGGGGTTTCA CCGTTTTAGC CGGGATGGTC TCGATCTCCT    7020

GACCTCGTGA TCCGCCCGCC TCGGCCTCCC AAAGTGCTGG GATTACAGGC GTGAGCACCG    7080
```

```
CGCCCGGCCG AATTCTTTTT TTTAAAAAAA GTTTTATTCT TATTTTTTAT GGCTATATAG    7140

CCGGTATATT TATGTGGTAC GTGAGATATT TTGATGCAGG CATACAATGC ATAATAATCA    7200

CATCAGGGTA AATGAGGTTT CCATCACCTC AAGCATTTAT CCTTCCTTTT GTTACAGACA    7260

TTCCAATTAT ACTATTTAGT TATTTTTAAA TGTACAATAC ATTGTTGACT GTAGTCACTC    7320

TGTTGTGCTA TAATATACTA GATCTTATTC TTACTATATT TTTGTACTTG TTAACCATCT    7380

CCACTGCCCT TCCTAGTCTC TGGTAACTAT CATCTCCACT ATCTCCATGA GTTCAATTGT    7440

TTTAATTTTT CACTCCCACA AATGAATGAG AACATGCAAA GTTTGTCTTT CTGTGCCTGG    7500

CTTATTTCAC CTAACATAAT GTCCTTCAGT TCCATCCATG TTATTCCAGA TGACAGGATC    7560

TCATTTTATT TTATGGCTGA ATAGCACTCC ATTGTATATA TGAACAACTT TTTTTTTTTT    7620

TTGAGACGGA GTCTCTGTCT CCCAGGCTGA AGTGCAGTGG TGTGATTTCA GCTCACTGCA    7680

ACCTCCACCT CAGCCTCCGA GTAGCTGGAA TTACAGGTTC CTGCCACCAC ACCTGGCTAA    7740

TTTTTGTATT TTTAGTAGAA ACAGGGTTTT GCCATGTAGG CCATATTGAT CTCGAACTCC    7800

TGACCTCAAA TGATCCACCC GCCTCAGCCT CCCACAGTGC TGGAATTAGA CGTGAGCCAC    7860

CGCGCCCGAG AGGAACCACA TTTTCTTTAT CCATTTATCT GTTGATGGAC ACTTAGGTTG    7920

CTTCCAAATC TTAGGTATTA TGAACAGTGC TGCAATAAAT ATGGGAGTGC AGATATCTCC    7980

TCAACCTAAT GATTTCATTT CCTTTGCGTA AATATCCAGT AAGTGGGATT GCAGAATCAT    8040

ATGGTAGTTC TGTCTTTAGT TTTTTTAGGA ACCTCCATAC TATTCTCCAT AGTGGTGATT    8100

TTGAGTCCTG ACTGAAGATA TTTAGCAAAT TATTTAGACA CTCTGAGTTT CCGTTTCCTC    8160

ATCTATAAAA TAGAATTTTT AAAAATCTAT ACTATTATTC AGTATAGAGT CAGAAAAGCT    8220

CAGAGGCGAT TTAGTCCAGC TTCCTTTGTC ATGTTCCATT CTTTAATGTA AGTTAAGTTC    8280

TTAAATTCTC TATTCTTTAA TAGCACTAAA GAACTAAATT CATTAAGAAA ACGTAGGTTT    8340

CTGTTCCCAT TTAAACATTC TTTGAGGTTG AGGGCTGTGC ATAGAAGACA ATAATAGCAA    8400

TTGAATACTA CATGATAGCA TAATCGATTT AATTATTGTA TCTAACTCTG TTTTAAAGGG    8460

CAAGTATTTA TCAGACAGAT TAAGCAGGCT ACCCAAGATT ACCCAGGTAA ATGGTAGAGA    8520

TAAAATTAGA TATCAGAACC ACTGTGACAT GCTGCTACCA TAGTGGCCCC CTGCTTTTTT    8580

TTTTATTTTT CTGGAGACGG AGTCTCACTG GTTCTCTCAG CTCTCTCAGG CTGGAGTGCA    8640

GTGGCGTGAT CTCTGCTCAC TGTAACCTCT GCCTCTTGGG TTCAAGCGAT TCTCATGCCT    8700

CAGCCTTCTA AGTAGCTGGG ATTACAGGCA TGTGCTACCA CACTGGGCTA ATTTTTGTAT    8760

TTTTAGTAGA AACGAGGTTT CGCCATGATG ACCAGGCTAG TTTTGAACTC CTGGCCTCAA    8820

GTGATCCACC CTCCTCAGCC TCCCAAAGTG CTGGGATTAC GGGCATGACC TTTTTTTATA    8880

ACCGTTAAAA AACTAGTATT TATATAAAAG CATTTTAACT GTTACTTATA CTTCCTGGTT    8940

TAGAACCATA ACTTATTTCT ATATATTTTG TAACTCTTCA GTGAGGTGCT TGTGTACATA    9000

ATACATAGTT GTATATTAGG ATTTTGTTCA ATAAAAATTT GAGTACATAA ATGCTTGATA    9060

CTGTTCTAGA TACTAAGTAT ATAAGGATGA AGAAACAAAA TTAAGAAATA AATTAATAAC    9120

AAAATGGGTA GTAGTGGTAG GTATTACAGT GAAAATGAAC AATGTGAGCA TAACAGATGG    9180

GCCTTTAAGC TGGGACCTGA TTGATGAGAA GGGAGCAAGA TATGCAAAAA ATGGGGTGCA    9240

GGCGTTCCAG GTAGAGAGAA TAGTTACTGC AGCAGCCAAG ACCAGTACGA ACAGAAAGTG    9300

TTCAAGGACC AGGAAGAAGG CAAGCATGGG TGGAATATAG TCAGGGATAG ACCATTCCCA    9360

GAGTATGTCA TGCCTTGTAG CCTTGGTAAA CAAACAGTTT TATTTCATTC TAACTGCATT    9420

GGGCAGTCAC TGGAGGGTTT GAAGCAGGGA AGTAATATAA TCTGATTTCT AGTTGGAAGA    9480
```

```
AATTGCACTG GCTGCTGGGT GTGGAGAATG GATTGTAAAG GGCAAGAGTA AAAGCAGAGA    9540

CTGATGAGGA GACTTGTAGT AACCAAGAGA TGGTGGTGGG CTAGATCAGG TGGTAGCAGT    9600

GAAAATGGAG AGAAGTGATA GACTTGGGAT TTGTTCTGGA GAGAGAGTTG ACAGGCCTTG    9660

CTTCTGAATT GAGTGTAAGG GAGGGAAAGT AAAATAACCA AAGGTTGCTC CTACATATTT    9720

TTGCTTGAAC AACAGGATAT TGGGAGAACA GGTTGCCATT CCCTAAAATG GGTGGGACTG    9780

GGGAGAGAAA ATCAGTAGTT CCGTTTTGTA CACTTTAAGT TTGAAGTGCC TGTAGATATC    9840

TAAGCAGAGC TGTCAAGCAG GCAGTTGGAT ATATAACCTC GAGCCTAGAG TTCAAGTGAA    9900

AGGTGTACAC TGGGGAGTCA TCAGCATATC CACGGCATTT AACCCATGAG ATGAGATCAC    9960

ATGTGGAATG AGCATAGAGA GAGAAGGGAA AGGTCCCACC ACTAGTTATG TTTGCAAATC   10020

CAGTAAATAA GCAGCTGGTG ATGTGGGAAA AGATTTTAAA AGATGTGGTA TCTTGAAAAC   10080

CAAGTGAAGC AAATATATCA AGAATCTAAT GCTATTTGGA GTCAAATAAG ATAAGGACTA   10140

AGAAGTGGCC CTTAAATTTG ACAAAATGGA AGTTGTTAAT GACTGAGGAG CAGTCAGTGG   10200

CACAGTTGGA ACTGAAGCCC GGTCAAGTTG GGTGGGGAGA GAATGGGTAG TAAGAAATGG   10260

AGACAGCAGC CGGGCACGGT GGCTCACACC TGTAATCCCA GCACTTTGGG AGGCCAGGGC   10320

GGGTGGATCA CCTGAAGTCA GGAGTTCGAG ACCAGCCTGA CCAACATGGG GAAACCACGT   10380

CTCTACTAAA AATGCAAAAA TTAGCTGGGC CTGGTGGTGC CTAGCCTGTA ATCCCAGCTA   10440

CTCAGGAGGC TGAGGCAGGA GAATCGCCTG AACCCGGGAG GCGGAGGTTG CAGTGAGCCA   10500

AGATCGTGCC ATTGTACTCC AGCCTGGGCA ACAAGAGAAA AAAACTGTCT CAGAAAAAAA   10560

AAAGAAAAAG AAATGGAGAC AGAGAATATA GATAATTCTT ATAACAACTT CTCCTGTGAC   10620

GGGGAGCAAG AAAAATGGGG CAATGGTTAG AGTGGACCAG GGACCAAGTT AAATAGGCAG   10680

GTTGGTTTTG TTTTCAATTT TACTTGTAAG TATTTTGCTG CAAGGTCAGC TCTTCTCTTA   10740

CAGCCCATTG ACCTGCAGAC CTGGGGTTTC ATATGTATTC ACTGAATAGA AAAACATACG   10800

TAGGAGCTCT CCAGCTATCC CTGCATACCC TGAGAACCAG TGGCAGCAGG AATAAGAATT   10860

CCCTTCACTT CCAAGATTAG GCTATAAGAG AAAAAATAAA AAAGAATTCA ACAACCCTTG   10920

CTCTGCCACT TTCTTGTCAG GCTCTGGGAA AACAGGAATA TCTTTCCCTG TCCCTCCTCC   10980

AAACTGCTGA CAGTCTGTCT GATGGAGACC TTGGTAGGTG CTCCATAGTC TGTTTTTGAC   11040

CTGGGCCTGG GATAAGAAGG AAGGGCTTTT CAGCAGAGAA AAGTGCCTCA GTCACAGAGG   11100

CATGCTGAGC AGAATGAGGA CCTATGAGGG AGCTTGGTGG AGCCTGGCGG GGTGGAGAGG   11160

TACAGGAGTG CTTTCTAGCA ATTTAGGCTT GTTAAGGAAC AAAGCCAGGC TGTTTACTGA   11220

GTTCTCTTAC CTGGTACTCA GATGGATTCT TCTAAATGAA AAGAGGTGAT ACAAATTTCC   11280

CCAAAATTGA GTCTTTGTGG CTTATGCTCG CAAACAGTGG CCTTCTCAAG ATTTATACGG   11340

TGAGCCCTAA ATTTGCCTTC TCACCCAGAA GAAAGTAAGG TACAAAATTT CCCTCATTCT   11400

TTCACGTCTT AGAATAAAGC ATGCAGTCAG TGTAATTGTT GCGTTCAGCT GTCTATTTAA   11460

GGTAACACAG GAAGTCAGCA GTGCATTTTC AAGAAAAGCT GATTACCATC TGTTATTAGT   11520

AATCATCTAA AAACATCACT AAGATAAGCA TTGGCAGTGG TCAGAGACAC ATAGATGAAA   11580

AGGGGGAAAT TATCCATCAT TTGGAATGTA TTACCCCATA CTAATACAAT ATACCAATTT   11640

AAATGATGTT AGAATATATC ACTCAAGATA TGGTGTTCTA CCCCATGCCC AAAATGTTCT   11700

ACTCTCATTT TTCCCCAGAT GTGGAAGGTT GCATATTAGG TAATACTTTT TTTTTTTTTT   11760

TTGAGACAGA GTTTCGCTCT TTTTGCCCAG GCTGGACTCC AATGGTGCGA TCTCAGCTCA   11820

CTGCCATCTC CACCTCCCGG GTTCAAGCAA TTCTTCTGCC TCGGCCTCCC AAGTAGCTGG   11880
```

```
GATTACAGGC GCCTGCCACC ACACCCGGCT AATTTTTTGT ATTTTAAGTA GAGACGGGGT    11940

TTCACCATGT TGGCCAGGAT GGTCTTGATC TCTTGACCTT GTGATCCACC TGCCTTGGCC    12000

TCCCAAAGTG CTGGGATTAC AAGCATGAGC CACGCACCTG GCCAGGTCAT GCTTCTTTTA    12060

AGACTCATTG TAAACACGTA ACCTTTACAG TTTTGCATCC AAGGTAGCCA GCTTTCTGTG    12120

AGGCTCTTCA GAGCCTGGGT CCCTGCATTC GAGGGGAGCT TCAGATGAGG GCTTTATTCA    12180

GGGCTCACCT TAGAGTCACC ATCTCTATCA TGACCATGGA TGCAGTAAGG TTTCACAGTA    12240

GCTCCTGCAA CCTCAAGAGG GTAGATTACA AAACCCAAAG ATAGCCAGTG GTGTTTCACA    12300

CCTAAACAAA TGTTTATCTT GCCATAGTGA TTGAACCATA GGCTGAATTG TAAAAGCTGA    12360

TGTTTGGGAG TCTAGCTAAA GAAAACTAAG TTAATAGGTT TAAAGAAGCA AGAGCTGGAA    12420

GGGTCTTCTC CTGGAAGGTG AGATATTGGT CTGTGGGGTG TCCAAGGGAG AGAATCCAGT    12480

CATGGGTTCT TAGCTTCTCT TTCTGGTTGG ACCAGTAAAG CCTCTTCCTC ATCCCTCTTT    12540

TCTGCTCATC ACTAGAGACA AAACTAAAAA CCATGGCTTC AGTCTGCTAA AAGCCTAGAA    12600

CAAAACAGAA CAACAAAATA AGGCAGGCTG GACAAGCTTG TTAAGACTTT CATGGATTAC    12660

CAGAAATATA AATGCCATTA AAGCCATCAT TTTTCCTCAT AAAATGCAAT CGATTGTTAC    12720

TGAAATTTTT AATGAAATCT TTCAGACTCT TAATGAGTAT TTAAATATCA GACTAAAGTA    12780

ATTTATAAAT CATTATTTTC TGAGCTCCGA GAGAGTCTCA CTTTTTTTTT TTTTTTTTTT    12840

TAAGACAGAG TCTGGCTCTG TCACCCAGGC TGGAGTTCAT TCTTGCAAAC TCGGCTCACT    12900

GTAACCTCCA CCTCCCAGGT TCAAGCGATC CTCCTGCCTC AGCCTCCCAA ATAGCTGGGA    12960

TTACAGGTGC CCACCACCAC ACCGGCTAAT TTTTGTATTT TTAGTAGAGA TAGAGTTTTA    13020

CCATGTTGGC CAGGGTGGTC TCTAACATCT GACCTCAAGT GATTTACCCA CCTTGGCCTC    13080

CCAAAGTGCT GGGATTACAG GCGTGAGCAC CTCACCTGGC CTCTCACTTT AAGAGCCAGT    13140

TTTCACAAAG AAATCATA                                                  13158
```

(2) INFORMATION FOR SEQ ID NO:106:

(i) SEQUENCE CHARACTERISTICS:
        (A) LENGTH: 230 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 3' END OF INTRON 21 OF RAD50 GENOMIC
            SEQUENCE (xi) SEQUENCE DESCRIPTION: SEQ ID NO:106:

```
CCTGGAGCAC TAGAAATAAG CCTGCCAATT TCAGTATTA GCCAAGCAGC AAAGTTTTGC      60

TGCTGTTTAT TTTTGTAGCT CTTACTATAT TCTACTTTTA CCATTGAAAA TATTGAGGAA    120

GTTATTTATA TTTCTATTTT TTATATATTA TATATTTTAT GTATTTAAT ATTACTATTA    180

CACATAATTA TTTTTTATAT ATATGAAGTA CCAATGACTT CCTTTTCCAG               230
```

(2) INFORMATION FOR SEQ ID NO:107:

(i) SEQUENCE CHARACTERISTICS:
        (A) LENGTH: 86 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (C) INDIVIDUAL ISOLATE: EXON 22 OF RAD50 GENOMIC SEQUENCE (xi) SEQUENCE DESCRIPTION: SEQ ID NO:107:

AGCAATAATG AAATTTCACA GTATGAAAAT GGAAGAAATC AATAAAATTA TACGTGACCT        60

GTGGCGAAGT ACCTATCGTG GACAAG                                           86

(2) INFORMATION FOR SEQ ID NO:108:

(i) SEQUENCE CHARACTERISTICS:
          (A) LENGTH: 233 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (C) INDIVIDUAL ISOLATE: 5' END OF INTRON 22 OF RAD50 GENOMIC
               SEQUENCE (xi) SEQUENCE DESCRIPTION: SEQ ID NO:108:

GTGAGTACCA TGGTGTATCA CAAATGCTCT TTCCAAAGCC CTCTCCGCAG CTCTTCCCCT        60

TATGACCTCT CATCATGCCA GCATTACCTC CCTGGACCCC TTTCTAAGCA TGTCTTTGAG      120

ATTTTCTAAG AATTCTTATC TTGGCAACAT CTTGTAGCAA GAAATGTAA AGTTTTCTGT      180

TCCAGAGCCT AACAGGACTT ACATATTTGA CTGCAGTAGG CATTATATTT AGC             233

(2) INFORMATION FOR SEQ ID NO:109:

(i) SEQUENCE CHARACTERISTICS:
          (A) LENGTH: 179 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (C) INDIVIDUAL ISOLATE: 3' END OF INTRON 22 OF RAD50 GENOMIC
               SEQUENCE (xi) SEQUENCE DESCRIPTION: SEQ ID NO:109:

TGGCCAGACC ACCAGGCTCT TGAATCCTCC CAGCCAGAGA AAGAGTTTCC ACACCAGCCA        60

TTGTTTTCCT CTGGTAATGT CAGCCTCATC TGTTGTTCCT AGGCTTACTT GATATGTTTG      120

TAAATGACAA AAGGCTACAG AGCATAGGTT CCTCTAAAAT ATTCTTCTTC CTGTGTCAG       179

(2) INFORMATION FOR SEQ ID NO:110:

(i) SEQUENCE CHARACTERISTICS:
          (A) LENGTH: 143 base pairs
          (B) TYPE: nucleic acid
          (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (C) INDIVIDUAL ISOLATE: EXON 23 OF RAD50 GENOMIC SEQUENCE (xi) SEQUENCE DESCRIPTION: SEQ ID NO:110:

ATATTGAATA CATAGAAATA CGGTCTGATG CCGATGAAAA TGTATCAGCT TCTGATAAAA      60

GGCGGAATTA TAACTACCGA GTGGTGATGC TGAAGGGAGA CACAGCCTTG GATATGCGAG     120

GACGATGCAG TGCTGGACAA AAG                                            143

(2) INFORMATION FOR SEQ ID NO:111:

(i) SEQUENCE CHARACTERISTICS:
          (A) LENGTH: 2448 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (C) INDIVIDUAL ISOLATE: INTRON 23 OF RAD50 GENOMIC SEQUENCE (xi) SEQUENCE DESCRIPTION: SEQ ID NO:111:

GCAGGTATCT CAAAAGCCTG GGGAGCCAAC TCACCCAAGT AACTGAAAGA GAGAAACAAA      60

CATCAGTGCA GTGGAAGCAC CCAAGGCTAC ACCTGAATGG TGGGAAGCTC TTTGCTGCTA     120

TATAAAATGA ATCAGGCTCA GCTACTATTA TTACACTCTC CTGAAGCTAA CCAACATTTC     180

CTGCAACATT ATGTAGACTT TTAAAAGAAG GGCCTGAAGC ATTCTCACAG GATAGGCTAA     240

ATGTAGAACA AGAAGCTGAA GACCCGTTAG AGTTTTCATG GCACTCCTTA TCAGAATAAG     300

GTCACTGTCT CATCAGTTAT AAGACATACC ACTATTTTAT GTGCCAGCAG GAATGAAAAA     360

ATGCAATTAT AACCATAAGA TGTTTCAGAA TCAATGACAT AATAGTATTG CAAACCAGAT     420

TCTAGCTTAA GCTAGAATGA ATATTCCAGT ATAGTAAGGA GTCTCATTAA GAAAGTAGCC     480

CCTCATAGAA CTAAGTCCCT ACCACAGCAT ACACAAAGAC TTAGCTGCTG GGTCAGGCCA     540

TCTGGCTTCA GGTAAGGCTC TGTGAGGACA GCCTACATTG GAAATCAGGA AGAGGAATGA     600

AGTTTTAAAG AATCAGGAAT ATGGCATCCT TGGGGAACAA GGCTGGATCC TTCACTGTGC     660

ACAGGTTTGT AACAAAGATG TCACAGATAC TTGAGCTTTC TGCTTTCAGA TCAAGGCAGA     720

AGATTACACT TGATAACACC TCTAGGCCCT TGACTTTTTT TAAATAAAAT TCTAAAATCA     780

TAGAAATAGA TGCTTACATT ATCTAACTCA TTTTCATAGT TTGCAGTTTT TGCTTAAAGA     840

ACATGCCATG CAGCTGGGCA TGGTGTCTCA CACCTGTAAT CGCAGCACTT TGGAAGGCCG     900

AGGCGGGCAG ATCACCTGAG GTCAGGAGTT CGAGACCAGC CTAACATGGT GAAACTCCGT     960

CTCTATTAAA AATACAAAAA TTAGCTGGGC ATGGTAGCAT GTGCCTGTAA TCCCAGCTAC    1020

TCGGGAGGCT GAGGCAGGAG AATTGCTTGA ACCTGGGAGG CGGAGGTTGC AGTGAGCCGA    1080

GATCGTGCCA TTGCACTCCA GCCCAGGCAA CAAGAGCGAA ACTCCGTCTC AAAAAAAAAA    1140

AAAAAAAGA ACATGCCATG CATATATGTA TTATGTTGTC AGCCTAGACA GCTGATCCCA     1200

ATTTAAAGCA TCTGCAGATT ACTGTCTAAA TCATAGTCTA CAAAAATGAC AAACTTGTGA    1260

-continued

```
TCTGTAATCA GTATCCCTAC GTGCTTTGAT GATTTTTAGT GGTAATTATA AATGAGAAAA    1320

TACAGAGTTT GAAACATGGT CTCTTTGAAT TAAAAATACT TTCAAAAATA TCTTGAGGAA    1380

AAAGATTTTT TGTAGCTATT CTGAGTTATG AAAATTAATT AGCAATAATT GTCTCCTTGG    1440

TGTGAGGGGA GAGAACAAAT AATGGAGGTG GGCCTCCAGC CTACCTAACA CTGGCTTTTG    1500

CTGAGGCTCT AGCAGCCAGC CAGGGGCTCT GCATGTGAGT GGGTGGTGGT AGAGTTGACA    1560

GCAGTTTGGA TTCAAAGACA GGAAGGAAAT GCCTGTCCCT CACAGGGCCA AGCTGTGGCC    1620

CTGTCTTCTG GCTTGCCTAG GCATTAAAGA AAAGACATAA ACTATTCTAA AATTACCAAC    1680

TCACTGATGT GTGCGCACCC ACCCACAAAC TGAGGGGGAA AGGGGACTTA CAGCTCACAC    1740

CAGAGTAGTT TATACTTCCT AGAATAGCCC TACTCTCTCA ATTCTGTGTG TCTTGTATCC    1800

TCAGATGGTT TCAGTGGGTC TGAGGGTTTT AGTATTAGGT TTCTAGTAAC CACGAAAATG    1860

CCTAACAGTT CCAGTTACTT GGATTTTCTA CAGGTAAGCT TAACTGAAAC CACATTTCTA    1920

TACTCCTGAT ACTTTGACCT AGGATTTTCT TTTTTATTCT CTCAGTCTCA GGATTATACA    1980

CAAGAATATG GAAATTTAAA GGTAGCAGAG AAAAAGTGAG AGGCTCTAGA AAACGTGTCG    2040

AAGTTTTCTA ACAGATCCCA TTATCAGGCA AATAGCCAGG TCAAGAATTT TTAAGGTTGC    2100

TCATCTTACA GGATTATTAA AATTACAGAT AAATGGCATT GTCTCTGTTT CTAGCCTTTG    2160

GTCTCAAGTT GGTTGTAGCT GATGTAATTT TTTATGTGAG AGCATCAGCG TTGTTCTGAG    2220

CATTTTGTTT TGTGGTGAAT GATAGGCTGA GATCATGCAG GTTCTCCTTC TGGAGGACAT    2280

AAGAATCTGG TCCCAGTGCT GGGCTCTCCC AGAGGGCAGT GCTTTACCTA ACAGTGAACC    2340

TGTGACGTTT CCCACTTTTC CCTGCTGAAA AGATCATGTC AGGACTGCTT GCCTGCCATG    2400

AGATGAGAAG GTCTGTGCTG GGCTTCTCAC ATAGGGGCTT TTTTCCAG              2448
```

(2) INFORMATION FOR SEQ ID NO:112:

(i) SEQUENCE CHARACTERISTICS:
        (A) LENGTH: 134 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 24 OF RAD50 GENOMIC SEQUENCE (xi) SEQUENCE DESCRIPTION: SEQ ID NO:112:

```
GTATTAGCCT CACTCATCAT TCGCCTGGCC CTGGCTGAAA CGTTCTGCCT CAACTGTGGC      60

ATCATTGCCT TGGATGAGCC AACAACAAAT CTTGACCGAG AAAACATTGA ATCTCTTGCA     120

CATGCTCTGG TTGA                                                        134
```

(2) INFORMATION FOR SEQ ID NO:113:

(i) SEQUENCE CHARACTERISTICS:
        (A) LENGTH: 1371 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (C) INDIVIDUAL ISOLATE: INTRON 24 OF RAD50 GENOMIC SEQUENCE (xi) SEQUENCE DESCRIPTION: SEQ ID NO:113:

```
GTAAGTATCT CTTGCACATG CTCTGGTTGA GTAAGTATCT CACATTTGGG GACAGGTTGT      60
GATAGTTCTT CAAAACCAAG AGAGTTCTGT GATGAAAACG TTCTCTAGCT GTGTTCCCCA     120
CTTCTTGGGG AAGCCAGTTG GTGCCAGGCC CTGGGCTTTA CCTTTTGATA GTAATTCTTC     180
AGATCCCTCC TAAAGGAACT AGATGGTGAA CAGCAGCCCC AGACACATCC TGCAGCTCCC     240
CAAGTGTGTT CACAGGGAGA GAGTCACTGT GAGGGGTTCC TGGCCTGGTT TTCCTGTAAA     300
CCTACCAGAG GAACCCACAT GTCATGCACA GCAATTAGCA TGCCCTGCTA AGACATCTGC     360
AGGTAGTGGT AGTGGGTTTA GGACTGTCTC CCCAGCTTTC CACATGTGTC AGAGAACTGT     420
GAGGAATGAC AGAGCTCTTA CTCAAAAAGC TTATTTGAGA TTAGGTAAAG TCCAGTGAGG     480
GTAAAATTGC ACACCTTTTA CCACATTCAC CTGGGGTCAG TGTAGACGCC AAGGTTGTCA     540
AGCAGCTCTT GCATAAGGAC TATGCTGGCA GAGAAAAAGG CAGTTTCCCT GAGGTCAAAG     600
GAGGTGTTTC AGGCACTCCT GGCTCCAGAC AGTCCCTTTC TGGCAGAGAG GGCCAGAAGG     660
AGAGCTCAGC AGCGCAGGGC CACCTTTCTG CAGCCATCAT CACAAGTAAG GGCGAGTGCT     720
TTTGAAACCT CAAATGCATC CAGCTCCAGG AAGGGGATAA GTGGCTAGCT AAAAGAAAAA     780
GTCTTTCAGG TTTCAGTCAC ATTGCTGGTT ACCTCAGCAA AATGTTCCCA GAACACCCAC     840
TCAGGTCCCT GTGTGTCATA GTAATGATGC ATCTAGTGAC TGGTGGTGGC AGAATTCTAA     900
GTAGACCCAG CTCTTAAGAA AGCAGTGTTA TTCCCCTTAC CTGTAGTTTG TCTTTATTAC     960
TTTTAAATTT TTCTTCCAGA GAAAAGTAGT AACAGGTCAG GAAAATCCCA GGCGAAGGAG    1020
TAAGCCTTCT ATAGTTGAAC AGTTTGGATA TTAAGGAAAA CTCAATAAAA TATTTATACC    1080
TGCTTTAGTG AGAACTTCTG ATCTGGAAGA AACTAGTTCT TGTATTCCTG TGAGTCCCTA    1140
AGCCAGACCT AAGTGAGGAG TCAGGCCATG TGTCCCTACT GTCTGGAGAG GAGAAGAGAC    1200
TCCTGCCTGG CTGCCTGAAG GCCTGGGGCC ACCCCTCCAC TTCCTGCAGG GTAGCTGGGG    1260
CCCTGACACA CAGCACAAGT TCATGTGTCT GACAAGGTTT GCGGTGACTT TTCAAATCAA    1320
AGAAGGGGTT ATGCTCTTTA CTAATAATAT GTTCTGAATA TATTGTTGCA G            1371
```

(2) INFORMATION FOR SEQ ID NO:114:

(i) SEQUENCE CHARACTERISTICS:
        (A) LENGTH: 1730 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EXON 25 OF RAD50 GENOMIC SEQUENCE (xi) SEQUENCE DESCRIPTION: SEQ ID NO:114:

```
GATAATAAAA AGTCGCTCAC AGCAGCGTAA CTTCCAGCTT CTGGTAATCA CTCATGATGA      60
AGATTTTGTG GAGCTTTTAG GACGTTCTGA ATATGTGGAG AAATTCTACA GGATTAAAAA     120
GAACATCGAT CAGTGCTCAG AGATTGTGAA ATGCAGTGTT AGCTCCCTGG GATTCAATGT     180
TCATTAAAAA TATCCAAGAT TTAAATGCCA TAGAAATGTA GGTCCTCAGA AAGTGTATAA     240
```

```
TAAGAAACTT ATTTCTCATA TCAACTTAGT CAATAAGAAA ATATATTCTT TCAAAGGAAC      300

ATTGTGTCTA GGATTTTGGA TGTTGAGAGG TTCTAAAATC ATGAAACTTG TTTCACTGAA      360

AATTGGACAG ATTGCCTGTT TCTGATTTGC TGCTCTTCAT CCCATTCCAG GCAGCCTCTG      420

TCAGGCCTTC AGGGTTCAGC AGTACAGCCG AGACTCGACT CTGTGCCTCC CTCCCCAGTG      480

CAAATGCATG CTTCTTCTCA AAGCACTGTT GAGAAGGAGA TAATTACTGC CTTGAAAATT      540

TATGGTTTTG GTATTTTTTT AAATCATAGT TAAATGTTAC CTCTGAATTT ACTTCCTTGC      600

ATGTGGTTTG AAAAACTGAG TATTAATATC TGAGGATGAC CAGAAATGGT GAGATGTATG      660

TTTGGCTCTG CTTTTAACTT TATAAATCCA GTGACCTCTC TCTCTGGGAC TTGGTTTCCC      720

CAACTAAAAT TTGAAGTAGT TGAATGGGGT CTCAAAGTTT GACAGGAACC TTAAGTAATC      780

ATCTAAGTCA GTACCCACCA CCTTCTTCTC CTACATATCC CTTCCAGATG GTCATCCAGA      840

CTCAGAGCTC TCTCTACAGA GAGGAAATTC TCCACTGTGC ACACCCACCT TTGGAAAGCT      900

CTGACCACTT GAGGCCTGAT CTGCCCATCG TGAAGAAGCC TGTAACACTC CTCTGCGTCT      960

ATCCTGTGTA GCATACTGGC TTCACCATCA ATCCTGATTC CTCTCTAAGT GGGCATTGCC     1020

ATGTGGAAGG CAAGCCAGGC TCACTCACAG AGTCAAGGCC TGCTCCCTGT AGGGTCCAAC     1080

CAGACCTGGA AGAACAGGCC TCTCCATTTG CTCTTCAGAT GCCACTTCTA AGAAAAGCCT     1140

AATCACAGTT TTTCCTGGAA TTGCCAGCTG ACATCTTGAA TCCTTCCATT CCACACAGAA     1200

TGCAACCAAG TCACACGCTT TTGAATTATG CTTTGTAGAG TTTTGTCATT CAGAGTCAGC     1260

CAGGACCATA CCGGGTCTTG ATTCAGTCAC ATGGCATGGT TTTGTGCCAT CTGTAGCTAT     1320

AATGAGCATG TTTGCCTAGA CAGCTTTTCT CAACTGGGTC CAGAAGAGAA TTAAGCCCTA     1380

AGGTCCTAAG GCATCTATCT GTGCTAGGTT AAATGGTTGG CCCCCAAAGA TAGACAGGTC     1440

CTGATTTCTA GAACCCGTGA CTGTTACTTT ATACAGCAAA GGAAACTTTG CAGATGTGAT     1500

TAAAGCTAAG GACCTTAAGA CAGAGTATCC TGGGGGTGGT GGTGGGGTGG GGGGGGGTCC     1560

TAAATGTAAT CACGAGTAAG ATTAAGAGCA AATCAATTCT AGTCATATAT TAAACATCCA     1620

CAATAACCAA GATATTTTTA TCCCAAGAAT GCAAGATTTC AGAAAATGAA AAATCTGTTG     1680

ATAAATCCAT CACTATAATA AAACCGAAGG TGAAAAAAAT TCTGAAAAAA              1730
```

(2) INFORMATION FOR SEQ ID NO:115:

(i) SEQUENCE CHARACTERISTICS:
        (A) LENGTH: 7705 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 3' END OF RAD50 GENOMIC SEQUENCE (xi) SEQUENCE DESCRIPTION: SEQ ID NO:115:

```
TTCTAGCAGC TATATTTGAT AAAATTCAAC ATCTCCTAGC TTTAGCAAAC TCACAGTTTT       60

GCAAATAATA TTTTCTTAAT GTTATCTGTT GCTAAATCAA AATTAAACAG TCATCTTAAC      120

TGCAAAATAA AACATTTCTC AGTAAATATT AAAGCCAGTT ACCTTCTATC AACATGTTAA      180

TGAAAGTGCT AGTTGTTGCA GCAAAGAATA ACAAAGGCAA TACACGATCA ATATAGGCAG      240

TGAAACAAAA GTATCATTTG CAAGTTAAAA CAGACTTCCC AATTTTAAAT CTGGTTTCCC      300
```

```
CCTGAATATG TGGCATCCTT GGCAGCACTT CTGAGAGTGG CTGCTTTCAT TCCAAGAAGC      360

CCATGGGTTT GGAGGTGGGA TAGGTGCCTT TCTGGCTTCT CATTGCTGCT TCTAGATCAG      420

TCTCCAAATA TCCCCCTTCC CCACATTGGA ATGAATAGCC ATCACAGCAT GGATGGAGGT      480

TAGAATGAGC CAGACTGCCT GGGCTCAAAT CCTAGCACAC CACTCACTAG CTGGGGACCT      540

TGAGCAAGTT ATTTGTCCTG TTTTCTGTTT CCTTATATGT AAAAGTGGGT AAAATGGTAC      600

ATATTTTGTA GGGTTGTTAT GAAGATTGAA TGACATTATT TACAAACTGC TTAGAACTGC      660

TTGCCACCTA CTAAATACTG TGTAAGTGTT CAAGAAAAAG CTGTCTTCAT TTCACTCTTG      720

TTGCAGTTAT CTTTCATTCC CAGCTTGGTC ACTCCCTCTT ATTTGTTGAA GAGTTTAGCT      780

CCCGGTTCAG TGTCACCCCA TTACTAATAA TCATTGCTGA TTTCAATATC CAAGTGATGG      840

TCTAATACAA CTCCTTGGCC TCTCAGTCTT TTTTATTTTT TGAGGTGGAG TCTTGCTCTG      900

TCACCCAGGC TGGAGTGCAA TGGCACCATC TCAGCTCACT GCAACCTCTG CCTCCCTGAT      960

ACAAGCAATC CTCCTGCCTC AGCCTCCCAA GTAGCTAGGA TTACAGGCAT GTACCACCAC     1020

ACCAGGCTAA TTTTTGTATT TTAGTAGAGA CAGGGTTTCG CCTTGTTGGC CAGGCTGGTC     1080

TTGAACGTCT GGCCTCAAGT GATCTGCCTA CCTTGGCCTC CCTCAGCCCC TTTTTGTTTC     1140

CTCCAGTGAG AAGATACTCA GTTCTATGGT CTTATTCTAG AGCCCCGTCC TTTTAATAAC     1200

AATAACTGCA CCCCTCCAAA ATCTCAGTTT TAAGCATCTC ACTCTCCAAT AACCCCATGG     1260

TGTCTACAAT TTTCCTGTGG TCCTCAACCC CAGCAATTCT TTGACCCCAC TGAGATTTCA     1320

ATCCATTGAT TCTATGGCTT TTTCACAGGT TGTTTCCCTG ATGCCTGTAC TTCTCTCCTT     1380

ATTCAACTTA AATTCCATGG CTCATCATTA TGTCACCCTC CACTGCATTG TACTCAAACT     1440

GTCCCGACAA TCCCCAGCCC TACTGGAATC CAGCTCTGCC TCCTCCCTGC AACACCTGCA     1500

CATCCCGTTT CCTTTGCTGT TTCCTCCTCA TTTCCCTGGC CCCTCAATGT CACAGGTTTT     1560

AGTACTCAGA GTCTGCACCT CTTTTCTTCT CTGTGCTCAC TTATTTGGTG ATCTCATCCA     1620

GTCTCATAGC TTTAAATTAT CTTAGTTTGG GTTCTCCCAG AAGCAGAGCG TAAAACAATG     1680

CTTCACGTGA AAGTAATCAG TAGGAAATTG GGGAAATTGT GTATGAAAGA GAAAGCAGCC     1740

AATGAAAAGT TTACTATTAA GCCAGCTACG GTAAGTGGGC AATTAGAGTT TGGTGCCCCA     1800

GGGAGACTCT GGGGAGTTTG GCAAAATATA TACCTCAGAA TTATCCCACC TAAGGGGCAA     1860

GAGACCTGGA GTATTTATAT AACAACTTGC CAGGGTTACT GAGTGAAGGC TATTCTAGCA     1920

CATGTTAGTT ACTGGCTTGC CATGTGTACC GACACAGCTG CTTTCCACAG TTTAAAAGA      1980

AAGTCTGAGC AACATAGTGA CATCCCATCT TTACATAAAA TTTTTAAAAA ATTAGCAAGG     2040

CATGGTGGTG CACACCTGTA GTCTCAGCTA CTTGGCTGAG ATAGGATCCC TGGAGTCTGA     2100

GGGTTCAAGG CTGCAGTGAG CTGTGATTTG TGCCACTGCA CCCCAGCCTG GGTGGGTGGC     2160

AGAGTGAGAC CCTGTCTAAA AAGACAAAAA AAAAAAAAA AAAAAAGCAG CAGCAGCTGA     2220

AAGTTGGCAG GAGCACACTG GCAGTTCCTA GGATCATAGG ATATAGGCAG GGCACTGACC     2280

ACTCCTACAA CCACCATCTA TACACTGATA ACTCATAAAT GTTTGTGTCC AATCCAGATC     2340

TCTCCTAAAT GCTTGACTGA TATATTCAGC TGCCTGTGGA TAACTGGGCA TCTATCTGCA     2400

CTTGAATATC TAATAAACGT CTAAAACTTA AAATGACCAA AACCAGTCTT TCTCCCAGAA     2460

CTTGAATCTC TTCTGTTAAT GGCAACTCCA TTATTCCAAT TGCTCAGGCA AAAATTGGCA     2520

TTATCCTTGA TTCTTTATCT TACATCTTAT ATCTAATTCG TCAGTTTAAT ACTATGGGTT     2580

CAATTTTCAA AACATCCGGA ATCTGACCAT GCCTCACCAT TTAAACCAGC AGTCCCCAAC     2640

CATTTTGGCA CCAGAGACCG ATTTAGTGGA AGACAATTTT TCCATGGACG GGTGGGGTGA     2700
```

```
GGGGGATGGT TTCGGGATGA AACTGTTCCA TCTCAGATCA TCAGGCATTA GTCAGATTCT    2760

CATAAGGAGC ACGCAACCTA GATCCCTCAC GTGCAAATTC ACAATAGAGT TTGCACTCCC    2820

GTGAGAATCT AATGCCACCA CCAATCTGAT AGGAGGTAGA GCTCAGGCGG TAATGCTCCC    2880

TCACCTGTCA CTCACCTCCT GTTGTGCGAC TCTGTTCCTA ACAGGCTGAG GACAGGTAAT    2940

GGTCTGCAGC CCGGGGGTTG GGGACCCCTG ATCTAAACCA TCATTGCTCT GGTCCAAGCC    3000

ACTGCCATCT CTAACCTGAA TAATCTGAGT AACCACGTAA CTGCTCCCAC TGATTTGGGG    3060

CCTGCTCCCT GTAGTTCTCA ACACAGCAGC CAGTGATCTT TTTAAAAAGT AACTCAAGAA    3120

AATGTGTTTC TCACAGGGGT GTGGGTTAGC AATTTCGAAA TTTTTATGTA CATACTAAAG    3180

TCAAACAAAT ACATACCTGT GTTGTAGATA ATACGAACTG AGTTTCTCAC TGTTGGAAAA    3240

AGGTGTTTGC ATATCAGGAA AGGAGGCCAT AAAAAGAACC CCTTGGTGTT GATTGAATCC    3300

AAAGGATCTG TACAAATTTA TAATTTTAAT ATCTAAAGGA TTTCTACTTC CATAAGGGTG    3360

GAGTAAAAGC CATCCAAAAT CTGCTTCTTC ATAAAAGCAA TAAGACTGGC AAAAATGTCA    3420

AAATCAACTT TTTCAGAACT TTGGAAATTA ACTAATGGAT AGCGACAAAC TGAGGTGTGT    3480

TTATTAAAGG AAAACAGCTG AATCTCAGAG CAGAAAGTGG CATTTTAAGT TGCCCTAATC    3540

CCATGCCCTT CTCTCTTAAT CCATGGTAAC TTGAAAACCA ACAGCCCTCT TAGTATCTGT    3600

GAAAATCAGC AACCTAGTAG CCACTGGAGG AGACAGAATA GATTTGGAGG TCCCCCAGAT    3660

CTCCACTACT AGAGAACTGC CTCTATTTGT CTTGTCTGGC AACTCACTGA AAAGCTCCAT    3720

TTTCAGGACC TATCTTTATT TGACTTAACT CAGAGCTCAC TCTGAAAACA GCCCTTCCTG    3780

CAGAATAATC AGTGGCAACT GATTAACCCT GTGGCTGCCT GAGGCAGCGT TACCAGGTGG    3840

AGCTAACAAA AGGCTGACCA AGAAACTTAA AAGGAAAAAT CTGGGAAGAA GATGTCCACG    3900

GGAGCTTTGA CAAGCTCAAG CATATTCCTG GGAATCTAGA AGTCCATGTG CATGTGCAGG    3960

GATGTATGCA TGTCCTGAGA GGGTCCTAAG CTCTCATCTC TGACTGACCT TGAAACTCAA    4020

TTCATGCCAG AAATGAAGAT AAAGGCAGTT GTAAACTGTC TGCTGACACA TCAATGACAT    4080

GACTCCACAA ATACACACAC ATGCACACAC TTGACAAAAG CTAGAAAATT TATTGGTTCA    4140

AGGCATTAGA AAGAAATATC TGTCCAATTA TTCGCTTACC CACTAGGCTG AGTAGAGACT    4200

TCAGGAACCA AACATGACAA AGCATATAGA ATTTGCAGAA TTAGTCCAGG AAAGACACAG    4260

AACAAACCAA CAGCAGCAAC AATAAGAAAT AGTAACAGGT GCAAGCCCTG GAGAGTAGGT    4320

AATCTGACTT CAATAATTGA TAGAGTATTT AAAACAAGAC ACACAAAGAA CAGGAACATC    4380

TGACCCATGC CATAAACAGC AATTTAAAAA ACAGTCAATA GAAACAATCT ATGAGGAAGC    4440

CCAGATGTTA GACTTACTAG GCAAAGACTT TAGATATCAG CTATTATAAA CATGTTCAAG    4500

GAACTAACAG AAACAAAGTC TAAAGAATTA AAGGAAATTA TGAGAATGAT GTTTCACCAA    4560

ATTATCAGGA CTATCAGTAA GGAGACAAAC ATTATAAAAA AGAATCAAAT AGATATTCTG    4620

GAGTTGAGAA ATACAGTAAT GGAAATAAAA ATTCACTAGA TGGGGGTCAA CAGCAAATTT    4680

GAACTGGCAG AAGAAAGAAT CAGTGAGTTC AAAGACCGGT CAATTGAGAT TATACAGTCT    4740

GAGGAATAGA CAGAAGAATG AAGAAAAATG AAGAGAGCTT CAGAGACCTT TGAGACACTA    4800

TCAAGTGTAC CAAAATGCCA AGTATACCAA TCATAATGAG AATCCCAGAA GAGAGAGAGA    4860

GAGAAAGGAG CAGAAAGACT ATTTGAAGAA ATAGTAGCCC AAAACTTCCC AAATTTTATG    4920

AAAACATTAA TCTTCGTATC CAAGAAATTG AACAAACTCC AAGTAGGGTA AACTCAAAGG    4980

GATTCACATT TAGATGCATC ATGGTCAAAT TGTTGAAAAA GAGATCTCAA ACGAAAGAAG    5040

CAAGTAAAGC TAAGAAGTGA CTTCTCTTAA GAAACAATGC AGGCCTGAAA GCAGTGAGAT    5100
```

-continued

```
GACATATTCA AAGTGCTGAA TGAAAAAGAC TATCAACCAA GAATTATTTT TGCAGTGGTG    5160

CAATCATAGC TCACTGTAGC TTCAAACTCC TGGGCTCAAG CAATTCTCTT TCCTCAGCCT    5220

CTCAAATAGG ACTACCAGCA TGTGCCACCA CACTCAAAAA AAAAAATTTT TTAAGAGACA    5280

GGGGGTCTTG CTGTCTTGCC CAGGCTGGTC TTAAACTCCT AGTCTTAAGC AGTCCTCCCA    5340

CCTTGGCCTC CCAAAGTGCT GGGATTAAGG TGTGGGCTAC TGTGCCCAGC CTCAATCAAG    5400

AATTCTGTAT CCAGAAAAAC TGTCCTTCAA AAACAAGAAA TGAAGACACT CCCATATAAA    5460

CAAACATTGT GATAATCTGT CTTCACCAGA CTTGCCCTAC AAGAAATATA AAGGAGAAT    5520

GAATCCTTTA GGGTAAAATG AAACTAGACT CAAATGCTCA TGAATACTCA AATAAAGAGT    5580

ACTGGTAAAG GTAAATATAT AGGTAATATA AAAGTATAAA TGTATTTTGG GGGCTGGGAG    5640

CAGTGGCTCA TGCCTGTAAT CCCAACACTT TGAGAGGCCG AGGTGGGCGG ATCACCTGAG    5700

GTCAGGAGTT TGAGACCAGC CTGCCCAACA TGGTGAAACC CTGTCTCTAC TAAAAATACA    5760

AAAAATCAGC CAGGCGTTGT GGTGGGCGCC TGTAATCCCA GCTACTCAGG AGGCTGAGGC    5820

AGGAGAATCT CTTGAACCCA GGAGGCGGAG GTTGCGGTGA GCTGAGATCA CGCCACTGCA    5880

CTCCAGCCTT GGTGACAAGA GCAAAACTCG GTCTCAAAAA AAAAAAAAAA GTATTTTGGG    5940

TTGTAACTCT TTTCCTACAT GATTGAAAGG GAACTGCATT AAGAATTTTA ACACTGTTGA    6000

TGGGCTTATA ATGTATAAAA ATATAATTTA TATGACAATA ATGCTACAAA AGAGAGAGGC    6060

AACAGAGCTA TATAGGAACT TTTGAAATGG AAATTAAGTT GACATTCATC TAAATTAAGG    6120

TGTTCATTTG TAATCCCCAG GGTAACCACT AAGAAAATAA TGAAAACTTA TAGTGAAAGT    6180

AACAAAGTTA TTTAAAGAGG GCCCAGTGTG ATGACACCCC AGTAATAATG AGGACACCTA    6240

CTTCCAAGAT CTCGATTTTA AAACACGCTC TTCAATAAAA AGAACTCTGG CTCCTTGGTG    6300

AAGTGGTTGA CTTCAGGGCT GAGGCAAGGA AAATACAAAA TGACCCTAGA ATTTTTTGTG    6360

GTGCCAGAAA TTAAGAAAAT ATTTTTTTTA AAAAAAAGG TAGAGTTTGT TCAAAGAACA     6420

CAGAACCCAA CCTGAAGTAA CTCCCAATGA TCAAAGGTAG AACAATTTGA GAAACAAAAT    6480

AAAGACAGTA TTGGATTATA ACCGATAGAG TAAAATAAAT ATTCATGAAC TTATGTGGCT    6540

ATACACAAGT ACTTACTTTA AAAAAAATGA GGGACAAGGA CAGCACTTCT TTATAGTAGA    6600

ATTACAAGTA ATAAATGTAG AAGGAAAGGG AAAAAGAAAA GTCATCACTA GGCAAATACC    6660

ACAATAAAAA TCATTTCAGA CAAGAGTCAC TGATGAAGCT AATATTAGTA GGCACAAATC    6720

TGAGAAAAAA TTTATATAAT CTCAAACTAT CTTTCCCAAT ATATTAACTA AAAGGGAAA    6780

GATAGTAATT TTATCATGGA AGAACCTGAC AGAAACCATC TTAACCAAGT GGTCAGGGTC    6840

AACATCACCA ATAAGAAGGC ATGTACCTCA TGAACCCTGT GACCTGATGC AGTGAGAAGG    6900

CCCCAACTTC ATCTCTGTGA AAATGTAGAA CCTCAGTGCA ATTAGGAGAA ACACCAAGG    6960

GGACCAAACT GAGGAACATT TGACAGCATA ACTCATCAGT ATTCCTGGAA AATGTAAGCG    7020

TTATGAAAGA CAAGACTGAG GAACCATTCA GACTGCAGGA GACCAAAGAG AATTAACTCA    7080

ATGCACTGTG AGATCCTGGG TTGATCTTGA AACTGAAAAA GGATGTGAAT GGAAACACTG    7140

GTGAGATTAG AATAGGATCC AGTTACTTA ATAAATCCAT GCTCATTTTT CTGTTTTTGA    7200

TCATTGCACT ATGATTATGT AATGTGTTAC CATTGGGAGA AGCTGGGTAA GTGGAGGGA    7260

TATGGAAACT GTCTGTACTA TTTTTGTATC TTTTCCGTAA ATATAACGTT AATTCAAATT    7320

TTTTTAAAAA AAGAAAAAAG GTAAATTGAG TCATGTCACT CCTCTGCTCA AAACCTCCAG    7380

TGGCTCCCTA TGTCACTCAT CATGAAATCC TCAGTCCTCT CAATGGCTTA CAAGTCTCCA    7440

TATGCTCTGG ACATACTTCT CTGACAGTAT CTTCTCCCAT GCCTCCCCTC ACTCCTTCTG    7500
```

```
GCTTTCCTTG CTAATTCTCA GCACAGTGGG CATTTTCCTG CTTTGGTGCT ACTATGGTTT      7560

GAGTGTATGT TTCCCTCCAA AATTCATACA TTGGAACTTA ATCCCCAAGG TGATGCTATT      7620

AAGAAGTGGG GCACTTAAAA GGTGATTAGG CCATGGAGGA ATGGGATTCA TGACCTCATA     7680

AAAGGGCTTG AGGGAGAAAG TTCTT                                          7705

(2) INFORMATION FOR SEQ ID NO:116:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R1

(xi) SEQUENCE DESCRIPTION: SEQ ID NO:116:

TCTCACGTCC CGTGCACGCC T                                              21

(2) INFORMATION FOR SEQ ID NO:117:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R2

(xi) SEQUENCE DESCRIPTION: SEQ ID NO:117:

ACTGAAGGCG GCTACTGAAG ACTT                                           24

(2) INFORMATION FOR SEQ ID NO:118:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R3

(xi) SEQUENCE DESCRIPTION: SEQ ID NO:118:

ATGGTAAACT TCTGTGGTTC TCTT                                           24

(2) INFORMATION FOR SEQ ID NO:119:

(i) SEQUENCE CHARACTERISTICS:
        (A) LENGTH: 26 base pairs
```

(B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R4

(xi) SEQUENCE DESCRIPTION: SEQ ID NO:119:

ATACAAAATT GTACTAGCAC CATTAC                                          26

(2) INFORMATION FOR SEQ ID NO:120:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R5

(xi) SEQUENCE DESCRIPTION: SEQ ID NO:120:

ACACTGGTGC TTATTAAAGT AACA                                            24

(2) INFORMATION FOR SEQ ID NO:121:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R6

(xi) SEQUENCE DESCRIPTION: SEQ ID NO:121:

AATTCAAATA TCATATAAAC ACCTAC                                          26

(2) INFORMATION FOR SEQ ID NO:122:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R7

(xi) SEQUENCE DESCRIPTION: SEQ ID NO:122:

CAATAGAATA GATACACTGA AGGT                                              24

(2) INFORMATION FOR SEQ ID NO:123:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R8

(xi) SEQUENCE DESCRIPTION: SEQ ID NO:123:

GGACTACAAA GTCTATTTAA GGGT                                              24

(2) INFORMATION FOR SEQ ID NO:124:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R9

(xi) SEQUENCE DESCRIPTION: SEQ ID NO:124:

ATCCCACTGT ATGAATATAT ACCA                                              24

(2) INFORMATION FOR SEQ ID NO:125:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R10

(xi) SEQUENCE DESCRIPTION: SEQ ID NO:125:

AGCCAGTCCA CGATGTATAC TT                                                22

(2) INFORMATION FOR SEQ ID NO:126:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
               (C) INDIVIDUAL ISOLATE: SSCP RAD50 PRIMER R11

(xi) SEQUENCE DESCRIPTION: SEQ ID NO:126:

ATCAGCCATG TAAGCTATAG TGAG                                              24

(2) INFORMATION FOR SEQ ID NO:127:

(i) SEQUENCE CHARACTERISTICS:
               (A) LENGTH: 24 base pairs
               (B) TYPE: nucleic acid
               (C) STRANDEDNESS: single
               (D) TOPOLOGY: linear (ii) MOLECULE TYPE: DNA (iii) HYPOTHETICAL: NO (iv) ANTI-SENSE: NO (vi) ORIGINAL SOURCE:
               (C) INDIVIDUAL ISOLATE: SSCP RAD50 PRIMER R12

(xi) SEQUENCE DESCRIPTION: SEQ ID NO:127:

GAAGCAGAAC AAAATTCTAC CACC                                              24

(2) INFORMATION FOR SEQ ID NO:128:

(i) SEQUENCE CHARACTERISTICS:
               (A) LENGTH: 24 base pairs
               (B) TYPE: nucleic acid
               (C) STRANDEDNESS: single
               (D) TOPOLOGY: linear (ii) MOLECULE TYPE: DNA (iii) HYPOTHETICAL: NO (iv) ANTI-SENSE: NO (vi) ORIGINAL SOURCE:
               (C) INDIVIDUAL ISOLATE: SSCP RAD50 PRIMER R13

(xi) SEQUENCE DESCRIPTION: SEQ ID NO:128:

GCTTTTTATT TTGGTGTTAC ACAG                                              24

(2) INFORMATION FOR SEQ ID NO:129:

(i) SEQUENCE CHARACTERISTICS:
               (A) LENGTH: 24 base pairs
               (B) TYPE: nucleic acid
               (C) STRANDEDNESS: single
               (D) TOPOLOGY: linear (ii) MOLECULE TYPE: DNA (iii) HYPOTHETICAL: NO (iv) ANTI-SENSE: NO (vi) ORIGINAL SOURCE:
               (C) INDIVIDUAL ISOLATE: SSCP RAD50 PRIMER R14

(xi) SEQUENCE DESCRIPTION: SEQ ID NO:129:

TAAGTCCTTG GAGATTCTTC ATTC                                              24

(2) INFORMATION FOR SEQ ID NO:130:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R15

(xi) SEQUENCE DESCRIPTION: SEQ ID NO:130:

GTGAATCTGC AGCTATCTCA ACTT                                              24

(2) INFORMATION FOR SEQ ID NO:131:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R16

(xi) SEQUENCE DESCRIPTION: SEQ ID NO:131:

AACAAATACT GTATTTCAAA ATACTTG                                           27

(2) INFORMATION FOR SEQ ID NO:132:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R17

(xi) SEQUENCE DESCRIPTION: SEQ ID NO:132:

ATGCTCATTC TTTACATATG CATTTAG                                           27

(2) INFORMATION FOR SEQ ID NO:133:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R18

(xi) SEQUENCE DESCRIPTION: SEQ ID NO:133:

GCTATAATCT TAGGATCAAA AATAGAC                                                27

(2) INFORMATION FOR SEQ ID NO:134:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: SSCP RAD50 PRIMER R19

(xi) SEQUENCE DESCRIPTION: SEQ ID NO:134:

ACCTTTGCAT TTGTATGAAT TATTGAC                                                27

(2) INFORMATION FOR SEQ ID NO:135:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: SSCP RAD50 PRIMER R20

(xi) SEQUENCE DESCRIPTION: SEQ ID NO:135:

GCAAGGTAGG CTATTTTAAG TACC                                                   24

(2) INFORMATION FOR SEQ ID NO:136:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: SSCP RAD50 PRIMER R21

(xi) SEQUENCE DESCRIPTION: SEQ ID NO:136:

GTTCTTGATA TAATGTGGAG ATATAGA                                                27

(2) INFORMATION FOR SEQ ID NO:137:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: SSCP RAD50 PRIMER R22

(xi) SEQUENCE DESCRIPTION: SEQ ID NO:137:

CTATTACATC TCCAAATGTT GCAACTT                                                  27

(2) INFORMATION FOR SEQ ID NO:138:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: SSCP RAD50 PRIMER R23

(xi) SEQUENCE DESCRIPTION: SEQ ID NO:138:

ACTCTTGTCA TGATTTGTTG GCAG                                                     24

(2) INFORMATION FOR SEQ ID NO:139:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: SSCP RAD50 PRIMER R24

(xi) SEQUENCE DESCRIPTION: SEQ ID NO:139:

TTCAAAGGTG TCAAAGTATC CTGA                                                     24

(2) INFORMATION FOR SEQ ID NO:140:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: SSCP RAD50 PRIMER R25

(xi) SEQUENCE DESCRIPTION: SEQ ID NO:140:

GATACAACCG TATTCAGAAT ACTGT                                                    25

(2) INFORMATION FOR SEQ ID NO:141:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R26

(xi) SEQUENCE DESCRIPTION: SEQ ID NO:141:

GTACAGTGAA GGTAAATCCC ATTCT                                              25

(2) INFORMATION FOR SEQ ID NO:142:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R27

(xi) SEQUENCE DESCRIPTION: SEQ ID NO:142:

TACATAACCT CAGTCTAACT GTGAG                                              25

(2) INFORMATION FOR SEQ ID NO:143:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R28

(xi) SEQUENCE DESCRIPTION: SEQ ID NO:143:

TTCTGCCTTA AACTACAATA AACTT                                              25

(2) INFORMATION FOR SEQ ID NO:144:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO -continued

```
    (vi) ORIGINAL SOURCE:
         (C) INDIVIDUAL ISOLATE: SSCP RAD50 PRIMER R29

(xi) SEQUENCE DESCRIPTION: SEQ ID NO:144:

GAATAATGCA GTAAGTTTAT TAAAGGA                                       27

(2) INFORMATION FOR SEQ ID NO:145:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: SSCP RAD50 PRIMER R30

(xi) SEQUENCE DESCRIPTION: SEQ ID NO:145:

TCTATGAGTA CAGAAGGACA CAGA                                          24

(2) INFORMATION FOR SEQ ID NO:146:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: SSCP RAD50 PRIMER R31

(xi) SEQUENCE DESCRIPTION: SEQ ID NO:146:

CTATGCCCTT ACATTAATTA CTGTGA                                        26

(2) INFORMATION FOR SEQ ID NO:147:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: SSCP RAD50 PRIMER R32

(xi) SEQUENCE DESCRIPTION: SEQ ID NO:147:

GGGTGACAGA ACGAGACTGT CTAA                                          24

(2) INFORMATION FOR SEQ ID NO:148:

(i) SEQUENCE CHARACTERISTICS:
        (A) LENGTH: 24 base pairs
        (B) TYPE: nucleic acid
        (C) STRANDEDNESS: single
```

(D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: SSCP RAD50 PRIMER R33

(xi) SEQUENCE DESCRIPTION: SEQ ID NO:148:

GTGAAGTCTG ACCCCTAAAG TAAG                                             24

(2) INFORMATION FOR SEQ ID NO:149:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: SSCP RAD50 PRIMER R34

(xi) SEQUENCE DESCRIPTION: SEQ ID NO:149:

CCGACGTGGT GCTATGAACA TAAG                                             24

(2) INFORMATION FOR SEQ ID NO:150:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: SSCP RAD50 PRIMER R35

(xi) SEQUENCE DESCRIPTION: SEQ ID NO:150:

CTCTCCTGTT ATGTGCCCTT AAGT                                             24

(2) INFORMATION FOR SEQ ID NO:151:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: SSCP RAD50 PRIMER R36

(xi) SEQUENCE DESCRIPTION: SEQ ID NO:151:

GTCATAGGTG TAAGTGATAT CATAAG                                           26

(2) INFORMATION FOR SEQ ID NO:152:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R37

(xi) SEQUENCE DESCRIPTION: SEQ ID NO:152:

CAGATTTCAT GTTAGTAACT TGGT      24

(2) INFORMATION FOR SEQ ID NO:153:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R38

(xi) SEQUENCE DESCRIPTION: SEQ ID NO:153:

TCACATTCCA GTAATAAAGA CGTT      24

(2) INFORMATION FOR SEQ ID NO:154:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R39

(xi) SEQUENCE DESCRIPTION: SEQ ID NO:154:

CTATGACTTT TCCACTTCAG GTTG      24

(2) INFORMATION FOR SEQ ID NO:155:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: SSCP RAD50 PRIMER R40

(xi) SEQUENCE DESCRIPTION: SEQ ID NO:155:

AAGAAAATCC CCAGTCTAAT ACTT                                              24

(2) INFORMATION FOR SEQ ID NO:156:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: SSCP RAD50 PRIMER R41

(xi) SEQUENCE DESCRIPTION: SEQ ID NO:156:

GAAGTACCAA TGACTTCCTT TTCC                                              24

(2) INFORMATION FOR SEQ ID NO:157:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: SSCP RAD50 PRIMER R42

(xi) SEQUENCE DESCRIPTION: SEQ ID NO:157:

CATTTGTGAT ACACCATGGT ACTC                                              24

(2) INFORMATION FOR SEQ ID NO:158:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: SSCP RAD50 PRIMER R43

(xi) SEQUENCE DESCRIPTION: SEQ ID NO:158:

AAGGCTACAG AGCATAGGTT CCTC                                              24

(2) INFORMATION FOR SEQ ID NO:159:

(i) SEQUENCE CHARACTERISTICS:
            (A) LENGTH: 24 base pairs (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: SSCP RAD50 PRIMER R44

(xi) SEQUENCE DESCRIPTION: SEQ ID NO:159:

GCTCCCCAGG CTTTTGAGAT ACCT                                            24

(2) INFORMATION FOR SEQ ID NO:160:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: SSCP RAD50 PRIMER R45

(xi) SEQUENCE DESCRIPTION: SEQ ID NO:160:

TCTGTGCTGG GCTTCTCACA TAGG                                            24

(2) INFORMATION FOR SEQ ID NO:161:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: SSCP RAD50 PRIMER R46

(xi) SEQUENCE DESCRIPTION: SEQ ID NO:161:

ACTCAACCAG AGCATGTGCA AGAG                                            24

(2) INFORMATION FOR SEQ ID NO:162:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: SSCP RAD50 PRIMER R47

(xi) SEQUENCE DESCRIPTION: SEQ ID NO:162:

```
GCGGTGACTT TTCAAATCAA AGAAGG                                    26

(2) INFORMATION FOR SEQ ID NO:163:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: SSCP RAD50 PRIMER R48

(xi) SEQUENCE DESCRIPTION: SEQ ID NO:163:

CAACATCCAA AATCCATGAC ACAATG                                    26

(2) INFORMATION FOR SEQ ID NO:164:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer 2B-8

(xi) SEQUENCE DESCRIPTION: SEQ ID NO:164:

CCAGGCTCAC TCACAGAGTC AAGG                                      24

(2) INFORMATION FOR SEQ ID NO:165:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer A106-AR (xi) SEQUENCE DESCRIPTION: SEQ ID NO:165:

TTTCTATGGC ATTTAAATCT TGGATATTT                                 29

(2) INFORMATION FOR SEQ ID NO:166:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA
```

-continued (iii) HYPOTHETICAL: NO (iv) ANTI-SENSE: NO (vi) ORIGINAL SOURCE:
         (C) INDIVIDUAL ISOLATE: Primer B4-2

(xi) SEQUENCE DESCRIPTION: SEQ ID NO:166:

CCTTGTTCAC AAGTTCTGTT GTCCTC                                                26

(2) INFORMATION FOR SEQ ID NO:167:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Primer N6Z-1

(xi) SEQUENCE DESCRIPTION: SEQ ID NO:167:

CATAATTGAT TTGAGGGAGA AGGA                                                  24

(2) INFORMATION FOR SEQ ID NO:168:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Primer N6Z-2

(xi) SEQUENCE DESCRIPTION: SEQ ID NO:168:

GTAACATCTG TCAGGCATAC TTTGGCACT                                             29

(2) INFORMATION FOR SEQ ID NO:169:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Primer G10-2

(xi) SEQUENCE DESCRIPTION: SEQ ID NO:169:

GCATTGTGGC TACGGCTTGC GTCC                                                  24

(2) INFORMATION FOR SEQ ID NO:170:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (vi) ORIGINAL SOURCE:
       (C) INDIVIDUAL ISOLATE: Primer G10-14

(xi) SEQUENCE DESCRIPTION: SEQ ID NO:170:

TCTAATCTCA CCAGGGACCT G                                                  21

(2) INFORMATION FOR SEQ ID NO:171:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (vi) ORIGINAL SOURCE:
       (C) INDIVIDUAL ISOLATE: Primer G10-N (xi) SEQUENCE DESCRIPTION: SEQ ID NO:171:

GAGAGGATCC TTTGTGGACT CCAGGTCCCT GGTGAGATT                                39

(2) INFORMATION FOR SEQ ID NO:172:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (vi) ORIGINAL SOURCE:
       (C) INDIVIDUAL ISOLATE: Primer G10-C1

(xi) SEQUENCE DESCRIPTION: SEQ ID NO:172:

GAGAGGATCC ATGAACATTG AATCCCAGGG AG                                      32

(2) INFORMATION FOR SEQ ID NO:173:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: NO (vi) ORIGINAL SOURCE:
       (C) INDIVIDUAL ISOLATE: Primer A106-21

```
        (xi) SEQUENCE DESCRIPTION: SEQ ID NO:173:

TCCCTTCAGC ATCACCACTC GGTAG                                             25

(2) INFORMATION FOR SEQ ID NO:174:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: Primer S1

(xi) SEQUENCE DESCRIPTION: SEQ ID NO:174:

CTTCTAAGCG GCCGCACCTA GCCCTCTGCT TCGCCGT                                 37

(2) INFORMATION FOR SEQ ID NO:175:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: Primer S2

(xi) SEQUENCE DESCRIPTION: SEQ ID NO:175:

CTCTCTCGAG TCAACAACGG TTACTACTGG GTGCTAA                                 37
```